US012767939B2

(12) United States Patent
Chen et al.

(10) Patent No.: US 12,767,939 B2
(45) **Date of Patent: *Oct. 20, 2026**

(54) COMPOSITIONS AND METHODS FOR GENE EDITING

(71) Applicant: The Regents of the University of California, Oakland, CA (US)

(72) Inventors: Jin Chen, San Francisco, CA (US); Luke Gilbert, San Francisco, CA (US); James Nunez, San Francisco, CA (US); Jonathan Weissman, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 713 days.

This patent is subject to a terminal disclaimer.

(21) Appl. No.: 17/726,290

(22) Filed: Apr. 21, 2022

(65) Prior Publication Data

US 2023/0103909 A1 Apr. 6, 2023

Related U.S. Application Data

(63) Continuation of application No. 17/073,588, filed on Oct. 19, 2020, now Pat. No. 11,434,491, which is a (Continued)

(51) Int. Cl.
*C12N 15/62* (2006.01)
*C07K 14/47* (2006.01)

(Continued)

(52) U.S. Cl.
CPC .......... *C12N 15/62* (2013.01); *C07K 14/4702* (2013.01); *C12N 9/1007* (2013.01);

(Continued)

(58) Field of Classification Search
CPC ........ C12N 15/62; C12N 9/1007; C12N 9/22; C07K 2319/00; C07K 2319/09; C12Y 201/01072
See application file for complete search history.

(56) References Cited

U.S. PATENT DOCUMENTS

| | | | |
|---|---|---|---|
| 6,919,204 | B2 | 7/2005 | Wolffe et al. |
| 8,658,393 | B2 | 2/2014 | Reik et al. |

(Continued)

FOREIGN PATENT DOCUMENTS

| | | | |
|---|---|---|---|
| WO | WO-03/072788 | A1 | 9/2003 |
| WO | WO-2013/141680 | A1 | 9/2013 |

(Continued)

OTHER PUBLICATIONS

DeWitt, Mark A., et al. "Genome Editing via Delivery of Cas9 Ribonucleoprotein." Methods, vol. 121-122, May 2017, pp. 9-15, https://doi.org/10.1016/j.ymeth.2017.04.003. Accessed May 6, 2020. (Year: 2017).*

(Continued)

*Primary Examiner* — Kimberly Chong
*Assistant Examiner* — Africa M McLeod
(74) *Attorney, Agent, or Firm* — Mintz Levin Cohn Ferris Glovsky and Popeo, P.C.

(57) ABSTRACT

Provided herein are, inter alia, compositions and methods for manipulation of genomes of living organisms. Provided herein also are fusion protein compositions that can turn off genes permanently and reversibly in mammalian cells using CRISPR-based epigenome editing. In addition, provided herein are fusion proteins including, from N-terminus to C-terminus, a DNA methyltransferase domain, a nuclease deficient RNA-guided endonuclease enzyme, and a Krüppel associated box domain.

14 Claims, 24 Drawing Sheets

Specification includes a Sequence Listing.

Related U.S. Application Data continuation of application No. PCT/US2019/028377, filed on Apr. 19, 2019.

(60) Provisional application No. 62/660,023, filed on Apr. 19, 2018.

(51) Int. Cl.

| | |
|---|---|
| ***C12N 9/10*** | (2006.01) |
| ***C12N 9/22*** | (2006.01) |
| ***C12N 15/113*** | (2010.01) |
| ***C12N 15/63*** | (2006.01) |

(52) U.S. Cl.

CPC ............ *C12N 15/113* (2013.01); *C12N 15/63* (2013.01); *C07K 2319/00* (2013.01); *C07K 2319/09* (2013.01); *C07K 2319/33* (2013.01); *C12N 9/22* (2013.01); *C12N 2310/20* (2017.05); *C12Y 201/01072* (2013.01); *C12Y 301/00* (2013.01)

(56) References Cited

U.S. PATENT DOCUMENTS

| | | | |
|---|---|---|---|
| 8,697,359 | B1 | 4/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,993,233 | B2 | 3/2015 | Zhang et al. |
| 8,999,641 | B2 | 4/2015 | Zhang et al. |
| 9,139,628 | B2 | 9/2015 | Minczuk et al. |
| 9,267,135 | B2 | 2/2016 | Church et al. |
| 9,322,006 | B2 | 4/2016 | Liu et al. |
| 9,526,784 | B2 | 12/2016 | Liu et al. |
| 9,771,601 | B2 | 9/2017 | May et al. |
| 9,840,713 | B2 | 12/2017 | Zhang |
| 9,850,500 | B2 | 12/2017 | Yun et al. |
| 10,266,850 | B2 | 4/2019 | Doudna et al. |
| 10,323,073 | B2 | 6/2019 | Tremblay et al. |
| 10,329,587 | B2 | 6/2019 | Church et al. |
| 10,378,027 | B2 | 8/2019 | Joung et al. |
| 10,443,076 | B2 | 10/2019 | Doudna et al. |
| 10,525,082 | B2 | 1/2020 | Crane et al. |
| 10,526,589 | B2 | 1/2020 | Tsai et al. |
| 10,570,378 | B2 | 2/2020 | Ji et al. |
| 10,583,201 | B2 | 3/2020 | Chen et al. |
| 10,604,752 | B2 | 3/2020 | Chen et al. |
| 10,612,044 | B2 | 4/2020 | Hatada et al. |
| 10,676,726 | B2 | 6/2020 | Gersbach et al. |
| 10,676,735 | B2 | 6/2020 | Gersbach et al. |
| 10,704,060 | B2 | 7/2020 | Gersbach et al. |
| 10,760,064 | B2 | 9/2020 | Joung et al. |
| 11,072,782 | B2 | 7/2021 | Cathomen et al. |
| 11,434,491 | B2 | 9/2022 | Chen et al. |
| 2007/0192880 | A1 | 8/2007 | Muyan et al. |
| 2009/0023153 | A1 | 1/2009 | Wolffe et al. |
| 2012/0207744 | A1 | 8/2012 | Mendlein et al. |
| 2014/0377868 | A1 | 12/2014 | Joung et al. |
| 2015/0191744 | A1 | 7/2015 | Wolfe et al. |
| 2015/0232883 | A1 | 8/2015 | Dahlman et al. |
| 2015/0247150 | A1 | 9/2015 | Zhang et al. |
| 2016/0010076 | A1 | 1/2016 | Joung et al. |
| 2016/0153005 | A1 | 6/2016 | Zhang et al. |
| 2016/0168594 | A1 | 6/2016 | Zhang et al. |
| 2016/0201089 | A1 | 7/2016 | Gersbach et al. |
| 2016/0298135 | A1 | 10/2016 | Chen et al. |
| 2016/0304872 | A1 | 10/2016 | Elowitz et al. |
| 2016/0319281 | A1 | 11/2016 | Tsai et al. |
| 2017/0191082 | A1 | 7/2017 | Chen et al. |
| 2017/0204407 | A1 | 7/2017 | Gilbert et al. |
| 2017/0219596 | A1 | 8/2017 | Tanenbaum et al. |
| 2017/0233762 | A1 | 8/2017 | Zalatan et al. |
| 2018/0030425 | A1 | 2/2018 | Joung et al. |
| 2018/0059373 | A1 | 3/2018 | Chen et al. |
| 2018/0216104 | A1 | 8/2018 | Abul-Husn et al. |
| 2018/0273976 | A1 | 9/2018 | Umit et al. |
| 2019/0010481 | A1 | 1/2019 | Joung et al. |
| 2019/0024072 | A1 | 1/2019 | Cathomen et al. |
| 2019/0024090 | A1 | 1/2019 | Cathomen et al. |
| 2019/0032049 | A1 | 1/2019 | Naldini et al. |
| 2019/0062739 | A1 | 2/2019 | Church et al. |
| 2019/0100732 | A1 | 4/2019 | Hellman et al. |
| 2019/0127713 | A1 | 5/2019 | Gersbach et al. |
| 2019/0194633 | A1 | 6/2019 | Gersbach et al. |
| 2019/0218261 | A1 | 7/2019 | Cheng et al. |
| 2019/0300868 | A1 | 10/2019 | Gilbert et al. |
| 2019/0328732 | A1 | 10/2019 | Deutzmann et al. |
| 2019/0343865 | A1 | 11/2019 | Jones et al. |
| 2019/0350938 | A1 | 11/2019 | Hoch et al. |
| 2019/0351074 | A1 | 11/2019 | Ahituv et al. |
| 2019/0376090 | A1 | 12/2019 | Joung et al. |
| 2019/0382752 | A1 | 12/2019 | Zeisberg et al. |
| 2020/0002710 | A1 | 1/2020 | Khalil et al. |
| 2020/0003761 | A1 | 1/2020 | Studer et al. |
| 2020/0071730 | A1 | 3/2020 | Joung et al. |
| 2020/0109406 | A1 | 4/2020 | Miller et al. |

FOREIGN PATENT DOCUMENTS

| | | | |
|---|---|---|---|
| WO | WO-2013/176772 | A1 | 11/2013 |
| WO | WO-2014/065596 | A1 | 5/2014 |
| WO | WO-2014/089290 | A1 | 6/2014 |
| WO | WO-2014/099744 | A1 | 6/2014 |
| WO | WO-2016/011080 | A2 | 1/2016 |
| WO | WO-2016/011080 | A3 | 1/2016 |
| WO | WO-2016/063264 | A1 | 4/2016 |
| WO | WO-2018/031762 | A1 | 2/2018 |
| WO | WO-2018/053035 | A1 | 3/2018 |
| WO | WO-2018/195540 | A1 | 10/2018 |
| WO | WO-2019/092507 | A2 | 5/2019 |
| WO | WO-2019/092507 | A3 | 5/2019 |
| WO | WO-2019/109051 | A1 | 6/2019 |
| WO | WO-2019/113061 | A1 | 6/2019 |
| WO | WO-2019/117660 | A2 | 6/2019 |
| WO | WO-2019/117660 | A3 | 6/2019 |
| WO | WO-2019/117662 | A2 | 6/2019 |
| WO | WO-2019/117662 | A3 | 6/2019 |
| WO | WO-2019/126799 | A1 | 6/2019 |
| WO | WO-2019/168950 | A1 | 9/2019 |
| WO | WO-2019/204503 | A1 | 10/2019 |
| WO | WO-2019/204766 | A1 | 10/2019 |
| WO | WO-2019/209869 | A2 | 10/2019 |
| WO | WO-2019/209869 | A3 | 10/2019 |
| WO | WO-2019/210279 | A1 | 10/2019 |
| WO | WO-2019/222437 | A1 | 11/2019 |
| WO | WO-2019/232069 | A1 | 12/2019 |
| WO | WO-2020/041679 | A1 | 2/2020 |
| WO | WO-2020/041679 | A4 | 2/2020 |
| WO | WO-2020/041776 | A1 | 2/2020 |
| WO | WO-2020/101042 | A1 | 5/2020 |
| WO | WO-2020/101042 | A8 | 5/2020 |

OTHER PUBLICATIONS

Georgios Vlachogiannis, et al. "The Dnmt3L ADD Domain Controls Cytosine Methylation Establishment during Spermatogenesis." Cell Reports, vol. 10, No. 6, Feb. 1, 2015, pp. 944-956, https://doi.org/10.1016/j.celrep.2015.01.021. Accessed Sep. 9, 2023. (Year: 2015).*

Gordana Apic, et al. "Multi-Domain Protein Families and Domain Pairs: Comparison with Known Structures and a Random Model of Domain Recombination." Journal of Structural and Functional Genomics, vol. 4, No. 2/3, Jan. 1, 2003, pp. 67-78, https://doi.org/10.1023/a:1026113408773. Accessed Jan. 16, 2025. (Year: 2003).*

Ley, Timothy J., et al. "DNMT3AMutations in Acute Myeloid Leukemia." New England Journal of Medicine, vol. 363, No. 25, Dec 16, 2010, pp. 2424-2433, https://doi.org/10.1056/nejmoa1005143. (Year: 2010).*

(56) References Cited

OTHER PUBLICATIONS

Park, Jong-Jin, et al. "RNA-Guided Transcriptional Activation via CRISPR/DCas9 Mimics Overexpression Phenotypes in Arabidopsis." PLOS ONE, vol. 12, No. 6, Jun. 16, 2017, p. e0179410, https://doi.org/10.1371/journal.pone.0179410. (Year: 2017).*
Peng, Hongzhuang, et al. "Epigenetic Gene Silencing by the SRY Protein Is Mediated by a KRAB-O Protein That Recruits the KAP1 Co-Repressor Machinery." Journal of Biological Chemistry, vol. 284, No. 51, Dec 2009, pp. 35670-35680, https://doi.org/10.1074/jbcm109.032086. Accessed Jul. 20, 2021. (Year: 2009).*
Swarts, Daan C., et al. "Structural Basis for Guide RNA Processing and Seed-Dependent DNA Targeting by CRISPR-Cas12a." Molecular Cell, vol. 66, No. 2, Apr. 2017, pp. 221-233.e4, https://doi.org/10.1016/j.molcel.2017.03.016. (Year: 2017).*
Yamano, Takashi, et al. "Structural Basis for the Canonical and Non-Canonical PAM Recognition by CRISPR-Cpf1." Molecular Cell, vol. 67, No. 4, Aug. 2017, pp. 633-645.e3, https://doi.org/10.1016/j.molcel.2017.06.035. Accessed Apr. 17, 2021. (Year: 2017).*
Jinek, M. et al. (Aug. 17, 2012). "A programmable dual-RNA-guided DNA endonuclease in adaptive bacterial immunity," *Science* 337(6096):816-821.
Lupo, A. et al. (Jun. 2013). "KRAB-Zinc Finger Proteins: A Repressor Family Displaying Multiple Biological Functions," *Curr Genomics* 4(4):268-278.
Petrossian, T. (Oct. 1, 2009). "Bioinformatic Identification of Novel Methyltransferases," *Epigenomics* 1(1):163-175.
Adamson, B. et al. (Dec 15, 2016). "A Multiplexed Single-Cell CRISPR Screening Platform Enables Systematic Dissection of the Unfolded Protein Response," *Cell* 167(7):1867-1882.e21.
Amabile, A. et al. (Sep. 22, 2016). "Inheritable Silencing of Endogenous Genes by Hit-and-Run Targeted Epigenetic Editing," *Cell* 167(1):219-232.
Braun, C.J. et al. (Jul. 5, 2016, e-published Jun. 20, 2016). "Versatile in vivo regulation of tumor phenotypes by dCas9-mediated transcriptional perturbation," *PNAS USA* 113(27):E3892-E3900.
Chen, B. et al. (Dec 19, 2013). "Dynamic imaging of genomic loci in living human cells by an optimized CRISPR/Cas system," *Cell* 155(7):1479-1491.
Choudhury, S.R. et al. (Jul. 19, 2016). "CRISPR-dCas9 mediated TET1 targeting for selective DNA demethylation at BRCA1 promoter," *Oncotarget* 7(29):46545-46556.
Deans, R.M. et al. (May 2016, e-published Mar. 28, 2016). "Parallel shRNA and CRISPR-Cas9 screens enable antiviral drug target identification," *Nat Chem Biol* 12(5):361-366.
Deuschle U. et al. (Apr. 1995). "Tetracycline-reversible silencing of eukaryotic promoters," *Mol Cell Biol.* 15(4):1907-1914.
Ecco, G. et al. (Aug. 1, 2017). "KRAB zinc finger proteins," *Development* 144(15):2719-2729.
Extended European Search Report dated Jan. 4, 2022, for EP Patent Application No. 19789200.3, 9 pages.
Gilbert, L.A. et al. (Jul. 18, 2013, e-published Jul. 11, 2013). "CRISPR-mediated modular RNA-guided regulation of transcription in eukaryotes," *Cell* 154(2):442-451.
Gilbert, L.A. et al. (Oct. 23, 2014, e-published Oct. 9, 2014). "Genome-Scale CRISPR-Mediated Control of Gene Repression and Activation," *Cell* 159(3):647-661.
Gowher, H. et al. (Apr. 8, 2005, e-published Jan. 24, 2005). "Mechanism of Stimulation of Catalytic Activity of Dnmt3A and Dnmt3B DNA-(Cytosine-C5)-methyltransferases By Dnmt3L", *The Journal of Biological Chemistry*, 280(14):13341-13348.
Guilinger, J.P. et al. (Apr. 25, 2014). "Fusion of catalytically inactive Cas9 to FokI nuclease improves the specificity of genome modification," *Nature Biotechnology* 32(6): 577-582.
Horlbeck, M.A. et al. (2016). "Compact and highly active next-generation libraries for CRISPR-mediated gene repression and activation," *eLife* 5:e19760.
Horlbeck, M.A. et al. (2016). "Nucleosomes impede Cas9 access to DNA in vivo and in vitro," *eLife* 5:e12677.
International Search Report mailed on Sep. 10, 2019, for PCT/US2019/028377, filed Apr. 19, 2019, 6 pages.
Kearns, N.A. et al. (Jan. 2014). "Cas9 effector-mediated regulation of transcription and differentiation in human pluripotent stem cells," *Development* 141(1):219-223.
Kocak, D. D. (2013). "Synthetic Transcription Factors and their Effects on Endogenous DNA Methylation in Human Cells," [Unpublished Master's Thesis]. Duke University. Located at https://dukespace.lib.duke.edu/dspace/bitstream/handle/10161/8802/Kocak_duke_0066N_12237.pdf?sequence=1, 35 pages.
Larson, M.H. et al. (Nov. 2013, e-published Oct. 17, 2013). "CRISPR interference (CRISPRi) for sequence-specific control of gene expression," *Nat Protoc* 8(11):2180-2196.
Li, H. et al. (Jul. 14, 2006, e-published May 8, 2006). "The Histone Methyltransferase SETDB1 and the DNA Methyltransferase DNMT3A Interact Directly and Localize to Promoters Silenced in Cancer Cells," *The Journal of Biological Chemistry* 281(28):19489-19500.
Lin, L. et al. (Mar. 1, 2018). "Genome-wide determination of on-target and off-target characteristics for RNA-guided DNA methylation by dCas9 methyltransferases," *Gigascience* 7(3):1-19.
Liu, X.S. et al. Sep. 22, 2016). "Editing DNA Methylation in the Mammalian Genome," *Cell* 167(1):233-247.e17.
Liu, S.J. et al. (Jan. 6, 2017, e-published Dec 15, 2016). "CRISPRi-based genome-scale identification of functional long noncoding RNA loci in human cells," *Science* 355(6320):aah7111.
Mandegar, M.A. et al. (Apr. 7, 2016, e-published Mar. 10, 2016). "CRISPR Interference Efficiently Induces Specific and Reversible Gene Silencing in Human iPSCs," *Cell Stem Cell* 18(4):541-553.
Mlambo, T. et al. (May 18, 2018). "Designer epigenome modifiers enable robust and sustained gene silencing in clinically relevant human cells," *Nucleic Acids Res* 46(9):4456-4468.
Nemudryi, A.A. et al. (Jul. 2014). "TALEN and CRISPR/Cas Genome Editing Systems: Tools of Discovery," *Acta Naturae* 6(3):19-40.
Nguyen, D.P. et al. (Jul. 1, 2016). "Ligand-binding domains of nuclear receptors facilitate tight control of split CRISPR activity," *Nat Commun* 7:12009.
O'Geen, H. et al. (Sep. 29, 2017). "dCas9-based epigenome editing suggests acquisition of histone methylation is not sufficient for target gene repression," *Nucleic Acids Research* 45(17):9901-9916.
O'Geen, H. et al. (Apr. 8, 2022). "Determinants of heritable gene silencing for KRAB-dCas9 + DNMT3 and Ezh2-dCas9 + DNMT3 hit-and-run epigenome editing," *Nucleic Acids Res* 50(6):3239-3253.
Qi, L.S. et al. (Feb. 28, 2013). "Repurposing CRISPR as an RNA-guided platform for sequence-specific control of gene expression," *Cell* 152(5):1173-1183.
Rivenbark, A.G. et al. (Apr. 2012). "Epigenetic reprogramming of cancer cells via targeted DNA methylation," *Epigenetics* 7(4):350-360.
Schellenberger, V. et al. (Dec 2009). "A recombinant polypeptide extends the in vivo half-life of peptides and proteins in a tunable manner," *Nature Biotechnology* 27(12):1186-1190.
Siddique, A.N. et al. (Feb. 8, 2013, e-published Dec. 4, 2012). "Targeted methylation and gene silencing of VEGF-A in human cells by using a designed Dnmt3a-Dnmt3L single-chain fusion protein with increased DNA methylation activity," *J Mol Biol* 425(3):479-491.
Stepper, P. et al. (Feb. 28, 2017, e-published Nov. 28, 2016). "Efficient targeted DNA methylation with chimeric dCas9-Dnmt3a-Dnmt3L methyltransferase," *Nucleic Acids Res* 45(4):1703-1713.
Vojta, A. et al. (Jul. 8, 2016, e-published Mar. 11, 2016). "Repurposing the CRISPR-Cas9 system for targeted DNA methylation," *Nucleic Acids Research* 44(12):5615-5628.
Wilson, R.C. et al. (Feb. 16, 2018, e-published Oct. 19, 2017). "The Promise and Challenge of In Vivo Delivery for Genome Therapeutics," *ACS Chem Biol* 13(2):376-382.
Written Opinion mailed on Sep. 10, 2019, for PCT/US2019/028377, filed Apr. 19, 2019, 10 pages.
Zalatan, J.G. et al. (Jan. 15, 2015, e-published Dec 18, 2014). "Engineering complex synthetic transcriptional programs with CRISPR RNA scaffolds," *Cell* 160(1-2):339-350.
Zhang Z. et al. (Aug. 15, 2013). "Dissecting the roles of miR-302/367 cluster in cellular reprogramming using TALE-based repressor and TALEN," *Stem Cell Reports* 1(3):218-225.

(56) References Cited

OTHER PUBLICATIONS

Miao, C. et al. (Apr. 9, 2018). "Systematically investigating the key features of the nuclease deactivated Cpf1 for tunable multiplex genetic regulation," *bioRxiv* No. 297903; doi: doi.org/10.1101/297903.
Zetsche, B. et al. (Oct. 22, 2015). "Cpf1 is a single RNA-guided endonuclease of a class 2 CRISPR-Cas system," *Cell* 163(3):759-771.
Zhang, X. et al. (Jun. 6, 2017). "Multiplex gene regulation by CRISPR-ddCpf1," *Cell Discov* 3:17018.
Zhang, X. et al. (Apr. 2018). "Gene activation in human cells using CRISPR/Cpf1-p300 and CRISPR/Cpf1-SunTag systems," *Protein Cell* 9(4):380-383, and S1-S8.

* cited by examiner

FIG. 13B
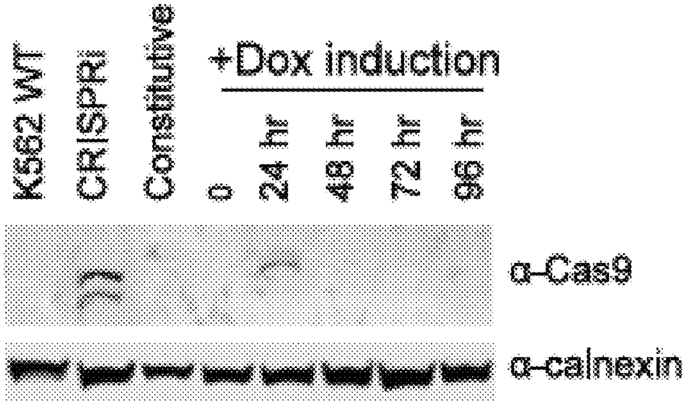
FIG. 13C
FIG. 13D
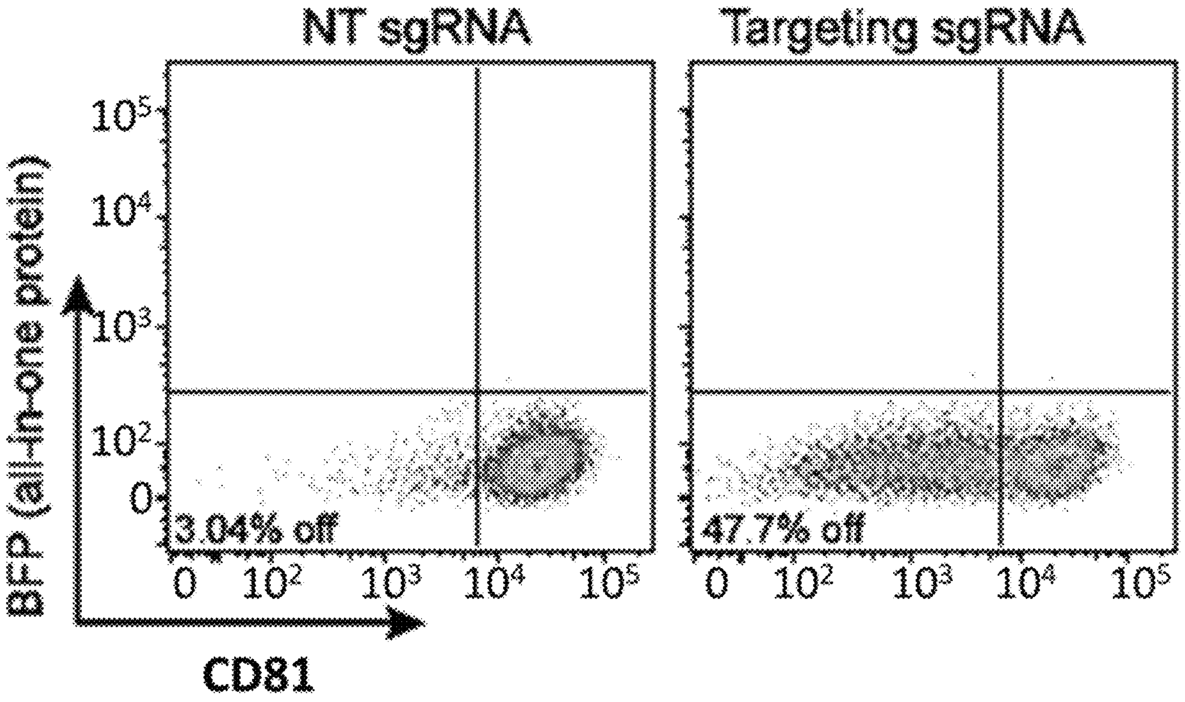

FIG. 13E
FIG. 13F
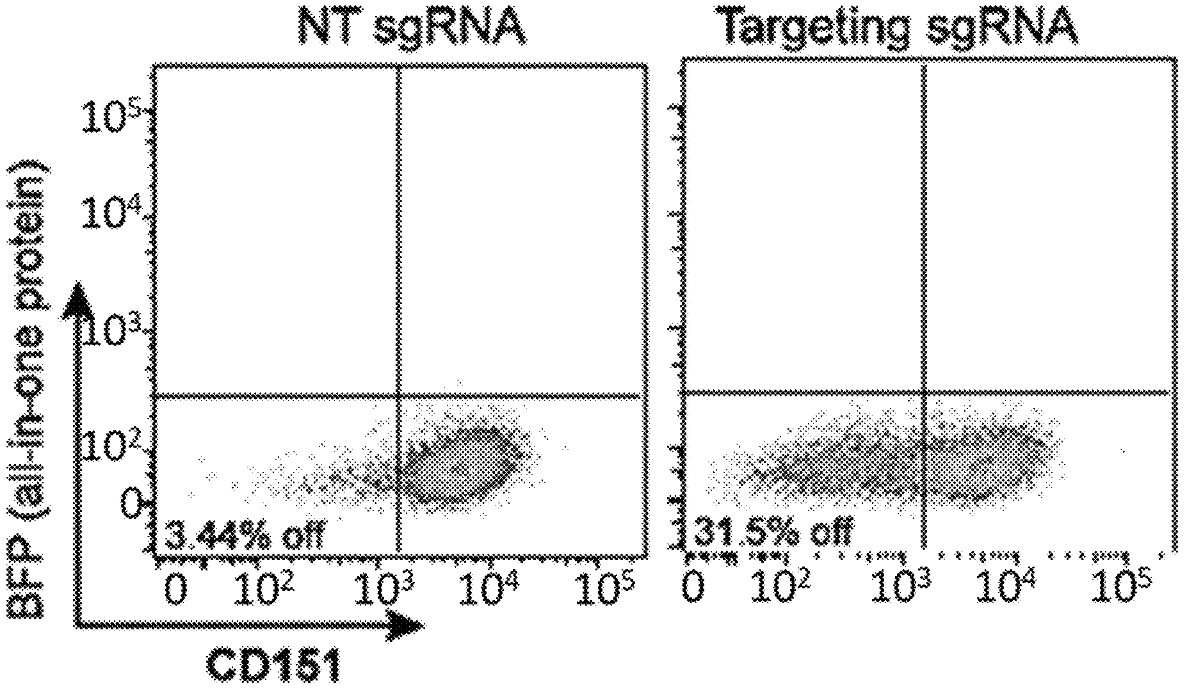
FIG. 13G
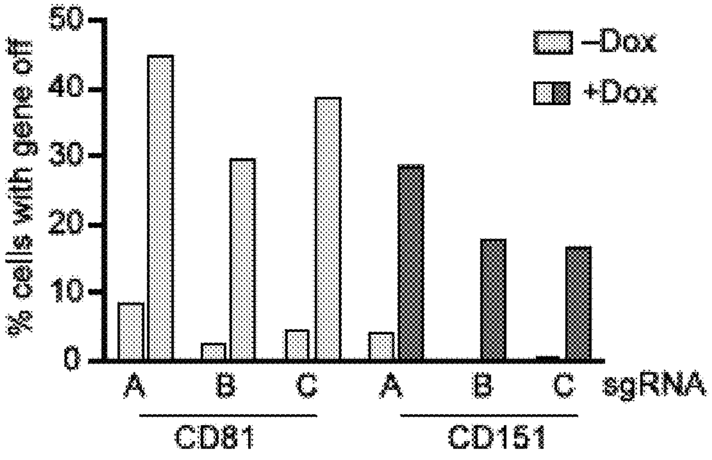

COMPOSITIONS AND METHODS FOR GENE EDITING

CROSS-REFERENCE TO RELATED APPLICATIONS

This application is a continuation of U.S. patent application Ser. No. 17/073,588 filed Oct. 19, 2020, now U.S. Pat. No. 11,434,491, issued on Sep. 6, 2022, which is a continuation under 35 USC § 120 of International Application No. PCT/US2019/028377 filed Apr. 19, 2019, which claims priority to U.S. Application No. 62/660,023 filed Apr. 19, 2018, the disclosure of which is incorporated by reference herein in their entireties.

STATEMENT AS TO RIGHTS TO INVENTIONS MADE UNDER FEDERALLY SPONSORED RESEARCH AND DEVELOPMENT

This invention was made with government support under grant no. HR0011-17-2-0043 awarded by the Department of Defense, Defense Advanced Research Projects Agency and grant no. R01 DA036858 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048536-620001WO_SequenceListing_ST25.txt, created May 14, 2019, 382,771 bytes, machine format IBM-PC, MS Windows operating system, is hereby incorporated by reference.

BACKGROUND

Although considered a promising therapeutic approach for treatment of disease, genome editing carries inherent risks due to the potential for genotoxicity from double strand breaks. Further, genome editing often is associated with an all-or-none effect on the target gene (i.e., it produces a full knockout). In contrast, targeted epigenome engineering does not carry the risk of DSB-induced genotoxicity; further, it affords the opportunity to create a more graded effect on gene expression and thus function from a complete silencing through a less pronounced effect.

Provided herein are solutions to these and other needs in the art.

BRIEF SUMMARY

In an aspect is provided a fusion protein including a nuclease-deficient RNA-guided DNA endonuclease enzyme, a Krüppel associated box (KRAB) domain and a DNA methyltransferase domain. In an aspect is provided a fusion protein of any one of SEQ ID NOS: 1-15.

In an aspect is provided a nucleic acid sequence encoding the fusion protein as described herein, including embodiments and aspects thereof.

In an aspect is provided a complex including a fusion protein as described herein, including embodiments and aspects thereof, and a polynucleotide including (1) a DNA-targeting sequence that is complementary to a target polynucleotide sequence and (2) a binding sequence for the nuclease-deficient RNA-guided DNA endonuclease enzyme, wherein the nuclease-deficient RNA-guided DNA endonuclease enzyme is bound to the polynucleotide via the binding sequence.

In an aspect is provided a vector including the nucleic acid sequence of a fusion protein as described herein, including embodiments and aspects thereof.

In an aspect is provided a cell including a fusion protein as described herein, including embodiments and aspects thereof, a nucleic acid as described herein, including embodiments and aspects thereof, a complex as described herein, including embodiments and aspects thereof, or a vector as described herein, including embodiments and aspects thereof.

In an aspect is provided a method of silencing a target nucleic acid sequence in a cell, including delivering a first polynucleotide encoding a fusion protein as described herein, including embodiments and aspects thereof, to a cell containing the target nucleic acid, and delivering to the cell a second polynucleotide including (i) a DNA-targeting sequence that is complementary to the target nucleic acid sequence, and (ii) a binding sequence for the nuclease-deficient RNA-guide DNA endonuclease enzyme. Without intending to be bound by any theory, it is believed that the fusion protein silences the target nucleic acid sequence in the cell by methylating a chromatin containing the target nucleic acid sequence and/or by introducing repressive chromatin marks to a chromatin containing the target nucleic acid sequence. Thus, in aspects, the fusion protein silences the target nucleic acid sequence in the cell by methylating a chromatin containing the target nucleic acid sequence and/or by introducing repressive chromatin marks to a chromatin containing the target nucleic acid sequence.

In an aspect is provided a method of silencing a target nucleic acid sequence in a cell, including delivering a complex as described herein, including embodiments and aspects thereof, to a cell containing the target nucleic acid, wherein the complex silences the target nucleic acid sequence in the cell. Without intending to be bound by any theory, it is believed that the complex silences the target nucleic acid sequence in the cell by methylating a chromatin containing the target nucleic acid sequence and/or by introducing repressive chromatin marks to a chromatin containing the target nucleic acid sequence. Thus, in aspects, the complex silences the target nucleic acid sequence in the cell by methylating a chromatin containing the target nucleic acid sequence and/or by introducing repressive chromatin marks to a chromatin containing the target nucleic acid sequence

BRIEF DESCRIPTION OF THE DRAWINGS

FIG. 1A is a schematic of an all-in-one protein (SEQ ID NO:1) of the disclosure that has the KRAB domain fused to the -N-terminus of dCas9 (SEQ ID NO:23), separated by a GGSGGGS (SEQ ID NO: 17) linker, and Dnmt3A-Dnmt3L at the C-terminus of dCas9 (separated by a EASGSGRASPGIPGSTR (SEQ ID NO:19) linker). FIG. 1B provides schematics of dCas9-fused epigenetic modulators tested for permanent gene silencing. The dCas9-KRAB protein is adapted from Gilbert et al., Cell 2013 for CRISPR interference (CRISPRi) applications. The dCas9-Dnmt3A-Dnmt3L fusion is adapted from Stepper et al., Nucleic Acids Research, 2016. The inventors engineered a novel all-in-one protein that combines the KRAB domain (SEQ ID NO:16), dCas9 (D10A, H208A), Dnmt3A-Dnmt3L (SEQ ID NO:33; where Dnmt3A is SEQ ID NO:26 and Dnmt3L is SEQ ID NO:28) into one polypeptide. FIG. 1C provides schematics of a methylation-sensitive GFP reporter (adapted from Stelzer et al., Cell 2015) that was used to assess long-term silencing by the all-in-one protein. FIGS. 1D-1E provide a diagram and results of a hit-and-run experimental workflow in HEK293T cells expressing the GFP reporter shown in FIG. 3. FIG. 1D shows that plasmids were co-transfected into cells, one encoding the hit-and-run protein and the other plasmid encoding a sgRNA. FIG. 1E shows the results of the hit-and-run assay sorted for cells that were co-transfected with the all-in-one plasmid and sgRNA plasmid. FIG. 1F shows the results of the silencing of the GFP reporter is dependent on the sgRNA sequence.

FIGS. 2A-2C are representative flow cytometry data shown taken 22 days post-transfection following gene (CD29, CD81, CD151) targeting for long term silencing using the all-in-one protein. Quadrant IV represents cells that have turned off the gene, indicated by the percentage of cells with the gene off (i.e., 45%, 66%, and 53%, respectively). FIG. 2D provides quantification of silencing of CD29, CD81, and CD151 with three different sgRNA. FIG. 2E provides quantification of silencing of two or three genes simultaneously to show that the all-in-protein can be multiplexed by co-delivery of sgRNAs targeting different genes. FIG. 2F provides a plot representing a time point taken 9 months post transfection of the all-in-one protein and sgRNA targeting the CLTA gene, signifying that the majority of cells have stably turned off the CLTA gene.

FIGS. 3A-3C shows that harvested cells lost expression of CD29 (FIG. 3A), CD81 (FIG. 3B), and CD151 (FIG. 3C) thirty-six days post-transfection, as determined by their RNA expression profiles. FIGS. 3D-3F are volcano plots showing that the targeted genes CD29 (FIG. 3D), CD81 (FIG. 3E) and CD151 (FIG. 3F) is the only significant gene knocked down for each experiment, signifying high specificity of gene silencing. FIGS. 3G-3I provides quantification of transcript levels of CD151 (FIG. 3G), CD81 (FIG. 3H), and CD29 (FIG. 3I) showing more than 96% knockdown of each of the targeted genes.

FIGS. 4A-4F are flow cytometry plots showing BFP expression (which is fused to the all-in-one protein) in HeLa (cervical) (FIG. 4A), U2OS (bone) (FIG. 4B), and human induced pluripotent cells (iPSC) (FIG. 4C). FIGS. 4D-4F are the untransfected controls for FIGS. 4A-4C, respectively. FIG. 4G shows that stable silencing of endogenous genes in HeLa and U2OS cells, measured at 18 days post-transfection with the all-in-one protein, was achieved. In FIGS. 4A-4F, the x-axis is BFP (fused to all-in-one protein), and the y-axis is mCherry. FIG. 4H shows that gene silencing was detected 14 days post transfection by qPCR in AML12 mouse hepatocyte cell lines when targeting Pcsk9, Npc1, Spcs1 and Cd81.

FIGS. 6A-6-B shows the gene silencing results 18 days post-transfection of the fusion proteins of SEQ ID NOS: 1-15 transfected into HEK293T cells for targeted silencing of the CLTA gene. The dCas9-KRAB and dCas9-Dnmt3A-Dnmt3L designs showed transient and lower efficiency of long term silencing. FIGS. 6C-6D provide a comparison of SEQ ID NO:1 (p76) and SEQ ID NO:15 (p112) for silencing the HIST2H2BE (H2B) endogenous gene (FIG. 6C) and a synthetic Snrpn-GFP reporter gene (FIG. 6D) stably expressed in HEK293T cells. FIG. 6E provides a plot of protein expression (dotted lines) of p76 and p112 over the 50 day time course to turn off the HIST2H2BE (H2B) gene. Protein levels were measured by flow cytometry detection of BFP, which is co-expressed with the all-in-one protein.

FIG. 7A is a Western blot analysis of the all-in-one protein variants p76 and p90-p102 using an antibody against *Streptococcus pyogenes* Cas9. The top band represents full-length protein and smaller-sized bands represent proteolysis of the all-in-one protein. FIG. 7B is a Western blot analysis of all-in-one protein variants to detect free Dnmt3A that is cleaved from the fusion protein.

FIG. 8A is a schematic of a pooled screen to determine the optimal sgRNAs that leads to long term gene silencing. FIGS. 8B-8E are flow cytometry histograms of the percent of cells undergoing gene silencing four weeks post-transfection. Four HEK293T cell lines were used, each with a different gene with a GFP tag, including CLTA (FIG. 8B), VIM (FIG. 8C), HIST2H2BE (H2B) (FIG. 8D), and RAB11A (FIG. 8E).

FIG. 10A is a workflow of a pooled screen in HEK293T cells to determine optimal sgRNA targeting positions for the all-in-one protein, adapted from a previous ricin tiling screen in K562 cells to determine optimal sgRNAs for dCas9-KRAB (Gilbert, Horlbeck et al., Cell 2014). FIGS. 10B-10E are representative plots showing growth phenotypes for four genes, including ARLI (FIG. 10B), EIF6 (FIG. 10C), SMC3 (FIG. 10D), HEATR1 (FIG. 10E), from existing dCas9-KRAB/CRISPRi datasets in K562 cells (Gilbert, Horlbeck et al., 2014) and with the all-in-one protein (bottom plot). Each dot represents an sgRNA. The TSS and annotated CpG island are shown for each gene.

FIG. 12A shows the in vitro transcription of two all-in-one variants (p102 and p112) show full length synthesis of each design. FIG. 12B provides a flow cytometry plot showing expression of p102 and p112 one day post-transfection of mRNA into HEK293T cells. FIG. 12C provides the time course of CLTA endogenous gene silencing in HEK293T cells after transfecting mRNA expressing the p102 and p112 all-in-one variants.

FIGS. 13A-13G describe controlled expression of the all-in-one protein by doxycycline induction. FIG. 13A provides flow cytometry plots showing induced expression of the all-in-one protein by addition of doxycycline in K562 cells that stably encode the all-in-one protein under a doxycycline-inducible promoter. The dotted line represents the baseline median BFP fluorescence without doxycycline administration. FIG. 13B provides a Western blot of cells to detect expression of the all-in-one protein before and after doxycycline treatment. FIGS. 13C-13F are flow cytometry plots of CD81 (FIGS. 13C-13D) and CD151 (FIGS. 13E-13F) knockdown 14 days post-doxycycline treatment of K562 cells. FIG. 13G shows the quantification of CD81 and CD151 knockdown 14 days post-doxycycline treatment or without doxycycline treatment.

DETAILED DESCRIPTION

Figure 1A:
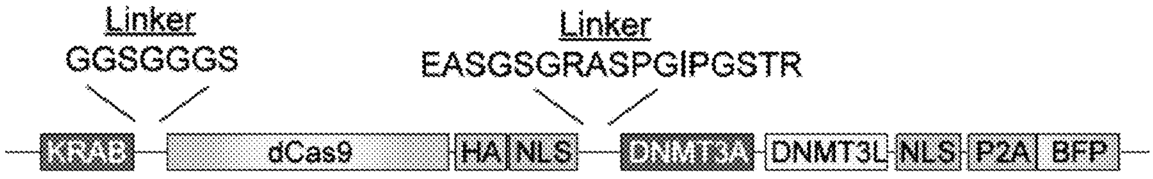
FIG. 1A-1F describe engineering of an all-in-one protein for long-term gene silencing.

The technology described herein allows for, inter alia, permanent silencing of genes in mammalian cells without generating double stranded DNA breaks in the host genome. In embodiments, the central component is a single polypeptide chain composed of catalytically inactive Cas9 (dCas9) fused to Dnmt3A, Dnmt3L, and a KRAB domain (herein referred to as an "all-in-one protein"). This fusion protein provided herein can be directed to a specific site in a mammalian genome using a single guide RNA (sgRNA) and may add DNA methylation and/or repressive chromatin marks to the site. In embodiments, the result is gene silencing that is inheritable across subsequent cell divisions. In embodiments, the fusion protein provided herein (and sgRNA) are only expressed transiently, bypassing the use of viral delivery methods to induce permanent silencing.

In embodiments, the fusion proteins provided herein provide a robust long-term or permanent silencing of endogenous gene expression by epigenome editing rather than genome editing. Both alleles of a gene may be targeted or a single pathogenic allele may be selectively targeted. In embodiments, an advantage of the fusion protein provided herein is that epigenetic editing is reversible and therefore inherently safer than genome editing. Thus, in embodiments, fusion protein provided herein is useful in prophylactic applications. For example, gene silencing can enable acute protection from an infection/biologic toxin and then be reversed after the risk of infection or intoxication is absent. Thus, in embodiments, fusion protein provided herein is useful for viral or toxin that enters a cell through interaction with a protein that is required for long term organ function or homeostasis. In embodiments, fusion protein provided herein is useful in genome editing based therapeutics.

In embodiments, permanent gene silencing in mammalian cells can be accomplished with two components: a single polypeptide chain composed of dCas9 fused to three epigenetic modulators and a single guide RNA that directs the protein to a specific site in the host genome. In embodiments, the components are only expressed transiently in the host cell, thus reducing toxicity and off-target events.

In embodiments, the fusion protein provided herein does not induce DNA breaks in the host cell for permanent gene silencing. In embodiments, the epigenetic marks that are added to the genomic site of interest are reversible, thus allowing for removal of any off-target events that may occur.

Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

The use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

"Nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acids, e.g. polynucleotides, contemplated herein include, but are not limited to, any type of RNA, e.g., mRNA, siRNA, miRNA, sgRNA, and guide RNA and any type of DNA, genomic DNA, plasmid DNA, and minicircle DNA, and any fragments thereof. In aspects, the nucleic acid is messenger RNA. In aspects, the messenger RNA is messenger ribonucleoprotein (RNP). The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, sgRNA, guide RNA, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amio acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In aspects, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

The term "complementary" or "complementarity" refers to the ability of a nucleic acid to form hydrogen bond(s) with another nucleic acid sequence by either traditional Watson-Crick or other non-traditional types. For example, the sequence A-G-T is complementary to the sequence T-C-A. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions (i.e., stringent hybridization conditions).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. One of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al., supra.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., sgRNA) may be detected by standard PCR or Northern blot methods well known in the art. See, Sambrook et al., 1989 Molecular Cloning: A Laboratory Manual, 18.1-18.88.

The term "transcriptional regulatory sequence" as provided herein refers to a segment of DNA that is capable of increasing or decreasing transcription (e.g., expression) of a specific gene within an organism. Non-limiting examples of transcriptional regulatory sequences include promoters, enhancers, and silencers.

The terms "transcription start site" and transcription initiation site" may be used interchangeably to refer herein to the 5' end of a gene sequence (e.g., DNA sequence) where RNA polymerase (e.g., DNA-directed RNA polymerase) begins synthesizing the RNA transcript. The transcription start site may be the first nucleotide of a transcribed DNA sequence where RNA polymerase begins synthesizing the RNA transcript. A skilled artisan can determine a transcription start site via routine experimentation and analysis, for example, by performing a run-off transcription assay or by definitions according to FANTOM5 database.

The term "promoter" as used herein refers to a region of DNA that initiates transcription of a particular gene. Promoters are typically located near the transcription start site of a gene, upstream of the gene and on the same strand (i.e., 5' on the sense strand) on the DNA. Promoters may be about 100 to about 1000 base pairs in length.

The term "enhancer" as used herein refers to a region of DNA that may be bound by proteins (e.g., transcription factors) to increase the likelihood that transcription of a gene will occur. Enhancers may be about 50 to about 1500 base pairs in length. Enhancers may be located downstream or upstream of the transcription initiation site that it regulates and may be several hundreds of base pairs away from the transcription initiation site.

The term "silencer" as used herein refers to a DNA sequence capable of binding transcription regulation factors known as repressors, thereby negatively effecting transcription of a gene. Silencer DNA sequences may be found at many different positions throughout the DNA, including, but not limited to, upstream of a target gene for which it acts to repress transcription of the gene (e.g., silence gene expression).

A "guide RNA" or "gRNA" as provided herein refers to any polynucleotide sequence having sufficient complementarity with a target polynucleotide sequence to hybridize with the target sequence and direct sequence-specific binding of a CRISPR complex to the target sequence. In aspects, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

In embodiments, the polynucleotide (e.g., gRNA) is a single-stranded ribonucleic acid. In aspects, the polynucleotide (e.g., gRNA) is 10, 20, 30, 40, 50, 60, 70, 80, 90, 100 or more nucleic acid residues in length. In aspects, the polynucleotide (e.g., gRNA) is from 10 to 30 nucleic acid residues in length. In aspects, the polynucleotide (e.g., gRNA) is 20 nucleic acid residues in length. In aspects, the length of the polynucleotide (e.g., gRNA) can be at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleic acid residues or sugar residues in length. In aspects, the polynucleotide (e.g., gRNA) is from 5 to 50, 10 to 50, 15 to 50, 20 to 50, 25 to 50, 30 to 50, 35 to 50, 40 to 50, 45 to 50, 5 to 75, 10 to 75, 15 to 75, 20 to 75, 25 to 75, 30 to 75, 35 to 75, 40 to 75, 45 to 75, 50 to 75, 55 to 75, 60 to 75, 65 to 75, 70 to 75, 5 to 100, 10 to 100, 15 to 100, 20 to 100, 25 to 100, 30 to 100, 35 to 100, 40 to 100, 45 to 100, 50 to 100, 55 to 100, 60 to 100, 65 to 100, 70 to 100, 75 to 100, 80 to 100, 85 to 100, 90 to 100, 95 to 100, or more residues in length. In aspects, the polynucleotide (e.g., gRNA) is from 10 to 15, 10 to 20, 10 to 30, 10 to 40, or 10 to 50 residues in length.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may, in aspects, be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. The following eight groups each contain amino acids that are conservative substitutions for one another: (1) Alanine (A), Glycine (G); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); (6) Phenylalanine (F), Tyrosine (Y), Tryptophan (W); (7) Serine(S), Threonine (T); and (8) Cysteine (C), Methionine (M) (see, e.g., Creighton, *Proteins* (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

For specific proteins described herein (e.g., KRAB, dCas9, Dnmt3A, Dnmt3L), the named protein includes any of the protein's naturally occurring forms, or variants or homologs that maintain the protein activity (e.g., within at least 50%, 80%, 90%, 95%, 96%, 97%, 98%, 99% or 100% activity compared to the native protein). In aspects, variants or homologs have at least 50%, 55%, 60%, 65%, 70%, 75%, 80%, 85%, 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In aspects, the protein is the protein as identified by its NCBI sequence reference. In aspects, the protein is the protein as identified by its NCBI sequence reference or functional fragment or homolog thereof.

The term "Krüppel associated box domain" or "KRAB domain" as provided herein refers to a category of transcriptional repression domains present in approximately 400 human zinc finger protein-based transcription factors. KRAB domains typically include about 45 to about 75 amino acid residues. A description of KRAB domains, including their function and use, may be found, for example, in Ecco, G., Imbeault, M., Trono, D., KRAB zinc finger proteins, Development 144, 2017; Lambert et al. The human transcription factors, Cell 172, 2018; Gilbert et al., Cell (2013); and Gilbert et al., Cell (2014), all of which are incorporated herein by reference in their entirety. In aspects, the KRAB domain is a KRAB domain of Kox 1. In aspects, the KRAB domain includes the sequence set forth by SEQ ID NO:16. In aspects, the KRAB domain is the sequence of SEQ ID NO: 16. In aspects, the KRAB domain includes an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:16. In aspects, the KRAB domain includes an amino acid sequence that has at least 75% sequence identity to SEQ ID NO:16. In aspects, the KRAB domain includes an amino acid sequence that has at least 80% sequence identity to SEQ ID NO:16. In aspects, the KRAB domain includes an amino acid sequence that has at least 85% sequence identity to SEQ ID NO:16. In aspects, the KRAB domain includes an amino acid sequence that has at least 90% sequence identity to SEQ ID NO:16. In aspects, the KRAB domain includes an amino acid sequence that has at least 95% sequence identity to SEQ ID NO:16.

The term "DNA methyltransferase" as provided herein refers to an enzyme that catalyzes the transfer of a methyl group to DNA. Non-limiting examples of DNA methyltransferases include Dnmt1, Dnmt3A, Dnmt3B, and Dnmt3L. In aspects, the DNA methyltransferase is a bacterial cytosine methyltransferase and/or a bacterial non-cytosine methyltransferase. Depending on the specific DNA methyltransferase, different regions of DNA are methylated. For example, Dnmt3A typically targets CpG dinucleotides for methylation. Through DNA methylation, DNA methyltransferases can modify the activity of a DNA segment (e.g., gene expression) without altering the DNA sequence. In aspects, DNA methylation results in repression of gene transcription and/or modulation of methylation sensitive transcription factors or CTCF. As described herein, fusion proteins may include one or more (e.g., two) DNA methyltransferases. When a DNA methyltransferase is included as part of a fusion protein, the DNA methyltransferase may be referred to as a "DNA methyltransferase domain." In aspects, a DNA methyltransferase domain includes one or more DNA methyltransferases. In aspects, a DNA methyltransferase domain includes two DNA methyltransferases. In aspects, the DNA methyltransferase domain is Dnmt3A. In aspects, the DNA methyltransferase domain has the amino acid sequence of SEQ ID NO:26. In aspects, the DNA methyltransferase domain has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:26. In aspects, the DNA methyltransferase domain has an amino acid sequence that has at least 75% sequence identity to SEQ ID NO:26. In aspects, the DNA methyltransferase domain has an amino acid sequence that has at least 80% sequence identity to SEQ ID NO:26. In aspects, the DNA methyltransferase domain has an amino acid sequence that has at least 85% sequence identity to SEQ ID NO:26. In aspects, the DNA methyltransferase domain has an amino acid sequence that has at least 90% sequence identity to SEQ ID NO:26. In aspects, the DNA methyltransferase domain has an amino acid sequence that has at least 95% sequence identity to SEQ ID NO:26. In aspects, the DNA methyltransferase domain is Dnmt3L. In aspects, the DNA methyltransferase domain has the amino acid sequence of SEQ ID NO:28. In aspects, the DNA methyltransferase domain has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:28. In aspects, the DNA methyltransferase domain has an amino acid sequence that has at least 75% sequence identity to SEQ ID NO:28. In aspects, the DNA methyltransferase domain has an amino acid sequence that has at least 80% sequence identity to SEQ ID NO:28. In aspects, the DNA methyltransferase domain has an amino acid sequence that has at least 85% sequence identity to SEQ ID NO:28. In aspects, the DNA methyltransferase domain has an amino acid sequence that has at least 90% sequence identity to SEQ ID NO:28. In aspects, the DNA methyltransferase domain has an amino acid sequence that has at least 95% sequence identity to SEQ ID NO:28. In aspects, the DNA methyltransferase domain includes Dnmt3A and Dnmt3L. In aspects, the DNA methyltransferase domain has the amino acid sequence of SEQ ID NO: 33. In aspects, the DNA methyltransferase domain has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:33. In aspects, the DNA methyltransferase domain has an amino acid sequence that has at least 75% sequence identity to SEQ ID NO:33. In aspects, the DNA methyltransferase domain has an amino acid sequence that has at least 80% sequence identity to SEQ ID NO:33. In aspects, the DNA methyltransferase domain has an amino acid sequence that has at least 85% sequence identity to SEQ ID NO:33. In aspects, the DNA methyltransferase domain has an amino acid sequence that has at least 90% sequence identity to SEQ ID NO:33. In aspects, the DNA methyltransferase domain has an amino acid sequence that has at least 95% sequence identity to SEQ ID NO:33. A description of Dnmt3A-3L domain structure and use may be found, for example, in Siddique et al, Targeted methylation and gene silencing of VEGF-A in human cells by using a designed Dnmt3a-Dnmt3L single-chain fusion protein with increased DNA methylation activity, J. Mol. Biol. 425, 2013 and Stepper et al, Efficient targeted DNA methylation with chimeric dCas9-Dnmt3a-Dnmt3L methyltransferase, Nucleic Acids Res. 45, 2017, which are incorporated herein by reference in their entirety and for all purposes.

A "Dnmt3A", "Dnmt3a," "DNA (cytosine-5)-methyltransferase 3A" or "DNA methyltransferase 3a" protein as referred to herein includes any of the recombinant or naturally-occurring forms of the Dnmt3A enzyme or variants or homologs thereof that maintain Dnmt3A enzyme activity (e.g. within at least 50%, 55%, 60%, 65%, 70%, 75%, 80%, 85%, 90%, 91%, 92%, 93%, 94%, 95%, 96%, 97%, 98%, 99% or 100% activity compared to Dnmt3A). In aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring Dnmt3A protein. In aspects, the Dnmt3A protein is substantially identical to the protein identified by the UniProt reference number Q9Y6K1 or a variant or homolog having substantial identity thereto. In aspects, the Dnmt3A polypeptide is encoded by a nucleic acid sequence identified by the NCBI reference sequence Accession number NM_022552, homologs or functional fragments thereof. In aspects, Dnmt3A includes the sequence set forth by SEQ ID NO:26. In aspects, Dnmt3A is the sequence set forth by SEQ ID NO:26. In aspects, Dnmt3A has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:26. In aspects, the DNA methyltransferase domain has an amino acid sequence that has at least 75% sequence identity to SEQ ID NO:26. In aspects, the DNA methyltransferase domain has an amino acid sequence that has at least 80% sequence identity to SEQ ID NO:26. In aspects, the DNA methyltransferase domain has an amino acid sequence that has at least 85% sequence identity to SEQ ID NO:26. In aspects, Dnmt3A has an amino acid sequence that has at least 90% sequence identity to SEQ ID NO:26. In aspects, Dnmt3A has an amino acid sequence that has at least 95% sequence identity to SEQ ID NO:26.

A "Dnmt3L", "DNA (cytosine-5)-methyltransferase 3L" or "DNA methyltransferase 3L" protein as referred to herein includes any of the recombinant or naturally-occurring forms of the Dnmt3L enzyme or variants or homologs thereof that maintain Dnmt3L enzyme activity (e.g., within at least 50%, 55%, 60%, 65%, 70%, 75%, 80%, 85%, 90%, 91%, 92%, 93%, 94%, 95%, 96%, 97%, 98%, 99% or 100% activity compared to Dnmt3L). In aspects, the variants or homologs have at least 50%, 55%, 60%, 65%, 70%, 75%, 80%, 85%, 90%, 91%, 92%, 93%, 94%, 95%, 96%, 97%, 98%, 99% or 100% amino acid sequence identity across the whole sequence or a portion of the sequence (e.g., a 50, 100, 150 or 200 continuous amino acid portion) compared to a naturally occurring Dnmt3L protein. In aspects, the Dnmt3L protein is substantially identical to the protein identified by the UniProt reference number Q9CWR8 or a variant or homolog having substantial identity thereto. In aspects, the Dnmt3L protein is identical to the protein identified by the UniProt reference number Q9CWR8. In aspects, the Dnmt3L protein has at least 75% sequence identity to the amino acid sequence of the protein identified by the UniProt reference number Q9CWR8. In aspects, the Dnmt3L protein has at least 80% sequence identity to the amino acid sequence of the protein identified by the UniProt reference number Q9CWR8. In aspects, the Dnmt3L protein has at least 85% sequence identity to the amino acid sequence of the protein identified by the UniProt reference number Q9CWR8. In aspects, the Dnmt3L protein has at least 95% sequence identity to the amino acid sequence of the protein identified by the UniProt reference number Q9CWR8.

In aspects, the Dnmt3L protein is substantially identical to the protein identified by the UniProt reference number Q9UJW or a variant or homolog having substantial identity thereto. In aspects, the Dnmt3L protein is identical to the protein identified by the UniProt reference number Q9UJW. In aspects, the Dnmt3L protein has at least 50% sequence identity to the amino acid sequence of the protein identified by the UniProt reference number Q9UJW. In aspects, the Dnmt3L protein has at least 55% sequence identity to the protein identified by the UniProt reference number Q9UJW. In aspects, the Dnmt3L protein has at least 60% sequence identity to the amino acid sequence of the protein identified by the UniProt reference number Q9UJW. In aspects, the Dnmt3L protein has at least 65% sequence identity to the amino acid sequence of the protein identified by the UniProt reference number Q9UJW. In aspects, the Dnmt3L protein has at least 70% sequence identity to the amino acid sequence of the protein identified by the UniProt reference number Q9UJW. In aspects, the Dnmt3L protein has at least 75% sequence identity to the amino acid sequence of the protein identified by the UniProt reference number Q9UJW. In aspects, the Dnmt3L protein has at least 80% sequence identity to the amino acid sequence of the protein identified by the UniProt reference number Q9UJW. In aspects, the Dnmt3L protein has at least 85% sequence identity to the amino acid sequence of the protein identified by the UniProt reference number Q9UJW. In aspects, the Dnmt3L protein has at least 90% sequence identity to the amino acid sequence of the protein identified by the UniProt reference number Q9UJW. In aspects, the Dnmt3L protein has at least 95% sequence identity to the amino acid sequence of the protein identified by the UniProt reference number Q9UJW. In aspects, the Dnmt3L polypeptide is encoded by a nucleic acid sequence identified by the NCBI reference sequence Accession number NM_001081695, or homologs or functional fragments thereof. In aspects, Dnmt3L includes the sequence set forth by SEQ ID NO:28. In aspects, Dnmt3L is the sequence set forth by SEQ ID NO:28. In aspects, Dnmt3L has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO: 28. In aspects, Dnmt3L has an amino acid sequence that has at least 50% sequence identity to SEQ ID NO:28. In aspects, Dnmt3L has an amino acid sequence that has at least 55% sequence identity to SEQ ID NO:28. In aspects, Dnmt3L has an amino acid sequence that has at least 60% sequence identity to SEQ ID NO:28. In aspects, Dnmt3L has an amino acid sequence that has at least 65% sequence identity to SEQ ID NO:28. In aspects, Dnmt3L has an amino acid sequence that has at least 97% sequence identity to SEQ ID NO:28. In aspects, Dnmt3L has an amino acid sequence that has at least 75% sequence identity to SEQ ID NO:28. In aspects, Dnmt3L has an amino acid sequence that has at least 80% sequence identity to SEQ ID NO:28. In aspects, Dnmt3L has an amino acid sequence that has at least 85% sequence identity to SEQ ID NO:28. In aspects, Dnmt3L has an amino acid sequence that has at least 90% sequence identity to SEQ ID NO:28. In aspects, Dnmt3L has an amino acid sequence that has at least 95% sequence identity to SEQ ID NO: 28.

The term "RNA-guided DNA endonuclease" and the like refer, in the usual and customary sense, to an enzyme that cleave a phosphodiester bond within a DNA polynucleotide chain, wherein the recognition of the phosphodiester bond is facilitated by a separate RNA sequence (for example, a single guide RNA).

The term "Class II CRISPR endonuclease" refers to endonucleases that have similar endonuclease activity as Cas9 and participate in a Class II CRISPR system. An example Class II CRISPR system is the type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). The Cpf1 enzyme belongs to a putative type V CRISPR-Cas system. Both type II and type V systems are included in Class II of the CRISPR-Cas system.

A "nuclear localization sequence" or "nuclear localization signal" or "NLS" is a peptide that directs proteins to the nucleus. In aspects, the NLS includes five basic, positively charged amino acids. The NLS may be located anywhere on the peptide chain. In aspects, the NLS is an NLS derived from SV40. In aspects, the NLS includes the sequence set forth by SEQ ID NO:25. In aspects, the NLS is the sequence set forth by SEQ ID NO:25. In aspects, NLS has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO: 25. In aspects, NLS has an amino acid sequence that has at least 75% sequence identity to SEQ ID NO:25. In aspects, NLS has an amino acid sequence that has at least 80% sequence identity to SEQ ID NO:25. In aspects, NLS has an amino acid sequence that has at least 85% sequence identity to SEQ ID NO:25. In aspects, NLS has an amino acid sequence that has at least 90% sequence identity to SEQ ID NO: 25. In aspects, NLS has an amino acid sequence that has at least 95% sequence identity to SEQ ID NO: 25. In aspects, NLS has an amino acid sequence of SEQ ID NO:25.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *Spodoptera*) and human cells. Cells may be useful when they are naturally nonadherent or have been treated not to adhere to surfaces, for example by trypsinization.

As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically. Replication-incompetent viral vectors or replication-defective viral vectors refer to viral vectors that are capable of infecting their target cells and delivering their viral payload, but then fail to continue the typical lytic pathway that leads to cell lysis and death.

The terms "transfection", "transduction", "transfecting" or "transducing" can be used interchangeably and are defined as a process of introducing a nucleic acid molecule and/or a protein to a cell. Nucleic acids may be introduced to a cell using non-viral or viral-based methods. The nucleic acid molecule can be a sequence encoding complete proteins or functional portions thereof. Typically, a nucleic acid vector, comprising the elements necessary for protein expression (e.g., a promoter, transcription start site, etc.). Non-viral methods of transfection include any appropriate method that does not use viral DNA or viral particles as a delivery system to introduce the nucleic acid molecule into the cell. Exemplary non-viral transfection methods include nanoparticle encapsulation of the nucleic acids that encode the fusion protein (e.g., lipid nanoparticles, gold nanoparticles, and the like), calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In aspects, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) Gene Therapy 8:1-4 and Prochiantz (2007) Nat. Methods 4:119-20.

A "peptide linker" as provided herein is a linker including a peptide moiety. In embodiments, the peptide linker is a divalent peptide, such as an amino acid sequence attached at the N-terminus and the C-terminus to the remainder of the compound (e.g., fusion protein provided herein. The peptide linker may be a peptide moiety (a divalent peptide moiety) capable of being cleaved (e.g., a P2A cleavable polypeptide). A peptide linker as provided herein may also be referred to interchangeably as an amino acid linker. In aspects, the peptide linker includes 1 to about 80 amino acid residues. In aspects, the peptide linker includes 1 to about 70 amino acid residues. In aspects, the peptide linker includes 1 to about 60 amino acid residues. In aspects, the peptide linker includes 1 to about 50 amino acid residues. In aspects, the peptide linker includes 1 to about 40 amino acid residues. In aspects, the peptide linker includes 1 to about 30 amino acid residues. In aspects, the peptide linker includes 1 to about 25 amino acid residues. In aspects, the peptide linker includes 1 to about 20 amino acid residues. In aspects, the peptide linker includes about 2 to about 20 amino acid residues. In aspects, the peptide linker includes about 2 to about 19 amino acid residues. In aspects, the peptide linker includes about 2 to about 18 amino acid residues. In aspects, the peptide linker includes about 2 to about 17 amino acid residues. In aspects, the peptide linker includes about 2 to about 16 amino acid residues. In aspects, the peptide linker includes about 2 to about 15 amino acid residues. In aspects, the peptide linker includes about 2 to about 14 amino acid residues. In aspects, the peptide linker includes about 2 to about 13 amino acid residues. In aspects, the peptide linker includes about 2 to about 12 amino acid residues. In aspects, the peptide linker includes about 2 to about 11 amino acid residues. In aspects, the peptide linker includes about 2 to about 10 amino acid residues. In aspects, the peptide linker includes about 2 to about 9 amino acid residues. In aspects, the peptide linker includes about 2 to about 8 amino acid residues. In aspects, the peptide linker includes about 2 to about 7 amino acid residues. In aspects, the peptide linker includes about 2 to about 6 amino acid residues. In aspects, the peptide linker includes about 2 to about 5 amino acid residues. In aspects, the peptide linker includes about 2 to about 4 amino acid residues. In aspects, the peptide linker includes about 2 to about 3 amino acid residues. In aspects, the peptide linker includes about 3 to about 19 amino acid residues. In aspects, the peptide linker includes about 3 to about 18 amino acid residues. In aspects, the peptide linker includes about 3 to about 17 amino acid residues. In aspects, the peptide linker includes about 3 to about 16 amino acid residues. In aspects, the peptide linker includes about 3 to about 15 amino acid residues. In aspects, the peptide linker includes about 3 to about 14 amino acid residues. In aspects, the peptide linker includes about 3 to about 13 amino acid residues. In aspects, the peptide linker includes about 3 to about 12 amino acid residues. In aspects, the peptide linker includes about 3 to about 11 amino acid residues. In aspects, the peptide linker includes about 3 to about 10 amino acid residues. In aspects, the peptide linker includes about 3 to about 9 amino acid residues. In aspects, the peptide linker includes about 3 to about 8 amino acid residues. In aspects, the peptide linker includes about 3 to about 7 amino acid residues. In aspects, the peptide linker includes about 3 to about 6 amino acid residues. In aspects, the peptide linker includes about 3 to about 5 amino acid residues. In aspects, the peptide linker includes about 3 to about 4 amino acid residues. In aspects, the peptide linker includes about 10 to about 20 amino acid residues. In aspects, the peptide linker includes about 15 to about 20 amino acid residues. In aspects, the peptide linker includes about 2 amino acid residues. In aspects, the peptide linker includes about 3 amino acid residues. In aspects, the peptide linker includes about 4 amino acid residues. In aspects, the peptide linker includes about 5 amino acid residues. In aspects, the peptide linker includes about 6 amino acid residues. In aspects, the peptide linker includes about 7 amino acid residues. In aspects, the peptide linker includes about 8 amino acid residues. In aspects, the peptide linker includes about 9 amino acid residues. In aspects, the peptide linker includes about 10 amino acid residues. In aspects, the peptide linker includes about 11 amino acid residues. In aspects, the peptide linker includes about 12 amino acid residues. In aspects, the peptide linker includes about 13 amino acid residues. In aspects, the peptide linker includes about 14 amino acid residues. In aspects, the peptide linker includes about 15 amino acid residues. In aspects, the peptide linker includes about 16 amino acid residues. In aspects, the peptide linker includes about 17 amino acid residues. In aspects, the peptide linker includes about 18 amino acid residues. In aspects, the peptide linker includes about 19 amino acid residues. In aspects, the peptide linker includes about 20 amino acid residues. In aspects, the peptide linker includes about 21 amino acid residues. In aspects, the peptide linker includes about 22 amino acid residues. In aspects, the peptide linker includes about 23 amino acid residues. In aspects, the peptide linker includes about 24 amino acid residues. In aspects, the peptide linker includes about 25 amino acid residues.

In aspects, the peptide linker includes the sequence set forth by SEQ ID NO:17. In aspects, the peptide linker is the sequence set forth by SEQ ID NO:17. In aspects, the peptide linker includes the sequence set forth by SEQ ID NO:18. In aspects, the peptide linker is the sequence set forth by SEQ ID NO:18. In aspects, the peptide linker includes the sequence set forth by SEQ ID NO:19. In aspects, the peptide linker is the sequence set forth by SEQ ID NO:19. In aspects, the peptide linker includes the sequence set forth by SEQ ID NO:20. In aspects, the peptide linker is the sequence set forth by SEQ ID NO:20. In aspects, the peptide linker includes the sequence set forth by SEQ ID NO: 21. In aspects, the peptide linker is the sequence set forth by SEQ ID NO:21. In aspects, the peptide linker includes the sequence set forth by SEQ ID NO:22. In aspects, the peptide linker is the sequence set forth by SEQ ID NO:22. In aspects, the peptide linker includes the sequence set forth by SEQ ID NO:27. In aspects, the peptide linker is the sequence set forth by SEQ ID NO:27. In aspects, the peptide linker includes the sequence set forth by SEQ ID NO:24. In aspects, the peptide linker is the sequence set forth by SEQ ID NO:24. In aspects, the peptide linker includes the sequence set forth by SEQ ID NO:29. In aspects, the peptide linker is the sequence set forth by SEQ ID NO: 29. In aspects, the peptide linker is an XTEN polypeptide. In aspects, the peptide linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:17, 18, 19, 20, 21, 22, 24, 27, or 29. In aspects, the peptide linker has an amino acid sequence that has at least 90% sequence identity to SEQ ID NO:17, 18, 19, 20, 21, 22, 24, 27, or 29.

In aspects, the peptide linker has an amino acid sequence that has at least 90% sequence identity to SEQ ID NO:17. In aspects, the peptide linker has an amino acid sequence that has at least 90% sequence identity to SEQ ID NO:18. In aspects, the peptide linker has an amino acid sequence that has at least 90% sequence identity to SEQ ID NO:19. In aspects, the peptide linker has an amino acid sequence that has at least 90% sequence identity to SEQ ID NO:20. In aspects, the peptide linker has an amino acid sequence that has at least 90% sequence identity to SEQ ID NO: 21. In aspects, the peptide linker has an amino acid sequence that has at least 90% sequence identity to SEQ ID NO:22. In aspects, the peptide linker has an amino acid sequence that has at least 90% sequence identity to SEQ ID NO:24. In aspects, the peptide linker has an amino acid sequence that has at least 90% sequence identity to SEQ ID NO:27. In aspects, the peptide linker has an amino acid sequence that has at least 90% sequence identity to SEQ ID NO:29. In aspects, the peptide linker has an amino acid sequence that has at least 95% sequence identity to SEQ ID NO: 17, 18, 19, 20, 21, 22, 24, 27, or 29. In aspects, the peptide linker has an amino acid sequence that has at least 95% sequence identity to SEQ ID NO:17. In aspects, the peptide linker has an amino acid sequence that has at least 95% sequence identity to SEQ ID NO:18. In aspects, the peptide linker has an amino acid sequence that has at least 95% sequence identity to SEQ ID NO: 19. In aspects, the peptide linker has an amino acid sequence that has at least 95% sequence identity to SEQ ID NO:20. In aspects, the peptide linker has an amino acid sequence that has at least 95% sequence identity to SEQ ID NO:21. In aspects, the peptide linker has an amino acid sequence that has at least 95% sequence identity to SEQ ID NO:22. In aspects, the peptide linker has an amino acid sequence that has at least 95% sequence identity to SEQ ID NO:24. In aspects, the peptide linker has an amino acid sequence that has at least 95% sequence identity to SEQ ID NO: 27. In aspects, the peptide linker has an amino acid sequence that has at least 95% sequence identity to SEQ ID NO:29.

The terms "XTEN," "XTEN linker," or "XTEN polypeptide" as used herein refer to an recombinant polypeptide (e.g. unstructured recombinant peptide) lacking hydrophobic amino acid residues. The development and use of XTEN can be found in, for example, Schellenberger et al., Nature Biotechnology 27, 1186-1190 (2009), which is incorporated herein by reference in its entirety and for all purposes. In aspects, the XTEN linker includes the sequence set forth by SEQ ID NO: 31. In aspects, the XTEN linker is the sequence set forth by SEQ ID NO:31. In aspects, the XTEN linker includes the sequence set forth by SEQ ID NO:32. In aspects, the XTEN linker is the sequence set forth by SEQ ID NO:32. In aspects, the XTEN linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:31. In aspects, the XTEN linker has an amino acid sequence that has at least 90% sequence identity to SEQ ID NO:31. In aspects, the XTEN linker has an amino acid sequence that has at least 95% sequence identity to SEQ ID NO:31. In aspects, the XTEN linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:32. In aspects, the XTEN linker has an amino acid sequence that has at least 90% sequence identity to SEQ ID NO:32. In aspects, the XTEN linker has an amino acid sequence that has at least 95% sequence identity to SEQ ID NO:32.

A "detectable agent" or "detectable moiety" is a composition detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y. $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorocarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide.

A detectable moiety is a monovalent detectable agent or a detectable agent capable of forming a bond with another composition. In aspects, the detectable agent is an HA tag. In aspects, the HA tag includes the sequence set forth by SEQ ID NO:24. In aspects, the HA tag is the sequence set forth by SEQ ID NO:24. In aspects, the HA tag has an amino acid sequence that has at least 80% sequence identity to SEQ ID NO:24. In aspects, the HA tag has an amino acid sequence that has at least 85% sequence identity to SEQ ID NO:24. In aspects, the HA tag has an amino acid sequence that has at least 90% sequence identity to SEQ ID NO:24. In aspects, the HA tag has an amino acid sequence that has at least 95% sequence identity to SEQ ID NO:24. In aspects, the detectable agent is blue fluorescent protein (BFP). In aspects, the BFP includes the sequence set forth by SEQ ID NO:30. In aspects, the BFP is the sequence set forth by SEQ ID NO:30. In aspects, the BFP has an amino acid sequence that has at least 80% sequence identity to SEQ ID NO:30. In aspects, the BFP has an amino acid sequence that has at least 85% sequence identity to SEQ ID NO: 30. In aspects, the BFP has an amino acid sequence that has at least 90% sequence identity to SEQ ID NO:30. In aspects, the BFP has an amino acid sequence that has at least 95% sequence identity to SEQ ID NO:30.

Radioactive substances (e.g., radioisotopes) that may be used as imaging and/or labeling agents in accordance with the aspects of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y. $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the aspects of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

"Contacting" is used in accordance with its plain ordinary meaning and refers to the process of allowing at least two distinct species to become sufficiently proximal to react, interact or physically touch. It should be appreciated, however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a fusion protein as provided herein and a nucleic acid sequence (e.g., target DNA sequence).

As defined herein, the term "inhibition", "inhibit", "inhibiting," "repression," repressing," "silencing," "silence" and the like when used in reference to a composition as provided herein (e.g., fusion protein, complex, nucleic acid, vector) refer to negatively affecting (e.g., decreasing) the activity (e.g., transcription) of a nucleic acid sequence (e.g., decreasing transcription of a gene) relative to the activity of the nuclei acid sequence (e.g., transcription of a gene) in the absence of the composition (e.g., fusion protein, complex, nucleic acid, vector). In aspects, inhibition refers to reduction of a disease or symptoms of disease (e.g., cancer). Thus, inhibition includes, at least in part, partially or totally blocking activation (e.g., transcription), or decreasing, preventing, or delaying activation (e.g., transcription) of the nucleic acid sequence. The inhibited activity (e.g., transcription) may be 90%, 80%, 70%, 60%, 50%, 40%, 30%, 20%, 10%, or less than that in a control. In aspects, the inhibition is 1.5-fold, 2-fold, 3-fold, 4-fold, 5-fold, 10-fold, or more in comparison to a control.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

Fusion Proteins

Provided herein are, inter alia, fusion proteins that can turn off genes permanently (e.g., irreversibly) and reversibly in mammalian cells using CRISPR-based epigenome editing. In embodiments, the fusion protein includes a single polypeptide fusion of four proteins (e.g., catalytically inactive Cas9 (e.g., dCas9), a KRAB domain, Dnmt3A and Dnmt3L) which can be expressed transiently in cells. The fusion protein can be directed to a specific site in a mammalian genome using a polynucleotide complementary to a target nucleic acid sequence (e.g., DNA sequence) and that further includes a sequence (i.e., binding sequence) capable of binding the fusion protein. Once properly positioned and without intending to be bound by a theory, the fusion protein adds DNA methylation and/or repressive chromatin marks to the target nucleic acid, resulting in gene silencing that is inheritable across subsequent cell divisions. In this way, the fusion protein can perform epigenome editing that bypasses the need to generate DNA double-strand breaks in the host genome, making it a safe and reversible way of manipulating the genome of a living organism.

In embodiments, the fusion protein comprises a nuclease-deficient RNA-guided DNA endonuclease enzyme; a KRAB domain, and a DNA methyltransferase domain. In aspects, the fusion protein comprises, from N-terminus to C-terminus, a DNA methyltransferase domain, a nuclease-deficient RNA-guided DNA endonuclease enzyme, and KRAB domain. In aspects, the fusion protein comprises, from N-terminus to C-terminus, a KRAB domain a nuclease-deficient RNA-guided DNA endonuclease enzyme, and a DNA methyltransferase domain. In embodiments, the fusion protein further comprises one or more peptide linkers. In aspects, the fusion protein further comprises one or more detectable tags. In aspects, the fusion protein further comprises one or more nuclear localization sequences. In aspects, the fusion protein further comprises one or more peptide linkers, one or more detectable tags, one or more nuclear localization sequences, or a combination of two or more of the foregoing. When the fusion protein comprises one or more peptide linkers, each peptide liner can be the same or different. When the fusion protein comprises one or more detectable tags, each detectable tag can be the same or different. In aspects, the fusion protein comprises from 1 to 10 detectable tags. In aspects, the fusion protein comprises from 1 to 9 detectable tags. In aspects, the fusion protein comprises from 1 to 8 detectable tags. In aspects, the fusion protein comprises from 1 to 7 detectable tags. In aspects, the fusion protein comprises from 1 to 6 detectable tags. In aspects, the fusion protein comprises from 1 to 5 detectable tags. In aspects, the fusion protein comprises from 1 to 4 detectable tags. In aspects, the fusion protein comprises from 1 to 3 detectable tags. In aspects, the fusion protein comprises from 1 to 2 detectable tags. In aspects, the fusion protein comprises 1 detectable tag. In aspects, the fusion protein comprises 2 detectable tags. In aspects, the fusion protein comprises 3 detectable tags. In aspects, the fusion protein comprises 4 detectable tags. In aspects, the fusion protein comprises 5 detectable tags.

In embodiments, the fusion protein comprises the structure: A-B-C, or B-A-C or C-A-B, or C-B-A, or B-C-A, or A-C-B; where A comprises a nuclease-deficient RNA-guided DNA endonuclease enzyme; B comprises a KRAB domain, C comprises a DNA methyltransferase domain; and wherein the component on the left is the N-terminus and the component on the right is the C-terminus. In aspects, the fusion protein further comprises one or more peptide linkers and one or more detectable tags. In aspects, A-B, B-A, B-C, C-B, A-C, and C-A are each independently linked together via a covalent bond, a peptide linker, a detectable tag, a nuclear localization sequence, or a combination of two or more thereof. The peptide linker can be any known in the art (e.g., P2A cleavable peptide, XTEN linker, and the like). In aspects, the fusion protein comprises other components, such as detectable tags (e.g., HA tag, blue fluorescent protein, and the like).

In embodiments, the fusion protein comprises the structure: A-$L_1$-B-$L_2$-C, where A comprises a nuclease-deficient RNA-guided DNA endonuclease enzyme; B comprises a KRAB domain, C comprises a DNA methyltransferase domain, $L_1$ is a covalent bond or a peptide linker, and $L_2$ is a covalent bond or a peptide linker; and where A is at the N-terminus and C is at the C-terminus. In aspects, A is covalently linked to B via a peptide linker. In aspects, A is covalently linked to B via a covalent bond. In aspects, B is covalently linked to C via a peptide linker. In aspects, B is covalently linked to C via a covalent bond. The peptide linker can be any known in the art (e.g., P2A cleavable peptide, XTEN linker, and the like). In aspects, the fusion protein comprises other components, such as detectable tags, nuclear localization sequences, and the like. In aspects, $L_1$ is a covalent bond, a peptide linker, a detectable tag, a nuclear localization sequence, or a combination thereof. In aspects, $L_2$ is a covalent bond, a peptide linker, a detectable tag, a nuclear localization sequence, or a combination thereof.

Figure 5:
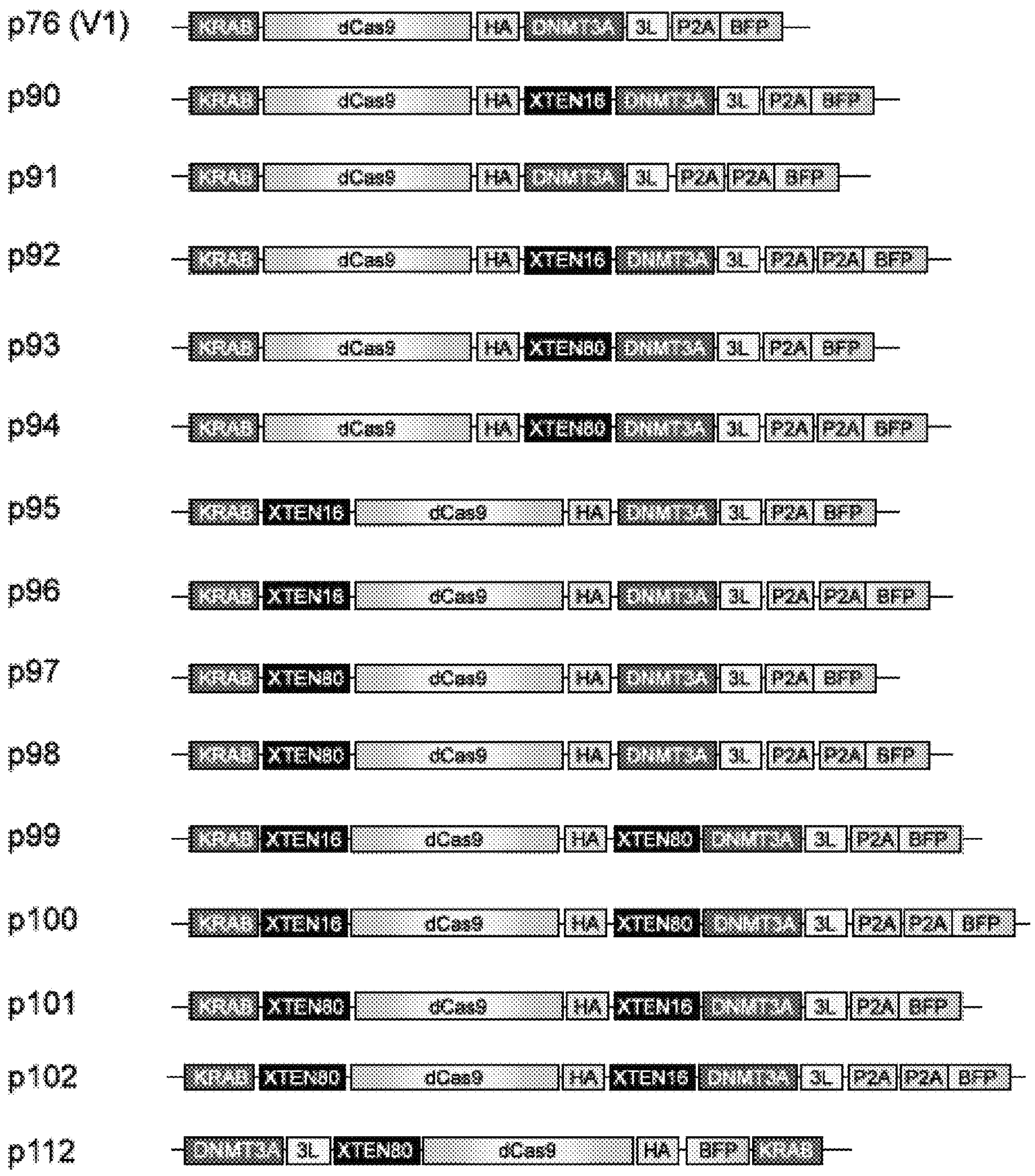
FIG. 5 provides schematics of the fusion proteins p76, p90-p102, and p112 which correspond to SEQ ID NOS: 1-15, respectively.

In embodiments, the fusion protein comprises the structure: B-$L_1$-A-$L_2$-C, where A comprise a nuclease-deficient RNA-guided DNA endonuclease enzyme; B comprises a KRAB domain, C comprises a DNA methyltransferase domain, $L_1$ is a covalent bond or a peptide linker, and $L_2$ is a covalent bond or a peptide linker; and where B is at the N-terminus and C is at the C-terminus. In aspects, $L_1$ is a peptide linker. In aspects, $L_1$ is a covalent bond. In aspects, $L_2$ is a peptide linker. In aspects, $L_2$ is a covalent bond. The peptide linker can be any known in the art or described herein (e.g., P2A cleavable peptide, XTEN linker, and the like). In aspects, the fusion protein comprises other components, such as detectable tags. In aspects, $L_1$ is a covalent bond, a peptide linker, a detectable tag, or a combination thereof. In aspects, $L_2$ is a covalent bond, a peptide linker, a detectable tag, or a combination thereof. In aspects, the fusion protein further comprises a nuclear localization sequence. Exemplary fusion proteins comprising the structure: B-$L_1$-A-$L_2$-C include p76, p90, p91, p92, p93, p94, p95, p96, p97, p98, p99, p100, p101, and p102 (FIG. 5)

In embodiments, the fusion protein comprises the structure: B-$L_3$-A-$L_4$-C-$L_5$-D; where A comprises a nuclease-deficient RNA-guided DNA endonuclease enzyme; B comprises a KRAB domain, C comprises a DNA methyltransferase domain, D is absent or D comprises one or more detectable tags, $L_3$ comprises a covalent bond, a peptide linker, a detectable tag, or a combination of two or more thereof, $L_4$ comprises a covalent bond, a peptide linker, a detectable tag, or a combination of two or more thereof, $L_5$ is absent or $L_5$ comprises a covalent bond or a peptide linker; and where B is at the N-terminus and D is at the C-terminus. In aspects, $L_3$ is a peptide linker. In aspects, $L_3$ is a covalent bond. In aspects, $L_3$ comprises a peptide linker and a detectable tag. In aspects, $L_3$ comprises a detectable tag. In aspects, $L_4$ is a peptide linker. In aspects, $L_4$ comprises a peptide linker and a detectable tag. In aspects, $L_4$ is a covalent bond. In aspects, $L_4$ comprises a detectable tag. In aspects, $L_5$ is a peptide linker. In aspects, $L_5$ is a covalent bond. In aspects, D comprises one or a plurality of detectable tags. In aspects, D comprises one detectable tag. In aspects, D comprises two detectable tags. In aspects, D comprises three detectable tags. In aspects, D comprises a plurality of detectable tags. D can be any detectable tag known in the art and/or described herein (e.g., HA tag, blue fluorescent protein, and the like). In aspects $L_5$ and D are absent. When $L_3$, $L_4$, $L_5$, and D comprise two or more detectable tags, each detectable tag is the same or different. The peptide linker can be any known in the art and/or described herein (e.g., P2A cleavable peptide, XTEN linker, and the like). In aspects, the fusion protein further comprises a nuclear localization sequence. Exemplary fusion proteins comprising the structure: B-$L_3$-A-$L_4$-C-$L_5$-D include p76, p90, p91, p92, p93, p94, p95, p96, p97, p98, p99, p100, p101, and p102, as shown in FIG. 5.

In embodiments, the fusion protein comprises the structure: C-$L_3$-A-$L_4$-B-$L_5$-D, where A comprises a nuclease-deficient RNA-guided DNA endonuclease enzyme; B comprises a KRAB domain, C comprises a DNA methyltransferase domain, D is absent or D comprises one or more detectable tags, $L_3$ comprises a covalent bond, a peptide linker, a detectable tag, or a combination of two or more thereof, $L_4$ comprises a covalent bond, a peptide linker, a detectable tag, or a combination of two or more thereof, $L_5$ is absent or $L_5$ comprises a covalent bond or a peptide linker; and where C is at the N-terminus and D is at the C-terminus. In aspects, $L_3$ is a peptide linker. In aspects, $L_3$ is a covalent bond. In aspects, $L_3$ comprises a detectable tag. In aspects, $L_3$ comprises a peptide linker and a detectable tag. In aspects, $L_4$ a peptide linker. In aspects, $L_4$ is a covalent bond. In aspects, $L_4$ comprises a detectable tag. In aspects, $L_4$ comprises a peptide linker and a detectable tag. In aspects, $L_5$ a peptide linker. In aspects, $L_5$ is a covalent bond. In aspects, D comprises one or a plurality of detectable tags. In aspects, D comprises one detectable tag. In aspects, D comprises two detectable tags. In aspects, D comprises three detectable tags. In aspects, D comprises a plurality of detectable tags. D can be any detectable tag known in the art and/or described herein (e.g., HA tag, blue fluorescent protein, and the like). In aspects $L_5$ and D are absent. When $L_3$, $L_4$, $L_5$, and D comprise two or more detectable tags, each detectable tag is the same or different. The peptide linker can be any known in the art and/or described herein (e.g., P2A cleavable peptide, XTEN linker, and the like). In aspects, the fusion protein further comprises a nuclear localization sequence. Exemplary fusion proteins comprising the structure: C-$L_3$-A-$L_4$-B-$L_5$-D include p112, as shown in FIG. 5.

The term "nuclease-deficient RNA-guided DNA endonuclease enzyme" and the like refer, in the usual and customary sense, to an RNA-guided DNA endonuclease (e.g. a mutated form of a naturally occurring RNA-guided DNA endonuclease) that targets a specific phosphodiester bond within a DNA polynucleotide, wherein the recognition of the phosphodiester bond is facilitated by a separate polynucleotide sequence (for example, a RNA sequence (e.g., single guide RNA (sgRNA)), but is incapable of cleaving the target phosphodiester bond to a significant degree (e.g. there is no measurable cleavage of the phosphodiester bond under physiological conditions). A nuclease-deficient RNA-guided DNA endonuclease thus retains DNA-binding ability (e.g. specific binding to a target sequence) when complexed with a polynucleotide (e.g., sgRNA), but lacks significant endonuclease activity (e.g. any amount of detectable endonuclease activity). In aspects, the nuclease-deficient RNA-guided DNA endonuclease enzyme is dCas9, ddCpf1, a nuclease-deficient Cas9 variant, or a nuclease-deficient Class II CRISPR endonuclease.

In embodiments, the nuclease-deficient RNA-guided DNA endonuclease enzyme is dCas9. The terms "dCas9" or "dCas9 protein" as referred to herein is a Cas9 protein in which both catalytic sites for endonuclease activity are defective or lack activity. In aspects, the dCas9 protein has mutations at positions corresponding to D10A and H840A of *S. pyogenes* Cas9. In aspects, the dCas9 protein lacks endonuclease activity due to point mutations at both endonuclease catalytic sites (RuvC and HNH) of wild type Cas9. The point mutations can be D10A and H840A. In aspects, the dCas9 has substantially no detectable endonuclease (e.g., endodeoxyribonuclease) activity. In aspects, dCas9 includes the amino acid sequence of SEQ ID NO:23. In aspects, dCas9 has the amino acid sequence of SEQ ID NO:23. In aspects, dCas9 has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:23. In aspects, dCas9 has an amino acid sequence that has at least 75% sequence identity to SEQ ID NO:23. In aspects, dCas9 has an amino acid sequence that has at least 80% sequence identity to SEQ ID NO:23. In aspects, dCas9 has an amino acid sequence that has at least 85% sequence identity to SEQ ID NO:23. In aspects, dCas9 has an amino acid sequence that has at least 90% sequence identity to SEQ ID NO:23. In aspects, dCas9 has an amino acid sequence that has at least 95% sequence identity to SEQ ID NO:23.

A "CRISPR associated protein 9," "Cas9," "Csn1" or "Cas9 protein" as referred to herein includes any of the recombinant or naturally-occurring forms of the Cas9 endonuclease or variants or homologs thereof that maintain Cas9 endonuclease enzyme activity (e.g. within at least 50%, 80%, 90%, 95%, 96%, 97%, 98%, 99% or 100% activity compared to Cas9). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cas9 protein. In aspects, the Cas9 protein is substantially identical to the protein identified by the UniProt reference number Q99ZW2 or a variant or homolog having substantial identity thereto. In aspects, the Cas9 protein has at least 75% sequence identity to the amino acid sequence of the protein identified by the UniProt reference number Q99ZW2. In aspects, the Cas9 protein has at least 80% sequence identity to the amino acid sequence of the protein identified by the UniProt reference number Q99ZW2. In aspects, the Cas9 protein has at least 85% sequence identity to the amino acid sequence of the protein identified by the UniProt reference number Q99ZW2. In aspects, the Cas9 protein has at least 90% sequence identity to the amino acid sequence of the protein identified by the UniProt reference number Q99ZW2. In aspects, the Cas9 protein has at least 95% sequence identity to the amino acid sequence of the protein identified by the UniProt reference number Q99ZW2.

In embodiments, the nuclease-deficient RNA-guided DNA endonuclease enzyme is "ddCpf1" or "ddCas12a". The terms "DNAse-dead Cpf1" or "ddCpf1" refer to mutated *Acidaminococcus* sp. Cpf1 (AsCpf1) resulting in the inactivation of Cpf1 DNAse activity. In aspects, ddCpf1 includes an E993A mutation in the RuvC domain of AsCpf1. In aspects, the ddCpf1 has substantially no detectable endonuclease (e.g., endodeoxyribonuclease) activity. In aspects, ddCpf1 includes the amino acid sequence of SEQ ID NO:34. In aspects, ddCpf1 has the amino acid sequence of SEQ ID NO:34. In aspects, ddCpf1 has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:34. In aspects, ddCpf1 has an amino acid sequence that has at least 75% sequence identity to SEQ ID NO:34. In aspects, ddCpf1 has an amino acid sequence that has at least 80% sequence identity to SEQ ID NO:34. In aspects, ddCpf1 has an amino acid sequence that has at least 85% sequence identity to SEQ ID NO:34. In aspects, ddCpf1 has an amino acid sequence that has at least 90% sequence identity to SEQ ID NO:34. In aspects, ddCpf1 has an amino acid sequence that has at least 95% sequence identity to SEQ ID NO: 34.

In embodiments, the nuclease-deficient RNA-guided DNA endonuclease enzyme is dLbCpf1. The term "dLbCpf1: refers to mutated Cpf1 from Lachnospiraceae bacterium ND2006 (LbCpf1) that lacks DNAse activity. In aspects, dLbCpf1 includes a D832A mutation. In aspects, the dLbCpf1 has substantially no detectable endonuclease (e.g., endodeoxyribo-nuclease) activity. In aspects, dLbCpf1 includes the amino acid sequence of SEQ ID NO:35. In aspects, dLbCpf1 has the amino acid sequence of SEQ ID NO:35. In aspects, dLbCpf1 has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:35. In aspects, dLbCpf1 has an amino acid sequence that has at least 75% sequence identity to SEQ ID NO:35. In aspects, dLbCpf1 has an amino acid sequence that has at least 80% sequence identity to SEQ ID NO:35. In aspects, dLbCpf1 has an amino acid sequence that has at least 85% sequence identity to SEQ ID NO:35. In aspects, dLbCpf1 has an amino acid sequence that has at least 90% sequence identity to SEQ ID NO:35. In aspects, dLbCpf1 has an amino acid sequence that has at least 95% sequence identity to SEQ ID NO: 35.

In embodiments, the nuclease-deficient RNA-guided DNA endonuclease enzyme is dFnCpf1. The term "dFnCpf1" refers to mutated Cpf1 from *Francisella novicida* U112 (FnCpf1) that lacks DNAse activity. In aspects, dFnCpf1 includes a D917A mutation. In aspects, the dFnCpf1 has substantially no detectable endonuclease (e.g., endodeoxyribo-nuclease) activity. In aspects, dFnCpf1 includes the amino acid sequence of SEQ ID NO: 36. In aspects, dFnCpf1 has the amino acid sequence of SEQ ID NO: 36. In aspects, dFnCpf1 has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:36. In aspects, dFnCpf1 has an amino acid sequence that has at least 75% sequence identity to SEQ ID NO:36. In aspects, dFnCpf1 has an amino acid sequence that has at least 80% sequence identity to SEQ ID NO:36. In aspects, dFnCpf1 has an amino acid sequence that has at least 85% sequence identity to SEQ ID NO:36. In aspects, dFnCpf1 has an amino acid sequence that has at least 90% sequence identity to SEQ ID NO:36. In aspects, dFnCpf1 has an amino acid sequence that has at least 95% sequence identity to SEQ ID NO:36.

A "Cpf1" or "Cpf1 protein" as referred to herein includes any of the recombinant or naturally-occurring forms of the Cpf1 (CRISPR from *Prevotella* and *Francisella* 1) endonuclease or variants or homologs thereof that maintain Cpf1 endonuclease enzyme activity (e.g. within at least 50%, 80%, 90%, 95%, 96%, 97%, 98%, 99% or 100% activity compared to Cpf1). In aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cpf1 protein. In aspects, the Cpf1 protein is substantially identical to the protein identified by the UniProt reference number U2UMQ6 or a variant or homolog having substantial identity thereto. In aspects, the Cpf1 protein is identical to the protein identified by the UniProt reference number U2UMQ6. In aspects, the Cpf1 protein has at least 75% sequence identity to the amino acid sequence of the protein identified by the UniProt reference number U2UMQ6. In aspects, the Cpf1 protein has at least 80% sequence identity to the amino acid sequence of the protein identified by the UniProt reference number U2UMQ6. In aspects, the Cpf1 protein is identical to the protein identified by the UniProt reference number U2UMQ6. In aspects, the Cpf1 protein has at least 85% sequence identity to the amino acid sequence of the protein identified by the UniProt reference number U2UMQ6. In aspects, the Cpf1 protein is identical to the protein identified by the UniProt reference number U2UMQ6. In aspects, the Cpf1 protein has at least 90% sequence identity to the amino acid sequence of the protein identified by the UniProt reference number U2UMQ6. In aspects, the Cpf1 protein is identical to the protein identified by the UniProt reference number U2UMQ6. In aspects, the Cpf1 protein has at least 95% sequence identity to the amino acid sequence of the protein identified by the UniProt reference number U2UMQ6.

In embodiments, the nuclease-deficient RNA-guided DNA endonuclease enzyme is a nuclease-deficient Cas9 variant. The term "nuclease-deficient Cas9 variant" refers to a Cas9 protein having one or more mutations that increase its binding specificity to PAM compared to wild type Cas9 and further include mutations that render the protein incapable of or having severely impaired endonuclease activity. Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). The binding specificity of nuclease-deficient Cas9 variants to PAM can be determined by any method known in the art. Descriptions and uses of known Cas9 variants may be found, for example, in Shmakov et al., Diversity and evolution of class 2 CRISPR-Cas systems. Nat. Rev. Microbiol. 15, 2017 and Cebrian-Serrano et al, CRISPR-Cas orthologues and variants: optimizing the repertoire, specificity and delivery of genome engineering tools. Mamm. Genome 7-8, 2017, which are incorporated herein by reference in their entirety and for all purposes. Exemplary Cas9 variants are listed in the Table 4 below.

TABLE 4

| Cas9 Variants | PAM domains | References |
|---|---|---|
| Strep pyogenes (Sp) Cas9 | NGG | Hsu et al. 2014 Cell |
| Staph aureus (Sa) Cas9 | NNGRRT or NNGRR NNGGGT, NNGAAT, NNGAGT (Zetsche) | Ran et al. 2015 Nature |
| SpCas9 VQR mutant (D1135V, R1335Q, T1337R) | NGAG > NGAT = NGAA > NGAC NGCG | Kleinstiver et al. 2015 Nature |
| SpCas9 VRER mutant (D1135V/G1218R/R1335E/T1337R) | NGCG | Kleinstiver et al. 2015 Nature |
| SpCas9 D1135E | NGG, greater fidelity, less cutting at NAG and NGA sites | Kleinstiver et al. 2015 Nature |
| eSpCas9 1.1 mutant (K848A/K1003A/R1060A) | NGG | Slaymaker et al. Science 2015 |
| SpCas9 HF1 (Q695A, Q926A, N497A, R661A) | NGG | Kleinstiver et al. 2016 Nature |
| AsCpf1 | TTTN (5' of sgRNA) | Zetsche et al. 2015 Cell |
| HypaCas9 (N692A, M694A, Q695A, H698A) | | Chen et al., Nature volume 550, pages 407-410 (19 Oct. 2017) |

In embodiments, the nuclease-deficient RNA-guided DNA endonuclease enzyme is a nuclease-deficient Class II CRISPR endonuclease. The term "nuclease-deficient Class II CRISPR endonuclease" as used herein refers to any Class II CRISPR endonuclease having mutations resulting in reduced, impaired, or inactive endonuclease activity.

In embodiments, the DNA methyltransferase domain is a Dnmt3A-3L domain. A "Dnmt3A-3L domain" as provided herein refers to a protein including both Dnmt3A and Dnmt3L. In aspects, the Dnmt3A and the Dnmt3L are covalently linked. In aspects, the Dnmt3A is covalently linked to the Dnmt3L through a peptide linker. In aspects, the peptide linker includes the sequence set forth by SEQ ID NO:27. In aspects, the peptide linker is the sequence set forth by SEQ ID NO: 27. In aspects, the peptide linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:27. In aspects, the peptide linker has an amino acid sequence that has at least 90% sequence identity to SEQ ID NO:27. In aspects, the peptide linker has an amino acid sequence that has at least 95% sequence identity to SEQ ID NO:27. In aspects, the Dnmt3A-3L domain includes the sequence set forth by SEQ ID NO:33. In aspects, the Dnmt3A-3L domain is the sequence set forth by SEQ ID NO:33. In aspects, the Dnmt3A-3L domain has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:33. In aspects, the Dnmt3A-3L domain has an amino acid sequence that has at least 75% sequence identity to SEQ ID NO: 33. In aspects, the Dnmt3A-3L domain has an amino acid sequence that has at least 80% sequence identity to SEQ ID NO:33. In aspects, the Dnmt3A-3L domain has an amino acid sequence that has at least 85% sequence identity to SEQ ID NO:33. In aspects, the Dnmt3A-3L domain has an amino acid sequence that has at least 90% sequence identity to SEQ ID NO:33. In aspects, the Dnmt3A-3L domain has an amino acid sequence that has at least 95% sequence identity to SEQ ID NO:33.

In embodiments, the peptide linker is a XTEN linker. In aspects, the XTEN linker includes about 16 to about 80 amino acid residues. In aspects, the XTEN linker includes about 17 to about 80 amino acid residues. In aspects, the XTEN linker includes about 18 to about 80 amino acid residues. In aspects, the XTEN linker includes about 19 to about 80 amino acid residues. In aspects, the XTEN linker includes about 20 to about 80 amino acid residues. In aspects, the XTEN linker includes about 30 to about 80 amino acid residues. In aspects, the XTEN linker includes about 40 to about 80 amino acid residues. In aspects, the XTEN linker includes about 50 to about 80 amino acid residues. In aspects, the XTEN linker includes about 60 to about 80 amino acid residues. In aspects, the XTEN linker includes about 70 to about 80 amino acid residues. In aspects, the XTEN linker includes about 16 to about 70 amino acid residues. In aspects, the XTEN linker includes about 16 to about 60 amino acid residues. In aspects, the XTEN linker includes about 16 to about 50 amino acid residues. In aspects, the XTEN linker includes about 16 to about 40 amino acid residues. In aspects, the XTEN linker includes about 16 to about 35 amino acid residues. In aspects, the XTEN linker includes about 16 to about 30 amino acid residues. In aspects, the XTEN linker includes about 16 to about 25 amino acid residues. In aspects, the XTEN linker includes about 16 to about 20 amino acid residues. In aspects, the XTEN linker includes about 16 amino acid residues. In aspects, the XTEN linker includes about 17 amino acid residues. In aspects, the XTEN linker includes about 18 amino acid residues. In aspects, the XTEN linker includes about 19 amino acid residues. In aspects, the XTEN linker includes about 20 amino acid residues.

In embodiments, the XTEN linker includes the sequence set forth by SEQ ID NO:31. In aspects, the XTEN linker is the sequence set forth by SEQ ID NO:31. In aspects, the XTEN linker includes the sequence set forth by SEQ ID NO:32. In aspects, the XTEN linker is the sequence set forth by SEQ ID NO:32. In aspects, the XTEN linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:31. In aspects, the XTEN linker has an amino acid sequence that has at least 85% sequence identity to SEQ ID NO:31. In aspects, the XTEN linker has an amino acid sequence that has at least 90% sequence identity to SEQ ID NO:31. In aspects, the XTEN linker has an amino acid sequence that has at least 95% sequence identity to SEQ ID NO:31. In aspects, the XTEN linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:32. In aspects, the XTEN linker has an amino acid sequence that has at least 75% sequence identity to SEQ ID NO:32. In aspects, the XTEN linker has an amino acid sequence that has at least 80% sequence identity to SEQ ID NO:32. In aspects, the XTEN linker has an amino acid sequence that has at least 85% sequence identity to SEQ ID NO:32. In aspects, the XTEN linker has an amino acid sequence that has at least 90% sequence identity to SEQ ID NO:32. In aspects, the XTEN linker has an amino acid sequence that has at least 95% sequence identity to SEQ ID NO:32.

The fusion protein may include amino acid sequences useful for targeting the fusion protein to specific regions of a cell (e.g., cytoplasm, nucleus). Thus, in aspects, the fusion protein further includes a nuclear localization signal (NLS) peptide. In aspects, the NLS includes the sequence set forth by SEQ ID NO:25. In aspects, the NLS is the sequence set forth by SEQ ID NO: 25. In aspects, the NLS has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO: 25. In aspects, the NLS has an amino acid sequence that has at least 75% sequence identity to SEQ ID NO:25. In aspects, the NLS has an amino acid sequence that has at least 80% sequence identity to SEQ ID NO:25. In aspects, the NLS has an amino acid sequence that has at least 85% sequence identity to SEQ ID NO:25. In aspects, the NLS has an amino acid sequence that has at least 90% sequence identity to SEQ ID NO:25. In aspects, the NLS has an amino acid sequence that has at least 95% sequence identity to SEQ ID NO:25.

In embodiments, the fusion protein includes, from N-terminus to C-terminus, a KRAB domain, a nuclease-deficient RNA-guided DNA endonuclease enzyme, and a DNA methyltransferase domain.

In embodiments, the nuclease-deficient RNA-guided DNA endonuclease enzyme is dCas9 and the DNA methyltransferase domain is a Dnmt3A-3L domain.

In embodiments, the dCas9 is covalently linked to the KRAB domain via a peptide linker and wherein the dCas9 is covalently linked to the Dnmt3A-3L domain via a peptide linker.

In embodiments, peptide linker is an XTEN linker. In aspects, the XTEN linker includes the sequence set forth by SEQ ID NO:31. In aspects, the XTEN linker is the sequence set forth by SEQ ID NO:31. In aspects, the XTEN linker has an amino acid sequence that has at least 75% sequence identity to SEQ ID NO:31. In aspects, the XTEN linker has an amino acid sequence that has at least 80% sequence identity to SEQ ID NO:31. In aspects, the XTEN linker has an amino acid sequence that has at least 85% sequence identity to SEQ ID NO:31. In aspects, the XTEN linker has an amino acid sequence that has at least 90% sequence identity to SEQ ID NO:31. In aspects, the XTEN linker has an amino acid sequence that has at least 95% sequence identity to SEQ ID NO:31. In aspects, the XTEN linker includes the sequence set forth by SEQ ID NO:32. In aspects, the XTEN linker is the sequence set forth by SEQ ID NO:32. In aspects, the XTEN linker has an amino acid sequence that has at least 75% sequence identity to SEQ ID NO:32. In aspects, the XTEN linker has an amino acid sequence that has at least 80% sequence identity to SEQ ID NO: 32. In aspects, the XTEN linker has an amino acid sequence that has at least 85% sequence identity to SEQ ID NO:32. In aspects, the XTEN linker has an amino acid sequence that has at least 90% sequence identity to SEQ ID NO:32. In aspects, the XTEN linker has an amino acid sequence that has at least 95% sequence identity to SEQ ID NO:32.

In embodiments, the fusion protein includes the amino acid sequence of SEQ ID NO: 1, 2, 3, 4, 5, 6, 7, 8, 9, 10, 11 12, 13, 14 or 15. In aspects, the fusion protein includes the amino acid sequence of SEQ ID NO:1. In aspects, the fusion protein is the amino acid sequence of SEQ ID NO: 1. In aspects, the fusion protein includes the amino acid sequence of SEQ ID NO:2. In aspects, the fusion protein is the amino acid sequence of SEQ ID NO:2 In aspects, the fusion protein includes the amino acid sequence of SEQ ID NO:3. In aspects, the fusion protein is the amino acid sequence of SEQ ID NO:3. In aspects, the fusion protein includes the amino acid sequence of SEQ ID NO: 4. In aspects, the fusion protein is the amino acid sequence of SEQ ID NO:4. In aspects, the fusion protein includes the amino acid sequence of SEQ ID NO:5. In aspects, the fusion protein is the amino acid sequence of SEQ ID NO:5. In aspects, the fusion protein includes the amino acid sequence of SEQ ID NO:6. In aspects, the fusion protein is the amino acid sequence of SEQ ID NO: 6. In aspects, the fusion protein includes the amino acid sequence of SEQ ID NO:7. In aspects, the fusion protein is the amino acid sequence of SEQ ID NO:7. In aspects, the fusion protein includes the amino acid sequence of SEQ ID NO:8. In aspects, the fusion protein is the amino acid sequence of SEQ ID NO:8. In aspects, the fusion protein includes the amino acid sequence of SEQ ID NO: 9. In aspects, the fusion protein is the amino acid sequence of SEQ ID NO:9. In aspects, the fusion protein includes the amino acid sequence of SEQ ID NO:10. In aspects, the fusion protein is the amino acid sequence of SEQ ID NO:10. In aspects, the fusion protein includes the amino acid sequence of SEQ ID NO: 11. In aspects, the fusion protein is the amino acid sequence of SEQ ID NO: 11. In aspects, the fusion protein includes the amino acid sequence of SEQ ID NO:12. In aspects, the fusion protein is the amino acid sequence of SEQ ID NO: 12. In aspects, the fusion protein includes the amino acid sequence of SEQ ID NO:13. In aspects, the fusion protein is the amino acid sequence of SEQ ID NO:13. In aspects, the fusion protein includes the amino acid sequence of SEQ ID NO:14. In aspects, the fusion protein is the amino acid sequence of SEQ ID NO: 14. In aspects, the fusion protein includes the amino acid sequence of SEQ ID NO:15. In aspects, the fusion protein is the amino acid sequence of SEQ ID NO:15.

In embodiments, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:1, 2, 3, 4, 5, 6, 7, 8, 9, 10, 11 12, 13, 14 or 15. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:1. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:2. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:3. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:4. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO: 5. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:6. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:7. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:8. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:9. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:10. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:11. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO: 12. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:13. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:14. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:15.

In embodiments, the fusion protein includes an amino acid sequence having at least 75% sequence identity to SEQ ID NO:1, 2, 3, 4, 5, 6, 7, 8, 9, 10, 11 12, 13, 14 or 15. In aspects, the fusion protein includes an amino acid sequence having at least 75% sequence identity to SEQ ID NO: 1. In aspects, the fusion protein includes an amino acid sequence having at least 75% sequence identity to SEQ ID NO:2. In aspects, the fusion protein includes an amino acid sequence having at least 75% sequence identity to SEQ ID NO:3. In aspects, the fusion protein includes an amino acid sequence having at least 75% sequence identity to SEQ ID NO:4. In aspects, the fusion protein includes an amino acid sequence having at least 75% sequence identity to SEQ ID NO:5. In aspects, the fusion protein includes an amino acid sequence having at least 75% sequence identity to SEQ ID NO: 6. In aspects, the fusion protein includes an amino acid sequence having at least 75% sequence identity to SEQ ID NO:7. In aspects, the fusion protein includes an amino acid sequence having at least 75% sequence identity to SEQ ID NO:8. In aspects, the fusion protein includes an amino acid sequence having at least 75% sequence identity to SEQ ID NO:9. In aspects, the fusion protein includes an amino acid sequence having at least 75% sequence identity to SEQ ID NO:10. In aspects, the fusion protein includes an amino acid sequence having at least 75% sequence identity to SEQ ID NO:11. In aspects, the fusion protein includes an amino acid sequence having at least 75% sequence identity to SEQ ID NO:12. In aspects, the fusion protein includes an amino acid sequence having at least 75% sequence identity to SEQ ID NO:13. In aspects, the fusion protein includes an amino acid sequence having at least 75% sequence identity to SEQ ID NO:14. In aspects, the fusion protein includes an amino acid sequence having at least 75% sequence identity to SEQ ID NO:15.

In embodiments, the fusion protein includes an amino acid sequence having at least 80% sequence identity to SEQ ID NO:1, 2, 3, 4, 5, 6, 7, 8, 9, 10, 11 12, 13, 14 or 15. In aspects, the fusion protein includes an amino acid sequence having at least 80% sequence identity to SEQ ID NO: 1. In aspects, the fusion protein includes an amino acid sequence having at least 80% sequence identity to SEQ ID NO:2. In aspects, the fusion protein includes an amino acid sequence having at least 80% sequence identity to SEQ ID NO:3. In aspects, the fusion protein includes an amino acid sequence having at least 80% sequence identity to SEQ ID NO:4. In aspects, the fusion protein includes an amino acid sequence having at least 80% sequence identity to SEQ ID NO:5. In aspects, the fusion protein includes an amino acid sequence having at least 80% sequence identity to SEQ ID NO: 6. In aspects, the fusion protein includes an amino acid sequence having at least 80% sequence identity to SEQ ID NO:7. In aspects, the fusion protein includes an amino acid sequence having at least 80% sequence identity to SEQ ID NO:8. In aspects, the fusion protein includes an amino acid sequence having at least 80% sequence identity to SEQ ID NO:9. In aspects, the fusion protein includes an amino acid sequence having at least 80% sequence identity to SEQ ID NO:10. In aspects, the fusion protein includes an amino acid sequence having at least 80% sequence identity to SEQ ID NO:11. In aspects, the fusion protein includes an amino acid sequence having at least 80% sequence identity to SEQ ID NO:12. In aspects, the fusion protein includes an amino acid sequence having at least 80% sequence identity to SEQ ID NO:13. In aspects, the fusion protein includes an amino acid sequence having at least 80% sequence identity to SEQ ID NO:14. In aspects, the fusion protein includes an amino acid sequence having at least 80% sequence identity to SEQ ID NO:15.

In embodiments, the fusion protein includes an amino acid sequence having at least 85% sequence identity to SEQ ID NO:1, 2, 3, 4, 5, 6, 7, 8, 9, 10, 11 12, 13, 14 or 15. In aspects, the fusion protein includes an amino acid sequence having at least 85% sequence identity to SEQ ID NO: 1. In aspects, the fusion protein includes an amino acid sequence having at least 85% sequence identity to SEQ ID NO:2. In aspects, the fusion protein includes an amino acid sequence having at least 85% sequence identity to SEQ ID NO:3. In aspects, the fusion protein includes an amino acid sequence having at least 85% sequence identity to SEQ ID NO:4. In aspects, the fusion protein includes an amino acid sequence having at least 85% sequence identity to SEQ ID NO:5. In aspects, the fusion protein includes an amino acid sequence having at least 85% sequence identity to SEQ ID NO: 6. In aspects, the fusion protein includes an amino acid sequence having at least 85% sequence identity to SEQ ID NO:7. In aspects, the fusion protein includes an amino acid sequence having at least 85% sequence identity to SEQ ID NO:8. In aspects, the fusion protein includes an amino acid sequence having at least 85% sequence identity to SEQ ID NO:9. In aspects, the fusion protein includes an amino acid sequence having at least 85% sequence identity to SEQ ID NO:10. In aspects, the fusion protein includes an amino acid sequence having at least 85% sequence identity to SEQ ID NO:11. In aspects, the fusion protein includes an amino acid sequence having at least 85% sequence identity to SEQ ID NO:12. In aspects, the fusion protein includes an amino acid sequence having at least 85% sequence identity to SEQ ID NO:13. In aspects, the fusion protein includes an amino acid sequence having at least 85% sequence identity to SEQ ID NO:14. In aspects, the fusion protein includes an amino acid sequence having at least 85% sequence identity to SEQ ID NO:15.

In embodiments, the fusion protein includes an amino acid sequence having at least 90% sequence identity to SEQ ID NO:1, 2, 3, 4, 5, 6, 7, 8, 9, 10, 11 12, 13, 14 or 15. In aspects, the fusion protein includes an amino acid sequence having at least 90% sequence identity to SEQ ID NO: 1. In aspects, the fusion protein includes an amino acid sequence having at least 90% sequence identity to SEQ ID NO:2. In aspects, the fusion protein includes an amino acid sequence having at least 90% sequence identity to SEQ ID NO:3. In aspects, the fusion protein includes an amino acid sequence having at least 90% sequence identity to SEQ ID NO:4. In aspects, the fusion protein includes an amino acid sequence having at least 90% sequence identity to SEQ ID NO:5. In aspects, the fusion protein includes an amino acid sequence having at least 90% sequence identity to SEQ ID NO: 6. In aspects, the fusion protein includes an amino acid sequence having at least 90% sequence identity to SEQ ID NO:7. In aspects, the fusion protein includes an amino acid sequence having at least 90% sequence identity to SEQ ID NO:8. In aspects, the fusion protein includes an amino acid sequence having at least 90% sequence identity to SEQ ID NO:9. In aspects, the fusion protein includes an amino acid sequence having at least 90% sequence identity to SEQ ID NO:10. In aspects, the fusion protein includes an amino acid sequence having at least 90% sequence identity to SEQ ID NO:11. In aspects, the fusion protein includes an amino acid sequence having at least 90% sequence identity to SEQ ID NO:12. In aspects, the fusion protein includes an amino acid sequence having at least 90% sequence identity to SEQ ID NO:13. In aspects, the fusion protein includes an amino acid sequence having at least 90% sequence identity to SEQ ID NO:14. In aspects, the fusion protein includes an amino acid sequence having at least 90% sequence identity to SEQ ID NO:15.

In embodiments, the fusion protein includes an amino acid sequence having at least 95% sequence identity to SEQ ID NO:1, 2, 3, 4, 5, 6, 7, 8, 9, 10, 11 12, 13, 14 or 15. In aspects, the fusion protein includes an amino acid sequence having at least 95% sequence identity to SEQ ID NO: 1. In aspects, the fusion protein includes an amino acid sequence having at least 95% sequence identity to SEQ ID NO:2. In aspects, the fusion protein includes an amino acid sequence having at least 95% sequence identity to SEQ ID NO:3. In aspects, the fusion protein includes an amino acid sequence having at least 95% sequence identity to SEQ ID NO:4. In aspects, the fusion protein includes an amino acid sequence having at least 95% sequence identity to SEQ ID NO:5. In aspects, the fusion protein includes an amino acid sequence having at least 95% sequence identity to SEQ ID NO: 6. In aspects, the fusion protein includes an amino acid sequence having at least 95% sequence identity to SEQ ID NO:7. In aspects, the fusion protein includes an amino acid sequence having at least 95% sequence identity to SEQ ID NO:8. In aspects, the fusion protein includes an amino acid sequence having at least 95% sequence identity to SEQ ID NO:9. In aspects, the fusion protein includes an amino acid sequence having at least 95% sequence identity to SEQ ID NO:10. In aspects, the fusion protein includes an amino acid sequence having at least 95% sequence identity to SEQ ID NO:11. In aspects, the fusion protein includes an amino acid sequence having at least 95% sequence identity to SEQ ID NO:12. In aspects, the fusion protein includes an amino acid sequence having at least 95% sequence identity to SEQ ID NO:13. In aspects, the fusion protein includes an amino acid sequence having at least 95% sequence identity to SEQ ID NO:14. In aspects, the fusion protein includes an amino acid sequence having at least 95% sequence identity to SEQ ID NO:15.

Complexes

In order for the fusion protein to carry out epigenome editing, the fusion protein interacts with (e.g. is non-covalently bound to) a polynucleotide (e.g., sgRNA) that is complementary to a target polynucleotide sequence (e.g., a target DNA sequence to be edited) and further includes a sequence (i.e., a binding sequence) to which the nuclease-deficient RNA-guided DNA endonuclease enzyme of the fusion protein as described herein can bind. By forming this complex, the fusion protein is appropriately positioned to perform epigenome editing. The term "complex" refers to a composition that includes two or more components, where the components bind together to make a functional unit. In aspects, a complex described herein includes a fusion protein described herein and a polynucleotide described herein. Thus, in an aspect is provided a fusion protein as described herein, including embodiments and aspects thereof, and a polynucleotide including: (1) a DNA-targeting sequence that is complementary to a target polynucleotide sequence; and (2) a binding sequence for the nuclease-deficient RNA-guided DNA endonuclease enzyme, wherein the nuclease-deficient RNA-guided DNA endonuclease enzyme is bound to the polynucleotide via the binding sequence (e.g., an amino acid sequence capable of binding to the DNA-targeting sequence).

A DNA-targeting sequence refers to a polynucleotide that includes a nucleotide sequence complementary to the target polynucleotide sequence (DNA or RNA). In aspects, a DNA-targeting sequence can be a single RNA molecule (single RNA polynucleotide), which may include a "single-guide RNA," or "sgRNA." In aspects, the DNA-targeting sequence includes two RNA molecules (e.g., joined together via hybridization at the binding sequence (e.g., dCas9-binding sequence). In aspects, the DNA-targeting sequence (e.g., sgRNA) is at least 50%, 55%, 60%, 65%, 70%, 75%, 80%, 85%, 90%, 95%, 96%, 97%, 98% or 99% complementary to the target polynucleotide sequence. In aspects, the DNA-targeting sequence (e.g., sgRNA) is at least 50%, 55%, 60%, 65%, 70%, 75%, 80%, 85%, 90%, 95%, 96%, 97%, 98% or 99% complementary to the sequence of a cellular gene. In aspects, the DNA-targeting sequence (e.g., sgRNA) binds a cellular gene sequence. In aspects, the DNA-targeting sequence (e.g., sgRNA) is at least 75% complementary to the sequence of a cellular gene. In aspects, the DNA-targeting sequence (e.g., sgRNA) is at least 80% complementary to the sequence of a cellular gene. In aspects, the DNA-targeting sequence (e.g., sgRNA) binds a cellular gene sequence. In aspects, the DNA-targeting sequence (e.g., sgRNA) is at least 85% complementary to the sequence of a cellular gene. In aspects, the DNA-targeting sequence (e.g., sgRNA) binds a cellular gene sequence. In aspects, the DNA-targeting sequence (e.g., sgRNA) is at least 90% complementary to the sequence of a cellular gene. In aspects, the DNA-targeting sequence (e.g., sgRNA) binds a cellular gene sequence. In aspects, the DNA-targeting sequence (e.g., sgRNA) is at least 95% complementary to the sequence of a cellular gene. In aspects, the DNA-targeting sequence (e.g., sgRNA) binds a cellular gene sequence.

A "target polynucleotide sequence" as provided herein is a nucleic acid sequence present in, or expressed by, a cell, to which a guide sequence (or a DNA-targeting sequence) is designed to have complementarity, where hybridization between a target sequence and a guide sequence (or a DNA-targeting sequence) promotes the formation of a CRISPR complex. Full complementarity is not necessarily required, provided there is sufficient complementarity to cause hybridization and promote formation of a CRISPR complex. In aspects, the target polynucleotide sequence is an exogenous nucleic acid sequence. In aspects, the target polynucleotide sequence is an endogenous nucleic acid sequence.

The target polynucleotide sequence may be any region of the polynucleotide (e.g., DNA sequence) suitable for epigenome editing. In aspects, the target polynucleotide sequence is part of a gene. In aspects, the target polynucleotide sequence is part of a transcriptional regulatory sequence. In aspects, the target polynucleotide sequence is part of a promoter, enhancer or silencer. In aspects, the target polynucleotide sequence is part of a promoter. In aspects, the target polynucleotide sequence is part of an enhancer. In aspects, the target polynucleotide sequence is part of a silencer.

In embodiments, the target polynucleotide sequence is a hypomethylated nucleic acid sequence. A "hypomethylated nucleic acid sequence" is used herein according to the standard meaning in the art and refers to a loss or lack of methyl groups on the 5-methylcytosine nucleotide (e.g., in CpG). The loss or lack of methyl groups may be relative to a standard control. Hypomethylation may occur, for example, in aging cells or in cancer (e.g., early stages of neoplasia) relative to the younger cell or non-cancer cell, respectively. Thus, the complex may be useful for reestablishing normal (e.g. non-aged of non-diseased) methylation levels.

In embodiments, the target polynucleotide sequence is within about 3000 base pairs (bp) flanking a transcription start site. In aspects, the target polynucleotide sequence is within about 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 200, or 100 base pairs (bp) flanking a transcription start site.

In embodiments, the target polynucleotide sequence is at, near, or within a promoter sequence. In aspects, the target polynucleotide sequence is within a CpG island. In aspects, the target polynucleotide sequence is known to be associated with a disease or condition characterized by DNA hypomethylation.

In embodiments, exemplary target polynucleotide sequences include those described in Tables 1 and 2. In aspects, the target polynucleotide sequence include the sequence of SEQ ID NO: 37, 39, 41, 43, 45, 47, 49, 51, 53, 55, 57, 59, 61, 63, 65, 67, 69, 71, 73, 75, 77, 79, 81, 83, 85, 87, 89, 91, 93, or 95. In aspects, the target polynucleotide sequence include an amino acid sequence having at least 80%, 85%, 90%, 91%, 92%, 93%, 94%, 95%, 96%, 97%, 98%, or 99% sequence identity to SEQ ID NO:37, 39, 41, 43, 45, 47, 49, 51, 53, 55, 57, 59, 61, 63, 65, 67, 69, 71, 73, 75, 77, 79, 81, 83, 85, 87, 89, 91, 93, or 95. In aspects, the target polynucleotide sequence is SEQ ID NO: 37. In aspects, the target polynucleotide sequence is SEQ ID NO:39. In aspects, the target polynucleotide sequence is SEQ ID NO:41. In aspects, the target polynucleotide sequence is SEQ ID NO: 43. In aspects, the target polynucleotide sequence is SEQ ID NO:45. In aspects, the target polynucleotide sequence is SEQ ID NO:47. In aspects, the target polynucleotide sequence is SEQ ID NO: 49. In aspects, the target polynucleotide sequence is SEQ ID NO:51. In aspects, the target polynucleotide sequence is SEQ ID NO:53. In aspects, the target polynucleotide sequence is SEQ ID NO: 55. In aspects, the target polynucleotide sequence is SEQ ID NO:57. In aspects, the target polynucleotide sequence is SEQ ID NO:59. In aspects, the target polynucleotide sequence is SEQ ID NO: 61. In aspects, the target polynucleotide sequence is SEQ ID NO:63. In aspects, the target polynucleotide sequence is SEQ ID NO:65. In aspects, the target polynucleotide sequence is SEQ ID NO: 67. In aspects, the target polynucleotide sequence is SEQ ID NO:69. In aspects, the target polynucleotide sequence is SEQ ID NO:71. In aspects, the target polynucleotide sequence is SEQ ID NO: 73. In aspects, the target polynucleotide sequence is SEQ ID NO:75. In aspects, the target polynucleotide sequence is SEQ ID NO:77. In aspects, the target polynucleotide sequence is SEQ ID NO: 79. In aspects, the target polynucleotide sequence is SEQ ID NO:81. In aspects, the target polynucleotide sequence is SEQ ID NO:83. In aspects, the target polynucleotide sequence is SEQ ID NO: 85. In aspects, the target polynucleotide sequence is SEQ ID NO:87. In aspects, the target polynucleotide sequence is SEQ ID NO:89. In aspects, the target polynucleotide sequence is SEQ ID NO: 91. In aspects, the target polynucleotide sequence is SEQ ID NO:93. In aspects, the target polynucleotide sequence is SEQ ID NO:95.

In aspects, the target polynucleotide sequence has at least 75%, 80%, 85%, 90%, 91%, 92%, 93%, 94%, 95%, 96%, 97%, 98%, or 99% sequence identity to SEQ ID NO:37. In aspects, the target polynucleotide sequence has at least 75%, 80%, 85%, 90%, 91%, 92%, 93%, 94%, 95%, 96%, 97%, 98%, or 99% sequence identity to SEQ ID NO:39. In aspects, the target polynucleotide sequence has at least 75%, 80%, 85%, 90%, 91%, 92%, 93%, 94%, 95%, 96%, 97%, 98%, or 99% sequence identity to SEQ ID NO:41. In aspects, the target polynucleotide sequence has at least 75%, 80%, 85%, 90%, 91%, 92%, 93%, 94%, 95%, 96%, 97%, 98%, or 99% sequence identity to SEQ ID NO:43. In aspects, the target polynucleotide sequence is SEQ ID NO:45. In aspects, the target polynucleotide sequence has at least 75%, 80%, 85%, 90%, 91%, 92%, 93%, 94%, 95%, 96%, 97%, 98%, or 99% sequence identity to SEQ ID NO:47. In aspects, the target polynucleotide sequence has at least 75%, 80%, 85%, 90%, 91%, 92%, 93%, 94%, 95%, 96%, 97%, 98%, or 99% sequence identity to SEQ ID NO:49. In aspects, the target polynucleotide sequence has at least 75%, 80%, 85%, 90%, 91%, 92%, 93%, 94%, 95%, 96%, 97%, 98%, or 99% sequence identity to SEQ ID NO:51. In aspects, the target polynucleotide sequence has at least 75%, 80%, 85%, 90%, 91%, 92%, 93%, 94%, 95%, 96%, 97%, 98%, or 99% sequence identity to SEQ ID NO:53. In aspects, the target polynucleotide sequence has at least 75%, 80%, 85%, 90%, 91%, 92%, 93%, 94%, 95%, 96%, 97%, 98%, or 99% sequence identity to SEQ ID NO:55. In aspects, the target polynucleotide sequence has at least 75%, 80%, 85%, 90%, 91%, 92%, 93%, 94%, 95%, 96%, 97%, 98%, or 99% sequence identity to SEQ ID NO:57. In aspects, the target polynucleotide sequence has at least 75%, 80%, 85%, 90%, 91%, 92%, 93%, 94%, 95%, 96%, 97%, 98%, or 99% sequence identity to SEQ ID NO:59. In aspects, the target polynucleotide sequence has at least 75%, 80%, 85%, 90%, 91%, 92%, 93%, 94%, 95%, 96%, 97%, 98%, or 99% sequence identity to SEQ ID NO: 61. In aspects, the target polynucleotide sequence has at least 75%, 80%, 85%, 90%, 91%, 92%, 93%, 94%, 95%, 96%, 97%, 98%, or 99% sequence identity to SEQ ID NO:63. In aspects, the target polynucleotide sequence has at least 75%, 80%, 85%, 90%, 91%, 92%, 93%, 94%, 95%, 96%, 97%, 98%, or 99% sequence identity to SEQ ID NO:65. In aspects, the target polynucleotide sequence has at least 75%, 80%, 85%, 90%, 91%, 92%, 93%, 94%, 95%, 96%, 97%, 98%, or 99% sequence identity to SEQ ID NO:67. In aspects, the target polynucleotide sequence has at least 75%, 80%, 85%, 90%, 91%, 92%, 93%, 94%, 95%, 96%, 97%, 98%, or 99% sequence identity to SEQ ID NO:69. In aspects, the target polynucleotide sequence has at least 75%, 80%, 85%, 90%, 91%, 92%, 93%, 94%, 95%, 96%, 97%, 98%, or 99% sequence identity to SEQ ID NO:71. In aspects, the target polynucleotide sequence has at least 75%, 80%, 85%, 90%, 91%, 92%, 93%, 94%, 95%, 96%, 97%, 98%, or 99% sequence identity to SEQ ID NO:73. In aspects, the target polynucleotide sequence has at least 75%, 80%, 85%, 90%, 91%, 92%, 93%, 94%, 95%, 96%, 97%, 98%, or 99% sequence identity to SEQ ID NO:75. In aspects, the target polynucleotide sequence has at least 75%, 80%, 85%, 90%, 91%, 92%, 93%, 94%, 95%, 96%, 97%, 98%, or 99% sequence identity to SEQ ID NO:77. In aspects, the target polynucleotide sequence has at least 75%, 80%, 85%, 90%, 91%, 92%, 93%, 94%, 95%, 96%, 97%, 98%, or 99% sequence identity to SEQ ID NO: 79. In aspects, the target polynucleotide sequence has at least 75%, 80%, 85%, 90%, 91%, 92%, 93%, 94%, 95%, 96%, 97%, 98%, or 99% sequence identity to SEQ ID NO:81. In aspects, the target polynucleotide sequence has at least 75%, 80%, 85%, 90%, 91%, 92%, 93%, 94%, 95%, 96%, 97%, 98%, or 99% sequence identity to SEQ ID NO:83. In aspects, the target polynucleotide sequence has at least 75%, 80%, 85%, 90%, 91%, 92%, 93%, 94%, 95%, 96%, 97%, 98%, or 99% sequence identity to SEQ ID NO:85. In aspects, the target polynucleotide sequence has at least 75%, 80%, 85%, 90%, 91%, 92%, 93%, 94%, 95%, 96%, 97%, 98%, or 99% sequence identity to SEQ ID NO:87. In aspects, the target polynucleotide sequence has at least 75%, 80%, 85%, 90%, 91%, 92%, 93%, 94%, 95%, 96%, 97%, 98%, or 99% sequence identity to SEQ ID NO:89. In aspects, the target polynucleotide sequence has at least 75%, 80%, 85%, 90%, 91%, 92%, 93%, 94%, 95%, 96%, 97%, 98%, or 99% sequence identity to SEQ ID NO:91. In aspects, the target polynucleotide sequence has at least 75%, 80%, 85%, 90%, 91%, 92%, 93%, 94%, 95%, 96%, 97%, 98%, or 99% sequence identity to SEQ ID NO:93. In aspects, the target polynucleotide sequence has at least 75%, 80%, 85%, 90%, 91%, 92%, 93%, 94%, 95%, 96%, 97%, 98%, or 99% sequence identity to SEQ ID NO:95.

In aspects, the target polynucleotide sequence has at least 90% sequence identity to SEQ ID NO: 37. In aspects, the target polynucleotide sequence has at least 90% sequence identity to SEQ ID NO: 39. In aspects, the target polynucleotide sequence has at least 90% sequence identity to SEQ ID NO: 41. In aspects, the target polynucleotide sequence has at least 90% sequence identity to SEQ ID NO: 43. In aspects, the target polynucleotide sequence is SEQ ID NO:45. In aspects, the target polynucleotide sequence has at least 90% sequence identity to SEQ ID NO:47. In aspects, the target polynucleotide sequence has at least 90% sequence identity to SEQ ID NO:49. In aspects, the target polynucleotide sequence has at least 90% sequence identity to SEQ ID NO:51. In aspects, the target polynucleotide sequence has at least 90% sequence identity to SEQ ID NO:53. In aspects, the target polynucleotide sequence has at least 90% sequence identity to SEQ ID NO:55. In aspects, the target polynucleotide sequence has at least 90% sequence identity to SEQ ID NO:57. In aspects, the target polynucleotide sequence has at least 90% sequence identity to SEQ ID NO:59. In aspects, the target polynucleotide sequence has at least 90% sequence identity to SEQ ID NO:61. In aspects, the target polynucleotide sequence has at least 90% sequence identity to SEQ ID NO:63. In aspects, the target polynucleotide sequence has at least 90% sequence identity to SEQ ID NO:65. In aspects, the target polynucleotide sequence has at least 90% sequence identity to SEQ ID NO:67. In aspects, the target polynucleotide sequence has at least 90% sequence identity to SEQ ID NO:69. In aspects, the target polynucleotide sequence has at least 90% sequence identity to SEQ ID NO:71. In aspects, the target polynucleotide sequence has at least 90% sequence identity to SEQ ID NO:73. In aspects, the target polynucleotide sequence has at least 90% sequence identity to SEQ ID NO:75. In aspects, the target polynucleotide sequence has at least 90% sequence identity to SEQ ID NO:77. In aspects, the target polynucleotide sequence has at least 90% sequence identity to SEQ ID NO:79. In aspects, the target polynucleotide sequence has at least 90% sequence identity to SEQ ID NO:81. In aspects, the target polynucleotide sequence has at least 90% sequence identity to SEQ ID NO:83. In aspects, the target polynucleotide sequence has at least 90% sequence identity to SEQ ID NO:85. In aspects, the target polynucleotide sequence has at least 90% sequence identity to SEQ ID NO:87. In aspects, the target polynucleotide sequence has at least 90% sequence identity to SEQ ID NO:89. In aspects, the target polynucleotide sequence has at least 90% sequence identity to SEQ ID NO:91. In aspects, the target polynucleotide sequence has at least 90% sequence identity to SEQ ID NO:93. In aspects, the target polynucleotide sequence has at least 90% sequence identity to SEQ ID NO:95.

In aspects, the target polynucleotide sequence has at least 95% sequence identity to SEQ ID NO: 37. In aspects, the target polynucleotide sequence has at least 95% sequence identity to SEQ ID NO: 39. In aspects, the target polynucleotide sequence has at least 95% sequence identity to SEQ ID NO: 41. In aspects, the target polynucleotide sequence has at least 95% sequence identity to SEQ ID NO: 43. In aspects, the target polynucleotide sequence is SEQ ID NO:45. In aspects, the target polynucleotide sequence has at least 95% sequence identity to SEQ ID NO:47. In aspects, the target polynucleotide sequence has at least 95% sequence identity to SEQ ID NO:49. In aspects, the target polynucleotide sequence has at least 95% sequence identity to SEQ ID NO:51. In aspects, the target polynucleotide sequence has at least 95% sequence identity to SEQ ID NO:53. In aspects, the target polynucleotide sequence has at least 95% sequence identity to SEQ ID NO:55. In aspects, the target polynucleotide sequence has at least 95% sequence identity to SEQ ID NO:57. In aspects, the target polynucleotide sequence has at least 95% sequence identity to SEQ ID NO:59. In aspects, the target polynucleotide sequence has at least 95% sequence identity to SEQ ID NO:61. In aspects, the target polynucleotide sequence has at least 95% sequence identity to SEQ ID NO:63. In aspects, the target polynucleotide sequence has at least 95% sequence identity to SEQ ID NO:65. In aspects, the target polynucleotide sequence has at least 95% sequence identity to SEQ ID NO:67. In aspects, the target polynucleotide sequence has at least 95% sequence identity to SEQ ID NO:69. In aspects, the target polynucleotide sequence has at least 95% sequence identity to SEQ ID NO:71. In aspects, the target polynucleotide sequence has at least 95% sequence identity to SEQ ID NO:73. In aspects, the target polynucleotide sequence has at least 95% sequence identity to SEQ ID NO:75. In aspects, the target polynucleotide sequence has at least 95% sequence identity to SEQ ID NO:77. In aspects, the target polynucleotide sequence has at least 95% sequence identity to SEQ ID NO:79. In aspects, the target polynucleotide sequence has at least 95% sequence identity to SEQ ID NO:81. In aspects, the target polynucleotide sequence has at least 95% sequence identity to SEQ ID NO:83. In aspects, the target polynucleotide sequence has at least 95% sequence identity to SEQ ID NO:85. In aspects, the target polynucleotide sequence has at least 95% sequence identity to SEQ ID NO:87. In aspects, the target polynucleotide sequence has at least 95% sequence identity to SEQ ID NO:89. In aspects, the target polynucleotide sequence has at least 95% sequence identity to SEQ ID NO:91. In aspects, the target polynucleotide sequence has at least 95% sequence identity to SEQ ID NO:93. In aspects, the target polynucleotide sequence has at least 95% sequence identity to SEQ ID NO:95.

In embodiments, the complex includes dCas9 bound to the polynucleotide through binding a binding sequence of the polynucleotide and thereby forming a ribonucleoprotein complex. In aspects, the binding sequence forms a hairpin structure. In aspects, the binding sequence is 30-100 nt, 35-50 nt, 37-47 nt, or 42 nt in length.

In embodiments, the binding sequence (e.g., Cas9-binding sequence) interacts with or binds to a Cas9 protein (e.g., dCas9 protein), and together they bind to the target polynucleotide sequence recognized by the DNA-targeting sequence. The binding sequence (e.g., Cas9-binding sequence) includes two complementary stretches of nucleotides that hybridize to one another to form a double stranded RNA duplex (a dsRNA duplex). These two complementary stretches of nucleotides may be covalently linked by intervening nucleotides known as linkers or linker nucleotides (e.g., in the case of a single-molecule polynucleotide), and hybridize to form the double stranded RNA duplex (dsRNA duplex, or "Cas9-binding hairpin") of the binding sequence (e.g., Cas9-binding sequence), thus resulting in a stem-loop structure. Alternatively, in some aspects, the two complementary stretches of nucleotides may not be covalently linked, but instead are held together by hybridization between complementary sequences (e.g., a two-molecule polynucleotide).

The binding sequence (e.g., Cas9-binding sequence) can have a length of from 10 nucleotides to 100 nucleotides, e.g., from 10 nucleotides (nt) to 20 nt, from 20 nt to 30 nt, from 30 nt to 40 nt, from 40 nt to 50 nt, from 50 nt to 60 nt, from 60 nt to 70 nt, from 70 nt to 80 nt, from 80 nt to 90 nt, or from 90 nt to 100 nt. In aspects, the binding sequence has a length of from 15 nucleotides (nt) to 80 nt. In aspects, the binding sequence has a length of from 15 nt to 50 nt. In aspects, the binding sequence has a length of from 15 nt to 40 nt. In aspects, the binding sequence has a length of from 15 nt to 30 nt. In aspects, the binding sequence has a length of from 37 nt to 47 nt (e.g., 42 nt). In aspects, the binding sequence has a length of from 15 nt to 25 nt.

The dsRNA duplex of the binding sequence (e.g., Cas9-binding sequence) can have a length from 6 base pairs (bp) to 50 bp. For example, the dsRNA duplex of the binding sequence (e.g., Cas9-binding sequence) can have a length from 6 bp to 40 bp, from 6 bp to 30 bp, from 6 bp to 25 bp, from 6 bp to 20 bp, from 6 bp to 15 bp, from 8 bp to 40 bp, from 8 bp to 30 bp, from 8 bp to 25 bp, from 8 bp to 20 bp or from 8 bp to 15 bp. In aspects, the dsRNA duplex of the binding sequence (e.g., Cas9-binding sequence) has a length from 8 bp to 10 bp. In aspects, the dsRNA duplex of the binding sequence (e.g., Cas9-binding sequence) has a length from 10 bp to 15 bp. In aspects, the dsRNA duplex of the binding sequence (e.g., Cas9-binding sequence) has a length from 15 bp to 18 bp. In aspects, the dsRNA duplex of the binding sequence (e.g., Cas9-binding sequence) has a length from 18 bp to 20 bp. In aspects, the dsRNA duplex of the binding sequence (e.g., Cas9-binding sequence) has a length from 20 bp to 25 bp. In aspects, the dsRNA duplex of the binding sequence (e.g., Cas9-binding sequence) has a length from 25 bp to 30 bp. In aspects, the dsRNA duplex of the binding sequence (e.g., Cas9-binding sequence) has a length from 30 bp to 35 bp. In aspects, the dsRNA duplex of the binding sequence (e.g., Cas9-binding sequence) has a length from 35 bp to 40 bp. In aspects, the dsRNA duplex of the binding sequence (e.g., Cas9-binding sequence) has a length from 40 bp to 50 bp.

In embodiments, the exemplary polynucleotide that forms a complex with a fusion protein described herein includes those described in Tables 1 and 2 as sgRNA. In aspects, the polynucleotide that forms a complex with a fusion protein described herein includes the sequence of SEQ ID NO: 38, 40, 42, 44, 46, 48, 50, 52, 54, 56, 58, 60, 62, 64, 66, 68, 70, 72, 74, 76, 78, 80, 82, 84, 86, 88, 90, 92, or 94 or their corresponding RNA sequence. In aspects, the polynucleotide that forms a complex with a fusion protein described herein includes the sequence having at least 80%, 85%, 90%, 91%, 92%, 93%, 94%, 95%, 96%, 97%, 98%, or 99% sequence identity to SEQ ID NO: 38, 40, 42, 44, 46, 48, 50, 52, 54, 56, 58, 60, 62, 64, 66, 68, 70, 72, 74, 76, 78, 80, 82, 84, 86, 88, 90, 92, or 94 or their corresponding RNA sequence. In aspects, the polynucleotide that forms a complex with a fusion protein described herein includes the sequence of SEQ ID NO:38. In aspects, the polynucleotide that forms a complex with a fusion protein described herein includes the sequence of SEQ ID NO:40. In aspects, the polynucleotide that forms a complex with a fusion protein described herein includes the sequence of SEQ ID NO:42. In aspects, the polynucleotide that forms a complex with a fusion protein described herein includes the sequence of SEQ ID NO: 44. In aspects, the polynucleotide that forms a complex with a fusion protein described herein includes the sequence of SEQ ID NO:46. In aspects, the polynucleotide that forms a complex with a fusion protein described herein includes the sequence of SEQ ID NO:48. In aspects, the polynucleotide that forms a complex with a fusion protein described herein includes the sequence of SEQ ID NO:50. In aspects, the polynucleotide that forms a complex with a fusion protein described herein includes the sequence of SEQ ID NO:52. In aspects, the polynucleotide that forms a complex with a fusion protein described herein includes the sequence of SEQ ID NO:54. In aspects, the polynucleotide that forms a complex with a fusion protein described herein includes the sequence of SEQ ID NO:56. In aspects, the polynucleotide that forms a complex with a fusion protein described herein includes the sequence of SEQ ID NO:58. In aspects, the polynucleotide that forms a complex with a fusion protein described herein includes the sequence of SEQ ID NO:60. In aspects, the polynucleotide that forms a complex with a fusion protein described herein includes the sequence of SEQ ID NO:62. In aspects, the polynucleotide that forms a complex with a fusion protein described herein includes the sequence of SEQ ID NO:64. In aspects, the polynucleotide that forms a complex with a fusion protein described herein includes the sequence of SEQ ID NO:66. In aspects, the polynucleotide that forms a complex with a fusion protein described herein includes the sequence of SEQ ID NO:68. In aspects, the polynucleotide that forms a complex with a fusion protein described herein includes the sequence of SEQ ID NO:70. In aspects, the polynucleotide that forms a complex with a fusion protein described herein includes the sequence of SEQ ID NO:72. In aspects, the polynucleotide that forms a complex with a fusion protein described herein includes the sequence of SEQ ID NO:74. In aspects, the polynucleotide that forms a complex with a fusion protein described herein includes the sequence of SEQ ID NO:76. In aspects, the polynucleotide that forms a complex with a fusion protein described herein includes the sequence of SEQ ID NO:78. In aspects, the polynucleotide that forms a complex with a fusion protein described herein includes the sequence of SEQ ID NO:80. In aspects, the polynucleotide that forms a complex with a fusion protein described herein includes the sequence of SEQ ID NO:82. In aspects, the polynucleotide that forms a complex with a fusion protein described herein includes the sequence of SEQ ID NO:84. In aspects, the polynucleotide that forms a complex with a fusion protein described herein includes the sequence of SEQ ID NO:86. In aspects, the polynucleotide that forms a complex with a fusion protein described herein includes the sequence of SEQ ID NO:88. In aspects, the polynucleotide that forms a complex with a fusion protein described herein includes the sequence of SEQ ID NO:90. In aspects, the polynucleotide that forms a complex with a fusion protein described herein includes the sequence of SEQ ID NO:92. In aspects, the polynucleotide that forms a complex with a fusion protein described herein includes the sequence of SEQ ID NO:94.

Nucleic Acids and Vectors

The fusion protein described herein, including embodiments and aspects thereof, may be provided as a nucleic acid sequence that encodes for the fusion protein. Thus, in an aspect is provided a nucleic acid sequence encoding the fusion protein described herein, including embodiments and aspects thereof. In an aspect is provided a nucleic acid sequence encoding the fusion protein described herein (including the DNA-targeting sequence), including embodiments and aspects thereof. In aspects, the nucleic acid sequence encodes for a fusion protein described herein, including fusion proteins having amino acid sequences with certain % sequence identities described herein. In aspects, the nucleic acid is RNA. In aspects, the nucleic acid is messenger RNA. In aspects, the messenger RNA is messenger RNP. In aspects, the nucleic acid sequence encodes for the fusion proteins described herein, including embodiments and aspects thereof. In aspects, the nucleic acid sequence encodes for the fusion protein of SEQ ID NO:1. In aspects, the nucleic acid sequence encodes for the fusion protein of SEQ ID NO:2. In aspects, the nucleic acid sequence encodes for the fusion protein of SEQ ID NO:3. In aspects, the nucleic acid sequence encodes for the fusion protein of SEQ ID NO:4. In aspects, the nucleic acid sequence encodes for the fusion protein of SEQ ID NO:5. In aspects, the nucleic acid sequence encodes for the fusion protein of SEQ ID NO:6. In aspects, the nucleic acid sequence encodes for the fusion protein of SEQ ID NO:7. In aspects, the nucleic acid sequence encodes for the fusion protein of SEQ ID NO: 8. In aspects, the nucleic acid sequence encodes for the fusion protein of SEQ ID NO:9. In aspects, the nucleic acid sequence encodes for the fusion protein of SEQ ID NO:10. In aspects, the nucleic acid sequence encodes for the fusion protein of SEQ ID NO:11. In aspects, the nucleic acid sequence encodes for the fusion protein of SEQ ID NO:12. In aspects, the nucleic acid sequence encodes for the fusion protein of SEQ ID NO:13. In aspects, the nucleic acid sequence encodes for the fusion protein of SEQ ID NO:14. In aspects, the nucleic acid sequence encodes for the fusion protein of SEQ ID NO:15.

It is further contemplated that the nucleic acid sequence encoding the fusion protein as described herein, including embodiments and aspects thereof, may be included in a vector. Therefore, in an aspect is provided a vector including a nucleic acid sequence as described herein, including embodiments and aspects thereof. In aspects, the vector comprises a nucleic acid sequence that encodes for a fusion protein described herein, including fusion proteins having amino acid sequences with certain % sequence identities described herein. In aspects, the nucleic acid is messenger RNA. In aspects, the messenger RNA is messenger RNP. In aspects, the vector comprises a nucleic acid sequence that encodes for the fusion protein of SEQ ID NO:1. In aspects, the vector comprises a nucleic acid sequence that encodes for the fusion protein of SEQ ID NO:2. In aspects, the vector comprises a nucleic acid sequence that encodes for the fusion protein of SEQ ID NO: 3. In aspects, the vector comprises a nucleic acid sequence that encodes for the fusion protein of SEQ ID NO:4. In aspects, the vector comprises a nucleic acid sequence that encodes for the fusion protein of SEQ ID NO:5. In aspects, the vector comprises a nucleic acid sequence that encodes for the fusion protein of SEQ ID NO:6. In aspects, the vector comprises a nucleic acid sequence that encodes for the fusion protein of SEQ ID NO:7. In aspects, the vector comprises a nucleic acid sequence that encodes for the fusion protein of SEQ ID NO:8. In aspects, the vector comprises a nucleic acid sequence that encodes for the fusion protein of SEQ ID NO:9. In aspects, the vector comprises a nucleic acid sequence that encodes for the fusion protein of SEQ ID NO:10. In aspects, the vector comprises a nucleic acid sequence that encodes for the fusion protein of SEQ ID NO: 11. In aspects, the vector comprises a nucleic acid sequence that encodes for the fusion protein of SEQ ID NO:12. In aspects, the vector comprises a nucleic acid sequence that encodes for the fusion protein of SEQ ID NO:13. In aspects, the vector comprises a nucleic acid sequence that encodes for the fusion protein of SEQ ID NO:14. In aspects, the vector comprises a nucleic acid sequence that encodes for the fusion protein of SEQ ID NO:15.

In embodiments, the vector further includes a polynucleotide, wherein the polynucleotide includes: (1) a DNA-targeting sequence that is complementary to a target polynucleotide sequence; and (2) a binding sequence for the nuclease-deficient RNA-guided DNA endonuclease enzyme. Thus, one or more vectors may include all necessary components for preforming epigenome editing.

Cells

The compositions described herein may be incorporated into a cell. Inside the cell, the compositions as described herein, including embodiments and aspects thereof, may perform epigenome editing. Accordingly, in an aspect is provided a cell including a fusion protein as described herein, including embodiments and aspects thereof, a nucleic acid as described herein, including embodiments and aspects thereof, a complex as described herein, including embodiments and aspects thereof, or a vector as described herein, including embodiments and aspects thereof. In aspects is provided a cell including a fusion protein as described herein, including embodiments and aspects thereof. In aspects is provided a cell including a nucleic acid as described herein, including embodiments and aspects thereof. In aspects is provided a cell including a complex as described herein, including embodiments and aspects thereof. In aspects is provided a cell including a vector as described herein, including embodiments and aspects thereof. In aspects, the cell is a eukaryotic cell. In aspects, the cell is a mammalian cell.

Methods

It is contemplated that the compositions described herein may be used for epigenome editing, and more particularly epigenome editing resulting in the repression or silencing of target nucleic acid sequences (e.g., genes). Without intending to be bound by any theory, silencing may result from methylation of and/or the introduction of repressive chromatin markers (e.g., mono-, di-, or tri-methylation of specific histones (e.g., H3K9, H3K27), deacetylation, acetylation, phosphorylation, ubiquitination) on chromatin containing a target nucleic acid sequence. Without intending to be bound by any theory, the method can be used to change epigenetic state by, for example, closing chromatin via methylation or introducing repressive chromatin markers on chromatin containing the target nuclei acid sequence (e.g., gene). Without intending to be bound by any theory, it is contemplated that the Dnmt3A-3L fusion functions to add methyl marks at CG DNA sites found in CpG islands and the KRAB domain recruits epigenetic factors that modify the histones by introducing repressive marks. Without intending to be bound by any theory, DNA is methylated at the C nucleotide of CG sequences found in CpG islands (i.e., adding methyl marks at the C nucleotide of CG DNA sites found in CpG islands).

In an aspect is provided a method of silencing a target nucleic acid sequence in a cell, including delivering a first polynucleotide encoding a fusion protein as described herein, including embodiments and aspects thereof, to a cell containing the target nucleic acid; and delivering to the cell a second polynucleotide including: (i) a DNA-targeting sequence that is complementary to the target nucleic acid sequence; and (ii) a binding sequence for the nuclease-deficient RNA-guide DNA endonuclease enzyme. Without intending to be bound by any theory, the fusion protein silences the target nucleic acid sequence in the cell by methylating a chromatin containing the target nucleic acid sequence and/or by introducing repressive chromatin marks to a chromatin containing the target nucleic acid sequence. Without intending to be bound by any theory, methylating a chromatin means that DNA is methylated at the C nucleotide of CG sequences found in CpG islands (i.e., adding methyl marks at the C nucleotide of CG DNA sites found in CpG islands). In aspects, the sequence that is within about 3000 base pairs of the target nucleic acid sequence is methylated. In aspects, the sequence that is within about 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 200, or 100 base pairs of the target nucleic acid sequence is methylated.

The term "repressive chromatin markers" as used herein refers to modifications made to the chromatin that result in silencing (e.g., decreasing or inhibiting of transcription) of the target nucleic acid sequence (e.g., a gene). Examples of repressive chromatin markers include, but are not limited to, mono-, di-, and/or tri-methylation, acetylation/deacetylation, phosphorylation, and ubiquitination of histones (e.g., H3K9, H3K27, H3K79, H2BK5).

In embodiments, silencing refers to a complete suppression of transcription. In aspects, silencing refers to a significant decrease in transcription compared to control levels of transcription.

In embodiments, the first polynucleotide is contained within a first vector. In aspects, the first polynucleotide is contained within a second vector. In aspects, the first vector and the second vector are the same. In aspects, the first vector is different from the second vector.

In embodiments, the polynucleotide described herein is delivered into the cell by any method known in the art, for example, by transfection, electroporation or transduction.

Alternatively, in an aspect is provided a method of silencing a target nucleic acid sequence in a cell, including delivering a complex as described herein, including embodiments and aspects thereof, to a cell containing the target nucleic acid. Without intending to be bound by any theory, the complex silences the target nucleic acid sequence in the cell by methylating a chromatin containing the target nucleic acid sequence and/or by introducing repressive chromatin marks to a chromatin containing the target nucleic acid sequence.

In embodiments, the cell is a mammalian cell.

In embodiments, the method has a specificity that is 2-fold higher than a specificity to a non-target nucleic acid sequence. In aspects, the method has a specificity that is at least 2-fold (e.g., 2-, 3-, 4-, 5-, 6-, 7-, 8-, 9-, 10-, 15-, 20-, 25-fold) higher than a specificity to a non-target nucleic acid sequence. Methods for determining specificity are well known in the art and include, but are not limited to, RNA-seq, bisulfite sequencing, chromatin immunoprecipitation, flow cytometry, and qPCR. Thus, in aspects, specificity is determined by RNA-seq. In aspects, specificity is determined by bisulfite sequencing. In aspects, specificity is determined by chromatin immunoprecipitation. In aspects, specificity is determined by flow cytometry. In aspects, specificity is determined by qPCR.

In aspects, the complex is delivered into the cell via any methods known in the art, for example, via ribonucleoprotein (RNP) delivery.

Embodiments N1-N41

Embodiment N1. A fusion protein comprising a nuclease-deficient RNA-guided DNA endonuclease enzyme, a Krüppel associated box domain, and a DNA methyltransferase domain.

Embodiment N2. The fusion protein of Embodiment N1, wherein the nuclease-deficient. RNA-guided DNA endonuclease enzyme is dCas9, ddCpf1, a nuclease-deficient Cas9 variant, or a nuclease-deficient Class II CRISPR endonuclease.

Embodiment N3. The fusion protein of Embodiment N1 or N2, wherein the DNA methyltransferase domain is a Dnmt3A-3L domain.

Embodiment N4. The fusion protein of Embodiment N1, wherein the fusion protein comprises, from N-terminus to C-terminus, the DNA methyltransferase domain, the nuclease-deficient RNA-guided DNA endonuclease enzyme, and the Krüppel associated box domain Embodiment N5. The fusion protein of Embodiment N4, wherein the nuclease-deficient RNA-guided DNA endonuclease enzyme is dCas9 and the DNA methyltransferase domain is a Dnmt3A-3L domain Embodiment N6. The fusion protein of Embodiment N5, wherein the nuclease-deficient RNA-guided DNA endonuclease enzyme is dCas9 and the DNA methyltransferase domain is a Dnmt3A-3L domain Embodiment N7. The fusion protein of Embodiment N6, wherein the peptide linker is a XTEN linker.

Embodiment N8. The fusion protein of Embodiment N1, wherein the fusion protein comprises, from N-terminus to C-terminus, the Krüppel associated box, the nuclease-deficient RNA-guided DNA endonuclease enzyme, and the DNA methyltransferase domain Embodiment N9. The fusion protein of Embodiment N8, wherein the nuclease-deficient RNA-guided DNA endonuclease enzyme is dCas9 and the DNA methyltransferase domain is a Dnmt3A-3L domain.

Embodiment N10. The fusion protein of Embodiment N9, wherein the dCas9 is covalently linked to the Dnmt3A-3L domain via a peptide linker and wherein the Krüppel associated box domain is covalently linked to the dCas9 via a peptide linker.

Embodiment N11. The fusion protein of Embodiment N10, wherein the peptide linker is a XTEN linker.

Embodiment N12. The fusion protein of any one of Embodiments N1 to N3, wherein the nuclease-deficient RNA-guided DNA endonuclease enzyme is covalently linked to the Krüppel associated box domain via a peptide linker.

Embodiment N13. The fusion protein of any one of Embodiments N1 to N3, wherein the nuclease-deficient RNA-guided DNA endonuclease enzyme is covalently linked to the DNA methyltransferase domain via a peptide linker.

Embodiment N14. The fusion protein of any one of Embodiments N1 to N3, wherein the Krüppel associated box domain is covalently linked to the DNA methyltransferase domain via a peptide linker.

Embodiment N15. The fusion protein of any one of Embodiments N12 to N14, wherein the peptide linker is a XTEN linker.

Embodiment N16. The fusion protein of Embodiment N15, wherein the XTEN linker comprises about 16 to 80 amino acid residues.

Embodiment N17. The fusion protein of any one of Embodiments N1 to N16, further comprising a nuclear localization signal peptide.

Embodiment N18. The fusion protein of Embodiment N1, wherein the fusion protein comprises the amino acid sequence of SEQ ID NO: 1, 2, 3, 4, 5, 6, 7, 8, 9, 10, 11 12, 13, 14, or 15.

Embodiment N19. A nucleic acid sequence encoding the fusion protein of any one of Embodiments N1 to N18.

Embodiment N20. The nucleic acid sequence of Embodiment N19, wherein the nucleic acid sequence is messenger RNA.

Embodiment N21. A complex comprising: (i) a fusion protein of any one of Embodiments N1 to N18; and (ii) a polynucleotide comprising: (a) a DNA-targeting sequence that is complementary to a target polynucleotide sequence; and (b) a binding sequence for the nuclease-deficient RNA-guided DNA endonuclease enzyme, wherein the nuclease-deficient RNA-guided DNA endonuclease enzyme is bound to the polynucleotide via the binding sequence.

Embodiment N22. The complex of Embodiment N21, wherein the target polynucleotide sequence is part of a gene.

Embodiment N23. The complex of Embodiment N21, wherein the target polynucleotide sequence is part of a transcriptional regulatory sequence.

Embodiment N24. The complex of Embodiment N21, wherein the target polynucleotide sequence is part of a promoter, enhancer, or silencer.

Embodiment N25. The complex of Embodiment N21, wherein the target polynucleotide sequence is within about 3000 bp flanking a transcription start site.

Embodiment N26. A vector comprising the nucleic acid sequence of Embodiment N19 or N20.

Embodiment N27. The vector of Embodiment N26, further comprising a polynucleotide, wherein the polynucleotide comprises: (a) a DNA-targeting sequence that is complementary to a target polynucleotide sequence; and (b) a binding sequence for the nuclease-deficient RNA-guided DNA endonuclease enzyme.

Embodiment N28. A cell comprising the fusion protein of any one of Embodiments N1 to N18; the nucleic acid of Embodiment N19 or N20; the complex of any one of Embodiments N21 to N25, or the vector of Embodiment N26 or N27.

Embodiment N29. The cell of Embodiment N28, wherein the cell is a eukaryotic cell.

Embodiment N30. The cell of Embodiment N28, wherein the cell is a mammalian cell.

Embodiment N31. A method of silencing a target nucleic acid sequence in a cell, comprising: (i) delivering a first polynucleotide encoding a fusion protein of any one of Embodiments N1 to N18 to a cell containing the target nucleic acid; and (ii) delivering to the cell a second polynucleotide comprising: (a) a DNA-targeting sequence that is complementary to the target nucleic acid sequence; and (b) a binding sequence for the nuclease-deficient RNA-guide DNA endonuclease enzyme Embodiment N32. The method of Embodiment N31, wherein the fusion protein silences the target nucleic acid sequence in the cell by methylating a chromatin containing the target nucleic acid sequence and/or by introducing repressive chromatin marks to a chromatin containing the target nucleic acid sequence.

Embodiment N33. The method of Embodiment N31 or N32, wherein the first polynucleotide is contained within a first vector.

Embodiment N34. The method of any one of Embodiments N31 to N33, wherein the first polynucleotide is contained within a second vector.

Embodiment N35. The method of Embodiment N34, wherein the first vector and the second vector are the same.

Embodiment N36. The method of Embodiment N34, wherein the first vector is different from the second vector.

Embodiment N37. The method of Embodiment N31, wherein the cell is a mammalian cell.

Embodiment N38. The method of Embodiment N31, wherein the method has a specificity that is 2-fold higher than a specificity to a non-target nucleic acid sequence.

Embodiment N39. A method of silencing a target nucleic acid sequence in a cell, the method comprising delivering the complex of any one of Embodiments N21 to N25 to a cell containing the target nucleic acid.

Embodiment N40. The method of Embodiment N39, wherein the complex silences the target nucleic acid sequence in the cell by methylating a chromatin containing the target nucleic acid sequence and/or by introducing repressive chromatin marks to a chromatin containing the target nucleic acid sequence.

Embodiment N41. The method of Embodiment N39 or N40, wherein the cell is a mammalian cell.

Embodiment N42. The method of any one of Embodiments N39 to N41, wherein the method has a specificity that is 2-fold higher than a specificity to a non-target nucleic acid sequence.

Embodiments 1 to 36

Embodiment 1. A fusion protein comprising a nuclease-deficient RNA-guided DNA endonuclease enzyme, a Krüppel associated box (KRAB) domain, and a DNA methyltransferase domain.

Embodiment 2. The fusion protein of Embodiment 1, wherein the nuclease-deficient RNA-guided DNA endonuclease enzyme is dCas9, ddCpf1, a nuclease-deficient Cas9 variant, or a nuclease-deficient Class II CRISPR endonuclease.

Embodiment 3. The fusion protein of Embodiment 1 or 2, wherein the DNA methyltransferase domain is a Dnmt3A-3L domain.

Embodiment 4. The fusion protein of any one of Embodiments 1 to 3, wherein the nuclease-deficient RNA-guided DNA endonuclease enzyme is covalently linked to the KRAB domain via a peptide linker.

Embodiment 5. The fusion protein of any one of Embodiments 1 to 4, wherein the nuclease-deficient RNA-guided DNA endonuclease enzyme is covalently linked to the DNA methyltransferase domain via a peptide linker.

Embodiment 6. The fusion protein of any one of Embodiments 1 to 5, wherein the KRAB domain is covalently linked to the DNA methyltransferase domain via a peptide linker.

Embodiment 7. The fusion protein of any one of Embodiments 4 to 6, wherein the peptide linker is a XTEN linker.

Embodiment 8. The fusion protein of Embodiment 7, wherein the XTEN linker comprises about 16 to 80 amino acid residues.

Embodiment 9. The fusion protein of any one of Embodiments 1 to 8, further comprising a nuclear localization signal peptide.

Embodiment 10. The fusion protein of any one of Embodiments 1 to 9, wherein the fusion protein comprises, from N-terminus to C-terminus, a KRAB domain, a nuclease-deficient RNA-guided DNA endonuclease enzyme, and a DNA methyltransferase domain.

Embodiment 11. The fusion protein of any one of Embodiments 1 to 10, wherein the nuclease-deficient RNA-guided DNA endonuclease enzyme is dCas9 and the DNA methyltransferase domain is a Dnmt3A-3L domain.

Embodiment 12. The fusion protein of Embodiment 11, wherein the dCas9 is covalently linked to the KRAB domain via a peptide linker and wherein the dCas9 is covalently linked to the Dnmt3A-3L domain via a peptide linker.

Embodiment 13. The fusion protein of Embodiment 12, wherein the peptide linker is a XTEN linker.

Embodiment 14. The fusion protein of any one of Embodiments 1 to 13, wherein the fusion protein comprises the amino acid sequence of SEQ ID NO:1, 2, 3, 4, 5, 6, 7, 8, 9, 10, 11 12, 13, 14, or 15.

Embodiment 15. A nucleic acid sequence encoding the fusion protein of any one of Embodiments 1 to 14.

Embodiment 16. A complex comprising: (i) a fusion protein of any one of Embodiments 1 to 18; and (ii) a polynucleotide comprising: (a) a DNA-targeting sequence that is complementary to a target polynucleotide sequence; and (b) a binding sequence for the nuclease-deficient RNA-guided DNA endonuclease enzyme, wherein the nuclease-deficient RNA-guided DNA endonuclease enzyme is bound to the polynucleotide via the binding sequence.

Embodiment 17. The complex of Embodiment 21, wherein the target polynucleotide sequence is part of a gene.

Embodiment 18. The complex of Embodiment 21, wherein the target polynucleotide sequence is part of a transcriptional regulatory sequence.

Embodiment 19. The complex of Embodiment 21, wherein the target polynucleotide sequence is part of a promoter, enhancer, or silencer.

Embodiment 20. The complex of Embodiment 21, wherein the target polynucleotide sequence is a hypomethylated nucleic acid sequence.

Embodiment 21. The complex of Embodiment 21, wherein the target polynucleotide sequence is within about 3000 bp flanking a transcription start site.

Embodiment 22. A vector comprising the nucleic acid sequence of Embodiment 19.

Embodiment 23. The vector of Embodiment 26 further comprising a polynucleotide, wherein the polynucleotide comprises: (a) a DNA-targeting sequence that is complementary to a target polynucleotide sequence; and (b) a binding sequence for the nuclease-deficient RNA-guided DNA endonuclease enzyme.

Embodiment 24. A cell comprising the fusion protein of any one of Embodiments 1 to 14; the nucleic acid of Embodiment 15; the complex of any one of Embodiments 16 to 21; or the vector of Embodiment 22 or 23.

Embodiment 25. The cell of Embodiment 28, wherein the cell is a eukaryotic cell.

Embodiment 26. The cell of Embodiment 28, wherein the cell is a mammalian cell.

Embodiment 27. A method of silencing a target nucleic acid sequence in a cell, comprising: (i) delivering a first polynucleotide encoding a fusion protein according to any one of Embodiments 1 to 14 to a cell containing the target nucleic acid; and (ii) delivering to the cell a second polynucleotide comprising: (a) a DNA-targeting sequence that is complementary to the target nucleic acid sequence; and (b) a binding sequence for the nuclease-deficient RNA-guide DNA endonuclease enzyme, wherein the fusion protein silences the target nucleic acid sequence in the cell by methylating a chromatin containing the target nucleic acid sequence and/or by introducing repressive chromatin marks to a chromatin containing the target nucleic acid sequence Embodiment 28. The method of Embodiment 27, wherein the first polynucleotide is contained within a first vector.

Embodiment 29. The method of Embodiment 27, wherein the first polynucleotide is contained within a second vector.

Embodiment 30. The method of Embodiment 28 or 29, wherein the first vector and the second vector are the same.

Embodiment 31. The method of Embodiment 28 or 29, wherein the first vector is different from the second vector.

Embodiment 32. The method of any one of Embodiments 27 to 31, wherein the cell is a mammalian cell.

Embodiment 33. The method of any one of Embodiments 27 to 32, wherein the method has a specificity that is 2-fold higher than a specificity to a non-target nucleic acid sequence.

Embodiment 34. A method of silencing a target nucleic acid sequence in a cell, the method comprising delivering the complex of any one of Embodiments 16 to 20 to a cell containing the target nucleic acid, wherein the complex silences the target nucleic acid sequence in the cell by: (i) methylating a chromatin containing the target nucleic acid sequence, (ii) introducing repressive chromatin marks to a chromatin containing the target nucleic acid sequence, or (iii) methylating a chromatin containing the target nucleic acid sequence and introducing repressive chromatin marks to a chromatin containing the target nucleic acid sequence.

Embodiment 35. The method of Embodiment 34, wherein the cell is a mammalian cell.

Embodiment 36. The method of Embodiment 34 or 35, wherein the method has a specificity that is 2-fold higher than a specificity to a non-target nucleic acid sequence.

EXAMPLES

Embodiments and aspects herein are further illustrated by the following examples. The examples are merely intended to illustrate embodiments and aspects, and are not to be construed to limit the scope herein.

Figure 1B:
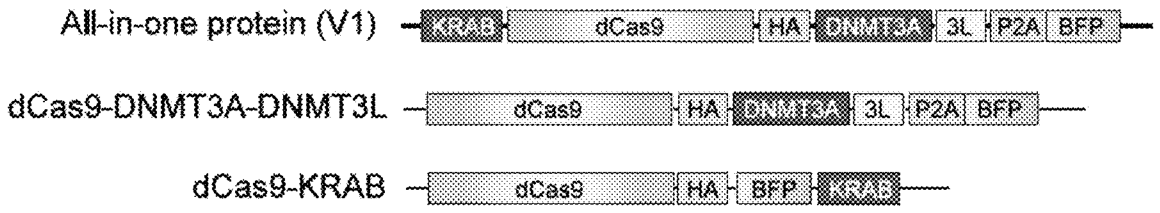

Example 1 dCas9-fused epigenetic modulators tested for permanent gene silencing. The initial version (V1, p76 (SEQ ID NO:1)) of the all-in-one protein (FIG. 1A) has the KRAB domain fused to the -N-terminus of dCas9 (SEQ ID NO:23), separated by a GGSGGGS (SEQ ID NO:17) linker, and Dnmt3A-Dnmt3L at the C-terminus of dCas9 (separated by a EASGSGRASPGIPGSTR (SEQ ID NO: 19) linker). Another all-in-one proteins that combined the KRAB domain (SEQ ID NO:16), dCas9 (D10A, H208A), Dnmt3A-Dnmt3L (SEQ ID NO:33; where SEQ ID NO:26 is Dnmt3A and SEQ ID NO:28 is Dnmt3L) into one polypeptide (FIG. 1B). With reference to FIG. 1B, the dCas9-KRAB protein was adapted from Gilbert et al., Cell 2013 for CRISPR interference (CRISPRi) applications, and the dCas9-Dnmt3A-Dnmt3L fusion was adapted from Stepper et al., Nucleic Acids Research, 2016.

Figure 1C:
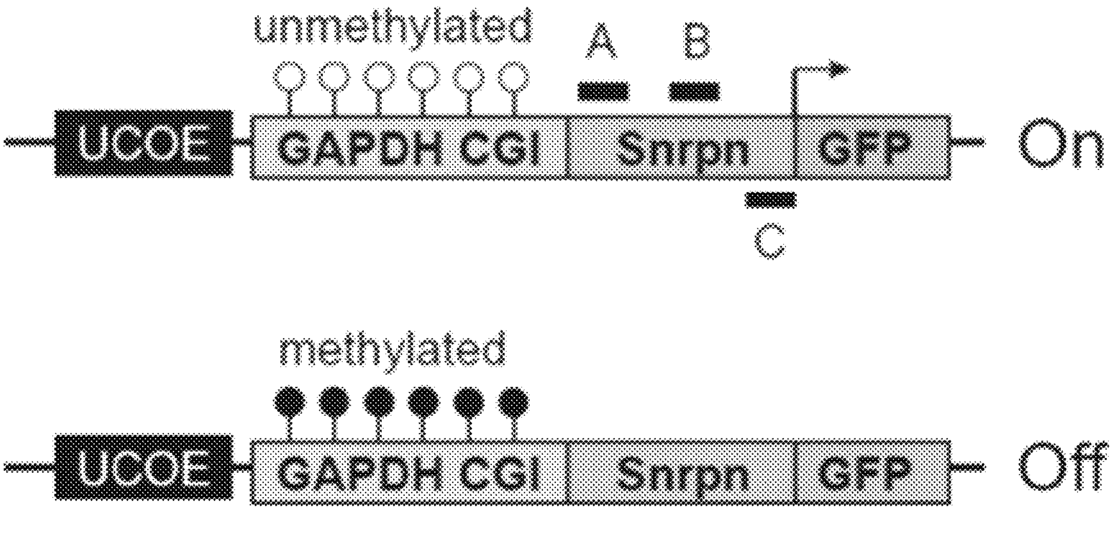
Figure 1D:
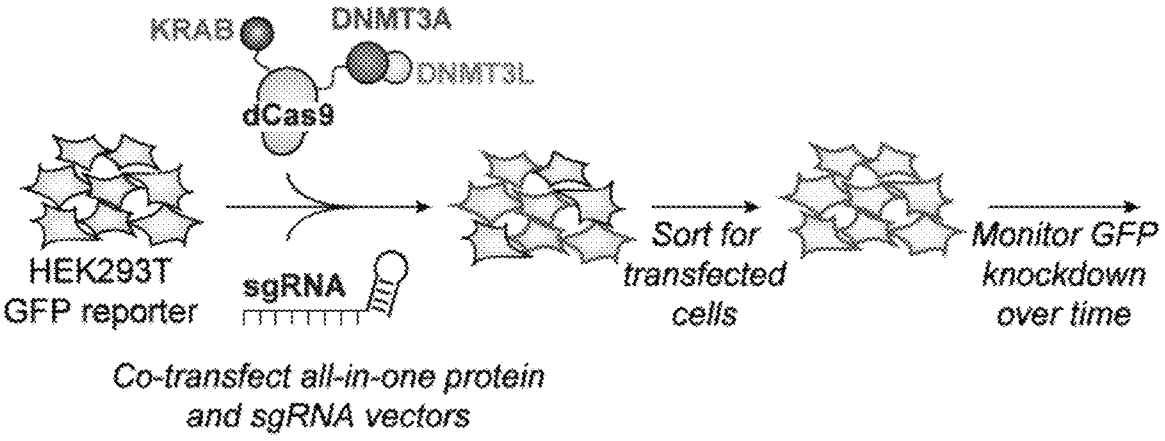
Figure 1E:
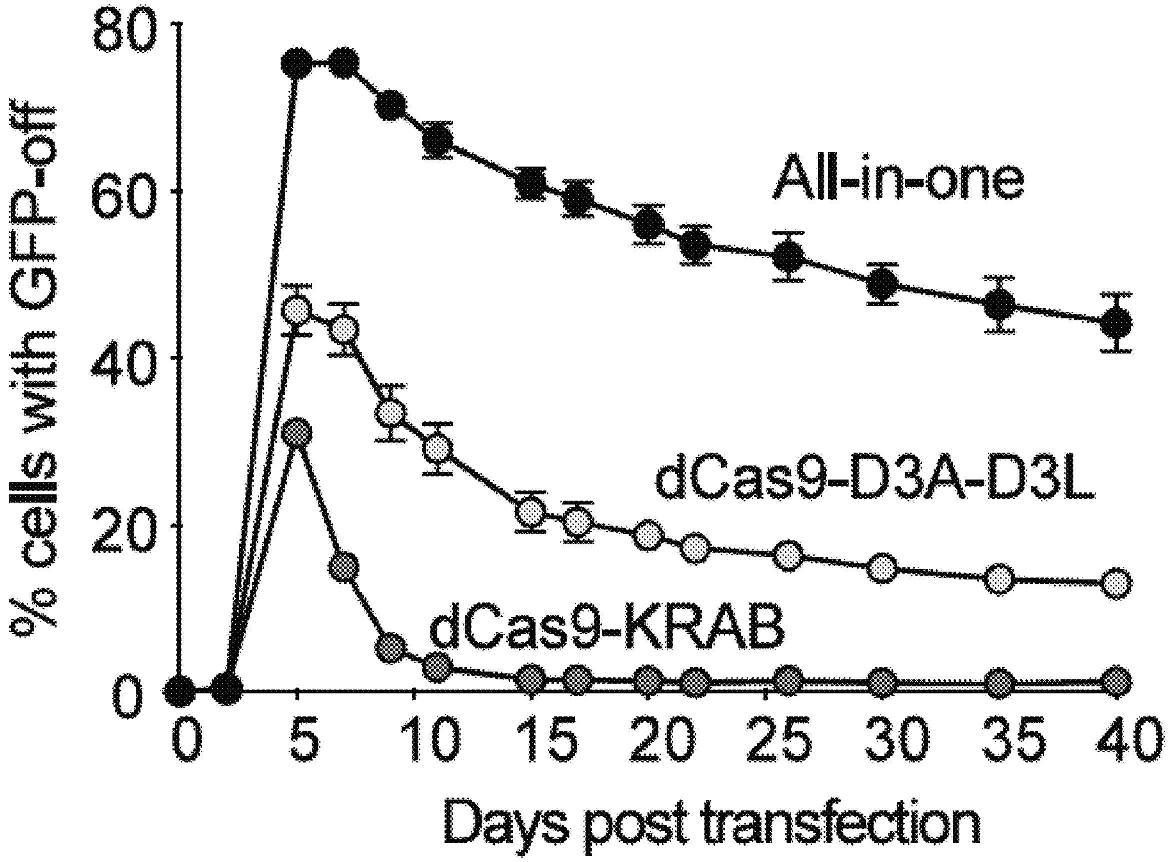
Figure 1F:
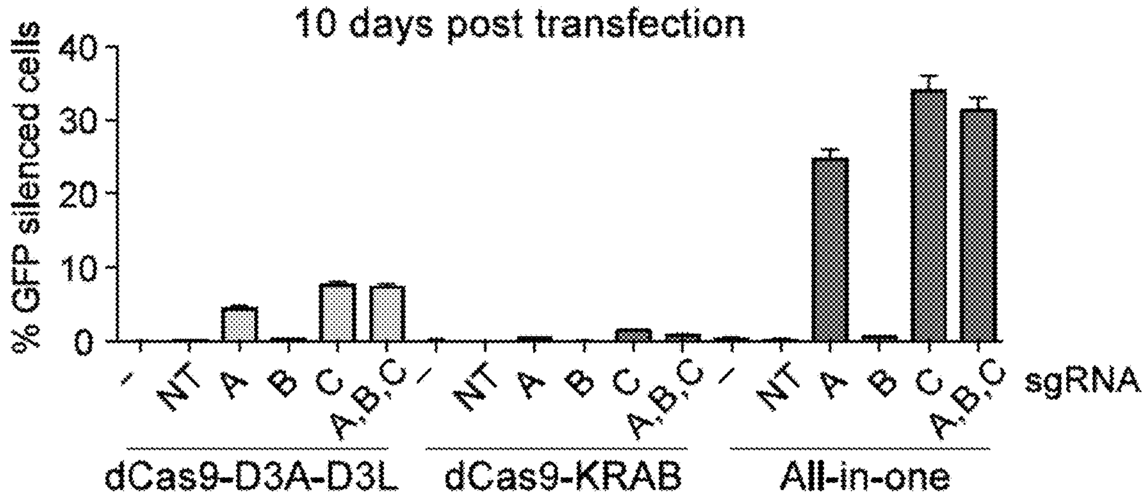

The activity of the V1 epigenetic editor was tested in HEK293T cells using a DNA-methylation sensitive GFP reporter (adapted from Stelzer et al., Cell 2015) to assess long-term silencing by the all-in-one protein (FIG. 1C). A ubiquitous chromatin opening element (UCOE) was added upstream of the GAPDH CpG island (CGI) to prevent background silencing of the lentiviral vector in mammalian cells. The gfp gene is turned off when the GAPDH CGI is methylated. A, B and C denote positions we encoded single guide RNAs (sgRNA) to target in the promoter. These targeted sequences and corresponding sgRNA sequences are listed in the Table 1 below. Two plasmids were co-transfected into cells, one encoding the hit-and-run protein and the other plasmid encoding a sgRNA (FIG. 1D). Two days post-transfection, cells that express the hit-and-run protein and sgRNA-expressing vector are sorted. GFP fluorescence is assessed over time by flow cytometry. A population of cells undergoing long-term silencing of the GFP reporter was observed when the all-in-one protein is expressed with sgRNAs (FIG. 1E). The number of cells undergoing long-term silencing was higher than dCas9-Dnmt3A-Dnmt3L (lacking the KRAB domain).

TABLE 1

| Name | Targeted sequence (5' to 3') | sgRNA sequence (5' to 3') |
|---|---|---|
| A (JKNg156) | ACTGCGGAAATTTGAGCGT (SEQ ID NO: 37) | ACGCTCAAATTTCCGCAGT (SEQ ID NO: 38) |
| B (JKNg158) | AGGCAATGGCTGCACATGC (SEQ ID NO: 39) | GCATGTGCAGCCATTGCCT (SEQ ID NO: 40) |
| C (JKNg160) | GACGCTTGGTTCTGAGGAG (SEQ ID NO: 41) | CTCCTCAGAACCAAGCGTC (SEQ ID NO: 42) |

Silencing of the GFP reporter is dependent on the sgRNA sequence, with guide C resulting in the highest level of silencing among the three sgRNA sequences tested. Pooling the sgRNAs encoding different sequences did not have a significant change in gene silencing.

Example 2

Figures 2A, 2B, 2C:
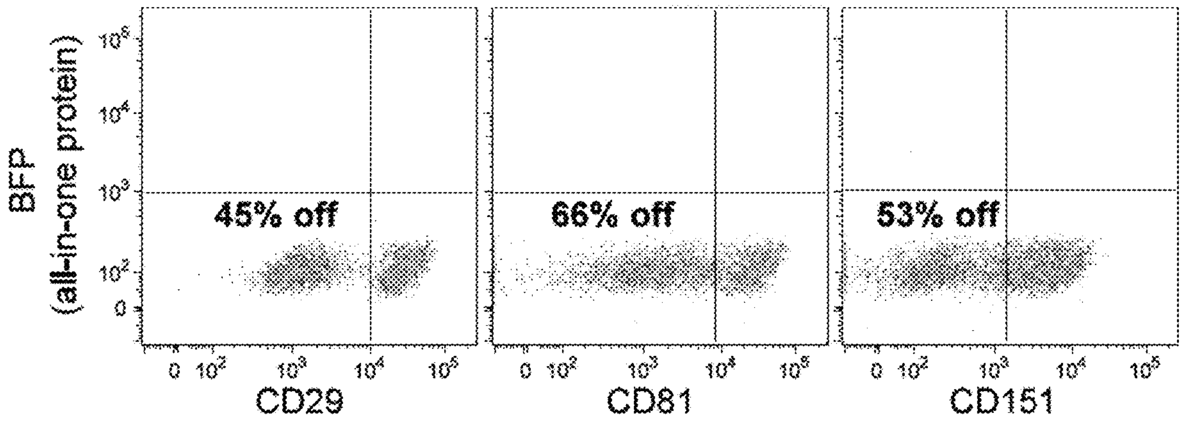
FIGS. 2A-2F describe long-term silencing of endogenous genes.
Figure 2D:
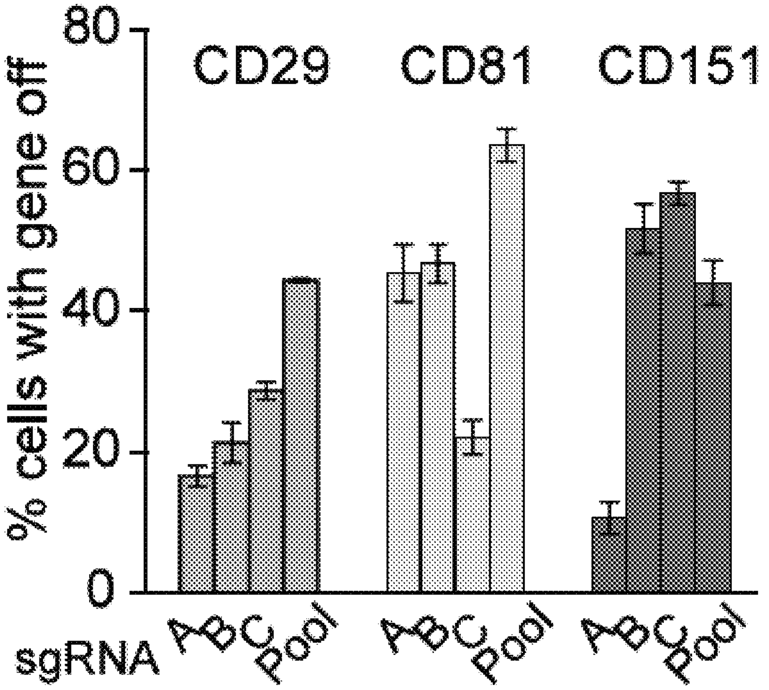

Three genes (CD29, CD81, CD151) were targeted for long term silencing using the hit-and-run fusion protein. All three proteins are cell surface-localized and knockdown was assessed by cell surface antibody staining of cells, followed by flow cytometry. Representative flow cytometry data are shown in FIGS. 2A-2C taken 22 days post-transfection. Quadrant IV represents cells that have turned off the gene, indicated by the percentage of cells with the gene off. The lack of cells in Quadrants I and II signify that the hit-and-run protein (marked by BFP) is no longer present in the cells. FIG. 2D provides quantification of silencing of CD29, CD81 and CD151 with three different sgRNA sequences or a pool of all three sgRNAs. The targeted DNA sequences and their sgRNAs used in this experiment are summarized in Table 2.

TABLE 2

| Name | Targeted sequence (5' to 3') | sgRNA sequence (5' to 3') |
|---|---|---|
| CD29, sgRNA-A | TCCGGAAACGCATTCCTCT (SEQ ID NO: 43) | AGAGGAATGCGTTTCCGGA (SEQ ID NO: 44) |
| CD29, sgRNA-B | CCGCGTCAGCCCGGCCCGG (SEQ ID NO: 45) | CCGGGCCGGGCTGACGCGG (SEQ ID NO: 46) |
| CD29, sgRNA-C | CGACTCCCGCTGGGCCTCT (SEQ ID NO: 47) | AGAGGCCCAGCGGGAGTCG (SEQ ID NO: 48) |

TABLE 2-continued

| Name | Targeted sequence (5' to 3') | sgRNA sequence (5' to 3') |
|---|---|---|
| CD81, sgRNA-A | ccgttgcgcgctcgctctc (SEQ ID NO: 49) | gagagcgagcgcgcaacgg (SEQ ID NO: 50) |
| CD81, sgRNA-B | CCGCGCATCCTGCCAGGCC (SEQ ID NO: 51) | GGCCTGGCAGGATGCGCGG (SEQ ID NO: 52) |
| CD81, sgRNA-C | CCAACTTGGCGCGTTTCGG (SEQ ID NO: 53) | CCGAAACGCGCCAAGTTGG (SEQ ID NO: 54) |
| CD151, sgRNA-A | ACCACGCGTCCGAGTCCGG (SEQ ID NO: 55) | CCGGACTCGGACGCGTGGT (SEQ ID NO: 56) |
| CD151, sgRNA-B | TGCTCATTGTCCCTGGACA (SEQ ID NO: 57) | TGTCCAGGGACAATGAGCA (SEQ ID NO: 58) |
| CD151, sgRNA-C | GGACACCCTGCTCATTGTC (SEQ ID NO: 59) | GACAATGAGCAGGGTGTCC (SEQ ID NO: 60) |

Figure 2E:
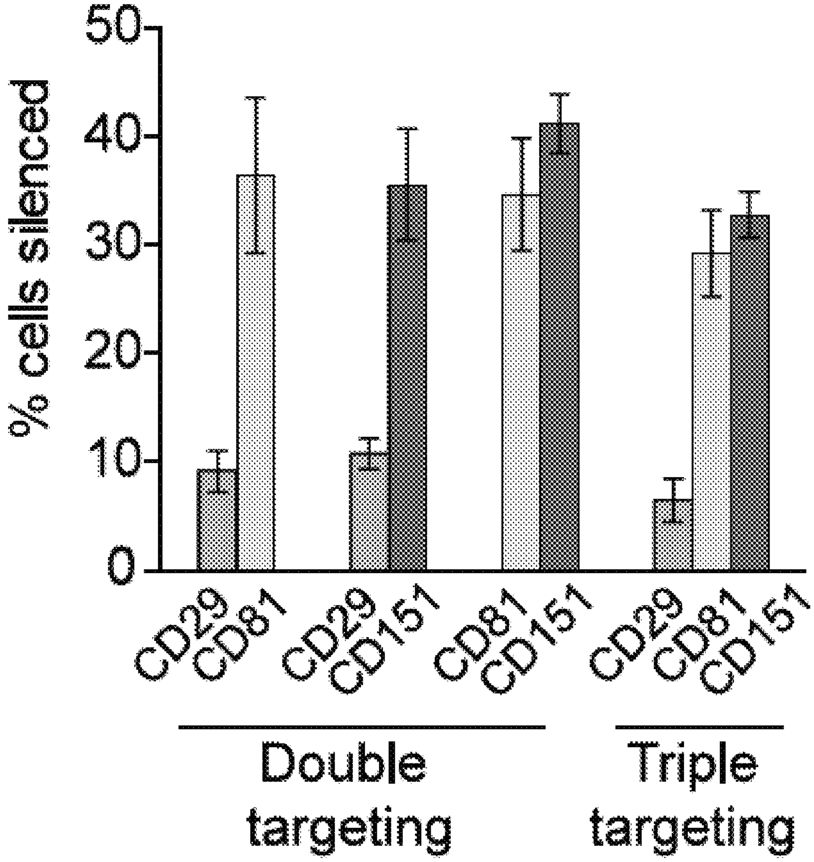

Two or three genes were simultaneously targeted to show that the all-in-protein can be multiplexed by co-delivery of sgRNAs targeting different genes. NT sgRNA refers to non-targeting sgRNA control. The results are shown in FIG. 2E.

Figure 2F:
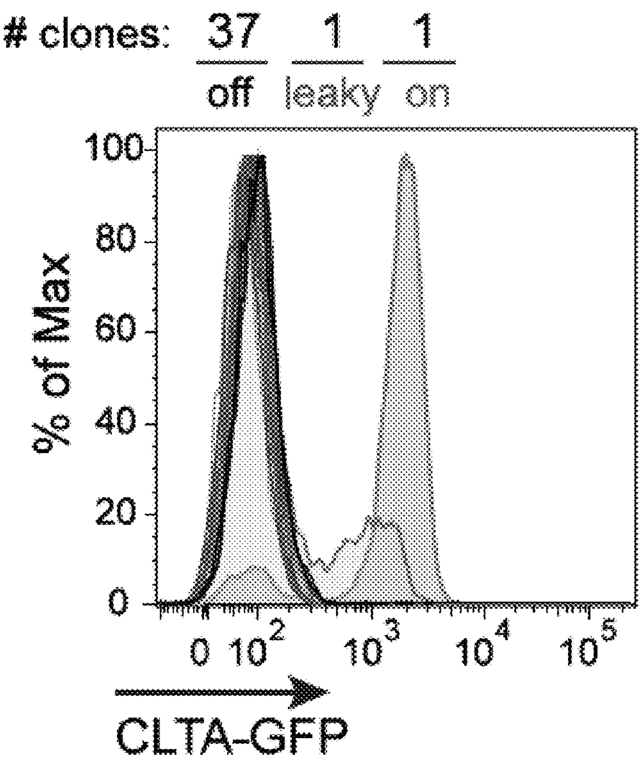

Gene silencing of cells that started as a single clone were followed and it was observed the majority of cells have maintained the targeted CLTA gene off (37 out of 39 clones). The plot in FIG. 2F represents a time point taken 9 months post transfection of the all-in-one protein and sgRNA targeting the CLTA gene.

The system described herein can target any genes in the mammalian genomes, especially those that contain CpG islands at the gene promoter. The Dnmt3A-Dnmt3L canonically targets CpG dinucleotides. Examples of genes that can be targeted include, but are not limited to, CXCR4, CD4, CD8, CD45, PD-1, CLTA-4, TGFBR, TCRa, TCRb, B2M.

Example 3

Figure 3A:
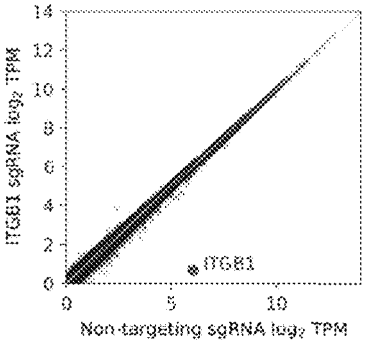
FIGS. 3A-3I describe long-term silencing of endogenous genes.
Figure 3B:
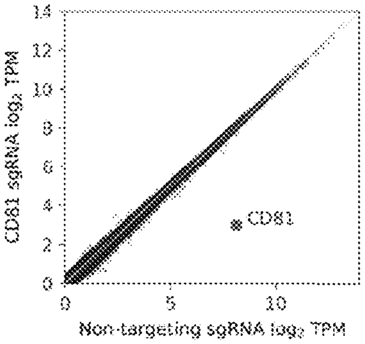
Figure 3C:
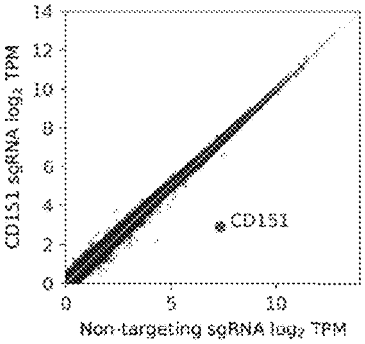
Figure 3D:
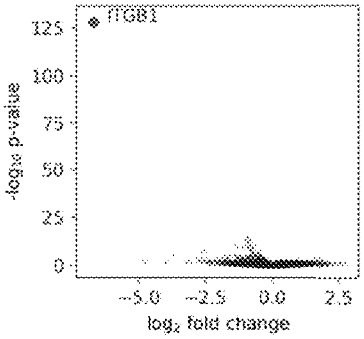
Figure 3E:
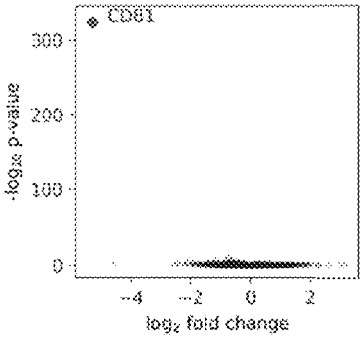
Figure 3F:
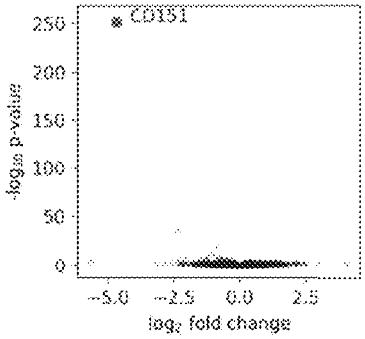
Figure 3G:
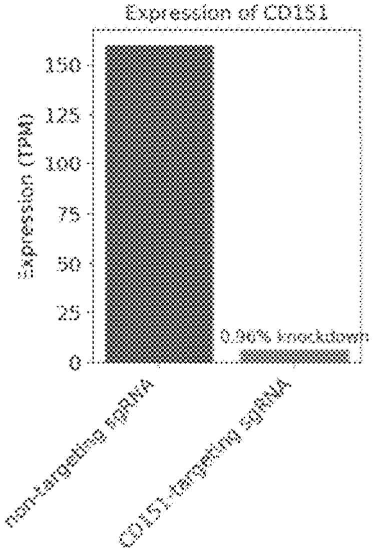
Figure 3H:
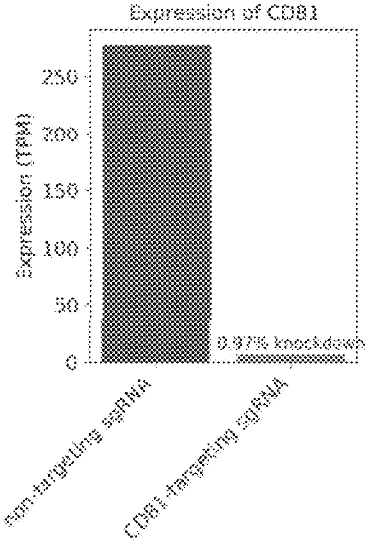
Figure 3I:
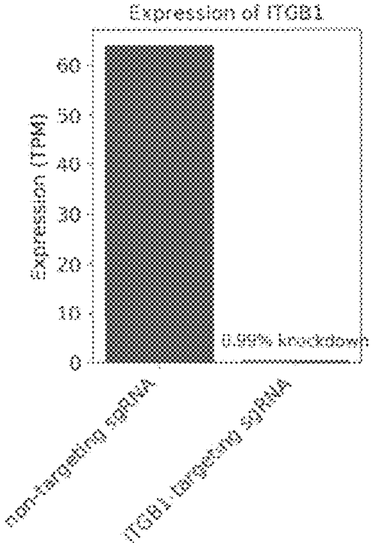

Cells were harvested that lost expression of ITGB1 (CD29), CD81 and CD151 thirty-six days post-transfection and analyzed their RNA expression profiles were analyzed. As shown in FIGS. 3A-3C, successful knockdown of the targeted genes was detected compared to the non-targeting sgRNA control. FIGS. 3D-3F are volcano plots show that the targeted gene is the only significant gene knocked down for each experiment, signifying high specificity of gene silencing. FIGS. 3G-31 are the quantification of transcript levels showing greater than 96% knockdown of the targeted gene.

Example 4

Figure 4A:
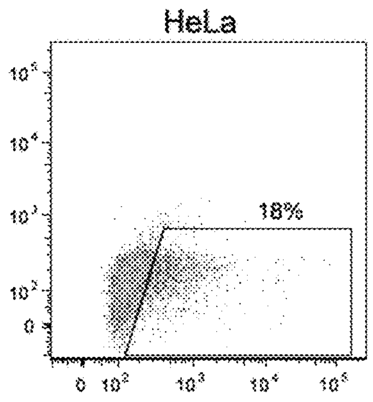
FIGS. 4A-4H describe long-term gene silencing in different mammalian cell lines.
Figure 4B:
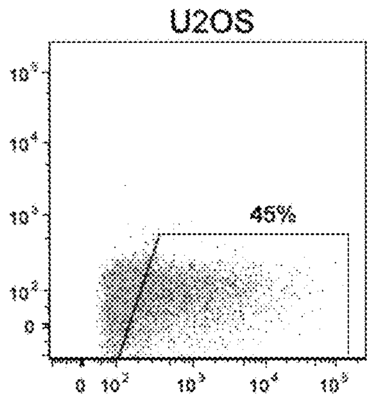
Figure 4C:
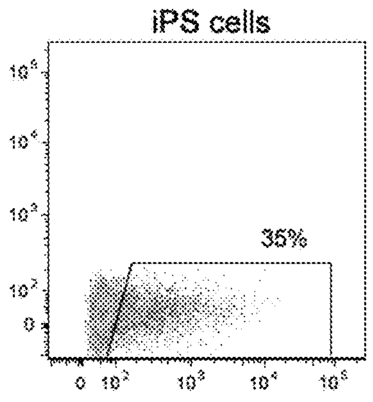
Figure 4D:
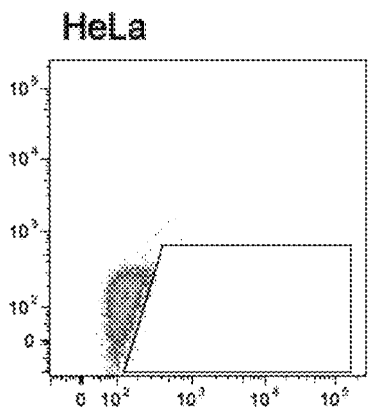
Figure 4E:
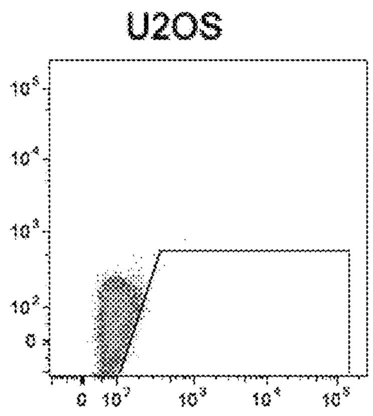
Figure 4F:
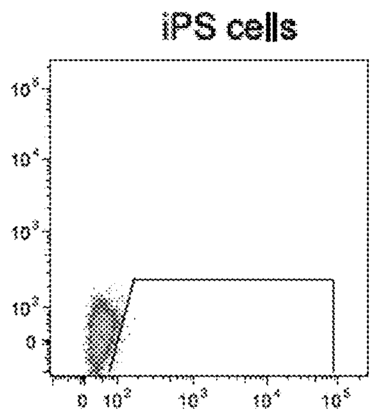
Figure 4G:
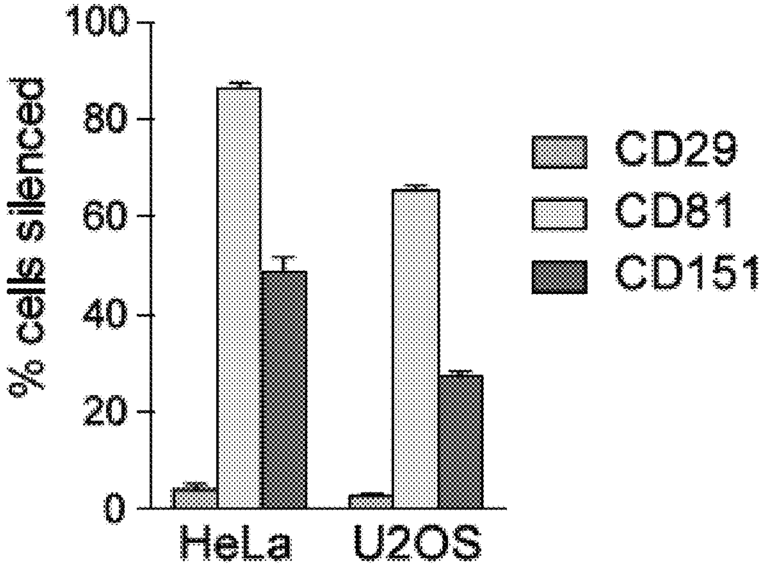
Figure 4H:
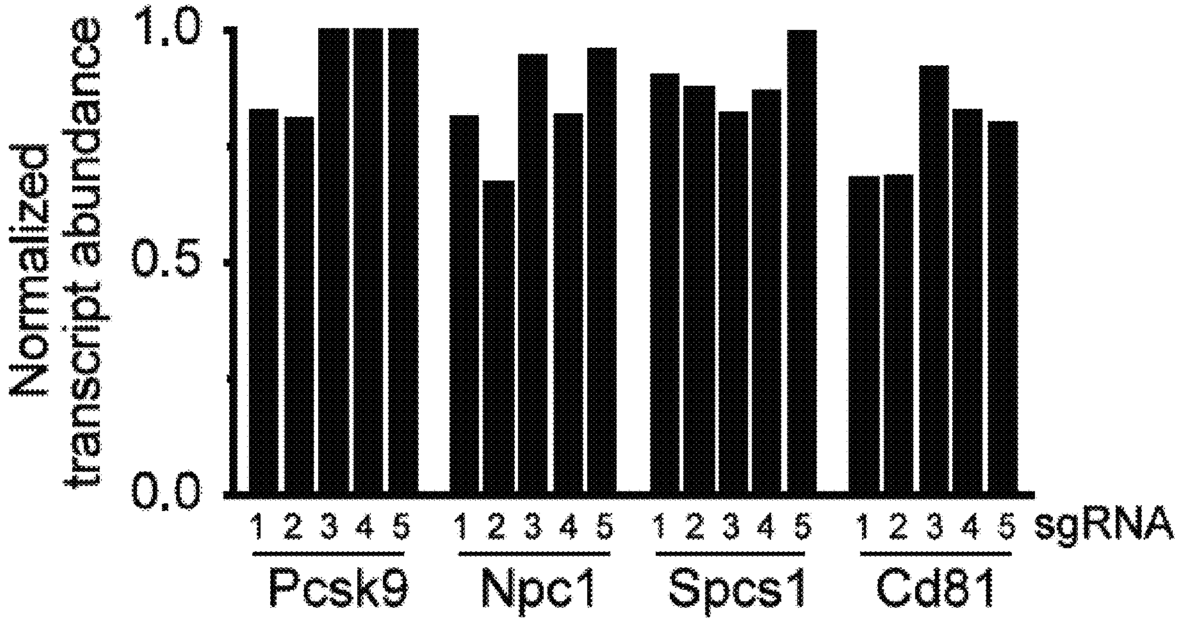

The all-in-one protein can be transfected and expressed in HeLa (cervical), U2OS (bone) and human induced pluripotent stem cells (iPSC). Flow cytometry plots in FIGS. 4A-4F show BFP expression, which is fused to the protein. Three endogenous genes in HeLa and U2OS cells (i.e., CD29, CD81, and CD151) were targeted. As shown in FIG. 4G, stable silencing, measured at 18 days post-transfection, was detected. Gene silencing in AML12 mouse hepatocyte cell lines was detected when targeting Pcsk9, Npc1, Spcs1 and Cd81. Silencing was detected by qPCR, measured 14 days post transfection, as shown in FIG. 4H. The sgRNA sequences used in this experiment are summarized in Table 3

TABLE 3

| Name | Targeted sequence (5' to 3') | sgRNA sequence (5' to 3') |
|---|---|---|
| Pcsk9 sgRNA-1 | TCCGGAAACGCATTCCTCT (SEQ ID NO: 43) | AGAGGAATGCGTTTCCGGA (SEQ ID NO: 44) |
| Pcsk9 sgRNA-2 | ACCGGCAGCCTGCGCGTCC (SEQ ID NO: 61) | GGACGCGCAGGCTGCCGGT (SEQ ID NO: 62) |
| Pcsk9 sgRNA-3 | CGATGGGCACCCACTGCTC (SEQ ID NO: 63) | GAGCAGTGGGTGCCCATCG (SEQ ID NO: 64) |
| Pcsk9 sgRNA-4 | CCTTCACGTGGACGCGCAG (SEQ ID NO: 65) | CTGCGCGTCCACGTGAAGG (SEQ ID NO: 66) |
| Pcsk9 sgRNA-5 | CGTGAAGGTGGAAGCCTTC (SEQ ID NO: 67) | GAAGGCTTCCACCTTCACG (SEQ ID NO: 68) |
| Npc1 sgRNA-1 | CTCCTTGGTCAGGCGCCGG (SEQ ID NO: 69) | CCGGCGCCTGACCAAGGAG (SEQ ID NO: 70) |
| Npc1 sgRNA-2 | TGGTCAGGCGCCGGTTCCG (SEQ ID NO: 71) | CGGAACCGGCGCCTGACCA (SEQ ID NO: 72) |
| Npc1 sgRNA-3 | TAGAGGTCGCCTTCTCCTC (SEQ ID NO: 73) | GAGGAGAAGGCGACCTCTA (SEQ ID NO: 74) |
| Npc1 sgRNA-4 | CGACGCTCGGGTCGCGGTG (SEQ ID NO: 75) | CACCGCGACCCGAGCGTCG (SEQ ID NO: 76) |
| Npc1 sgRNA-5 | ATGCTGTCGCCGCGCGGGG (SEQ ID NO: 77) | CCCCGCGCGGCGACAGCAT (SEQ ID NO: 78) |
| Spcs1 sgRNA-1 | CTCACCCTCACCGGAGCCA (SEQ ID NO: 79) | TGGCTCCGGTGAGGGTGAG (SEQ ID NO: 80) |
| Spcs1 sgRNA-2 | CCGCAAACTTTACTCCTTA (SEQ ID NO: 81) | TAAGGAGTAAAGTTTGCGG (SEQ ID NO: 82) |
| Spcs1 sgRNA-3 | CTCGGAGACATCCGCTTCC (SEQ ID NO: 60) | GGAAGCGGATGTCTCCGAG (SEQ ID NO: 60) |
| Spcs1 sgRNA-4 | CTCCTAAGATTGGCTTCAC (SEQ ID NO: 83) | GTGAAGCCAATCTTAGGAG (SEQ ID NO: 84) |
| Spcs1 sgRNA-5 | CCGGAGCCACTCCTAAGAT (SEQ ID NO: 85) | ATCTTAGGAGTGGCTCCGG (SEQ ID NO: 86) |
| Cd81 sgRNA-1 | TTCTCTACCCTACGTCTCA (SEQ ID NO: 87) | TGAGACGTAGGGTAGAGAA (SEQ ID NO: 88) |
| Cd81 sgRNA-2 | TACGTCTCATTCTCCGCAA (SEQ ID NO: 89) | TTGCGGAGAATGAGACGTA (SEQ ID NO: 90) |
| Cd81 sgRNA-3 | GCTAGGCCTCCAGCCCTTC (SEQ ID NO: 91) | GAAGGGCTGGAGGCCTAGC (SEQ ID NO: 92) |
| Cd81 sgRNA-4 | ACAGGTGGCGCCGCAACTT (SEQ ID NO: 93) | AAGTTGCGGCGCCACCTGT (SEQ ID NO: 94) |
| Cd81 sgRNA-5 | AGCCGGAGGCGCGAGAGTC (SEQ ID NO: 95) | GACTCTCGCGCCTCCGGCT (SEQ ID NO: 96) |

Example 5

FIG. 5 provides a schematic of the all-in-one protein constructs that were designed and tested for gene silencing. The initial design (p76, V1) of SEQ ID NO:1 was modified to encode XTEN linkers (e.g., 16 amino acids (SEQ ID NO: 31) or 80 amino acids (SEQ ID NO:32)) at either the N or C terminus of dCas9 (SEQ ID NO:29). All vectors contain HA tags (SEQ ID NO:24) at the C-terminus of dCas9. In aspects, CAG promoter is used since it provides good expression, for example, in constructs p76, and p90-102, p112 (V2). With reference to FIG. 5, the protein constructs of p90 to p102 correspond to SEQ ID NOS: 2-14, respectively, and protein construct p112 corresponds to SEQ ID NO:15.

Example 6

Figure 6A:
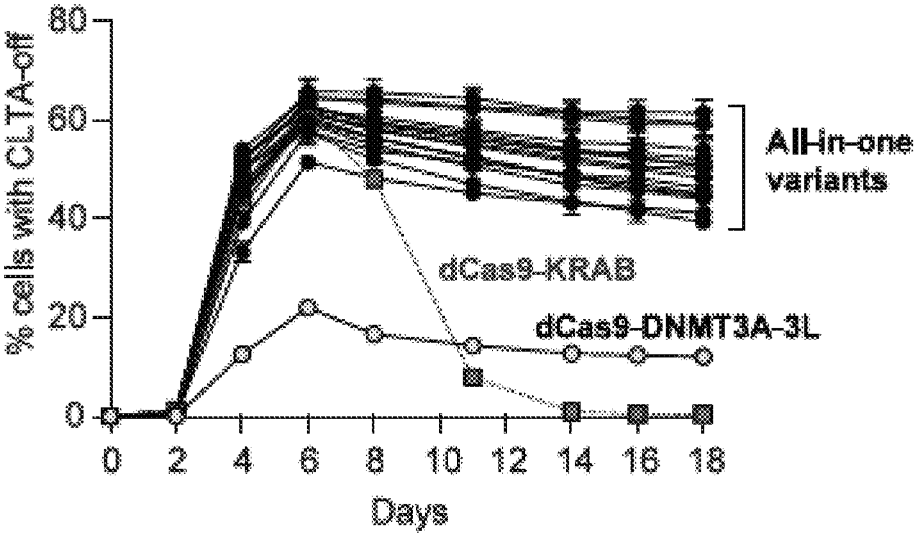
FIGS. 6A-6E describe gene silencing activities of all-in-one protein variants.
Figure 6B:
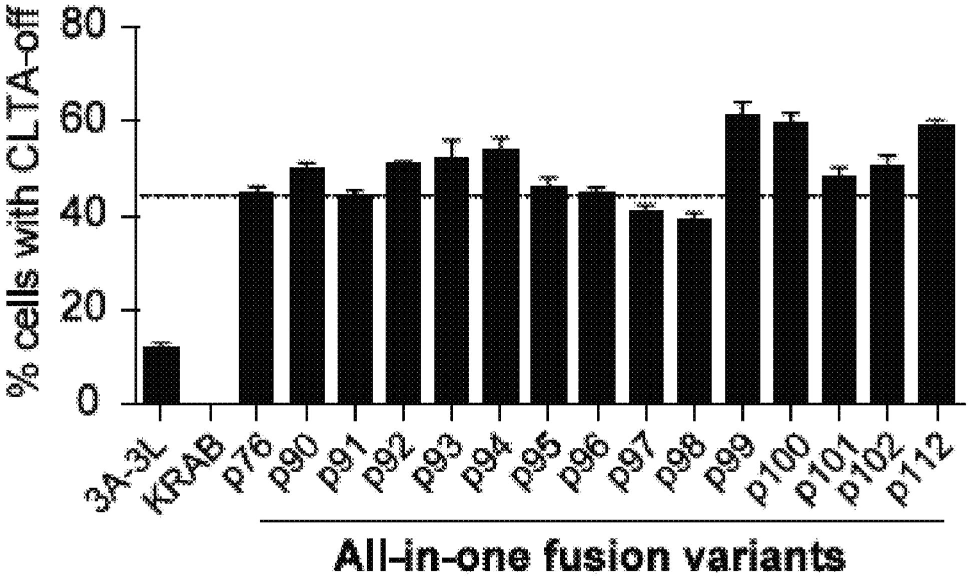
Figure 6C:
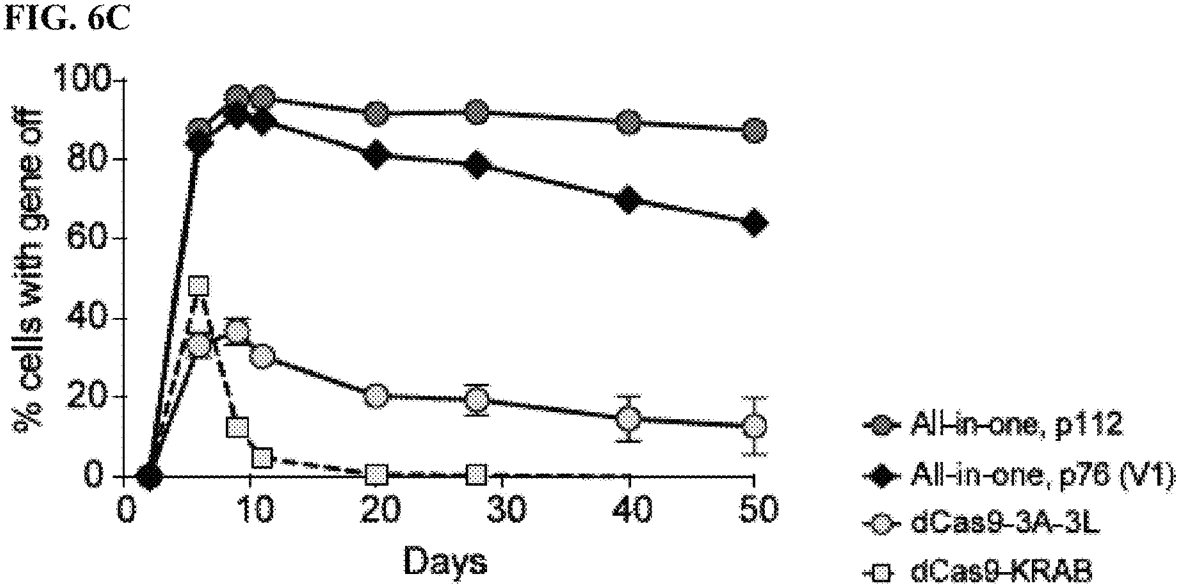
Figure 6D:
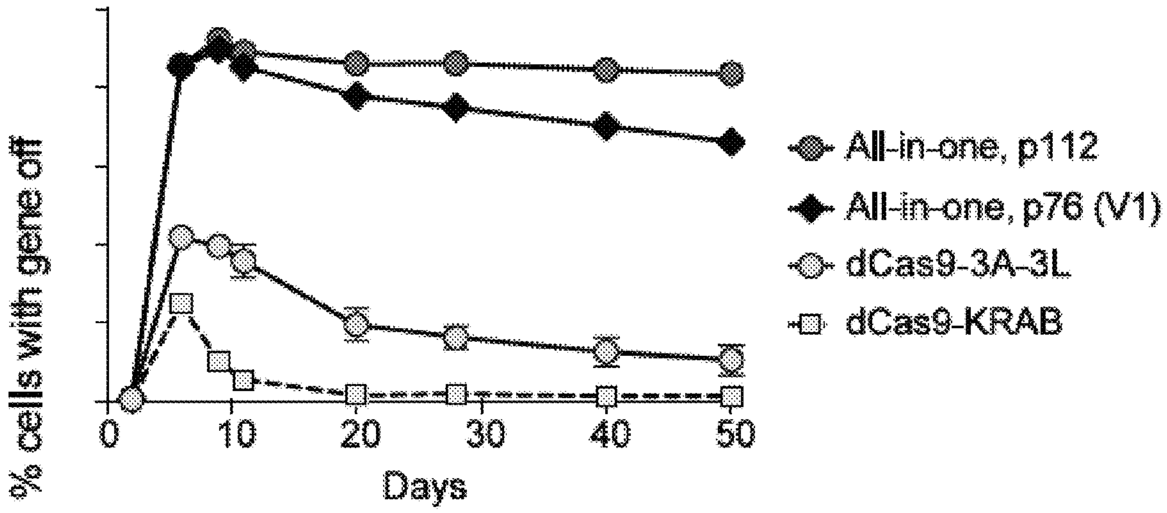
Figure 6E:
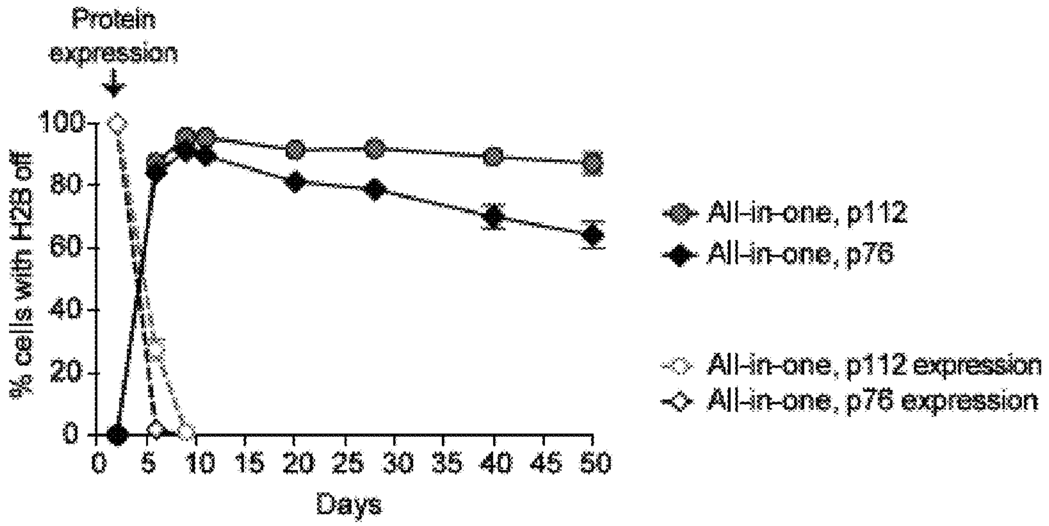

The protein constructs shown in FIG. 5 were tested for silencing of the CLTA gene in HEK293T cells for 18 days post-transfection (FIGS. 6A-6B). Variable levels of gene silencing activities were detected, including a panel of variants with more durable gene silencing compared to the p76 (V1) design such as p99 (SEQ ID NO:11), p100 (SEQ ID NO:12), and p112 (SEQ ID NO: 15). FIGS. 6A and 6B show that the dCas9-KRAB and dCas9-Dnmt3A-Dnmt3L constructs showed transient and lower efficiency of long term silencing.

p76 (SEQ ID NO:1), p112 (SEQ ID NO:15) were tested for silencing the HIST2H2BE (H2B) endogenous gene and a synthetic Snrpn-GFP reporter gene stably expressed in HEK293T cells (FIGS. 6C-6D). Cells were followed for 50 days post-transfection. The p112 variant sustained gene silencing at a higher efficiency than the p76 (V1) design. The dCas9-Dnmt3A-Dnmt3L and dCas9-KRAB fusion proteins have transient and lower efficiency of long term silencing. FIG. 6E provides a plot of protein expression of p76 and p112 over the 50 day time course to turn off the HIST2H2BE (H2B) gene. Protein levels were measured by flow cytometry detection of BFP, which is co-expressed with the all-in-one protein.

Example 7

Figure 7A:
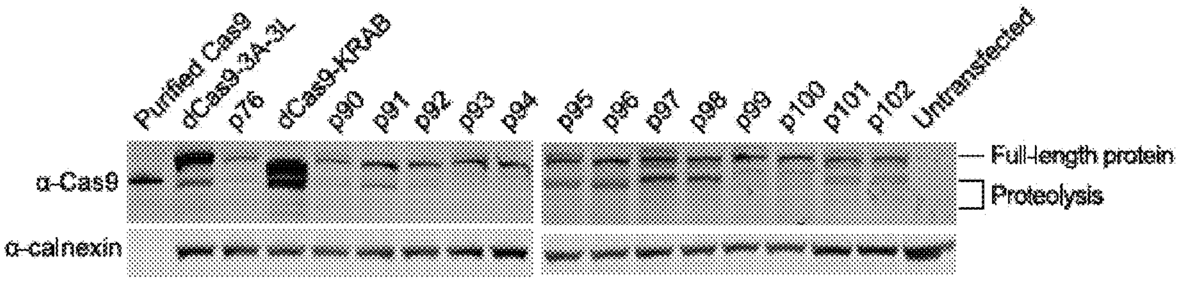
FIGS. 7A-7B provide Western blots of all-in-one-protein variants.

Western blot analysis was performed with the all-in-one protein variants p76, p90-p102 using an antibody against *Streptococcus pyogenes* Cas9. With reference to FIG. 7A, the top band represents full-length protein and smaller-sized bands represent proteolysis of the all-in-one protein. Variants that show little proteolysis, such as p99 (SEQ ID NO:11), p100 (SEQ ID NO:12), and p102 (SEQ ID NO:14), exhibited higher efficiency of gene silencing. Variants with high levels of proteolysis, such as p96 (SEQ ID NO:8) and p97 (SEQ ID NO:9), led to lower efficiency of sustained gene silencing.

Figure 7B:
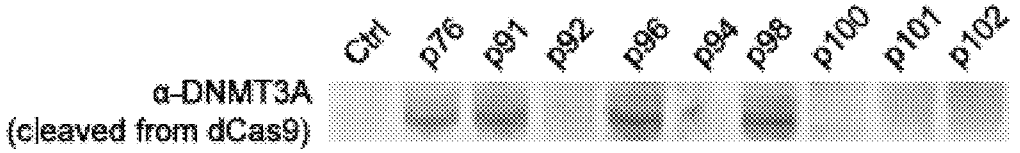

Western blot analysis was performed with the all-in-one protein variants to detect free Dnmt3A that is cleaved from the fusion protein. As shown in FIG. 7B, variants that had little or no detectable free Dnmt3, such as p92 (SEQ ID NO:4), p100 (SEQ ID NO:12), p101 (SEQ ID NO:13), and p102 (SEQ ID NO:14), had higher efficiency of sustained gene silencing compared to variants with detectable cleaved Dnmt3A, i.e., p76 (SEQ ID NO:1), p91 (SEQ ID NO:3), p96 (SEQ ID NO: 8), p98 (SEQ ID NO:10).

Example 8

Figure 8A:
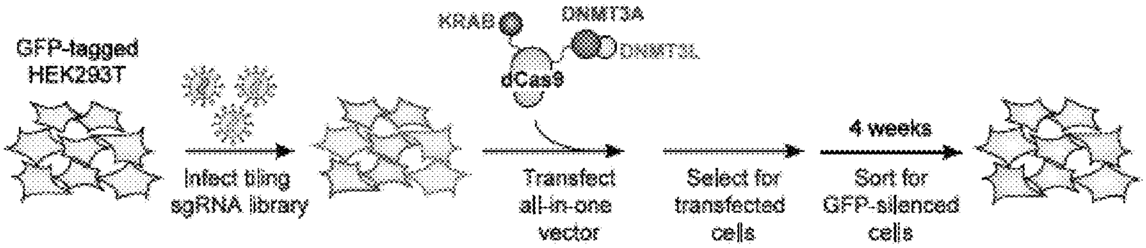
FIGS. 8A-8E describe pooled screen to determine optimal sgRNAs.
Figure 8B:
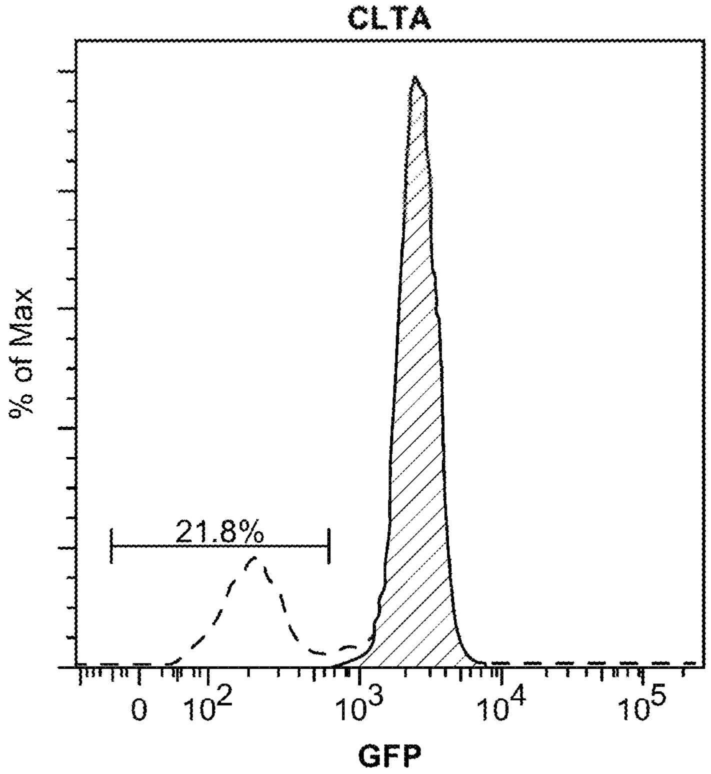
Figure 8C:
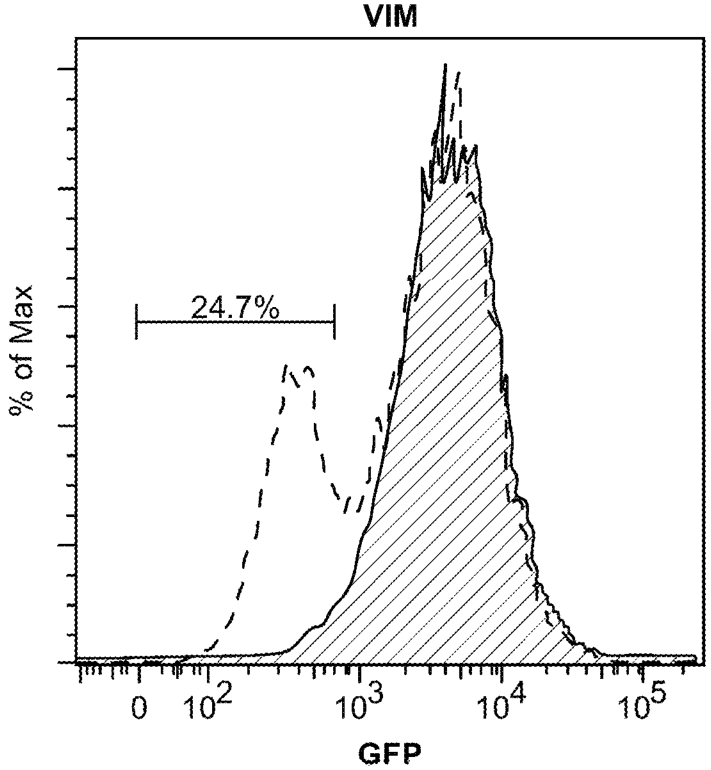
Figure 8D:
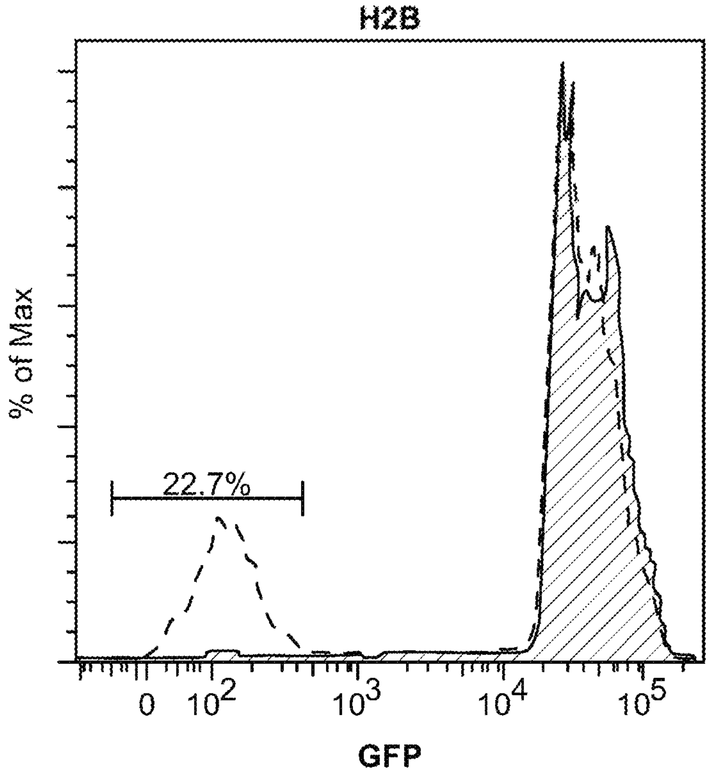
Figure 8E:
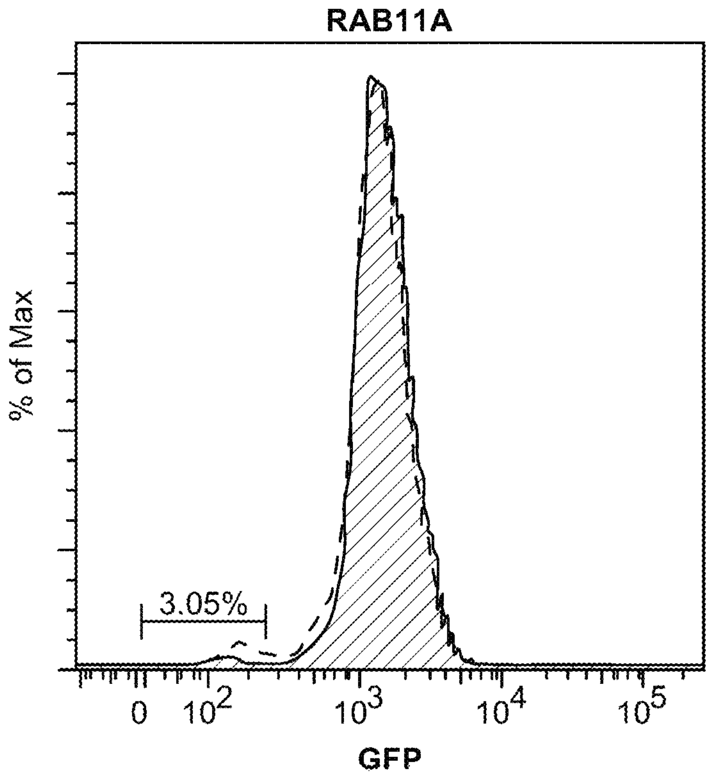
Figure 9A:
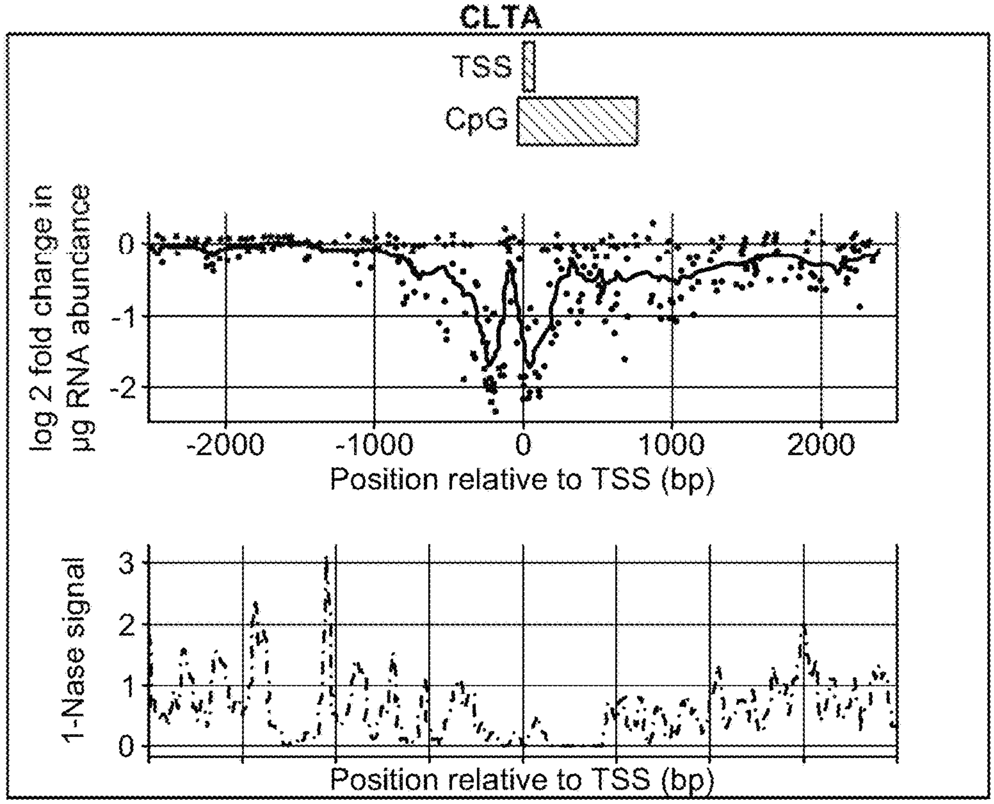
FIGS. 9A-9D are maps of sgRNA functionality across the transcription start site of the targeted gene, including CLTA (FIG. 9A), H2B (FIG. 9B), RAB11 (FIG. 9C), and VIM (FIG. 9D). The transcription start site (TSS) and CpG island are annotated above each plot. Each dot represents one sgRNA and its efficacy in long term gene silencing is plotted as the log 2 fold change in sgRNA abundance. Nucleosome occupancy (bottom plot) is plotted from MNase signal.
Figure 9B:
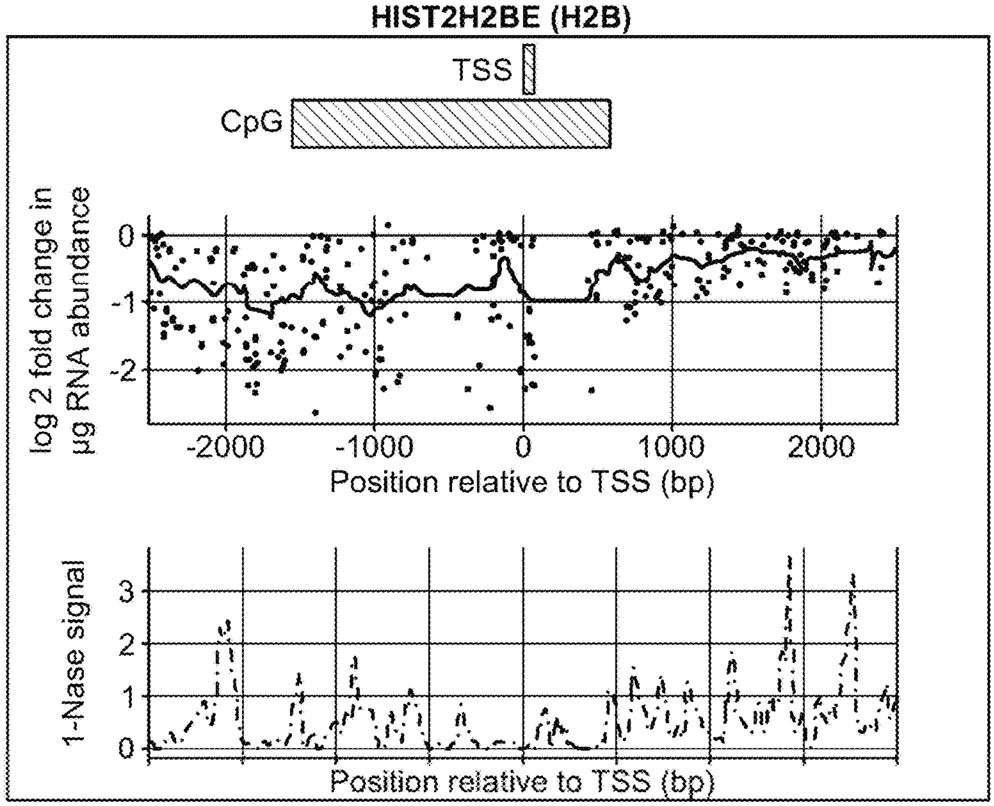
Figure 9C:
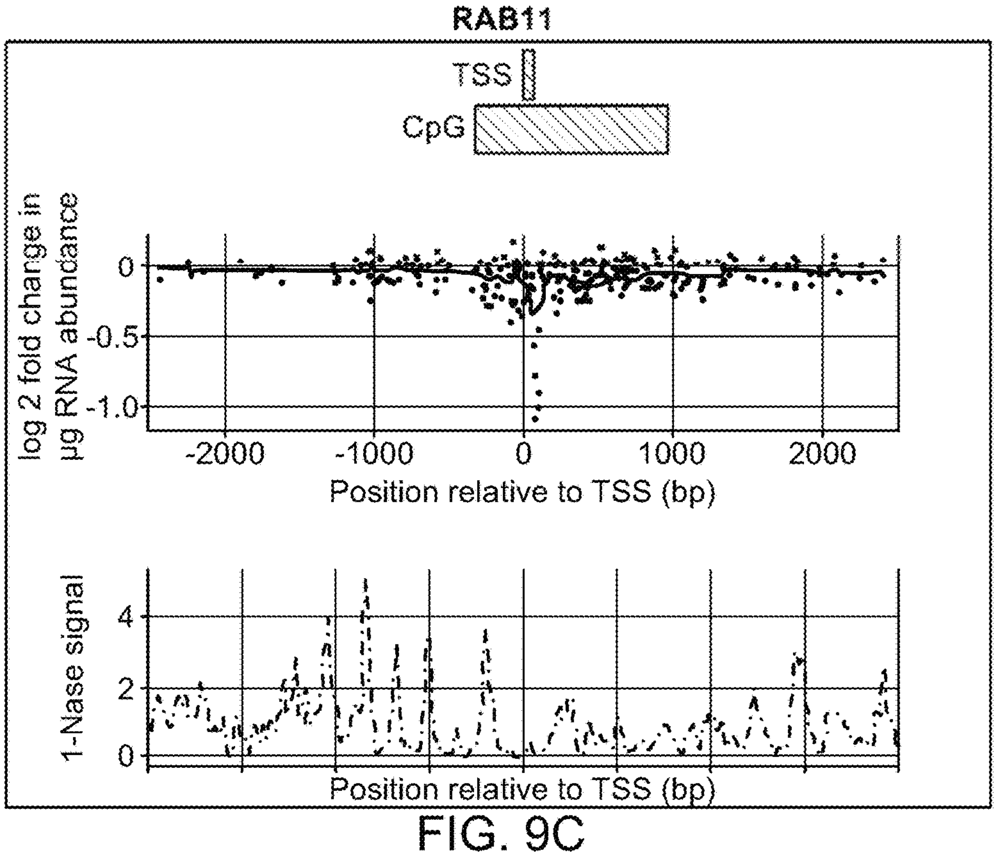
Figure 9D:
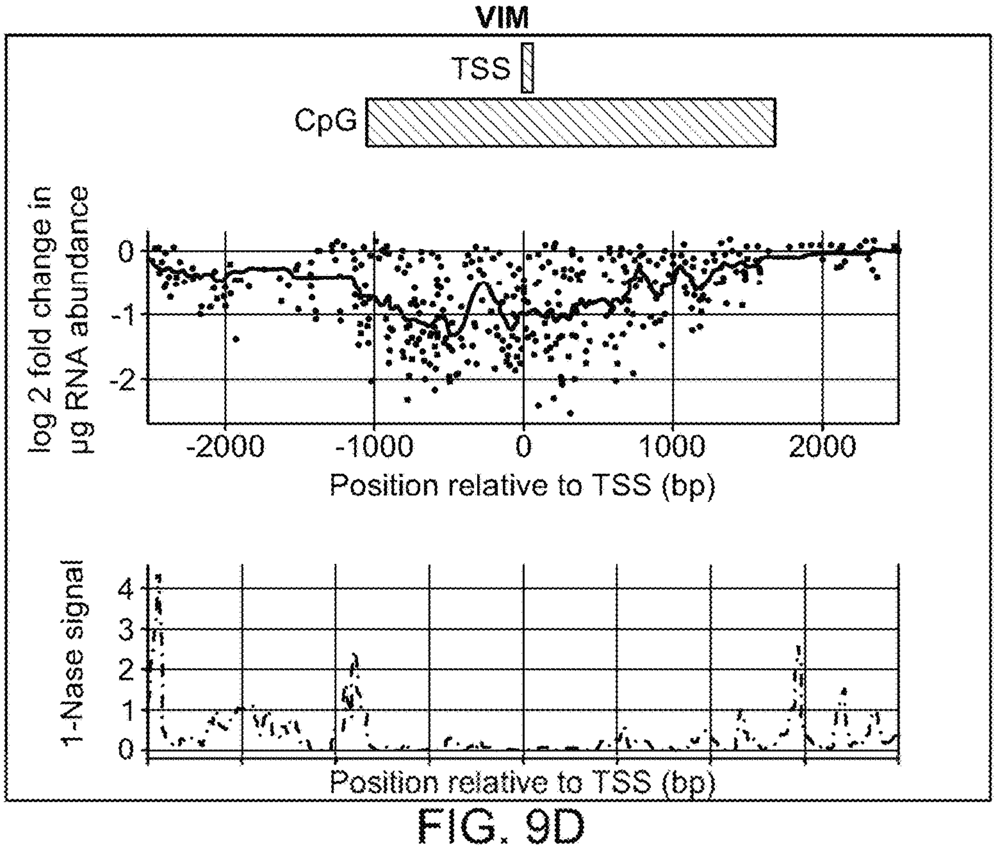

A pooled screen was assayed, as shown in FIG. 8A, to determine the optimal sgRNAs that leads to long term gene silencing. Four HEK293T cell lines were used, each with a different gene with a GFP tag (CLTA, VIM, HIST2H2BE (H2B), and RAB11A). Tiling libraries consisting of sgRNAs that span +/−2.5 kb from the transcription start site (TSS) of each gene were stably expressed in cells by lentiviral delivery, followed by transient expression plasmid DNA expressing the all-in-one protein. Four weeks post-transfection, cells that maintained gene silencing were sorted to determine the sgRNA identity. FIGS. 8B-8E are flow cytometry histograms showing the percent of cells undergoing gene silencing four weeks post-transfection.

FIGS. 9A-9D are maps of sgRNA functionality across the transcription start site of the targeted gene (CLTA, H2B, RAB11, VIM). The transcription start site (TSS) and CpG island are annotated above each plot. Each dot represents one sgRNA and its efficacy in long term gene silencing is plotted as the log 2 fold change in sgRNA abundance. Nucleosome occupancy (bottom plot) is plotted from MNase signal.

Example 9

Figure 10A:
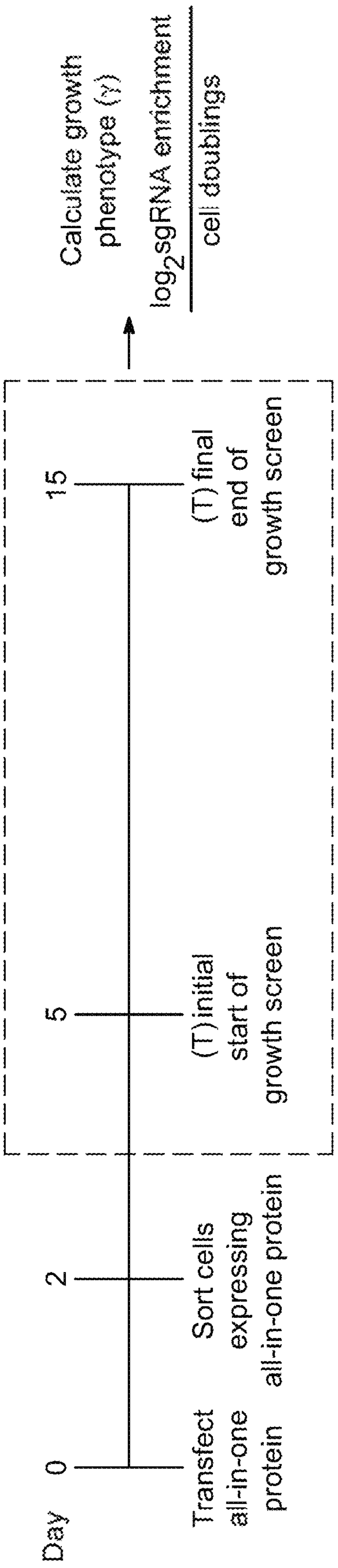
FIGS. 10A-10E describe functional sgRNAs for long term gene silencing.
Figure 10B:
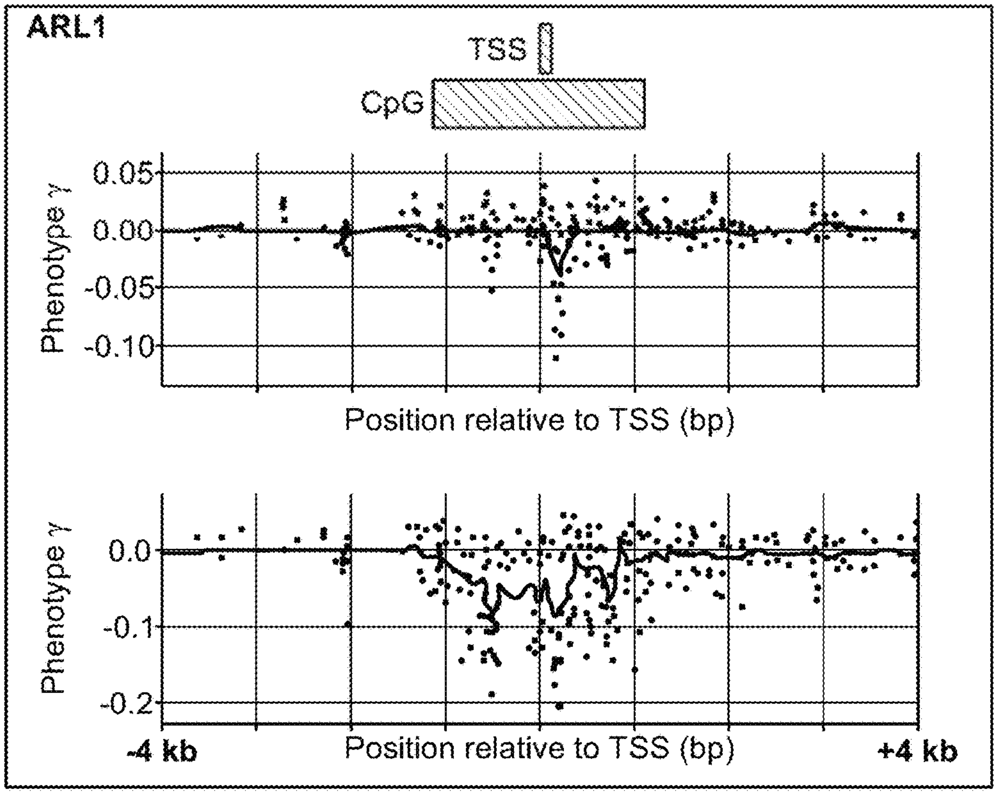
Figure 10C:
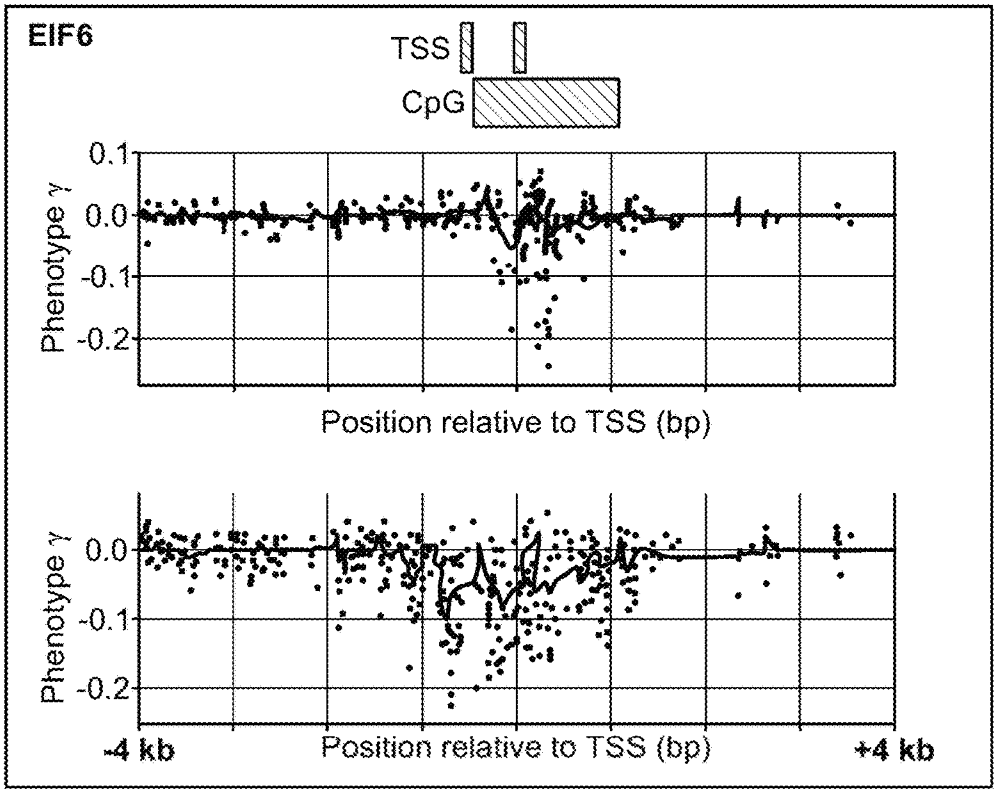
Figure 10D:
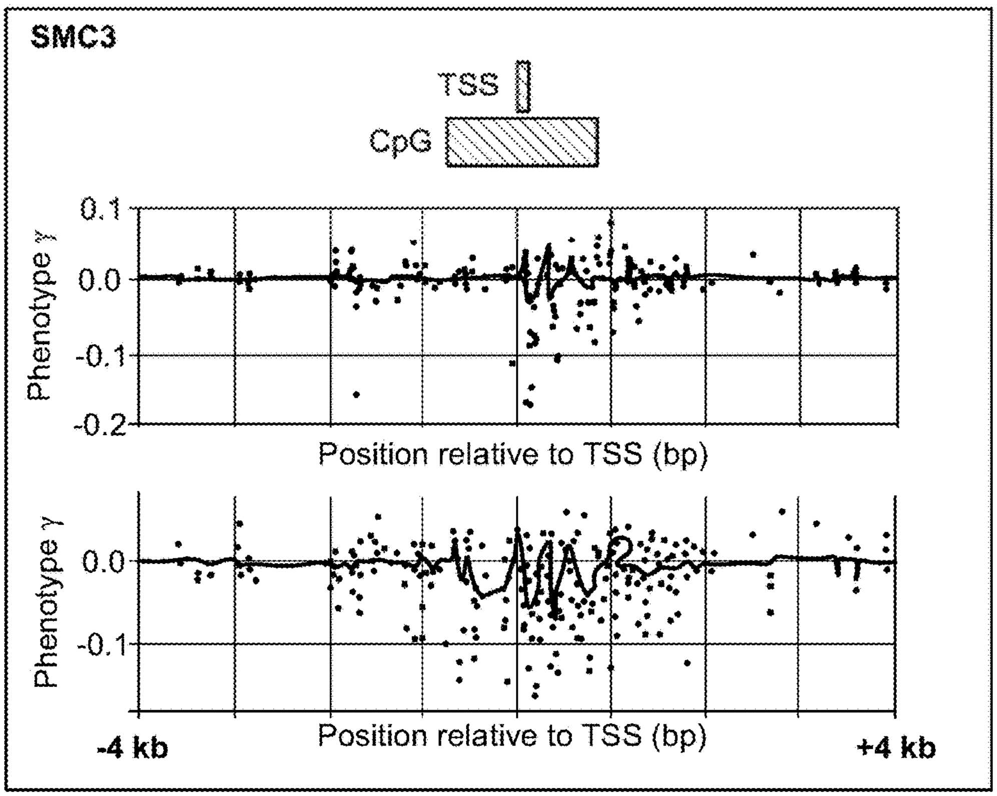
Figure 10E:
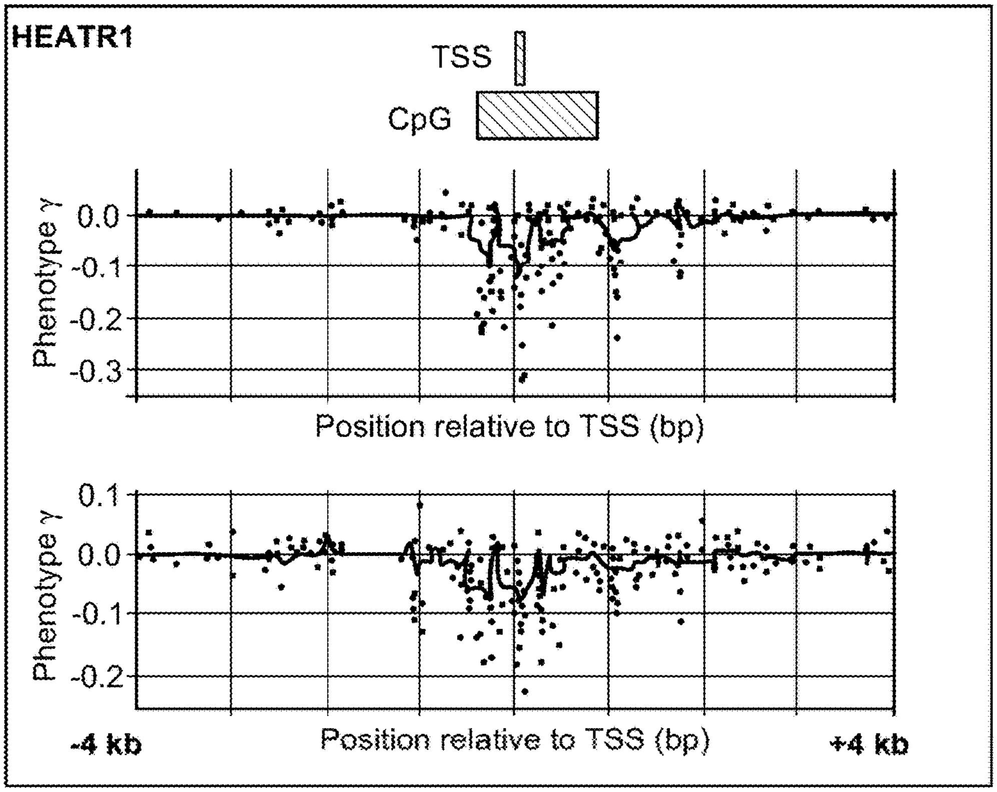

FIG. 10A shows the workflow of a pooled screen in HEK293T cells to determine optimal sgRNA targeting positions for the all-in-one protein, adapted from a previous ricin tiling screen in K562 cells to determine optimal sgRNAs for dCas9-KRAB (Gilbert, Horlbeck et al., Cell 2014). The sgRNAs are first stably expressed in HEK293T cells by lentiviral delivery, followed by transient transfection of a plasmid encoding the all-in-one protein (Day 0). Cells expressing the all-in-one protein are sorted (Day 2) and allowed to grow for three more days. Cells are split on Day 5, from which half are harvested as an initial time point, and the other half are passaged for ten more days (Day 15) for a final time point. The growth phenotype (γ) is calculated as the log 2 sgRNA enrichment divided by the number of cell doublings between T (initial) and T (final).

FIGS. 10B-10E are representative plots showing growth phenotypes for four genes (ARL1, EIF6, SMC3, HEATR1) from existing dCas9-KRAB/CRISPRi datasets in K562 cells (Gilbert, Horlbeck et al., 2014) and with the all-in-one protein (bottom plot). Each dot represents an sgRNA. The TSS and annotated CpG island are shown for each gene. The functional sgRNAs using the all-in-one protein spans a wider range than the functional sgRNAs, signifying a broader range of effective targeting.

Example 10

Figure 11A:
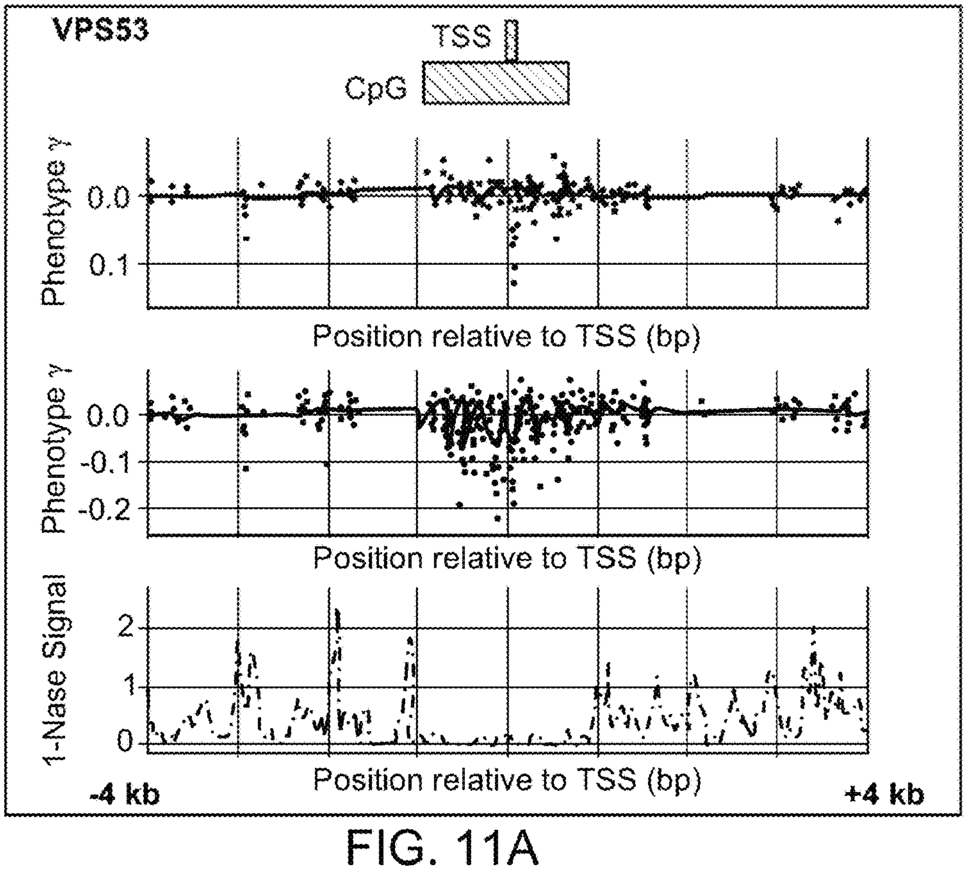
FIGS. 11A-11B provide a comparison of growth phenotypes and nucleosome positioning (from MNase signal) for VPS53 (FIG. 11A) and VPS54 (FIG. 11B) showing the location of functional sgRNAs at nucleosome-depleted regions.
Figure 11B:
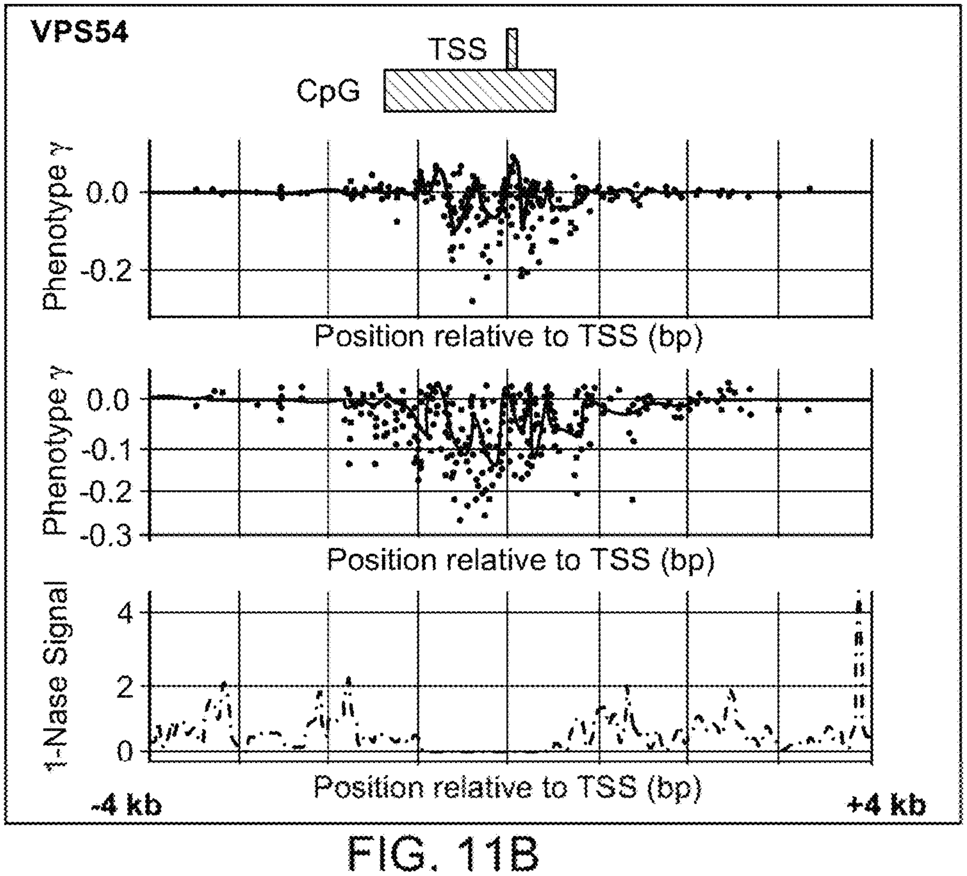

FIGS. 11A-11B provide a comparison of growth phenotypes and nucleosome positioning (from MNase signal) for VPS53 and VPS54 and show the location of functional sgRNAs at nucleosome-depleted regions. Furthermore, the range of functional sgRNAs is broader when using the all-in-one protein compared to dCas9-KRAB/CRISPRi.

Example 11

Figure 12A:
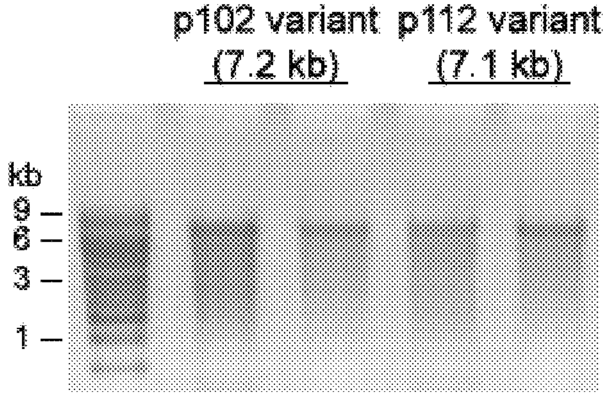
FIGS. 12A-12C show the delivery of the all-in-one protein by mRNA expression
Figure 12B:
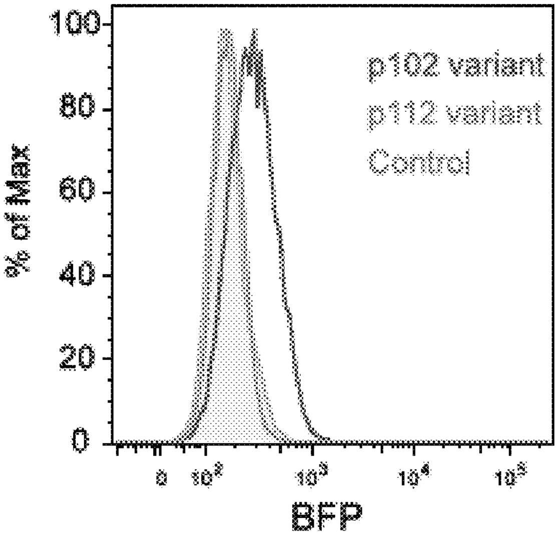
Figure 12C:
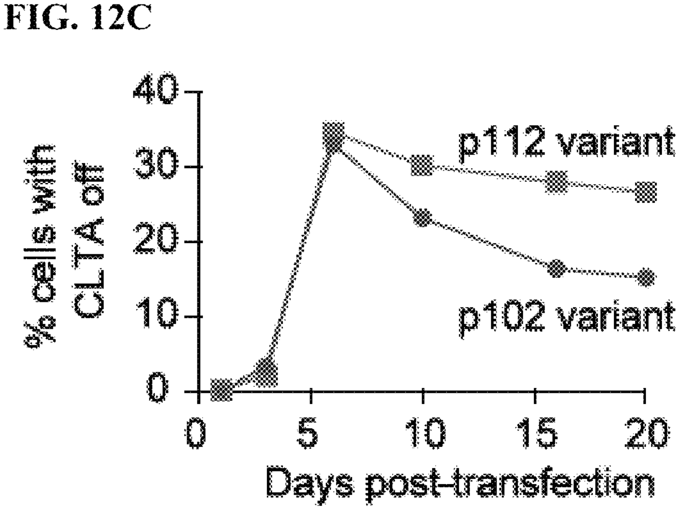

The in vitro transcription of two all-in-one variants (p102 (SEQ ID NO:14) and p112 (SEQ ID NO:15)) show full length synthesis of each design (FIG. 12A). FIG. 12B provides a flow cytometry plot showing expression of p102 and p112 one day post-transfection of mRNA into HEK293T cells. FIG. 12C shows the time course of CLTA endogenous gene silencing in HEK293T cells after transfecting mRNA expressing the p102 and p112 all-in-one variants.

Example 12

Figure 13A:
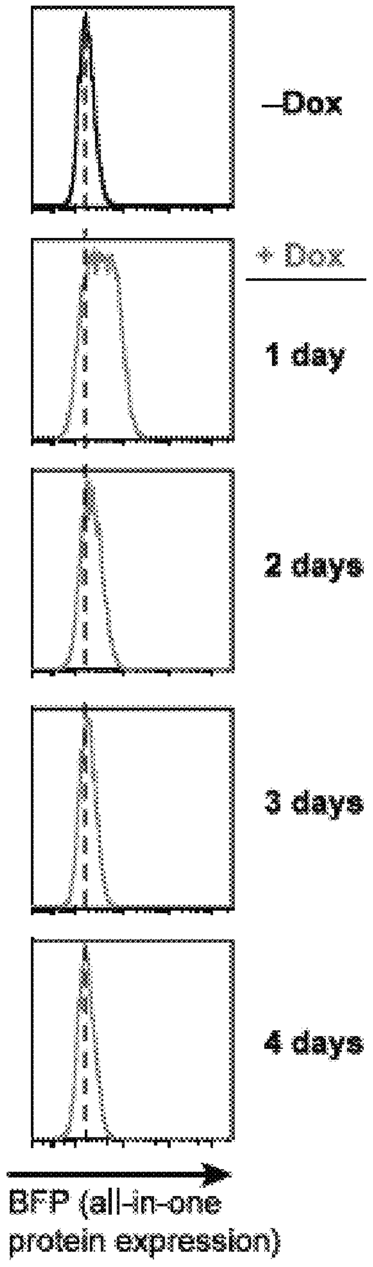

FIG. 13A provides flow cytometry plots showing induced expression of the all-in-one protein by addition of doxycycline in K562 cells that stably encode the all-in-one protein under a doxycycline-inducible promoter. Protein expression was followed for four days after doxycycline induction. The dotted lines in the panels in FIG. 13A represent the baseline median BFP fluorescence without doxycycline administration. Western blots of cells were performed to detect expression of the all-in-one protein before and after doxycycline treatment (FIG. 13B). The presence of the all-in-one protein is not detectable by 96 hours post-induction. Flow cytometry plots of CD81 and CD151 knockdown 14 days post-doxycycline treatment of K562 cells are shown in FIGS. 13C-13F. The percent of cells with the targeted gene knocked down is shown. There is no detectable expression of the all-in-one protein, as no cells are present in the BFP+ quadrants. Quantification of CD81 and CD151 knockdown 14 days post-doxycycline treatment or without doxycycline treatment is shown in FIG. 13G.

REFERENCES

Ecco et al, Development 144, 2017. Lambert et al, Cell 172, 2018. Siddique et al., J. Mol. Biol., 425, 2013. Stepper et al, Nucleic Acids Res., 45, 2017. Shmakov et al., Nat. Rev. Microbiol. 15, 2017. Cebrian-Serrano et al, Mamm. Genome 7-8, 2017. Pulecio et al., Cell Stem Cell 21, 2017.

Informal Sequence Listing (p76 (all-in-one protein sequence, version 1): KRAB (bold; from Gilbert et al., Cell, 2013, 2014), Linkers (underlined), dCas9 (italics), HA tag (lowercase), SV40 NLS (lowercase italics), Dnmt3A (bold italics; residues 612-912; from Siddique et al., JMB, 2013; Stepper et al., NAR, 2016), 27 amino acid linker (italics underlined; from Siddique et al., JMB, 2013; Stepper et al., NAR, 2016), Dnmt3L (bold underlined; from Siddique et al., JMB, 2013; Stepper et al., NAR, 2016), P2A peptide cleavage sequence (lowercase bold), BFP (lowercase underlined))

SEQ ID NO: 1

DAKSLTAWSRTLVTFKDVFVDFTREEWKLLDTAQQIVYRNVMLENYKNLVSLGYQL
TKPDVILRLEKGEEPGGSGGGSMDKKYSIGLAIGTNSVGWAVITDEYKVPSKKFKVLGNTDRH
SIKKNLIGALLFDSGETAEATRLKRTARRRYTRRKNRICYLQEIFSNEMAKVDDSFFHRLEESFLVE
EDKKHERHPIFGNIVDEVAYHEKYPTIYHLRKKLVDSTDKADLRLIYLALAHMIKFRGHFLIEGDL
NPDNSDVDKLFIQLVQTYNQLFEENPINASGVDAKAILSARLSKSRRLENLIAQLPGEKKNGLFGN
LIALSLGLTPNFKSNFDLAEDAKLQLSKDTYDDDLDNLLAQIGDQYADLFLAAKNLSDAILLSDIL
RVNTEITKAPLSASMIKRYDEHHQDLTLLKALVRQQLPEKYKEIFFDQSKNGYAGYIDGGASQEE
FYKFIKPILEKMDGTEELLVKLNREDLLRKQRTFDNGSIPHQIHLGELHAILRRQEDFYPFLKDN
REKIEKILTFRIPYYVGPLARGNSRFAWMTRKSEETITPWNFEEVVDKGASAQSFIERMTNFDKNL
PNEKVLPKHSLLYEYFTVYNELTKVKYVTEGMRKPAFLSGEQKKAIVDLLFKTNRKVTVKQLKED
YFKKIECFDSVEISGVEDRFNASLGTYHDLLKIIKDKDFLDNEENEDILEDIVLTLTLFEDREMIEE
RLKTYAHLFDDKVMKQLKRRRYTGWGRLSRKLINGIRDKQSGKTILDFLKSDGFANRNFMQLIH
DDSLTFKEDIQKAQVSGQGDSLHEHIANLAGSPAIKKGILQTVKVVDELVKVMGRHKPENIVIEM
ARENQTTQKGQKNSRERMKRIEEGIKELGSQILKEHPVENTQLQNEKLYLYYLQNGRDMYVDQE
LDINRLSDYDVDAIVPQSFLKDDSIDNKVLTRSDKNRGKSDNVPSEEVVKKMKNYWRQLLNAKLI
TQRKFDNLTKAERGGLSELDKAGFIKRQLVETRQITKHVAQILDSRMNTKYDENDKLIREVKVIT
LKSKLVSDFRKDFQFYKVREINNYHHAHDAYLNAVVGTALIKKYPKLESEFVYGDYKVYDVRKMI
AKSEQEIGKATAKYFFYSNIMNFFKTEITLANGEIRKRPLIETNGETGEIVWDKGRDFATVRKVLS
MPQVNIVKKTEVQTGGFSKESILPKRNSDKLIARKKDWDPKKYGGFDSPTVAYSVLVVAKVEKG
KSKKLKSVKELLGITIMERSSFEKNPIDFLEAKGYKEVKKDLIIKLPKYSLFELENGRKRMLASAGE
LQKGNELALPSKYVNFLYLASHYEKLKGSPEDNEQKQLFVEQHKHYLDEIIEQISEFSKRVILADA
NLDKVLSAYNKHRDKPIREQAENIIHLFTLTNLGAPAAFKYFDTTIDRKRYTSTKEVLDATLIHQSI
TGLYETRIDLSQLGGDSRADypydvpdyaSGSpkkkrkvEASGSGRASPGIPGSTRNHDQEFDPPKV
YPPVPAEKRKPIRVLSLFDGIATGLLVLKDLGIQVDRYIASEVCEDSITVGMVRHQGKIMYV
GDVRSVTQKHIQEWGPFDLVIGGSPCNDLSIVNPARKGLYEGTGRLFFEFYRLLHDARPKE
GDDRPFFWLFENVVAMGVSDKRDISRFLESNPVMIDAKEVSAAHRARYFWGNLPGMNRP
LASTVNDKLELQECLEHGRIAKFSKVRTITTRSNSIKQGKDQHFPVFMNEKEDILWCTEME
RVFGFPVHYTDVSNMSRLARQRLLGRSWSVPVIRHLFAPLKEYFACVSSGNSNANSRGPSFS
SGLVPLSLRGSHMGPMEIYKTVSAWKRQPVRVLSLFRNIDKVLKSLGFLESGSGSGGGT
LKYVEDVTNVVRRDVEKWGPFDLVYGSTQPLGSSCDRCPGWYMFQFHRILQYALPR
QESQRPFFWIFMDNLLLTEDDQETTTRFLQTEAVTLQDVRGRDYQNAMRVWSNIPGL
KSKHAPLTPKEEEYLQAQVRSRSKLDAPKVDLLVKNCLLPLREYFKYFSQNSLPLSRA
DpkkkrkvGSGatnfsllkqagdveenpgpselikenmhmklymegtvdnhhfkctsegegkpyegtqtmrikvveggplpfafd
ilatsflygsktfinhtqgipdffkqsfpegftwervttyedggvltatqdtslqdgcliynvkirgvnftsngpvmqkktlgweaftetlypad
gglegrndmalklvggshlianikttyrskkpaknlkmpgvyyvdyrlerikeannetyveghevavarycdlpsklghkln*

(p90 (KRAB-dCas9-XTEN16-Dnmt3A-Dnmt3L-P2A-BFP): KRAB (bold, from Gilbert et al., Cell, 2013, 2014); Linkers (underlined), dCas9 (italics); HA tag (lowercase), SV40 NLS (lowercase italics), XTEN16 (uppercase, 16 amino acid sequence), Dnmt3A (bold italics; from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

SEQ ID NO: 2

DAKSLTAWSRTLVTFKDVFVDFTREEWKLLDTAQQIVYRNVMLENYKNLVSLGYQL
TKPDVILRLEKGEEPGGSGGGSMDKKYSIGLAIGTNSVGWAVITDEYKVPSKKFKVLGNTDRH
SIKKNLIGALLFDSGETAEATRLKRTARRRYTRRKNRICYLQEIFSNEMAKVDDSFFHRLEESFLVE
EDKKHERHPIFGNIVDEVAYHEKYPTIYHLRKKLVDSTDKADLRLIYLALAHMIKFRGHFLIEGDL
NPDNSDVDKLFIQLVQTYNQLFEENPINASGVDAKAILSARLSKSRRLENLIAQLPGEKKNGLFGN
LIALSLGLTPNFKSNFDLAEDAKLQLSKDTYDDDLDNLLAQIGDQYADLFLAAKNLSDAILLSDIL
RVNTEITKAPLSASMIKRYDEHHQDLTLLKALVRQQLPEKYKEIFFDQSKNGYAGYIDGGASQEE
FYKFIKPILEKMDGTEELLVKLNREDLLRKQRTFDNGSIPHQIHLGELHAILRRQEDFYPFLKDN
REKIEKILTFRIPYYVGPLARGNSRFAWMTRKSEETITPWNFEEVVDKGASAQSFIERMTNFDKNL
PNEKVLPKHSLLYEYFTVYNELTKVKYVTEGMRKPAFLSGEQKKAIVDLLFKTNRKVTVKQLKED
YFKKIECFDSVEISGVEDRFNASLGTYHDLLKIIKDKDFLDNEENEDILEDIVLTLTLFEDREMIEE
RLKTYAHLFDDKVMKQLKRRRYTGWGRLSRKLINGIRDKQSGKTILDFLKSDGFANRNFMQLIH
DDSLTFKEDIQKAQVSGQGDSLHEHIANLAGSPAIKKGILQTVKVVDELVKVMGRHKPENIVIEM
ARENQTTQKGQKNSRERMKRIEEGIKELGSQILKEHPVENTQLQNEKLYLYYLQNGRDMYVDQE
LDINRLSDYDVDAIVPQSFLKDDSIDNKVLTRSDKNRGKSDNVPSEEVVKKMKNYWRQLLNAKLI
TQRKFDNLTKAERGGLSELDKAGFIKRQLVETRQITKHVAQILDSRMNTKYDENDKLIREVKVIT
LKSKLVSDFRKDFQFYKVREINNYHHAHDAYLNAVVGTALIKKYPKLESEFVYGDYKVYDVRKMI
AKSEQEIGKATAKYFFYSNIMNFFKTEITLANGEIRKRPLIETNGETGEIVWDKGRDFATVRKVLS
MPQVNIVKKTEVQTGGFSKESILPKRNSDKLIARKKDWDPKKYGGFDSPTVAYSVLVVAKVEKG
KSKKLKSVKELLGITIMERSSFEKNPIDFLEAKGYKEVKKDLIIKLPKYSLFELENGRKRMLASAGE
LQKGNELALPSKYVNFLYLASHYEKLKGSPEDNEQKQLFVEQHKHYLDEIIEQISEFSKRVILADA
NLDKVLSAYNKHRDKPIREQAENIIHLFTLTNLGAPAAFKYFDTTIDRKRYTSTKEVLDATLIHQSI
TGLYETRIDLSQLGGDSRADypydvpdyaSGSpkkkrkvSPGSGSETPGTSESATPESNHDQEFDPP -continued KVYPPVPAEKRKPIRVLSLFDGIATGLLVLKDLGIQVDRYIASEVCEDSITVGMVRHQGKIM
YVGDVRSVTQKHIQEWGPFDLVIGGSPCNDLSIVNPARKGLYEGTGRLFFEFYRLLHDARP
KEGDDRPFFWLFENVVAMGVSDKRDISRFLESNPVMIDAKEVSAAHRARYFWGNLPGMN
RPLASTVNDKLELQECLEHGRIAKFSKVRTITTRSNSIKQGKDQHFPVFMNEKEDILWCTE
MERVFGFPVHYTDVSNMSRLARQRLLGRSWSVPVIRHLFAPLKEYFACVSSGNSNANSRGP
SFSSGLVPLSLRGSHMGPMEIYKTVSAWKRQPVRVLSLFRNIDKVLKSLGFLESGSGSGG
GTLKYVEDVTNVVRRDVEKWGPFDLVYGSTQPLGSSCDRCPGWYMFQFHRILQYAL
PRQESQRPFFWIFMDNLLLTEDDQETTTRFLQTEAVTLQDVRGRDYQNAMRVWSNIP
GLKSKHAPLTPKEEEYLQAQVRSRSKLDAPKVDLLVKNCLLPLREYFKYFSQNSLPLS
RADpkkkrkvGSGatnfsllkqagdveenpgpselikenmhmklymegtvdnhhfkctsegegkpyegtqtmrikvveggplpf
afdilatsflygsktfinhtqgipdffkqsfpegftwervttyedggvltatqdtslqdgcliynvkirgvnftsngpvmqkktlgweaftetly
padgglegrndmalklvggshlianikttyrskkpaknlkmpgvyyvdyrlerikeannetyveghevavarycdlpsklghkln*

(p91 (KRAB-dCas9-Dnmt3A-Dnmt3L-P2A-P2A-BFP): KRAB (bold, from Gilbert et al., Cell, 2013, 2014), Linkers (underlined), dCas9 (italics), HA tag (lowercase), SV40 NLS (lowercase italics), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP(lowercase underlined))

SEQ ID NO: 3

DAKSLTAWSRTLVTFKDVFVDFTREEWKLLDTAQQIVYRNVMLENYKNLVSLGYQL
TKPDVILRLEKGEEPGGSGGGSMDKKYSIGLAIGTNSVGWAVITDEYKVPSKKFKVLGNTDRH
SIKKNLIGALLFDSGETAEATRLKRTARRRYTRRKNRICYLQEIFSNEMAKVDDSFFHRLEESFLVE
EDKKHERHPIFGNIVDEVAYHEKYPTIYHLRKKLVDSTDKADLRLIYLALAHMIKFRGHFLIEGDL
NPDNSDVDKLFIQLVQTYNQLFEENPINASGVDAKAILSARLSKSRRLENLIAQLPGEKKNGLFGN
LIALSLGLTPNFKSNFDLAEDAKLQLSKDTYDDDLDNLLAQIGDQYADLFLAAKNLSDAILLSDIL
RVNTEITKAPLSASMIKRYDEHHQDLTLLKALVRQQLPEKYKEIFFDQSKNGYAGYIDGGASQEE
FYKFIKPILEKMDGTEELLVKLNREDLLRKQRTFDNGSIPHQIHLGELHAILRRQEDFYPFLKDN
REKIEKILTFRIPYYVGPLARGNSRFAWMTRKSEETITPWNFEEVVDKGASAQSFIERMTNFDKNL
PNEKVLPKHSLLYEYFTVYNELTKVKYVTEGMRKPAFLSGEQKKAIVDLLFKTNRKVTVKQLKED
YFKKIECFDSVEISGVEDRFNASLGTYHDLLKIIKDKDFLDNEENEDILEDIVLTLTLFEDREMIEE
RLKTYAHLFDDKVMKQLKRRRYTGWGRLSRKLINGIRDKQSGKTILDFLKSDGFANRNFMQLIH
DDSLTFKEDIQKAQVSGQGDSLHEHIANLAGSPAIKKGILQTVKVVDELVKVMGRHKPENIVIEM
ARENQTTQKGQKNSRERMKRIEEGIKELGSQILKEHPVENTQLQNEKLYLYYLQNGRDMYVDQE
LDINRLSDYDVDAIVPQSFLKDDSIDNKVLTRSDKNRGKSDNVPSEEVVKKMKNYWRQLLNAKLI
TQRKFDNLTKAERGGLSELDKAGFIKRQLVETRQITKHVAQILDSRMNTKYDENDKLIREVKVIT
LKSKLVSDFRKDFQFYKVREINNYHHAHDAYLNAVVGTALIKKYPKLESEFVYGDYKVYDVRKMI
AKSEQEIGKATAKYFFYSNIMNFFKTEITLANGEIRKRPLIETNGETGEIVWDKGRDFATVRKVLS
MPQVNIVKKTEVQTGGFSKESILPKRNSDKLIARKKDWDPKKYGGFDSPTVAYSVLVVAKVEKG
KSKKLKSVKELLGITIMERSSFEKNPIDFLEAKGYKEVKKDLIIKLPKYSLFELENGRKRMLASAGE
LQKGNELALPSKYVNFLYLASHYEKLKGSPEDNEQKQLFVEQHKHYLDEIIEQISEFSKRVILADA
NLDKVLSAYNKHRDKPIREQAENIIHLFTLTNLGAPAAFKYFDTTIDRKRYTSTKEVLDATLIHQSI
TGLYETRIDLSQLGGDSRADypydvpdyaSGSpkkkrkvEASGSGRASPGIPGSTRNHDQEFDPPKV
YPPVPAEKRKPIRVLSLFDGIATGLLVLKDLGIQVDRYIASEVCEDSITVGMVRHQGKIMYV
GDVRSVTQKHIQEWGPFDLVIGGSPCNDLSIVNPARKGLYEGTGRLFFEFYRLLHDARPKE
GDDRPFFWLFENVVAMGVSDKRDISRFLESNPVMIDAKEVSAAHRARYFWGNLPGMNRP
LASTVNDKLELQECLEHGRIAKFSKVRTITTRSNSIKQGKDQHFPVFMNEKEDILWCTEME
RVFGFPVHYTDVSNMSRLARQRLLGRSWSVPVIRHLFAPLKEYFACVSSGNSNANSRGPSFS
SGLVPLSLRGSHMGPMEIYKTVSAWKRQPVRVLSLFRNIDKVLKSLGFLESGSGSGGGT
LKYVEDVTNVVRRDVEKWGPFDLVYGSTQPLGSSCDRCPGWYMFQFHRILQYALPR
QESQRPFFWIFMDNLLLTEDDQETTTRFLQTEAVTLQDVRGRDYQNAMRVWSNIPGL
KSKHAPLTPKEEEYLQAQVRSRSKLDAPKVDLLVKNCLLPLREYFKYFSQNSLPLSRA
DpkkkrkvGSGatnfsllkqagdveenpgpGSGatnfsllkqagdveenpgpselikenmhmklymegtvdnhhfkctsegeg
kpyegtqtmrikvveggplpfafdilatsflygsktfinhtqgipdffkqsfpegftwervttyedggvltatqdtslqdgcliynvkirgvnfts
ngpvmqkktlgweaftetlypadgglegrndmalklvggshlianikttyrskkpaknlkmpgvyyvdyrlerikeannetyvegheva
varycdlpsklghkln*

(p92 (KRAB-dCas9-XTEN16-Dnmt3A-Dnmt3L-P2A-P2A-BFP): KRAB (bold, from Gilbert et al., Cell, 2013, 2014), Linkers (underlined), dCas9 (italics), HA tag (lowercase), SV40 NLS (lowercase italics), XTEN16 (16 amino acid sequence), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

SEQ ID NO: 4

DAKSLTAWSRTLVTFKDVFVDFTREEWKLLDTAQQIVYRNVMLENYKNLVSLGYQL
TKPDVILRLEKGEEPGGSGGGSMDKKYSIGLAIGTNSVGWAVITDEYKVPSKKFKVLGNTDRH
SIKKNLIGALLFDSGETAEATRLKRTARRRYTRRKNRICYLQEIFSNEMAKVDDSFFHRLEESFLVE
EDKKHERHPIFGNIVDEVAYHEKYPTIYHLRKKLVDSTDKADLRLIYLALAHMIKFRGHFLIEGDL
NPDNSDVDKLFIQLVQTYNQLFEENPINASGVDAKAILSARLSKSRRLENLIAQLPGEKKNGLFGN
LIALSLGLTPNFKSNFDLAEDAKLQLSKDTYDDDLDNLLAQIGDQYADLFLAAKNLSDAILLSDIL
RVNTEITKAPLSASMIKRYDEHHQDLTLLKALVRQQLPEKYKEIFFDQSKNGYAGYIDGGASQEE
FYKFIKPILEKMDGTEELLVKLNREDLLRKQRTFDNGSIPHQIHLGELHAILRRQEDFYPFLKDN
REKIEKILTFRIPYYVGPLARGNSRFAWMTRKSEETITPWNFEEVVDKGASAQSFIERMTNFDKNL
PNEKVLPKHSLLYEYFTVYNELTKVKYVTEGMRKPAFLSGEQKKAIVDLLFKTNRKVTVKQLKED
YFKKIECFDSVEISGVEDRFNASLGTYHDLLKIIKDKDFLDNEENEDILEDIVLTLTLFEDREMIEE
RLKTYAHLFDDKVMKQLKRRRYTGWGRLSRKLINGIRDKQSGKTILDFLKSDGFANRNFMQLIH
DDSLTFKEDIQKAQVSGQGDSLHEHIANLAGSPAIKKGILQTVKVVDELVKVMGRHKPENIVIEM
ARENQTTQKGQKNSRERMKRIEEGIKELGSQILKEHPVENTQLQNEKLYLYYLQNGRDMYVDQE
LDINRLSDYDVDAIVPQSFLKDDSIDNKVLTRSDKNRGKSDNVPSEEVVKKMKNYWRQLLNAKLI
TQRKFDNLTKAERGGLSELDKAGFIKRQLVETRQITKHVAQILDSRMNTKYDENDKLIREVKVIT

-continued

LKSKLVSDFRKDFQFYKVREINNYHHAHDAYLNAVVGTALIKKYPKLESEFVYGDYKVYDVRKMI
AKSEQEIGKATAKYFFYSNIMNFFKTEITLANGEIRKRPLIETNGETGEIVWDKGRDFATVRKVLS
MPQVNIVKKTEVQTGGFSKESILPKRNSDKLIARKKDWDPKKYGGFDSPTVAYSVLVVAKVEKG
KSKKLKSVKELLGITIMERSSFEKNPIDFLEAKGYKEVKKDLIIKLPKYSLFELENGRKRMLASAGE
LQKGNELALPSKYVNFLYLASHYEKLKGSPEDNEQKQLFVEQHKHYLDEIIEQISEFSKRVILADA
NLDKVLSAYNKHRDKPIREQAENIIHLFTLTNLGAPAAFKYFDTTIDRKRYTSTKEVLDATLIHQSI
TGLYETRIDLSQLGGDSRADypydvpdyaSGSpkkkrkvSPGSGSETPGTSESATPESNHDQEFDPP
KVYPPVPAEKRKPIRVLSLFDGIATGLLVLKDLGIQVDRYIASEVCEDSITVGMVRHQGKIM
YVGDVRSVTQKHIQEWGPFDLVIGGSPCNDLSIVNPARKGLYEGTGRLFFEFYRLLHDARP
KEGDDRPFFWLFENVVAMGVSDKRDISRFLESNPVMIDAKEVSAAHRARYFWGNLPGMN
RPLASTVNDKLELQECLEHGRIAKFSKVRTITTRSNSIKQGKDQHFPVFMNEKEDILWCTE
MERVFGFPVHYTDVSNMSRLARQRLLGRSWSVPVIRHLFAPLKEYFACVSSGNSNANSRGP
SFSSGLVPLSLRGSHMGPMEIYKTVSAWKRQPVRVLSLFRNIDKVLKSLGFLESGSGSGG
GTLKYVEDVTNVVRRDVEKWGPFDLVYGSTQPLGSSCDRCPGWYMFQFHRILQYAL
PRQESQRPFFWIFMDNLLLTEDDQETTTRFLQTEAVTLQDVRGRDYQNAMRVWSNIP
GLKSKHAPLTPKEEEYLQAQVRSRSKLDAPKVDLLVKNCLLPLREYFKYFSQNSLPLS
RADpkkkrkvGSGatnfsllkqagdveenpgpGSGatnfsllkqagdveenpgpselikenmhmklymegtvdnhhfkctse
gegkpyegtqtmrikvveggplpfafdilatsflygsktfinhtqgipdffkqsfpegftwervttyedggvltatqdtslqdgcliynvkirgv
nftsngpvmqkktlgweaftetlypadgglegrndmalklvggshlianikttyrskkpaknlkmpgvyyvdyrlerikeannetyvegh
evavarycdlpsklghkln*

(p93 (KRAB-dCas9-XTEN80-Dnmt3A-Dnmt3L-P2A-BFP): KRAB (bold, from Gilbert et al., Cell, 2013, 2014), Linkers (underlined), dCas9 (italics), HA tag (lowercase), SV40 NLS (lowercase italics), XTEN80 (80 amino acid sequence), Dnmt3A (bold italics, from Siddique et al., JMB, 2013; Stepper et al., NAR, 2016), 27 amino acid linker (italics underlined; from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

SEQ ID NO: 5

DAKSLTAWSRTLVTFKDVFVDFTREEWKLLDTAQQIVYRNVMLENYKNLVSLGYQL
TKPDVILRLEKGEEPGGSGGGSMDKKYSIGLAIGTNSVGWAVITDEYKVPSKKFKVLGNTDRH
SIKKNLIGALLFDSGETAEATRLKRTARRRYTRRKNRICYLQEIFSNEMAKVDDSFFHRLEESFLVE
EDKKHERHPIFGNIVDEVAYHEKYPTIYHLRKKLVDSTDKADLRLIYLALAHMIKFRGHFLIEGDL
NPDNSDVDKLFIQLVQTYNQLFEENPINASGVDAKAILSARLSKSRRLENLIAQLPGEKKNGLFGN
LIALSLGLTPNFKSNFDLAEDAKLQLSKDTYDDDLDNLLAQIGDQYADLFLAAKNLSDAILLSDIL
RVNTEITKAPLSASMIKRYDEHHQDLTLLKALVRQQLPEKYKEIFFDQSKNGYAGYIDGGASQEE
FYKFIKPILEKMDGTEELLVKLNREDLLRKQRTFDNGSIPHQIHLGELHAILRRQEDFYPFLKDN
REKIEKILTFRIPYYVGPLARGNSRFAWMTRKSEETITPWNFEEVVDKGASAQSFIERMTNFDKNL
PNEKVLPKHSLLYEYFTVYNELTKVKYVTEGMRKPAFLSGEQKKAIVDLLFKTNRKVTVKQLKED
YFKKIECFDSVEISGVEDRFNASLGTYHDLLKIIKDKDFLDNEENEDILEDIVLTLTLFEDREMIEE
RLKTYAHLFDDKVMKQLKRRRYTGWGRLSRKLINGIRDKQSGKTILDFLKSDGFANRNFMQLIH
DDSLTFKEDIQKAQVSGQGDSLHEHIANLAGSPAIKKGILQTVKVVDELVKVMGRHKPENIVIEM
ARENQTTQKGQKNSRERMKRIEEGIKELGSQILKEHPVENTQLQNEKLYLYYLQNGRDMYVDQE
LDINRLSDYDVDAIVPQSFLKDDSIDNKVLTRSDKNRGKSDNVPSEEVVKKMKNYWRQLLNAKLI
TQRKFDNLTKAERGGLSELDKAGFIKRQLVETRQITKHVAQILDSRMNTKYDENDKLIREVKVIT
LKSKLVSDFRKDFQFYKVREINNYHHAHDAYLNAVVGTALIKKYPKLESEFVYGDYKVYDVRKMI
AKSEQEIGKATAKYFFYSNIMNFFKTEITLANGEIRKRPLIETNGETGEIVWDKGRDFATVRKVLS
MPQVNIVKKTEVQTGGFSKESILPKRNSDKLIARKKDWDPKKYGGFDSPTVAYSVLVVAKVEKG
KSKKLKSVKELLGITIMERSSFEKNPIDFLEAKGYKEVKKDLIIKLPKYSLFELENGRKRMLASAGE
LQKGNELALPSKYVNFLYLASHYEKLKGSPEDNEQKQLFVEQHKHYLDEIIEQISEFSKRVILADA
NLDKVLSAYNKHRDKPIREQAENIIHLFTLTNLGAPAAFKYFDTTIDRKRYTSTKEVLDATLIHQSI
TGLYETRIDLSQLGGDSRADypydvpdyaSGSpkkkrkvSPGGGPSSGAPPPSGGSPAGSPTSTEEGT
SESATPESGPGTSTEPSEGSAPGSPAGSPTSTEEGTSTEPSEGSAPGTSTEPSENHDQEFDPPK
VYPPVPAEKRKPIRVLSLFDGIATGLLVLKDLGIQVDRYIASEVCEDSITVGMVRHQGKIMY
VGDVRSVTQKHIQEWGPFDLVIGGSPCNDLSIVNPARKGLYEGTGRLFFEFYRLLHDARPK
EGDDRPFFWLFENVVAMGVSDKRDISRFLESNPVMIDAKEVSAAHRARYFWGNLPGMNR
PLASTVNDKLELQECLEHGRIAKFSKVRTITTRSNSIKQGKDQHFPVFMNEKEDILWCTEM
ERVFGFPVHYTDVSNMSRLARQRLLGRSWSVPVIRHLFAPLKEYFACVSSGNSNANSRGPSF
SSGLVPLSLRGSHMGPMEIYKTVSAWKRQPVRVLSLFRNIDKVLKSLGFLESGSGSGGG
TLKYVEDVTNVVRRDVEKWGPFDLVYGSTQPLGSSCDRCPGWYMFQFHRILQYALP
RQESQRPFFWIFMDNLLLTEDDQETTTRFLQTEAVTLQDVRGRDYQNAMRVWSNIPG
LKSKHAPLTPKEEEYLQAQVRSRSKLDAPKVDLLVKNCLLPLREYFKYFSQNSLPLSR
ADpkkkrkvGSGatnfsllkqagdveenpgpselikenmhmklymegtvdnhhfkctsegegkpyegtqtmrikvveggplpfaf
dilatsflygsktfinhtqgipdffkqsfpegftwervttyedggvltatqdtslqdgcliynvkirgvnftsngpvmqkktlgweaftetlypa
dgglegrndmalklvggshlianikttyrskkpaknlkmpgvyyvdyrlerikeannetyveghevavarycdlpsklghkln*

(p94 (KRAB-dCas9-XTEN80-Dnmt3A-Dnmt3L-P2A-P2A-BFP): KRAB (bold, from Gilbert et al., Cell, 2013, 2014), Linkers (underlined), dCas9 (italics), HA tag (lowercase), SV40 NLS (lowercase italics), XTEN80 (80 amino acid sequence), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

SEQ ID NO: 6

DAKSLTAWSRTLVTFKDVFVDFTREEWKLLDTAQQIVYRNVMLENYKNLVSLGYQL
TKPDVILRLEKGEEPGGSGGGSMDKKYSIGLAIGTNSVGWAVITDEYKVPSKKFKVLGNTDRH
SIKKNLIGALLFDSGETAEATRLKRTARRRYTRRKNRICYLQEIFSNEMAKVDDSFFHRLEESFLVE
EDKKHERHPIFGNIVDEVAYHEKYPTIYHLRKKLVDSTDKADLRLIYLALAHMIKFRGHFLIEGDL
NPDNSDVDKLFIQLVQTYNQLFEENPINASGVDAKAILSARLSKSRRLENLIAQLPGEKKNGLFGN
LIALSLGLTPNFKSNFDLAEDAKLQLSKDTYDDDLDNLLAQIGDQYADLFLAAKNLSDAILLSDIL
RVNTEITKAPLSASMIKRYDEHHQDLTLLKALVRQQLPEKYKEIFFDQSKNGYAGYIDGGASQEE

-continued

FYKFIKPILEKMDGTEELLVKLNREDLLRKQRTFDNGSIPHQIHLGELHAILRRQEDFYPFLKDN
REKIEKILTFRIPYYVGPLARGNSRFAWMTRKSEETITPWNFEEVVDKGASAQSFIERMTNFDKNL
PNEKVLPKHSLLYEYFTVYNELTKVKYVTEGMRKPAFLSGEQKKAIVDLLFKTNRKVTVKQLKED
YFKKIECFDSVEISGVEDRFNASLGTYHDLLKIIKDKDFLDNEENEDILEDIVLTLTLFEDREMIEE
RLKTYAHLFDDKVMKQLKRRRYTGWGRLSRKLINGIRDKQSGKTILDFLKSDGFANRNFMQLIH
DDSLTFKEDIQKAQVSGQGDSLHEHIANLAGSPAIKKGILQTVKVVDELVKVMGRHKPENIVIEM
ARENQTTQKGQKNSRERMKRIEEGIKELGSQILKEHPVENTQLQNEKLYLYYLQNGRDMYVDQE
LDINRLSDYDVDAIVPQSFLKDDSIDNKVLTRSDKNRGKSDNVPSEEVVKKMKNYWRQLLNAKLI
TQRKFDNLTKAERGGLSELDKAGFIKRQLVETRQITKHVAQILDSRMNTKYDENDKLIREVKVIT
LKSKLVSDFRKDFQFYKVREINNYHHAHDAYLNAVVGTALIKKYPKLESEFVYGDYKVYDVRKMI
AKSEQEIGKATAKYFFYSNIMNFFKTEITLANGEIRKRPLIETNGETGEIVWDKGRDFATVRKVLS
MPQVNIVKKTEVQTGGFSKESILPKRNSDKLIARKKDWDPKKYGGFDSPTVAYSVLVVAKVEKG
KSKKLKSVKELLGITIMERSSFEKNPIDFLEAKGYKEVKKDLIIKLPKYSLFELENGRKRMLASAGE
LQKGNELALPSKYVNFLYLASHYEKLKGSPEDNEQKQLFVEQHKHYLDEIIEQISEFSKRVILADA
NLDKVLSAYNKHRDKPIREQAENIIHLFTLTNLGAPAAFKYFDTTIDRKRYTSTKEVLDATLIHQSI
TGLYETRIDLSQLGGDSRADypydvpdyaSGSpkkkrkvSPGGGPSSGAPPPSGGSPAGSPTSTEEGT
SESATPESGPGTSTEPSEGSAPGSPAGSPTSTEEGTSTEPSEGSAPGTSTEPSENHDQEFDPPK
VYPPVPAEKRKPIRVLSLFDGIATGLLVLKDLGIQVDRYIASEVCEDSITVGMVRHQGKIMY
VGDVRSVTQKHIQEWGPFDLVIGGSPCNDLSIVNPARKGLYEGTGRLFFEFYRLLHDARPK
EGDDRPFFWLFENVVAMGVSDKRDISRFLESNPVMIDAKEVSAAHRARYFWGNLPGMNR
PLASTVNDKLELQECLEHGRIAKFSKVRTITTRSNSIKQGKDQHFPVFMNEKEDILWCTEM
ERVFGFPVHYTDVSNMSRLARQRLLGRSWSVPVIRHLFAPLKEYFACVSSGNSNANSRGPSF
SSGLVPLSLRGSHMGPMEIYKTVSAWKRQPVRVLSLFRNIDKVLKSLGFLESGSGSGGG
TLKYVEDVTNVVRRDVEKWGPFDLVYGSTQPLGSSCDRCPGWYMFQFHRILQYALP
RQESQRPFFWIFMDNLLLTEDDQETTTRFLQTEAVTLQDVRGRDYQNAMRVWSNIPG
LKSKHAPLTPKEEEYLQAQVRSRSKLDAPKVDLLVKNCLLPLREYFKYESQNSLPLSR
ADpkkkrkvGSGatnfsllkqagdveenpgpGSGatnfsllkqagdveenpgpselikenmhmklymegtvdnhhfkctseg
egkpyegtqtmrikvveggplpfafdilatsflygsktfinhtqgipdffkqsfpegftwervttyedggvltatqdtslqdgcliynvkirgvn
ftsngpvmqkktlgweaftetlypadgglegrndmalklvggshlianikttyrskkpaknlkmpgvyyvdyrlerikeannetyveqhe
vavarycdlpsklghkln*

(p95 (KRAB-XTEN16-dCas9-Dnmt3A-Dnmt3L-P2A-BFP): KRAB (bold, from Gilbert et al., Cell, 2013, 2014), Linkers (underlined), XTEN16 (16 amino acid sequence), dCas9 (italics), HA tag (lowercase), SV40 NLS (lowercase italics), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

SEQ ID NO: 7

DAKSLTAWSRTLVTFKDVFVDFTREEWKLLDTAQQIVYRNVMLENYKNLVSLGYQL
TKPDVILRLEKGEEPSGSETPGTSESATPESMDKKYSIGLAIGTNSVGWAVITDEYKVPSKKFK
VLGNTDRHSIKKNLIGALLFDSGETAEATRLKRTARRRYTRRKNRICYLQEIFSNEMAKVDDSFFH
RLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLFLAAKN
LSDAILLSDILRVNTEITKAPLSASMIKRYDEHHQDLTLLKALVRQQLPEKYKEIFFDQSKNGYAGY
IDGGASQEEFYKFIKPILEKMDGTEELLVKLNREDLLRKQRTFDNGSIPHQIHLGELHAILRRQE
DFYPFLKDNREKIEKILTFRIPYYVGPLARGNSRFAWMTRKSEETITPWNFEEVVDKGASAQSFIE
RMTNFDKNLPNEKVLPKHSLLYEYFTVYNELTKVKYVTEGMRKPAFLSGEQKKAIVDLLFKTNR
KVTVKQLKEDYFKKIECFDSVEISGVEDRFNASLGTYHDLLKIIKDKDFLDNEENEDILEDIVLTL
TLFEDREMIEERLKTYAHLFDDKVMKQLKRRRYTGWGRLSRKLINGIRDKQSGKTILDFLKSDG
FANRNFMQLIHDDSLTFKEDIQKAQVSGQGDSLHEHIANLAGSPAIKKGILQTVKVVDELVKVM
GRHKPENIVIEMARENQTTQKGQKNSRERMKRIEEGIKELGSQILKEHPVENTQLQNEKLYLYYL
QNGRDMYVDQELDINRLSDYDVDAIVPQSFLKDDSIDNKVLTRSDKNRGKSDNVPSEEVVKKMK
NYWRQLLNAKLITQRKFDNLTKAERGGLSELDKAGFIKRQLVETRQITKHVAQILDSRMNTKYDE
NDKLIREVKVITLKSKLVSDFRKDFQFYKVREINNYHHAHDAYLNAVVGTALIKKYPKLESEFVYG
DYKVYDVRKMIAKSEQEIGKATAKYFFYSNIMNFFKTEITLANGEIRKRPLIETNGETGEIVWDKG
RDFATVRKVLSMPQVNIVKKTEVQTGGFSKESILPKRNSDKLIARKKDWDPKKYGGFDSPTVAYS
VLVVAKVEKGKSKKLKSVKELLGITIMERSSFEKNPIDFLEAKGYKEVKKDLIIKLPKYSLFELENG
RKRMLASAGELQKGNELALPSKYVNFLYLASHYEKLKGSPEDNEQKQLFVEQHKHYLDEIIEQIS
EFSKRVILADANLDKVLSAYNKHRDKPIREQAENIIHLFTLTNLGAPAAFKYFDTTIDRKRYTSTKE
VLDATLIHQSITGLYETRIDLSQLGGDSRADypydvpdyaSGSpkkkrkvEASGSGRASPGIPGSTRNH
DQEFDPPKVYPPVPAEKRKPIRVLSLFDGIATGLLVLKDLGIQVDRYIASEVCEDSITVGMV
RHQGKIMYVGDVRSVTQKHIQEWGPFDLVIGGSPCNDLSIVNPARKGLYEGTGRLFFEFYR
LLHDARPKEGDDRPFFWLFENVVAMGVSDKRDISRFLESNPVMIDAKEVSAAHRARYFW
GNLPGMNRPLASTVNDKLELQECLEHGRIAKFSKVRTITTRSNSIKQGKDQHFPVFMNEKE
DILWCTEMERVFGFPVHYTDVSNMSRLARQRLLGRSWSVPVIRHLFAPLKEYFACVSSGNS
NANSRGPSFSSGLVPLSLRGSHMGPMEIYKTVSAWKRQPVRVLSLFRNIDKVLKSLGFLE
SGSGSGGGTLKYVEDVTNVVRRDVEKWGPFDLVYGSTQPLGSSCDRCPGWYMFQFH
RILQYALPRQESQRPFFWIFMDNLLLTEDDQETTTRFLQTEAVTLQDVRGRDYQNAM
RVWSNIPGLKSKHAPLTPKEEEYLQAQVRSRSKLDAPKVDLLVKNCLLPLREYFKYFS
QNSLPLSRADpkkkrkvGSGatnfsllkqagdveenpgpselikenmhmklymegtvdnhhfkctsegegkpyegtqtmri
kvveggplpfafdilatsflygsktfinhtqgipdffkqsfpegftwervttyedggvltatqdtslqdgcliynvkirgvnftsngpvmqkktl
gweaftetlypadgglegrndmalklvggshlianikttyrskkpaknlkmpgvyyvdyrlerikeannetyveghevavarycdlpskl
ghkln*

(p96 (KRAB-XTEN16-dCas9-Dnmt3A-Dnmt3L-P2A-P2A-BFP): KRAB · (bold, from Gilbert et al., Cell, 2013, 2014), Linkers (underlined), XTEN16 (16 amino acid sequence), dCas9 (italics), HA tag (lowercase), SV40 NLS (lowercase italics), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, -continued from Siddique et al., JMB, 2013; Stepper et al., NAR, 2016), P2A peptide cleavage sequence (lowercase bold); BFP (lowercase underlined))

SEQ ID NO: 8

DAKSLTAWSRTLVTFKDVFVDFTREEWKLLDTAQQIVYRNVMLENYKNLVSLGYQL
TKPDVILRLEKGEEPSGSETPGTSESATPES*MDKKYSIGLAIGTNSVGWAVITDEYKVPSKKFK*
*VLGNTDRHSIKKNLIGALLFDSGETAEATRLKRTARRRYTRRKNRICYLQEIFSNEMAKVDDSFFH*
*RLEESFLVEEDKKHERHPIFGNIVDEVAYHEKYPTIYHLRKKLVDSTDKADLRLIYLALAHMIKFR*
*GHFLIEGDLNPDNSDVDKLFIQLVQTYNQLFEENPINASGVDAKAILSARLSKSRRLENLIAQLPG*
*EKKNGLFGNLIALSLGLTPNFKSNFDLAEDAKLQLSKDTYDDDLDNLLAQIGDQYADLFLAAKN*
*LSDAILLSDILRVNTEITKAPLSASMIKRYDEHHQDLTLLKALVRQQLPEKYKEIFFDQSKNGYAGY*
*IDGGASQEEFYKFIKPILEKMDGTEELLVKLNREDLLRKQRTFDNGSIPHQIHLGELHAILRRQE*
*DFYPFLKDNREKIEKILTFRIPYYVGPLARGNSRFAWMTRKSEETITPWNFEEVVDKGASAQSFIE*
*RMTNFDKNLPNEKVLPKHSLLYEYFTVYNELTKVKYVTEGMRKPAFLSGEQKKAIVDLLFKTNR*
*KVTVKQLKEDYFKKIECFDSVEISGVEDRFNASLGTYHDLLKIIKDKDFLDNEENEDILEDIVLTL*
*TLFEDREMIEERLKTYAHLFDDKVMKQLKRRRYTGWGRLSRKLINGIRDKQSGKTILDFLKSDG*
*FANRNFMQLIHDDSLTFKEDIQKAQVSGQGDSLHEHIANLAGSPAIKKGILQTVKVVDELVKVM*
*GRHKPENIVIEMARENQTTQKGQKNSRERMKRIEEGIKELGSQILKEHPVENTQLQNEKLYLYYL*
*QNGRDMYVDQELDINRLSDYDVDAIVPQSFLKDDSIDNKVLTRSDKNRGKSDNVPSEEVVKKMK*
*NYWRQLLNAKLITQRKFDNLTKAERGGLSELDKAGFIKRQLVETRQITKHVAQILDSRMNTKYDE*
*NDKLIREVKVITLKSKLVSDFRKDFQFYKVREINNYHHAHDAYLNAVVGTALIKKYPKLESEFVYG*
*DYKVYDVRKMIAKSEQEIGKATAKYFFYSNIMNFFKTEITLANGEIRKRPLIETNGETGEIVWDKG*
*RDFATVRKVLSMPQVNIVKKTEVQTGGFSKESILPKRNSDKLIARKKDWDPKKYGGFDSPTVAYS*
*VLVVAKVEKGKSKKLKSVKELLGITIMERSSFEKNPIDFLEAKGYKEVKKDLIIKLPKYSLFELENG*
*RKRMLASAGELQKGNELALPSKYVNFLYLASHYEKLKGSPEDNEQKQLFVEQHKHYLDEIIEQIS*
*EFSKRVILADANLDKVLSAYNKHRDKPIREQAENIIHLFTLTNLGAPAAFKYFDTTIDRKRYTSTKE*
*VLDATLIHQSITGLYETRIDLSQLGGDSRAD*ypydvpdyaSGS*pkkkrkv*EASGSGRASPGIPGSTR*NH
*DQEFDPPKVYPPVPAEKRKPIRVLSLFDGIATGLLVLKDLGIQVDRYIASEVCEDSITVGMV*
*RHQGKIMYVGDVRSVTQKHIQEWGPFDLVIGGSPCNDLSIVNPARKGLYEGTGRLFFEFYR*
*LLHDARPKEGDDRPFFWLFENVVAMGVSDKRDISRFLESNPVMIDAKEVSAAHRARYFW*
*GNLPGMNRPLASTVNDKLELQECLEHGRIAKFSKVRTITTRSNSIKQGKDQHFPVFMNEKE*
*DILWCTEMERVFGFPVHYTDVSNMSRLARQRLLGRSWSVPVIRHLFAPLKEYFACV*SSGNS
*NANSRGPSFSSGLVPLSLRGSH*MGPMEIYKTVSAWKRQPVRVLSLFRNIDKVLKSLGFLE
SGSGSGGGTLKYVEDVTNVVRRDVEKWGPFDLVYGSTQPLGSSCDRCPGWYMFQFH
RILQYALPRQESQRPFFWIEMDNLLLTEDDQETTTRFLQTEAVTLQDVRGRDYQNAM
RVWSNIPGLKSKHAPLTPKEEEYLQAQVRSRSKLDAPKVDLLVKNCLLPLREYFKYFS
QNSLPLSRAD*pkkkrkv*GSGatnfsllkqagdveenpgpGSGatnfsllkqagdveenpgpselikenmhmklymegt
vdnhhfkctsegegkpyegtqtmrikvveggplpfafdilatsflygsktfinhtqgipdffkqsfpegftwervttyedggvltatqdtslgd
gcliynvkirgvnftsngpvmqkktlgweaftetlypadggleqrndmalklvggshlianikttyrskkpaknlkmpgvyyvdyrlerik
eannetyveqhevavarycdlpsklghkln*

(p97 (KRAB-XTEN80-dCas9-Dnmt3A-Dnmt3L-P2A-BFP): KRAB (bold, from Gilbert et al., Cell, 2013, 2014), Linkers (underlined), XTEN80 (80 amino acid sequence), dCas9 (italics); HA tag (lowercase), SV40 NLS (lowercase italics), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

SEQ ID NO: 9

DAKSLTAWSRTLVTFKDVFVDFTREEWKLLDTAQQIVYRNVMLENYKNLVSLGYQL
TKPDVILRLEKGEEPGGPSSGAPPPSGGSPAGSPTSTEEGTSESATPESGPGTSTEPSEGSAP
GSPAGSPTSTEEGTSTEPSEGSAPGTSTEPSE*MDKKYSIGLAIGTNSVGWAVITDEYKVPSKKFK*
*VLGNTDRHSIKKNLIGALLFDSGETAEATRLKRTARRRYTRRKNRICYLQEIFSNEMAKVDDSFFH*
*RLEESFLVEEDKKHERHPIFGNIVDEVAYHEKYPTIYHLRKKLVDSTDKADLRLIYLALAHMIKFR*
*GHFLIEGDLNPDNSDVDKLFIQLVQTYNQLFEENPINASGVDAKAILSARLSKSRRLENLIAQLPG*
*EKKNGLFGNLIALSLGLTPNFKSNFDLAEDAKLQLSKDTYDDDLDNLLAQIGDQYADLFLAAKN*
*LSDAILLSDILRVNTEITKAPLSASMIKRYDEHHQDLTLLKALVRQQLPEKYKEIFFDQSKNGYAGY*
*IDGGASQEEFYKFIKPILEKMDGTEELLVKLNREDLLRKQRTFDNGSIPHQIHLGELHAILRRQE*
*DFYPFLKDNREKIEKILTFRIPYYVGPLARGNSRFAWMTRKSEETITPWNFEEVVDKGASAQSFIE*
*RMTNFDKNLPNEKVLPKHSLLYEYFTVYNELTKVKYVTEGMRKPAFLSGEQKKAIVDLLFKTNR*
KVTVKQLKEDYFKKIECFDSVEISGVEDRFNASLGTYHDLLKIIKDKDFLDNEENEDILEDIVLTL
*TLFEDREMIEERLKTYAHLFDDKVMKQLKRRRYTGWGRLSRKLINGIRDKQSGKTILDFLKSDG*
*FANRNFMQLIHDDSLTFKEDIQKAQVSGQGDSLHEHIANLAGSPAIKKGILQTVKVVDELVKVM*
*GRHKPENIVIEMARENQTTQKGQKNSRERMKRIEEGIKELGSQILKEHPVENTQLQNEKLYLYYL*
*QNGRDMYVDQELDINRLSDYDVDAIVPQSFLKDDSIDNKVLTRSDKNRGKSDNVPSEEVVKKMK*
*NYWRQLLNAKLITQRKFDNLTKAERGGLSELDKAGFIKRQLVETRQITKHVAQILDSRMNTKYDE*
*NDKLIREVKVITLKSKLVSDFRKDFQFYKVREINNYHHAHDAYLNAVVGTALIKKYPKLESEFVYG*
*DYKVYDVRKMIAKSEQEIGKATAKYFFYSNIMNFFKTEITLANGEIRKRPLIETNGETGEIVWDKG*
*RDFATVRKVLSMPQVNIVKKTEVQTGGFSKESILPKRNSDKLIARKKDWDPKKYGGFDSPTVAYS*
*VLVVAKVEKGKSKKLKSVKELLGITIMERSSFEKNPIDFLEAKGYKEVKKDLIIKLPKYSLFELENG*
*RKRMLASAGELQKGNELALPSKYVNFLYLASHYEKLKGSPEDNEQKQLFVEQHKHYLDEIIEQIS*
*EFSKRVILADANLDKVLSAYNKHRDKPIREQAENIIHLFTLTNLGAPAAFKYFDTTIDRKRYTSTKE*
*VLDATLIHQSITGLYETRIDLSQLGGD*SRADypydvpdyaSGS*pkkkrkv*EASGSGRASPGIPGSTR*NH
*DQEFDPPKVYPPVPAEKRKPIRVLSLFDGIATGLLVLKDLGIQVDRYIASEVCEDSITVGMV*
*RHQGKIMYVGDVRSVTQKHIQEWGPFDLVIGGSPCNDLSIVNPARKGLYEGTGRLFFEFYR*
*LLHDARPKEGDDRPFFWLFENVVAMGVSDKRDISRFLESNPVMIDAKEVSAAHRARYFW*
*GNLPGMNRPLASTVNDKLELQECLEHGRIAKFSKVRTITTRSNSIKQGKDQHFPVFMNEKE*
*DILWCTEMERVFGFPVHYTDVSNMSRLARQRLLGRSWSVPVIRHLFAPLKEYFACV*SSGNS
*NANSRGPSFSSGLVPLSLRGSH*MGPMEIYKTVSAWKRQPVRVLSLFRNIDKVLKSLGFLE
SGSGSGGGTLKYVEDVTNVVRRDVEKWGPFDLVYGSTQPLGSSCDRCPGWYMFQFH
RILQYALPRQESQRPFFWIFMDNLLLTEDDQETTTRFLQTEAVTLQDVRGRDYQNAM
RVWSNIPGLKSKHAPLTPKEEEYLQAQVRSRSKLDAPKVDLLVKNCLLPLREYFKYFS

-continued

QNSLPLSRADpkkkrkvGSGatnfsllkqagdveenpgpselikenmhmklymegtvdnhhfkctsegegkpyegtqtmri
kvveggplpfafdilatsflygsktfinhtqgipdffkqsfpegftwervttyedggvltatqdtslQdgcliynvkirgvnftsngpvmqkktl
gweaftetlypadgglegrndmalklvggshlianikttyrskkpaknlkmpgvyyvdyrlerikeannetyveghevavarycdlpskl
ghkln*

(p98 (KRAB-XTEN80-dCas9-Dnmt3A-Dnmt3L-P2A-P2A-BFP): KRAB (bold, from Gilbert et al., Cell, 2013, 2014), Linkers (underlined), XTEN80 (80 amino acid sequence), dCas9 (italics), HA tag (lowercase), SV40 NLS (lowercase italics), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

SEQ ID NO: 10

DAKSLTAWSRTLVTFKDVFVDFTREEWKLLDTAQQIVYRNVMLENYKNLVSLGYQL
TKPDVILRLEKGEEPGGPSSGAPPPSGGSPAGSPTSTEEGTSESATPESGPGTSTEPSEGSAP
GSPAGSPTSTEEGTSTEPSEGSAPGTSTEPSEMDKKYSIGLAIGTNSVGWAVITDEYKVPSKKFK
VLGNTDRHSIKKNLIGALLFDSGETAEATRLKRTARRRYTRRKNRICYLQEIFSNEMAKVDDSFFH
RLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLFLAAKN
LSDAILLSDILRVNTEITKAPLSASMIKRYDEHHQDLTLLKALVRQQLPEKYKEIFFDQSKNGYAGY
IDGGASQEEFYKFIKPILEKMDGTEELLVKLNREDLLRKQRTFDNGSIPHQIHLGELHAILRRQE
DFYPFLKDNREKIEKILTFRIPYYVGPLARGNSRFAWMTRKSEETITPWNFEEVVDKGASAQSFIE
RMTNFDKNLPNEKVLPKHSLLYEYFTVYNELTKVKYVTEGMRKPAFLSGEQKKAIVDLLFKTNR
KVTVKQLKEDYFKKIECFDSVEISGVEDRFNASLGTYHDLLKIIKDKDFLDNEENEDILEDIVLTL
TLFEDREMIEERLKTYAHLFDDKVMKQLKRRRYTGWGRLSRKLINGIRDKQSGKTILDFLKSDG
FANRNFMQLIHDDSLTFKEDIQKAQVSGQGDSLHEHIANLAGSPAIKKGILQTVKVVDELVKVM
GRHKPENIVIEMARENQTTQKGQKNSRERMKRIEEGIKELGSQILKEHPVENTQLQNEKLYLYYL
QNGRDMYVDQELDINRLSDYDVDAIVPQSFLKDDSIDNKVLTRSDKNRGKSDNVPSEEVVKKMK
NYWRQLLNAKLITQRKFDNLTKAERGGLSELDKAGFIKRQLVETRQITKHVAQILDSRMNTKYDE
NDKLIREVKVITLKSKLVSDFRKDFQFYKVREINNYHHAHDAYLNAVVGTALIKKYPKLESEFVYG
DYKVYDVRKMIAKSEQEIGKATAKYFFYSNIMNFFKTEITLANGEIRKRPLIETNGETGEIVWDKG
RDFATVRKVLSMPQVNIVKKTEVQTGGFSKESILPKRNSDKLIARKKDWDPKKYGGFDSPTVAYS
VLVVAKVEKGKSKKLKSVKELLGITIMERSSFEKNPIDFLEAKGYKEVKKDLIIKLPKYSLFELENG
RKRMLASAGELQKGNELALPSKYVNFLYLASHYEKLKGSPEDNEQKQLFVEQHKHYLDEIIEQIS
EFSKRVILADANLDKVLSAYNKHRDKPIREQAENIIHLFTLTNLGAPAAFKYFDTTIDRKRYTSTKE
VLDATLIHQSITGLYETRIDLSQLGGDSRADypydvpdyaSGSpkkkrkvEASGSGRASPGIPGSTRNH
DQEFDPPKVYPPVPAEKRKPIRVLSLFDGIATGLLVLKDLGIQVDRYIASEVCEDSITVGMV
RHQGKIMYVGDVRSVTQKHIQEWGPFDLVIGGSPCNDLSIVNPARKGLYEGTGRLFFEFYR
LLHDARPKEGDDRPFFWLFENVVAMGVSDKRDISRFLESNPVMIDAKEVSAAHRARYFW
GNLPGMNRPLASTVNDKLELQECLEHGRIAKFSKVRTITTRSNSIKQGKDQHFPVFMNEKE
DILWCTEMERVFGFPVHYTDVSNMSRLARQRLLGRSWSVPVIRHLFAPLKEYFACVSSGNS
NANSRGPSFSSGLVPLSLRGSHMGPMEIYKTVSAWKRQPVRVLSLFRNIDKVLKSLGFLE
SGSGSGGGTLKYVEDVTNVVRRDVEKWGPFDLVYGSTQPLGSSCDRCPGWYMFQFH
RILQYALPRQESQRPFFWIFMDNLLLTEDDQETTTRFLQTEAVTLQDVRGRDYQNAM
RVWSNIPGLKSKHAPLTPKEEEYLQAQVRSRSKLDAPKVDLLVKNCLLPLREYFKYFS
QNSLPLSRADpkkkrkvGSGatnfsllkqagdveenpgpGSGatnfsllkqagdveenpgpselikenmhmklymegt
vdnhhfkctsegegkpyegtqtmrikvveggplpfafdilatsflygsktfinhtqgipdffkqsfpegftwervttyedggvltatqdtslqd
gcliynvkirgvnftsngpvmqkktlgweaftetlypadgglegrndmalklvggshlianikttyrskkpaknlkmpgvyyvdyrlerik
eannetyveghevavarycdlpsklghkln*

(p99 (KRAB-XTEN16-dCas9-XTEN80-Dnmt3A-Dnmt3L-P2A-BFP): KRAB (bold, from Gilbert et al:, Cell, 2013, 2014), XTEN16 (16 amino acid sequence), dCas9 (italics), HA tag (lowercase), Linkers (underlined), SV40 NLS (lowercase italics), XTEN80 (lowercase italics bold, 80 amino acid sequence), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (old underlined, from Siddique et al., JMB, 2013; Stepper et al., NAR, 2016), P2A peptide cleavage sequence (lowercase bold), BFP (lowercase underlined))

SEQ ID NO: 11

DAKSLTAWSRTLVTFKDVFVDFTREEWKLLDTAQQIVYRNVMLENYKNLVSLGYQL
TKPDVILRLEKGEEPSGSETPGTSESATPESMDKKYSIGLAIGTNSVGWAVITDEYKVPSKKFK
VLGNTDRHSIKKNLIGALLFDSGETAEATRLKRTARRRYTRRKNRICYLQEIFSNEMAKVDDSFFH
RLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLFLAAKN
LSDAILLSDILRVNTEITKAPLSASMIKRYDEHHQDLTLLKALVRQQLPEKYKEIFFDQSKNGYAGY
IDGGASQEEFYKFIKPILEKMDGTEELLVKLNREDLLRKQRTFDNGSIPHQIHLGELHAILRRQE
DFYPFLKDNREKIEKILTFRIPYYVGPLARGNSRFAWMTRKSEETITPWNFEEVVDKGASAQSFIE
RMTNFDKNLPNEKVLPKHSLLYEYFTVYNELTKVKYVTEGMRKPAFLSGEQKKAIVDLLFKTNR
KVTVKQLKEDYFKKIECFDSVEISGVEDRFNASLGTYHDLLKIIKDKDFLDNEENEDILEDIVLTL
TLFEDREMIEERLKTYAHLFDDKVMKQLKRRRYTGWGRLSRKLINGIRDKQSGKTILDFLKSDG
FANRNFMQLIHDDSLTFKEDIQKAQVSGQGDSLHEHIANLAGSPAIKKGILQTVKVVDELVKVM
GRHKPENIVIEMARENQTTQKGQKNSRERMKRIEEGIKELGSQILKEHPVENTQLQNEKLYLYYL
QNGRDMYVDQELDINRLSDYDVDAIVPQSFLKDDSIDNKVLTRSDKNRGKSDNVPSEEVVKKMK
NYWRQLLNAKLITQRKFDNLTKAERGGLSELDKAGFIKRQLVETRQITKHVAQILDSRMNTKYDE
NDKLIREVKVITLKSKLVSDFRKDFQFYKVREINNYHHAHDAYLNAVVGTALIKKYPKLESEFVYG
DYKVYDVRKMIAKSEQEIGKATAKYFFYSNIMNFFKTEITLANGEIRKRPLIETNGETGEIVWDKG
RDFATVRKVLSMPQVNIVKKTEVQTGGFSKESILPKRNSDKLIARKKDWDPKKYGGFDSPTVAYS
VLVVAKVEKGKSKKLKSVKELLGITIMERSSFEKNPIDFLEAKGYKEVKKDLIIKLPKYSLFELENG
RKRMLASAGELQKGNELALPSKYVNFLYLASHYEKLKGSPEDNEQKQLFVEQHKHYLDEIIEQIS

-continued

EFSKRVILADANLDKVLSAYNKHRDKPIREQAENIIHLFTLTNLGAPAAFKYFDTTIDRKRYTSTKE
VLDATLIHQSITGLYETRIDLSQLGGDSRADypydvpdyaSGSpkkkrkvSPGggpssgapppsggspagsptste
egtsesatpesgpgtstepsegsapgspagsptsteegtstepsegsapgtstepseNHDQEFDPPKVYPPVPAEKRKPIR
VLSLFDGIATGLLVLKDLGIQVDRYIASEVCEDSITVGMVRHQGKIMYVGDVRSVTQKHIQE
WGPFDLVIGGSPCNDLSIVNPARKGLYEGTGRLFFEFYRLLHDARPKEGDDRPFFWLFEN
VVAMGVSDKRDISRFLESNPVMIDAKEVSAAHRARYFWGNLPGMNRPLASTVNDKLELQE
CLEHGRIAKFSKVRTITTRSNSIKQGKDQHFPVFMNEKEDILWCTEMERVFGFPVHYTDVS
NMSRLARQRLLGRSWSVPVIRHLFAPLKEYFACVSSGNSNANSRGPSFSSGLVPLSLRGSHMG
PMEIYKTVSAWKRQPVRVLSLFRNIDKVLKSLGFLESGSGSGGGTLKYVEDVTNVVR
RDVEKWGPFDLVYGSTQPLGSSCDRCPGWYMFQFHRILQYALPRQESQRPFFWIEMD
NLLLTEDDQETTTRFLQTEAVTLQDVRGRDYQNAMRVWSNIPGLKSKHAPLTPKEEE
YLQAQVRSRSKLDAPKVDLLVKNCLLPLREYFKYFSQNSLPLSRADpkkkrkvGSGatnfsllk
qagdveenpgpselikenmhmklymegtvdnhhfkctsegegkpyegtgtmrikvveggplpfafdilatsflygsktfinhtqgipdff
kqsfpegftwervttyedggvltatqdtslqdgcliynvkirgvnftsngpvmqkktlgweaftetlypadgglegrndmalklvggshlia
nikttyrskkpaknlkmpgvyyvdyrlerikeannetyveghevavarycdlpsklghkln*

(p100 (KRAB-XTEN16-dCas9-XTEN80-Dnmt3A-Dnmt3L-P2A-P2A-BFP): KRAB (bold, from Gilbert et al., Cell, 2013, 2014), XTEN16 (16 amino acid sequence), dCas9 (italics), HA tag (lowercase), Linkers (underlined), SV40 NLS (lowercase italics), XTEN80 (lowercase bold italics, 80 amino acid sequence), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

SEQ ID NO: 12

DAKSLTAWSRTLVTFKDVFVDFTREEWKLLDTAQQIVYRNVMLENYKNLVSLGYQL
TKPDVILRLEKGEEPSGSETPGTSESATPESMDKKYSIGLAIGTNSVGWAVITDEYKVPSKKFK
VLGNTDRHSIKKNLIGALLFDSGETAEATRLKRTARRRYTRRKNRICYLQEIFSNEMAKVDDSFFH
RLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLFLAAKN
LSDAILLSDILRVNTEITKAPLSASMIKRYDEHHQDLTLLKALVRQQLPEKYKEIFFDQSKNGYAGY
IDGGASQEEFYKFIKPILEKMDGTEELLVKLNREDLLRKQRTFDNGSIPHQIHLGELHAILRRQE
DFYPFLKDNREKIEKILTFRIPYYVGPLARGNSRFAWMTRKSEETITPWNFEEVVDKGASAQSFIE
RMTNFDKNLPNEKVLPKHSLLYEYFTVYNELTKVKYVTEGMRKPAFLSGEQKKAIVDLLFKTNR
KVTVKQLKEDYFKKIECFDSVEISGVEDRFNASLGTYHDLLKIIKDKDFLDNEENEDILEDIVLTL
TLFEDREMIEERLKTYAHLFDDKVMKQLKRRRYTGWGRLSRKLINGIRDKQSGKTILDFLKSDG
FANRNFMQLIHDDSLTFKEDIQKAQVSGQGDSLHEHIANLAGSPAIKKGILQTVKVVDELVKVM
GRHKPENIVIEMARENQTTQKGQKNSRERMKRIEEGIKELGSQILKEHPVENTQLQNEKLYLYYL
QNGRDMYVDQELDINRLSDYDVDAIVPQSFLKDDSIDNKVLTRSDKNRGKSDNVPSEEVVKKMK
NYWRQLLNAKLITQRKFDNLTKAERGGLSELDKAGFIKRQLVETRQITKHVAQILDSRMNTKYDE
NDKLIREVKVITLKSKLVSDFRKDFQFYKVREINNYHHAHDAYLNAVVGTALIKKYPKLESEFVYG
DYKVYDVRKMIAKSEQEIGKATAKYFFYSNIMNFFKTEITLANGEIRKRPLIETNGETGEIVWDKG
RDFATVRKVLSMPQVNIVKKTEVQTGGFSKESILPKRNSDKLIARKKDWDPKKYGGFDSPTVAYS
VLVVAKVEKGKSKKLKSVKELLGITIMERSSFEKNPIDFLEAKGYKEVKKDLIIKLPKYSLFELENG
RKRMLASAGELQKGNELALPSKYVNFLYLASHYEKLKGSPEDNEQKQLFVEQHKHYLDEIIEQIS
EFSKRVILADANLDKVLSAYNKHRDKPIREQAENIIHLFTLTNLGAPAAFKYFDTTIDRKRYTSTKE
VLDATLIHQSITGLYETRIDLSQLGGDSRADypydvpdyaSGSpkkkrkvSPGggpssgapppsggspagsptste
egtsesatpesgpgtstepsegsapgspagsptsteegtstepsegsapgtstepseNHDQEFDPPKVYPPVPAEKRKPIR
VLSLFDGIATGLLVLKDLGIQVDRYIASEVCEDSITVGMVRHQGKIMYVGDVRSVTQKHIQE
WGPFDLVIGGSPCNDLSIVNPARKGLYEGTGRLFFEFYRLLHDARPKEGDDRPFFWLFEN
VVAMGVSDKRDISRFLESNPVMIDAKEVSAAHRARYFWGNLPGMNRPLASTVNDKLELQE
CLEHGRIAKFSKVRTITTRSNSIKQGKDQHFPVFMNEKEDILWCTEMERVFGFPVHYTDVS
NMSRLARQRLLGRSWSVPVIRHLFAPLKEYFACVSSGNSNANSRGPSFSSGLVPLSLRGSHMG
PMEIYKTVSAWKRQPVRVLSLFRNIDKVLKSLGFLESGSGSGGGTLKYVEDVTNVVR
RDVEKWGPFDLVYGSTQPLGSSCDRCPGWYMFQFHRILQYALPRQESQRPFFWIFMD
NLLLTEDDQETTTRFLQTEAVTLQDVRGRDYQNAMRVWSNIPGLKSKHAPLTPKEEE
YLQAQVRSRSKLDAPKVDLLVKNCLLPLREYFKYFSQNSLPLSRADpkkkrkvGSGatnfsllk
qagdveenpgpGSGatnfsllkqagdveenpgpselikenmhmklymegtvdnhhfkctsegegkpyegtqtmrikvveggplp
fafdilatsflygsktfinhtqgipdffkqsfpegftwervttyedggvltatqdtslqdgcliynvkirgvnftsngpvmqkktlgweaftetly
padgglegrndmalklvggshlianikttyrskkpaknlkmpgvyyvdyrlerikeannetyveghevavarycdlpsklghkln*

(p101 (KRAB-XTEN80-dCas9-XTEN16-Dnmt3A-Dnmt3L-P2A-BFP): KRAB (bold, from Gilbert et al., Cell, 2013, 2014), Linkers (underlined), XTEN80 (lowercase bold italics, 80 amino acid sequence), dCas9 (italics), HA tag (lowercase), SV40 NLS (lowercase italics), XTEN16 (16 amino acid sequence), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

SEQ ID NO: 13

DAKSLTAWSRTLVTFKDVFVDFTREEWKLLDTAQQIVYRNVMLENYKNLVSLGYQL
TKPDVILRLEKGEEPggpssgapppsggspagsptsteegtsesatpesgpgtstepsegsapgspagsptsteegtstepseg
sapgtstepseMDKKYSIGLAIGTNSVGWAVITDEYKVPSKKFKVLGNTDRHSIKKNLIGALLFDSGET
AEATRLKRTARRRYTRRKNRICYLQEIFSNEMAKVDDSFFHRLEESFLVEEDKKHERHPIFGNIVD
EVAYHEKYPTIYHLRKKLVDSTDKADLRLIYLALAHMIKFRGHFLIEGDLNPDNSDVDKLFIQLVQ
TYNQLFEENPINASGVDAKAILSARLSKSRRLENLIAQLPGEKKNGLFGNLIALSLGLTPNFKSNFD
LAEDAKLQLSKDTYDDDLDNLLAQIGDQYADLFLAAKNLSDAILLSDILRVNTEITKAPLSASMIK
RYDEHHQDLTLLKALVRQQLPEKYKEIFFDQSKNGYAGYIDGGASQEEFYKFIKPILEKMDGTE
ELLVKLNREDLLRKQRTFDNGSIPHQIHLGELHAILRRQEDFYPFLKDNREKIEKILTFRIPYYVG
PLARGNSRFAWMTRKSEETITPWNFEEVVDKGASAQSFIERMTNFDKNLPNEKVLPKHSLLYEYF
TVYNELTKVKYVTEGMRKPAFLSGEQKKAIVDLLFKTNRKVTVKQLKEDYFKKIECFDSVEISGV -continued EDRFNASLGTYHDLLKIIKDKDFLDNEENEDILEDIVLTLTLFEDREMIEERLKTYAHLFDDKVM
KQLKRRRYTGWGRLSRKLINGIRDKQSGKTILDFLKSDGFANRNFMQLIHDDSLTFKEDIQKAQ
VSGQGDSLHEHIANLAGSPAIKKGILQTVKVVDELVKVMGRHKPENIVIEMARENQTTQKGQKN
SRERMKRIEEGIKELGSQILKEHPVENTQLQNEKLYLYYLQNGRDMYVDQELDINRLSDYDVDAI
VPQSFLKDDSIDNKVLTRSDKNRGKSDNVPSEEVVKKMKNYWRQLLNAKLITQRKFDNLTKAER
GGLSELDKAGFIKRQLVETRQITKHVAQILDSRMNTKYDENDKLIREVKVITLKSKLVSDFRKDF
QFYKVREINNYHHAHDAYLNAVVGTALIKKYPKLESEFVYGDYKVYDVRKMIAKSEQEIGKATAK
YFFYSNIMNFFKTEITLANGEIRKRPLIETNGETGEIVWDKGRDFATVRKVLSMPQVNIVKKTEVQ
TGGFSKESILPKRNSDKLIARKKDWDPKKYGGFDSPTVAYSVLVVAKVEKGKSKKLKSVKELLGI
TIMERSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAYNKHR
DKPIREQAENIIHLFTLTNLGAPAAFKYFDTTIDRKRYTSTKEVLDATLIHQSITGLYETRIDLSQLG
GDSRADypydvpdyaSGSpkkkrkvSPGSGSETPGTSESATPESNHDQEFDPPKVYPPVPAEKRKPI
RVLSLFDGIATGLLVLKDLGIQVDRYIASEVCEDSITVGMVRHQGKIMYVGDVRSVTQKHIQ
EWGPFDLVIGGSPCNDLSIVNPARKGLYEGTGRLFFEFYRLLHDARPKEGDDRPFFWLFE
NVVAMGVSDKRDISRFLESNPVMIDAKEVSAAHRARYFWGNLPGMNRPLASTVNDKLELQ
ECLEHGRIAKFSKVRTITTRSNSIKQGKDQHFPVFMNEKEDILWCTEMERVFGFPVHYTD
VSNMSRLARQRLLGRSWSVPVIRHLFAPLKEYFACVSSGNSNANSRGPSFSSGLVPLSLRGSH
MGPMEIYKTVSAWKRQPVRVLSLFRNIDKVLKSLGFLESGSGSGGGTLKYVEDVTNV
VRRDVEKWGPFDLVYGSTQPLGSSCDRCPGWYMFQFHRILQYALPRQESQRPFFWIF
MDNLLLTEDDQETTTRFLQTEAVTLQDVRGRDYQNAMRVWSNIPGLKSKHAPLTPK
EEEYLQAQVRSRSKLDAPKVDLLVKNCLLPLREYFKYFSQNSLPLSRADpkkkrkvGSGatn
fsllkqagdveenpgpselikenmhmklymegtvdnhhfkctsegegkpyegtqtmrikvveggplpfafdilatsflygsktfinhtqg
ipdffkqsfpegftwervttyedggvltatqdtslqdgcliynvkirgvnftsngpvmqkktlgweaftetlypadgglegrndmalklvgg
shlianikttyrskkpaknlkmpgvyyvdyrlerikeannetyveghevavarycdlpsklghkln*

(p102 (KRAB-XTEN80-dCas9-XTEN16-Dnmt3A-Dnmt3L-P2A-BFP):
KRAB (bold, from Gilbert et al., Cell, 2013, 2014), Linkers (underlined), XTEN80 (lowercase bold italics, 80 amino acid sequence), dCas9 (italics), HA tag (lowercase), SV40 NLS (lowercase italics), XTEN16 (16 amino acid sequence), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et. al., NAR, 2016), P2A peptide cleavage sequence (lowercase bold), BFP (lowercase underlined))

SEQ ID NO: 14

DAKSLTAWSRTLVTFKDVFVDFTREEWKLLDTAQQIVYRNVMLENYKNLVSLGYQL
TKPDVILRLEKGEEPggpssgapppsggspagsptsteegtsesatpesgpgtstepsegsapgspagsptsteegtstepseg
sapgtstepseMDKKYSIGLAIGTNSVGWAVITDEYKVPSKKFKVLGNTDRHSIKKNLIGALLFDSGET
AEATRLKRTARRRYTRRKNRICYLQEIFSNEMAKVDDSFFHRLEESFLVEEDKKHERHPIFGNIVD
EVAYHEKYPTIYHLRKKLVDSTDKADLRLIYLALAHMIKFRGHFLIEGDLNPDNSDVDKLFIQLVQ
TYNQLFEENPINASGVDAKAILSARLSKSRRLENLIAQLPGEKKNGLFGNLIALSLGLTPNFKSNFD
LAEDAKLQLSKDTYDDDLDNLLAQIGDQYADLFLAAKNLSDAILLSDILRVNTEITKAPLSASMIK
RYDEHHQDLTLLKALVRQQLPEKYKEIFFDQSKNGYAGYIDGGASQEEFYKFIKPILEKMDGTE
ELLVKLNREDLLRKQRTFDNGSIPHQIHLGELHAILRRQEDFYPFLKDNREKIEKILTFRIPYYVG
PLARGNSRFAWMTRKSEETITPWNFEEVVDKGASAQSFIERMTNFDKNLPNEKVLPKHSLLYEYF
TVYNELTKVKYVTEGMRKPAFLSGEQKKAIVDLLFKTNRKVTVKQLKEDYFKKIECFDSVEISGV
EDRFNASLGTYHDLLKIIKDKDFLDNEENEDILEDIVLTLTLFEDREMIEERLKTYAHLFDDKVM
KQLKRRRYTGWGRLSRKLINGIRDKQSGKTILDFLKSDGFANRNFMQLIHDDSLTFKEDIQKAQ
VSGQGDSLHEHIANLAGSPAIKKGILQTVKVVDELVKVMGRHKPENIVIEMARENQTTQKGQKN
SRERMKRIEEGIKELGSQILKEHPVENTQLQNEKLYLYYLQNGRDMYVDQELDINRLSDYDVDAI
VPQSFLKDDSIDNKVLTRSDKNRGKSDNVPSEEVVKKMKNYWRQLLNAKLITQRKFDNLTKAER
GGLSELDKAGFIKRQLVETRQITKHVAQILDSRMNTKYDENDKLIREVKVITLKSKLVSDFRKDF
QFYKVREINNYHHAHDAYLNAVVGTALIKKYPKLESEFVYGDYKVYDVRKMIAKSEQEIGKATAK
YFFYSNIMNFFKTEITLANGEIRKRPLIETNGETGEIVWDKGRDFATVRKVLSMPQVNIVKKTEVQ
TGGFSKESILPKRNSDKLIARKKDWDPKKYGGFDSPTVAYSVLVVAKVEKGKSKKLKSVKELLGI
TIMERSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAYNKHR
DKPIREQAENIIHLFTLTNLGAPAAFKYFDTTIDRKRYTSTKEVLDATLIHQSITGLYETRIDLSQLG
GDSRADypydvpdyaSGSpkkkrkvSPGSGSETPGTSESATPESNHDQEFDPPKVYPPVPAEKRKPI
RVLSLFDGIATGLLVLKDLGIQVDRYIASEVCEDSITVGMVRHQGKIMYVGDVRSVTQKHIQ
EWGPFDLVIGGSPCNDLSIVNPARKGLYEGTGRLFFEFYRLLHDARPKEGDDRPFFWLFE
NVVAMGVSDKRDISRFLESNPVMIDAKEVSAAHRARYFWGNLPGMNRPLASTVNDKLELQ
ECLEHGRIAKFSKVRTITTRSNSIKQGKDQHFPVFMNEKEDILWCTEMERVFGFPVHYTD
VSNMSRLARQRLLGRSWSVPVIRHLFAPLKEYFACVSSGNSNANSRGPSFSSGLVPLSLRGSH
MGPMEIYKTVSAWKRQPVRVLSLFRNIDKVLKSLGFLESGSGSGGGTLKYVEDVTNV
VRRDVEKWGPFDLVYGSTQPLGSSCDRCPGWYMFQFHRILQYALPRQESQRPFFWIF
MDNLLLTEDDQETTTRFLQTEAVTLQDVRGRDYQNAMRVWSNIPGLKSKHAPLTPK
EEEYLQAQVRSRSKLDAPKVDLLVKNCLLPLREYFKYFSQNSLPLSRADpkkkrkvGSGatn
fsllkqagdveenpgpGSGatnfsllkqagdveenpgpselikenmhmklymegtvdnhhfkctsegegkpyegtqtmrikvve
ggplpfafdilatsflygsktfinhtqgipdffkqsfpegftwervttyedggvltatqdtslqdgcliynvkirgvnftsngpvmqkktlgwe
aftetlypadgglegrndmalklvggshlianikttyrskkpaknlkmpgvyyvdyrlerikeannetyveghevavarycdlpsklghkl
n*

(p112 (Dnmt3A-Dnmt3L-XTEN80-dCas9-BFP-KRAB); KRAB (bold, from Gilbert et al., Cell, 2013, 2014), Linkers (underlined), XTEN80 (lowercase bold italics, 80 amino acid sequence), dCas9 (italics), HA tag (lowercase), SV40 NLS (lowercase italics), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), BFP (lowercase underlined))

SEQ ID NO: 15

NHDQEFDPPKVYPPVPAEKRKPIRVLSLFDGIATGLLVLKDLGIQVDRYIASEVCEDSITVG

-continued

*MVRHQGKIMYVGDVRSVTQKHIQEWGPFDLVIGGSPCNDLSIVNPARKGLYEGTGRLFFE FYRLLHDARPKEGDDRPFFWLFENVVAMGVSDKRDISRFLESNPVMIDAKEVSAAHRARY FWGNLPGMNRPLASTVNDKLELQECLEHGRIAKFSKVRTITTRSNSIKQGKDQHFPVFMN EKEDILWCTEMERVFGFPVHYTDVSNMSRLARQRLLGRSWSVPVIRHLFAPLKEYFACV*SS GNSNANSRGPSFSSGLVPLSLRGSHMGPMEIYKTVSAWKRQPVRVLSLFRNIDKVLKSLG FLESGSGSGGGTLKYVEDVTNVVRRDVEKWGPFDLVYGSTQPLGSSCDRCPGWYMF QFHRILQYALPRQESQRPFFWIFMDNLLLTEDDQETTTRFLQTEAVTLQDVRGRDYQ NAMRVWSNIPGLKSKHAPLTPKEEEYLQAQVRSRSKLDAPKVDLLVKNCLLPLREYF KYFSQNSLPL*ggpssgapppsgggpsagsptsteegtsesatpesgpgtstepsegsapggspagsptsteegtstepsegsapgtste pse*MDKKYSIGLAIGTNSVGWAVITDEYKVPSKKFKVLGNTDRHSIKKNLIGALLFDSGETAEATRL KRTARRRYTRRKNRICYLQEIFSNEMAKVDDSFFHRLEESFLVEEDKKHERHPIFGNIVDEVAYH EKYPTIYHLRKKLVDSTDKADLRLIYLALAHMIKFRGHFLIEGDLNPDNSDVDKLFIQLVQTYNQL FEENPINASGVDAKAILSARLSKSRRLENLIAQLPGEKKNGLFGNLIALSLGLTPNFKSNFDLAEDA KLQLSKDTYDDDLDNLLAQIGDQYADLFLAAKNLSDAILLSDILRVNTEITKAPLSASMIKRYDEH HQDLTLLKALVRQQLPEKYKEIFFDQSKNGYAGYIDGGASQEEFYKFIKPILEKMDGTEELLVKL NREDLLRKQRTFDNGSIPHQIHLGELHAILRRQEDFYPFLKDNREKIEKILTFRIPYYVGPLARGN SRFAWMTRKSEETITPWNFEEVVDKGASAQSFIERMTNFDKNLPNEKVLPKHSLLYEYFTVYNEL TKVKYVTEGMRKPAFLSGEQKKAIVDLLFKTNRKVTVKQLKEDYFKKIECFDSVEISGVEDRFNA SLGTYHDLLKIIKDKDFLDNEENEDILEDIVLTLTLFEDREMIEERLKTYAHLFDDKVMKQLKRR RYTGWGRLSRKLINGIRDKQSGKTILDFLKSDGFANRNFMQLIHDDSLTFKEDIQKAQVSGQGD SLHEHIANLAGSPAIKKGILQTVKVVDELVKVMGRHKPENIVIEMARENQTTQKGQKNSRERMK RIEEGIKELGSQILKEHPVENTQLQNEKLYLYYLQNGRDMYVDQELDINRLSDYDVDAIVPQSFL KDDSIDNKVLTRSDKNRGKSDNVPSEEVVKKMKNYWRQLLNAKLITQRKFDNLTKAERGGLSEL DKAGFIKRQLVETRQITKHVAQILDSRMNTKYDENDKLIREVKVITLKSKLVSDFRKDFQFYKVR EINNYHHAHDAYLNAVVGTALIKKYPKLESEFVYGDYKVYDVRKMIAKSEQEIGKATAKYFFYSNI MNFFKTEITLANGEIRKRPLIETNGETGEIVWDKGRDFATVRKVLSMPQVNIVKKTEVQTGGFSK ESILPKRNSDKLIARKKDWDPKKYGGFDSPTVAYSVLVVAKVEKGKSKKLKSVKELLGITIMERSS FEKNPIDFLEAKGYKEVKKDLIIKLPKYSLFELENGRKRMLASAGELQKGNELALPSKYVNFLYLA SHYEKLKGSPEDNEQKQLFVEQHKHYLDEIIEQISEFSKRVILADANLDKVLSAYNKHRDKPIREQ AENIIHLFTLTNLGAPAAFKYFDTTIDRKRYTSTKEVLDATLIHQSITGLYETRIDLSQLGGD*Aypyd vpdyaSLGSGS*pkkkrkv*ED*pkkkrkv*DGIGSGSNGSSGSselikenmhmklymegtvdnhhfkctsegegkpyegtqt mrikvveggplpfafdilatsflygsktfinhtqgipdffkqsfpegftwervttyedggvltatqdtslqdgcliynvkirgvnftsngpvmq kktlgweaftetlypadgglegrndmalklvggshlianikttyrskkpaknlkmpgvyyvdyrlerikeannetyveqhevavarycdlp sklghklnGGGGGMDAKSLTAWSRTLVTFKDVFVDFTREEWKLLDTAQQIVYRNVMLEN YKNLVSLGYQLTKPDVILRLEKGEEP*

(KRAB; from Gilbert et al., Cell, 2013, 2014)

SEQ ID NO: 16

DAKSLTAWSRTLVTFKDVFVDFTREEWKLLDTAQQIVYRNVMLENYKNLVSLGYQLTKP DVILRLEKGEEP (Linker)

SEQ ID NO: 17

GGSGGGS (Linker)

SEQ ID NO: 18

SGS (Linker)

SEQ ID NO: 19

EASGSGRASPGIPGSTR (Linker)

SEQ ID NO: 20

SRAD (Linker)

SEQ ID NO: 21

GSG (Linker

SEQ ID NO: 22

SPG (dCas9)

SEQ ID NO: 23

MDKKYSIGLAIGTNSVGWAVITDEYKVPSKKFKVLGNTDRHSIKKNLIGALLFDSGETAEA TRLKRTARRRYTRRKNRICYLQEIFSNEMAKVDDSFFHRLEESFLVEEDKKHERHPIFGNIV DEVAYHEKYPTIYHLRKKLVDSTDKADLRLIYLALAHMIKFRGHFLIEGDLNPDNSDVDKL FIQLVQTYNQLFEENPINASGVDAKAILSARLSKSRRLENLIAQLPGEKKNGLFGNLIALSLG LTPNFKSNFDLAEDAKLQLSKDTYDDDLDNLLAQIGDQYADLFLAAKNLSDAILLSDILRV NTEITKAPLSASMIKRYDEHHQDLTLLKALVRQQLPEKYKEIFFDQSKNGYAGYIDGGASQ EEFYKFIKPILEKMDGTEELLVKLNREDLLRKQRTFDNGSIPHQIHLGELHAILRRQEDFYPF LKDNREKIEKILTFRIPYYVGPLARGNSRFAWMTRKSEETITPWNFEEVVDKGASAQSFIER MTNFDKNLPNEKVLPKHSLLYEYFTVYNELTKVKYVTEGMRKPAFLSGEQKKAIVDLLFK TNRKVTVKQLKEDYFKKIECFDSVEISGVEDRFNASLGTYHDLLKIIKDKDFLDNEENEDIL EDIVLTLTLFEDREMIEERLKTYAHLFDDKVMKQLKRRRYTGWGRLSRKLINGIRDKQSGK TILDFLKSDGFANRNFMQLIHDDSLTFKEDIQKAQVSGQGDSLHEHIANLAGSPAIKKGILQ TVKVVDELVKVMGRHKPENIVIEMARENQTTQKGQKNSRERMKRIEEGIKELGSQILKEHP VENTQLQNEKLYLYYLQNGRDMYVDQELDINRLSDYDVDAIVPQSFLKDDSIDNKVLTRS

-continued

DKNRGKSDNVPSEEVVKKMKNYWRQLLNAKLITQRKFDNLTKAERGGLSELDKAGFIKR
QLVETRQITKHVAQILDSRMNTKYDENDKLIREVKVITLKSKLVSDFRKDFQFYKVREINN
YHHAHDAYLNAVVGTALIKKYPKLESEFVYGDYKVYDVRKMIAKSEQEIGKATAKYFFYS
NIMNFFKTEITLANGEIRKRPLIETNGETGEIVWDKGRDFATVRKVLSMPQVNIVKKTEVQT
GGFSKESILPKRNSDKLIARKKDWDPKKYGGFDSPTVAYSVLVVAKVEKGKSKKLKSVKE
LLGITIMERSSFEKNPIDFLEAKGYKEVKKDLIIKLPKYSLFELENGRKRMLASAGELQKGN
ELALPSKYVNFLYLASHYEKLKGSPEDNEQKQLFVEQHKHYLDEIIEQISEFSKRVILADAN
LDKVLSAYNKHRDKPIREQAENIIHLFTLTNLGAPAAFKYFDTTIDRKRYTSTKEVLDATLI
HQSITGLYETRIDLSQLGGD (HA tag)

SEQ ID NO: 24

YPYDVPDYA (SV40 NLS)

SEQ ID NO: 25

PKKKRKV (Dnmt3A; residues 612-912; from Siddique et al., JMB, 2013; Stepper et al., NAR, 2016)

SEQ ID NO: 26

NHDQEFDPPKVYPPVPAEKRKPIRVLSLFDGIATGLLVLKDLGIQVDRYIASEVCEDSITVG
MVRHQGKIMYVGDVRSVTQKHIQEWGPFDLVIGGSPCNDLSIVNPARKGLYEGTGRLFFEF
YRLLHDARPKEGDDRPFFWLFENVVAMGVSDKRDISRFLESNPVMIDAKEVSAAHRARYF
WGNLPGMNRPLASTVNDKLELQECLEHGRIAKFSKVRTITTRSNSIKQGKDQHFPVFMNEK
EDILWCTEMERVFGFPVHYTDVSNMSRLARQRLLGRSWSVP.VIRHLFAPLKEYFACV (27 amino acid linker; from Siddique et al., JMB, 2013; Stepper et al., NAR, 2016)

SEQ ID NO: 27

SSGNSNANSRGPSFSSGLVPLSLRGSH (Dnmt3L; from Siddique et al., JMB, 2013; Stepper et al., NAR, 2016)

SEQ ID NO: 28

MGPMEIYKTVSAWKRQPVRVLSLFRNIDKVLKSLGFLESGSGSGGGTLKYVEDVTNVVRR
DVEKWGPFDLVYGSTQPLGSSCDRCPGWYMFQFHRILQYALPRQESQRPFFWIFMDNLLL
TEDDQETTTRFLQTEAVTLQDVRGRDYQNAMRVWSNIPGLKSKHAPLTPKEEEYLQAQVR
SRSKLDAPKVDLLVKNCLLPLREYFKYFSQNSLPL (P2A peptide cleave sequence)

SEQ ID NO: 29

ATNFSLLKQAGDVEENPGP (BFP)

SEQ ID NO: 30

SELIKENMHMKLYMEGTVDNHHFKCTSEGEGKPYEGTQTMRIKVVEGGPLPFAFDILATSF
LYGSKTFINHTQGIPDFFKQSFPEGFTWERVTTYEDGGVLTATQDTSLQDGCLIYNVKIRGV
NFTSNGPVMQKKTLGWEAFTETLYPADGGLEGRNDMALKLVGGSHLIANIKTTYRSKKPA
KNLKMPGVYYVDYRLERIKEANNETYVEQHEVAVARYCDLPSKLGHKLN*

(XTEN16 (16 amino acid sequence))

SEQ ID NO: 31

SGSETPGTSESATPES (XTEN80 (80 amino acid sequence))

SEQ ID NO: 32

GGPSSGAPPPSGGSPAGSPTSTEEGTSESATPESGPGTSTEPSEGSAPGSPAGSPTSTEEGTSTE
PSEGSAPGTSTEPSE (Dnmt3A-Dnmt3L domain)

SEQ ID NO: 33

NHDQEFDPPKVYPPVPAEKRKPIRVLSLFDGIATGLLVLKDLGIQVDRYIASEVCEDSITVG
MVRHQGKIMYVGDVRSVTQKHIQEWGPFDLVIGGSPCNDLSIVNPARKGLYEGTGRLFFEF
YRLLHDARPKEGDDRPFFWLFENVVAMGVSDKRDISRFLESNPVMIDAKEVSAAHRARYF
WGNLPGMNRPLASTVNDKLELQECLEHGRIAKFSKVRTITTRSNSIKQGKDQHFPVFMNEK
EDILWCTEMERVFGFPVHYTDVSNMSRLARQRLLGRSWSVPVIRHLFAPLKEYFACVSSGN
SNANSRGPSFSSGLVPLSLRGSHMGPMEIYKTVSAWKRQPVRVLSLFRNIDKVLKSLGFLES
GSGSGGGTLKYVEDVTNVVRRDVEKWGPFDLVYGSTQPLGSSCDRCPGWYMFQFHRILQ
YALPRQESQRPFFWIFMDNLLLTEDDQETTTRFLQTEAVTLQDVRGRDYQNAMRVWSNIP
GLKSKHAPLTPKEEEYLQAQVRSRSKLDAPKVDLLVKNCLLPLREYFKYFSQNSLPL (ddAsCfp1)

SEQ ID NO: 34

MTQFEGFTNLYQVSKTLRFELIPQGKTLKHIQEQGFIEEDKARNDHYKELKPIIDRIYKTYA
DQCLQLVQLDWENLSAAIDSYRKEKTEETRNALIEEQATYRNAIHDYFIGRTDNLTDAINK
RHAEIYKGLFKAELFNGKVLKQLGTVTTTEHENALLRSFDKFTTYFSGFYENRKNVFSAEDI
STAIPHRIVQDNFPKFKENCHIFTRLITA VPSLREHFENVKKAIGIFVSTSIEEVFSFPFYNQLL
TQTQIDLYNQLLGGISREAGTEKIKGLNEVLNLAIQKNDETAHIIASLPHRFIPLFKQILSDRN
TLSFILEEFKSDEEVIQSFCKYKTLLRNENVLETAEALFNELNSIDLTHIFISHKKLETISSALC
DHWDTLRNALYERRISELTGKITKSAKEKVQRSLKHEDINLQEIISAAGKELSEAFKQKTSEI
LSHAHAALDQPLPTTLKKQEEKEILKSQLDSLLGLYHLLDWFAVDESNEVDPEFSARLTGIK

-continued

LEMEPSLSFYNKARNYATKKPYSVEKFKLNFQMPTLASGWDVNKEKNNGAILFVKNGLY
YLGIMPKQKGRYKALSFEPTEKTSEGFDKMYYDYFPDAAKMIPKCSTQLKAVTAHFQTHT
TPILLSNNFIEPLEITKEIYDLNNPEKEPKKFQTAYAKKTGDQKGYREALCKWIDFTRDFLSK
YTKTTSIDLSSLRPSSQYKDLGEYYAELNPLLYHISFQRIAEKEIMDAVETGKLYLFQIYNKD
FAKGHHGKPNLHTLYWTGLFSPENLAKTSIKLNGQAELFYRPKSRMKRMAHRLGEKMLN
KKLKDQKTPIPDTLYQELYDYVNHRLSHDLSDEARALLPNVITKEVSHEIIKDRRFTSDKFF
FHVPITLNYQAANSPSKFNQRVNAYLKEHPETPIIGIDRGERNLIYITVIDSTGKILEQRSLNTI
QQFDYQKKLDNREKERVAARQAWSVVGTIKDLKQGYLSQVIHEIVDLMIHYQAVVVLAN
LNFGFKSKRTGIAEKAVYQQFEKMLIDKLNCLVLKDYPAEKVGGVLNPYQLTDQFTSFAK
MGTQSGFLFYVPAPYTSKIDPLTGFVDPFVWKTIKNHESRKHFLEGFDFLHYDVKTGDFILH
FKMNRNLSFQRGLPGFMPAWDIVFEKNETQFDAKGTPFIAGKRIVPVIENHRFTGRYRDLY
PANELIALLEEKGIVFRDGSNILPKLLENDDSHAIDTMVALIRSVLQMRNSNAATGEDYINSP
VRDLNGVCFDSRFQNPEWPMDADANGAYHIALKGQLLLNHLKESKDLKLQNGISNQDWL
AYIQELRN (ddLbCfp1)

SEQ ID NO: 35

MSKLEKFTNCYSLSKTLRFKAIPVGKTQENIDNKRLLVEDEKRAEDYKGVKKLLDRYYLSF
INDVLHSIKLKNLNNYISLFRKKTRTEKENKELENLEINLRKEIAKAFKGNEGYKSLFKKDII
ETILPEFLDDKDEIALVNSFNGFTTAFTGFFDNRENMFSEEAKSTSIAFRCINENLTRYISNMD
IFEKVDAIFDKHEVQEIKEKILNSDYDVEDFFEGEFFNFVLTQEGIDVYNAIIGGFVTESGEKI
KGLNEYINLYNQKTKQKLPKFKPLYKQVLSDRESLSFYGEGYTSDEEVLEVFRNTLNKNSE
IFSSIKKLEKLFKNFDEYSSAGIFVKNGPAISTISKDIFGEWNVIRDKWNAEYDDIHLKKKAV
VTEKYEDDRRKSFKKIGSFSLEQLQEYADADLSVVEKLKEIIIQKVDEIYKVYGSSEKLFDA
DFVLEKSLKKNDAVVAIMKDLLDSVKSFENYIKAFFGEGKETNRDESFYGDFVLAYDILLK
VDHIYDAIRNYVTQKPYSKDKFKLYFQNPQFMGGWDKDKETDYRATILRYGSKYYLAIM
DKKYAKCLQKIDKDDVNGNYEKINYKLLPGPNKMLPKVFFSKKWMAYYNPSEDIQKIYK
NGTFKKGDMFNLNDCHKLIDFFKDSISRYPKWSNAYDFNFSETEKYKDIAGFYREVEEQGY
KVSFESASKKEVDKLVEEGKLYMFQIYNKDFSDKSHGTPNLHTMYFKLLFDENNHGQIRLS
GGAELFMRRASLKKEELVVHPANSPIANKNPDNPKKTTTLSYDVYKDKRFSEDQYELHIPI
AINKCPKNIFKINTEVRVLLKHDDNPYVVIGIARGERNLLYIVVVDGKGNIVEQYSLNEIINNF
NGIRIKTDYHSLLDKKEKERFEARQNWTSIENIKELKAGYISQVVHKICELVEKYDAVIALA
DLNSGFKNSRVKVEKQVYQKFEKMLIDKLNYMVDKKSNPCATGGALKGYQITNKFESFKS
MSTQNGFIFYIPAWLTSKIDPSTGFVNLLKTKYTSIADSKKFISSFDRIMYVPEEDLFEFALDY
KNFSRTDADYIKKWKLYSYGNRIRIFRNPKKNNVFDWEEVCLTSAYKELFNKYGINYQQG
DIRALLCEQSDKAFYSSFMALMSLMLQMRNSITGRTDVDFLISPVKNSDGIFYDSRNYEAQ
ENAILPKNADANGAYNIARKVLWAIGQFKKAEDEKLDKVKIAISNKEWLEYAQTSVKH (ddFnCfp1)

SEQ ID NO: 36

MYPYDVPDYASGSGMSIYQEFVNKYSLSKTLRFELIPQGKTLENIKARGLILDDEKRAKDY
KKAKQIIDKYHQFFIEEILSSVCISEDLLQNYSDVYFKLKKSDDDNLQKDFKSAKDTIKKQIS
EYIKDSEKFKNLFNQNLIDAKKGQESDLILWLKQSKDNGIELFKANSDITDIDEALEIIKSFK
GWTTYFKGFHENRKNVYSSNDIPTSIIYRIVDDNLPKFLENKAKYESLKDKAPEAINYEQIK
KDLAEELTFDIDYKTSEVNQRVFSLDEVFEIANFNNYLNQSGITKENTIIGGKFVNGENTKR
KGINEYINLYSQQINDKTLKKYKMSVLFKQILSDTESKSFVIDKLEDDSDVVTTMQSFYEQI
AAFKTVEEKSIKETLSLLFDDLKAQKLDLSKIYFKNDKSLTDLSQQVFDDYSVIGTAVLEYI
TQQIAPKNLDNPSKKEQELIAKKTEKAKYLSLETIKLALEEFNKHRDIDKQCRFEEILANFA
AIPMIFDEIAQNKDNLAQISIKYQNQGKKDLLQASAEDDVKAIKDLLDQTNNLLHKLKIFHI
SQSEDKANILDKDEHFYLVFEECYFELANIVPLYNKIRNYITQKPYSDEKFKLNFENSTLAN
GWDKNKEPDNTAILFIKDDKYYLGVMNKKNNKIFDDKAIKENKGEGYKKIVYKLLPGAN
KMLPKVFFSAKSIKFYNPSEDILRIRNHSTHTKNGSPQKGYEKFEFNIEDCRKFIDFYKQSISK
HPEWKDFGFRFSDTQRYNSIDEFYREVENQGYKLTFENISESYIDSVVNQGKLYLFQIYNKD
FSAYSKGRPNLHTLYWKALFDERNLQDVVYKLNGEAELFYRKQSIPKKITHPAKEAIANKN
KDNPKKESVFEYDLIKDKRFTEDKFFFHCPITINFKSSGANKFNDEINLLLKEKANDVHILSI
ARGERHLAYYTLVDGKGNIIKQDTFNIIGNDRMKTNYHDKLAAIEKDRDSARKDWKKINN
IKEMKEGYLSQVVHEIAKLVIEYNAIVVFEDLNFGFKRGRFKVEKQVYQKLEKMLIEKLNY
LVFKDNEFDKTGGVLRAYQLTAPFETFKKMGKQTGIIYYVPAGFTSKICPVTGFVNQLYPK
YESVSKSQEFFSKFDKICYNLDKGYFEFSFDYKNFGDKAAKGKWTIASFGSRLINFRNSDKN
HNWDTREVYPTKELEKLLKDYSIEYGHGECIKAAICGESDKKFFAKLTSVLNTILQMRNSK
TGTELDYLISPVADVNGNFFDSRQAPKNMPQDADANGAYHIGLKGLMLLGRIKNNQEGKK
LNLVIKNEEYFEFVQNRN

What is claimed is:

1. A method of silencing a target nucleic acid sequence in a cell, wherein the method comprises: (i) delivering a first polynucleotide encoding a fusion protein to a cell containing the target nucleic acid, the fusion protein comprising from N-terminus to C-terminus: a DNA methyltransferase domain, a nuclease-deficient RNA-guided DNA endonuclease enzyme, and a Krüppel associated box domain wherein (1) the nuclease-deficient RNA-guided DNA endonuclease enzyme is dCas9 which comprises an amino acid sequence having at least 90% sequence identity to SEQ ID NO: 23; ddCas12a which comprises an amino acid sequence having at least 90% sequence identity to SEQ ID NO: 34; dLbCpf1 which comprises an amino acid sequence having at least 90% sequence identity to SEQ ID NO: 35; or dFnCpf1 which comprises an amino acid sequence having at least 90% sequence identity to SEQ ID NO: 36;

(2) the Krüppel associated box domain comprises an amino acid sequence having at least 90% sequence identity to SEQ ID NO: 16; and (3) the DNA methyltransferase domain comprises a Dnmt3A protein or a Dnmt3A protein and a Dnmt3L protein; wherein the Dnmt3A protein comprises an amino acid sequence with at least 90% sequence identity to SEQ ID NO: 26, and the Dnmt3L protein comprises an amino acid sequence with at least 90% sequence identity to SEQ ID NO: 28; and (ii) delivering to the cell a second polynucleotide comprising: (a) a DNA-targeting sequence that is complementary to the target nucleic acid sequence; and (b) a binding sequence for the nuclease-deficient RNA-guide DNA endonuclease enzyme.

2. The method of claim 1, wherein the Krüppel associated box domain comprises an amino acid sequence having at least 95% sequence identity to SEQ ID NO: 16.

3. The method of claim 2, wherein the Krüppel associated box domain comprises an amino acid sequence having at least 99% sequence identity to SEQ ID NO: 16.

4. The method of claim 1, wherein the Dnmt3A protein comprises an amino acid sequence with at least 95% sequence identity to SEQ ID NO: 26.

5. The method of claim 4, wherein the Dnmt3A protein comprises an amino acid sequence with at least 99% sequence identity to SEQ ID NO: 26.

6. The method of claim 1, wherein the Dnmt3L protein comprises an amino acid sequence with at least 95% sequence identity to SEQ ID NO: 28.

7. The method of claim 6, wherein the Dnmt3L protein comprises an amino acid sequence with at least 99% sequence identity to SEQ ID NO: 28.

8. The method of claim 1, wherein the dCas9 comprises an amino acid sequence having at least 95% sequence identity to SEQ ID NO: 23.

9. The method of claim 8, wherein the dCas9 comprises an amino acid sequence having at least 99% sequence identity to SEQ ID NO: 23.

10. The method of claim 1, wherein the Krüppel associated box domain comprises an amino acid sequence of SEQ ID NO: 16, the Dnmt3A protein comprises an amino acid sequence of SEQ ID NO: 26, the Dnmt3L protein comprises an amino acid sequence of SEQ ID NO: 28 and the dCas9 comprises an amino acid sequence of SEQ ID NO: 23.

11. The method of claim 1, wherein the fusion protein further comprises a nuclear localization sequence.

12. The method of claim 11, wherein the nuclear localization sequence comprises an amino acid sequence of SEQ ID NO: 25.

13. The method of claim 1, wherein the cell is a eukaryotic cell.

14. The method of claim 1, wherein the cell is a mammalian cell.

* * * * *

SEQUENCE LISTING

<160> NUMBER OF SEQ ID NOS: 96

<210> SEQ ID NO 1
<211> LENGTH: 2294
<212> TYPE: PRT
<213> ORGANISM: Artificial sequence
<220> FEATURE:
<223> OTHER INFORMATION: Synthetic polypeptide

<400> SEQUENCE: 1

Asp Ala Lys Ser Leu Thr Ala Trp Ser Arg Thr Leu Val Thr Phe Lys

-continued

```
1               5                   10                  15

Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Gly Gly Ser Gly Gly Gly Ser Met Asp
65                  70                  75                  80

Lys Lys Tyr Ser Ile Gly Leu Ala Ile Gly Thr Asn Ser Val Gly Trp
                85                  90                  95

Ala Val Ile Thr Asp Glu Tyr Lys Val Pro Ser Lys Lys Phe Lys Val
            100                 105                 110

Leu Gly Asn Thr Asp Arg His Ser Ile Lys Lys Asn Leu Ile Gly Ala
        115                 120                 125

Leu Leu Phe Asp Ser Gly Glu Thr Ala Glu Ala Thr Arg Leu Lys Arg
    130                 135                 140

Thr Ala Arg Arg Arg Tyr Thr Arg Arg Lys Asn Arg Ile Cys Tyr Leu
145                 150                 155                 160

Gln Glu Ile Phe Ser Asn Glu Met Ala Lys Val Asp Asp Ser Phe Phe
                165                 170                 175

His Arg Leu Glu Glu Ser Phe Leu Val Glu Glu Asp Lys Lys His Glu
            180                 185                 190

Arg His Pro Ile Phe Gly Asn Ile Val Asp Glu Val Ala Tyr His Glu
        195                 200                 205

Lys Tyr Pro Thr Ile Tyr His Leu Arg Lys Lys Leu Val Asp Ser Thr
    210                 215                 220

Asp Lys Ala Asp Leu Arg Leu Ile Tyr Leu Ala Leu Ala His Met Ile
225                 230                 235                 240

Lys Phe Arg Gly His Phe Leu Ile Glu Gly Asp Leu Asn Pro Asp Asn
                245                 250                 255

Ser Asp Val Asp Lys Leu Phe Ile Gln Leu Val Gln Thr Tyr Asn Gln
            260                 265                 270

Leu Phe Glu Glu Asn Pro Ile Asn Ala Ser Gly Val Asp Ala Lys Ala
        275                 280                 285

Ile Leu Ser Ala Arg Leu Ser Lys Ser Arg Arg Leu Glu Asn Leu Ile
    290                 295                 300

Ala Gln Leu Pro Gly Glu Lys Lys Asn Gly Leu Phe Gly Asn Leu Ile
305                 310                 315                 320

Ala Leu Ser Leu Gly Leu Thr Pro Asn Phe Lys Ser Asn Phe Asp Leu
                325                 330                 335

Ala Glu Asp Ala Lys Leu Gln Leu Ser Lys Asp Thr Tyr Asp Asp Asp
            340                 345                 350

Leu Asp Asn Leu Leu Ala Gln Ile Gly Asp Gln Tyr Ala Asp Leu Phe
        355                 360                 365

Leu Ala Ala Lys Asn Leu Ser Asp Ala Ile Leu Leu Ser Asp Ile Leu
    370                 375                 380

Arg Val Asn Thr Glu Ile Thr Lys Ala Pro Leu Ser Ala Ser Met Ile
385                 390                 395                 400

Lys Arg Tyr Asp Glu His His Gln Asp Leu Thr Leu Leu Lys Ala Leu
                405                 410                 415

Val Arg Gln Gln Leu Pro Glu Lys Tyr Lys Glu Ile Phe Phe Asp Gln
            420                 425                 430
```

```
Ser Lys Asn Gly Tyr Ala Gly Tyr Ile Asp Gly Gly Ala Ser Gln Glu
        435                 440                 445

Glu Phe Tyr Lys Phe Ile Lys Pro Ile Leu Glu Lys Met Asp Gly Thr
    450                 455                 460

Glu Glu Leu Leu Val Lys Leu Asn Arg Glu Asp Leu Leu Arg Lys Gln
465                 470                 475                 480

Arg Thr Phe Asp Asn Gly Ser Ile Pro His Gln Ile His Leu Gly Glu
                485                 490                 495

Leu His Ala Ile Leu Arg Arg Gln Glu Asp Phe Tyr Pro Phe Leu Lys
            500                 505                 510

Asp Asn Arg Glu Lys Ile Glu Lys Ile Leu Thr Phe Arg Ile Pro Tyr
        515                 520                 525

Tyr Val Gly Pro Leu Ala Arg Gly Asn Ser Arg Phe Ala Trp Met Thr
    530                 535                 540

Arg Lys Ser Glu Glu Thr Ile Thr Pro Trp Asn Phe Glu Glu Val Val
545                 550                 555                 560

Asp Lys Gly Ala Ser Ala Gln Ser Phe Ile Glu Arg Met Thr Asn Phe
                565                 570                 575

Asp Lys Asn Leu Pro Asn Glu Lys Val Leu Pro Lys His Ser Leu Leu
            580                 585                 590

Tyr Glu Tyr Phe Thr Val Tyr Asn Glu Leu Thr Lys Val Lys Tyr Val
        595                 600                 605

Thr Glu Gly Met Arg Lys Pro Ala Phe Leu Ser Gly Glu Gln Lys Lys
    610                 615                 620

Ala Ile Val Asp Leu Leu Phe Lys Thr Asn Arg Lys Val Thr Val Lys
625                 630                 635                 640

Gln Leu Lys Glu Asp Tyr Phe Lys Lys Ile Glu Cys Phe Asp Ser Val
                645                 650                 655

Glu Ile Ser Gly Val Glu Asp Arg Phe Asn Ala Ser Leu Gly Thr Tyr
            660                 665                 670

His Asp Leu Leu Lys Ile Ile Lys Asp Lys Asp Phe Leu Asp Asn Glu
        675                 680                 685

Glu Asn Glu Asp Ile Leu Glu Asp Ile Val Leu Thr Leu Thr Leu Phe
    690                 695                 700

Glu Asp Arg Glu Met Ile Glu Glu Arg Leu Lys Thr Tyr Ala His Leu
705                 710                 715                 720

Phe Asp Asp Lys Val Met Lys Gln Leu Lys Arg Arg Arg Tyr Thr Gly
                725                 730                 735

Trp Gly Arg Leu Ser Arg Lys Leu Ile Asn Gly Ile Arg Asp Lys Gln
            740                 745                 750

Ser Gly Lys Thr Ile Leu Asp Phe Leu Lys Ser Asp Gly Phe Ala Asn
        755                 760                 765

Arg Asn Phe Met Gln Leu Ile His Asp Asp Ser Leu Thr Phe Lys Glu
    770                 775                 780

Asp Ile Gln Lys Ala Gln Val Ser Gly Gln Gly Asp Ser Leu His Glu
785                 790                 795                 800

His Ile Ala Asn Leu Ala Gly Ser Pro Ala Ile Lys Lys Gly Ile Leu
                805                 810                 815

Gln Thr Val Lys Val Val Asp Glu Leu Val Lys Val Met Gly Arg His
            820                 825                 830

Lys Pro Glu Asn Ile Val Ile Glu Met Ala Arg Glu Asn Gln Thr Thr
        835                 840                 845
```

```
Gln Lys Gly Gln Lys Asn Ser Arg Glu Arg Met Lys Arg Ile Glu Glu
    850                 855                 860

Gly Ile Lys Glu Leu Gly Ser Gln Ile Leu Lys Glu His Pro Val Glu
865                 870                 875                 880

Asn Thr Gln Leu Gln Asn Glu Lys Leu Tyr Leu Tyr Tyr Leu Gln Asn
                885                 890                 895

Gly Arg Asp Met Tyr Val Asp Gln Glu Leu Asp Ile Asn Arg Leu Ser
            900                 905                 910

Asp Tyr Asp Val Asp Ala Ile Val Pro Gln Ser Phe Leu Lys Asp Asp
        915                 920                 925

Ser Ile Asp Asn Lys Val Leu Thr Arg Ser Asp Lys Asn Arg Gly Lys
    930                 935                 940

Ser Asp Asn Val Pro Ser Glu Glu Val Val Lys Lys Met Lys Asn Tyr
945                 950                 955                 960

Trp Arg Gln Leu Leu Asn Ala Lys Leu Ile Thr Gln Arg Lys Phe Asp
                965                 970                 975

Asn Leu Thr Lys Ala Glu Arg Gly Gly Leu Ser Glu Leu Asp Lys Ala
            980                 985                 990

Gly Phe Ile Lys Arg Gln Leu Val  Glu Thr Arg Gln Ile  Thr Lys His
        995                 1000                1005

Val Ala  Gln Ile Leu Asp Ser  Arg Met Asn Thr Lys  Tyr Asp Glu
    1010                1015                1020

Asn Asp  Lys Leu Ile Arg Glu  Val Lys Val Ile Thr  Leu Lys Ser
    1025                1030                1035

Lys Leu  Val Ser Asp Phe Arg  Lys Asp Phe Gln Phe  Tyr Lys Val
    1040                1045                1050

Arg Glu  Ile Asn Asn Tyr His  His Ala His Asp Ala  Tyr Leu Asn
    1055                1060                1065

Ala Val  Val Gly Thr Ala Leu  Ile Lys Lys Tyr Pro  Lys Leu Glu
    1070                1075                1080

Ser Glu  Phe Val Tyr Gly Asp  Tyr Lys Val Tyr Asp  Val Arg Lys
    1085                1090                1095

Met Ile  Ala Lys Ser Glu Gln  Glu Ile Gly Lys Ala  Thr Ala Lys
    1100                1105                1110

Tyr Phe  Phe Tyr Ser Asn Ile  Met Asn Phe Phe Lys  Thr Glu Ile
    1115                1120                1125

Thr Leu  Ala Asn Gly Glu Ile  Arg Lys Arg Pro Leu  Ile Glu Thr
    1130                1135                1140

Asn Gly  Glu Thr Gly Glu Ile  Val Trp Asp Lys Gly  Arg Asp Phe
    1145                1150                1155

Ala Thr  Val Arg Lys Val Leu  Ser Met Pro Gln Val  Asn Ile Val
    1160                1165                1170

Lys Lys  Thr Glu Val Gln Thr  Gly Gly Phe Ser Lys  Glu Ser Ile
    1175                1180                1185

Leu Pro  Lys Arg Asn Ser Asp  Lys Leu Ile Ala Arg  Lys Lys Asp
    1190                1195                1200

Trp Asp  Pro Lys Lys Tyr Gly  Gly Phe Asp Ser Pro  Thr Val Ala
    1205                1210                1215

Tyr Ser  Val Leu Val Val Ala  Lys Val Glu Lys Gly  Lys Ser Lys
    1220                1225                1230

Lys Leu  Lys Ser Val Lys Glu  Leu Leu Gly Ile Thr  Ile Met Glu
    1235                1240                1245

Arg Ser  Ser Phe Glu Lys Asn  Pro Ile Asp Phe Leu  Glu Ala Lys
```

```
    1250                1255                1260

Gly Tyr  Lys Glu Val Lys Lys  Asp Leu Ile Ile Lys  Leu Pro Lys
    1265                1270                1275

Tyr Ser  Leu Phe Glu Leu Glu  Asn Gly Arg Lys Arg  Met Leu Ala
    1280                1285                1290

Ser Ala  Gly Glu Leu Gln Lys  Gly Asn Glu Leu Ala  Leu Pro Ser
    1295                1300                1305

Lys Tyr  Val Asn Phe Leu Tyr  Leu Ala Ser His Tyr  Glu Lys Leu
    1310                1315                1320

Lys Gly  Ser Pro Glu Asp Asn  Glu Gln Lys Gln Leu  Phe Val Glu
    1325                1330                1335

Gln His  Lys His Tyr Leu Asp  Glu Ile Ile Glu Gln  Ile Ser Glu
    1340                1345                1350

Phe Ser  Lys Arg Val Ile Leu  Ala Asp Ala Asn Leu  Asp Lys Val
    1355                1360                1365

Leu Ser  Ala Tyr Asn Lys His  Arg Asp Lys Pro Ile  Arg Glu Gln
    1370                1375                1380

Ala Glu  Asn Ile Ile His Leu  Phe Thr Leu Thr Asn  Leu Gly Ala
    1385                1390                1395

Pro Ala  Ala Phe Lys Tyr Phe  Asp Thr Thr Ile Asp  Arg Lys Arg
    1400                1405                1410

Tyr Thr  Ser Thr Lys Glu Val  Leu Asp Ala Thr Leu  Ile His Gln
    1415                1420                1425

Ser Ile  Thr Gly Leu Tyr Glu  Thr Arg Ile Asp Leu  Ser Gln Leu
    1430                1435                1440

Gly Gly  Asp Ser Arg Ala Asp  Tyr Pro Tyr Asp Val  Pro Asp Tyr
    1445                1450                1455

Ala Ser  Gly Ser Pro Lys Lys  Lys Arg Lys Val Glu  Ala Ser Gly
    1460                1465                1470

Ser Gly  Arg Ala Ser Pro Gly  Ile Pro Gly Ser Thr  Arg Asn His
    1475                1480                1485

Asp Gln  Glu Phe Asp Pro Pro  Lys Val Tyr Pro Pro  Val Pro Ala
    1490                1495                1500

Glu Lys  Arg Lys Pro Ile Arg  Val Leu Ser Leu Phe  Asp Gly Ile
    1505                1510                1515

Ala Thr  Gly Leu Leu Val Leu  Lys Asp Leu Gly Ile  Gln Val Asp
    1520                1525                1530

Arg Tyr  Ile Ala Ser Glu Val  Cys Glu Asp Ser Ile  Thr Val Gly
    1535                1540                1545

Met Val  Arg His Gln Gly Lys  Ile Met Tyr Val Gly  Asp Val Arg
    1550                1555                1560

Ser Val  Thr Gln Lys His Ile  Gln Glu Trp Gly Pro  Phe Asp Leu
    1565                1570                1575

Val Ile  Gly Gly Ser Pro Cys  Asn Asp Leu Ser Ile  Val Asn Pro
    1580                1585                1590

Ala Arg  Lys Gly Leu Tyr Glu  Gly Thr Gly Arg Leu  Phe Phe Glu
    1595                1600                1605

Phe Tyr  Arg Leu Leu His Asp  Ala Arg Pro Lys Glu  Gly Asp Asp
    1610                1615                1620

Arg Pro  Phe Phe Trp Leu Phe  Glu Asn Val Val Ala  Met Gly Val
    1625                1630                1635

Ser Asp  Lys Arg Asp Ile Ser  Arg Phe Leu Glu Ser  Asn Pro Val
    1640                1645                1650
```

```
Met Ile Asp Ala Lys Glu Val Ser Ala Ala His Arg Ala Arg Tyr
    1655                1660                1665

Phe Trp Gly Asn Leu Pro Gly Met Asn Arg Pro Leu Ala Ser Thr
    1670                1675                1680

Val Asn Asp Lys Leu Glu Leu Gln Glu Cys Leu Glu His Gly Arg
    1685                1690                1695

Ile Ala Lys Phe Ser Lys Val Arg Thr Ile Thr Thr Arg Ser Asn
    1700                1705                1710

Ser Ile Lys Gln Gly Lys Asp Gln His Phe Pro Val Phe Met Asn
    1715                1720                1725

Glu Lys Glu Asp Ile Leu Trp Cys Thr Glu Met Glu Arg Val Phe
    1730                1735                1740

Gly Phe Pro Val His Tyr Thr Asp Val Ser Asn Met Ser Arg Leu
    1745                1750                1755

Ala Arg Gln Arg Leu Leu Gly Arg Ser Trp Ser Val Pro Val Ile
    1760                1765                1770

Arg His Leu Phe Ala Pro Leu Lys Glu Tyr Phe Ala Cys Val Ser
    1775                1780                1785

Ser Gly Asn Ser Asn Ala Asn Ser Arg Gly Pro Ser Phe Ser Ser
    1790                1795                1800

Gly Leu Val Pro Leu Ser Leu Arg Gly Ser His Met Gly Pro Met
    1805                1810                1815

Glu Ile Tyr Lys Thr Val Ser Ala Trp Lys Arg Gln Pro Val Arg
    1820                1825                1830

Val Leu Ser Leu Phe Arg Asn Ile Asp Lys Val Leu Lys Ser Leu
    1835                1840                1845

Gly Phe Leu Glu Ser Gly Ser Gly Ser Gly Gly Gly Thr Leu Lys
    1850                1855                1860

Tyr Val Glu Asp Val Thr Asn Val Val Arg Arg Asp Val Glu Lys
    1865                1870                1875

Trp Gly Pro Phe Asp Leu Val Tyr Gly Ser Thr Gln Pro Leu Gly
    1880                1885                1890

Ser Ser Cys Asp Arg Cys Pro Gly Trp Tyr Met Phe Gln Phe His
    1895                1900                1905

Arg Ile Leu Gln Tyr Ala Leu Pro Arg Gln Glu Ser Gln Arg Pro
    1910                1915                1920

Phe Phe Trp Ile Phe Met Asp Asn Leu Leu Leu Thr Glu Asp Asp
    1925                1930                1935

Gln Glu Thr Thr Thr Arg Phe Leu Gln Thr Glu Ala Val Thr Leu
    1940                1945                1950

Gln Asp Val Arg Gly Arg Asp Tyr Gln Asn Ala Met Arg Val Trp
    1955                1960                1965

Ser Asn Ile Pro Gly Leu Lys Ser Lys His Ala Pro Leu Thr Pro
    1970                1975                1980

Lys Glu Glu Glu Tyr Leu Gln Ala Gln Val Arg Ser Arg Ser Lys
    1985                1990                1995

Leu Asp Ala Pro Lys Val Asp Leu Leu Val Lys Asn Cys Leu Leu
    2000                2005                2010

Pro Leu Arg Glu Tyr Phe Lys Tyr Phe Ser Gln Asn Ser Leu Pro
    2015                2020                2025

Leu Ser Arg Ala Asp Pro Lys Lys Lys Arg Lys Val Gly Ser Gly
    2030                2035                2040
```

```
Ala Thr  Asn Phe Ser Leu Leu  Lys Gln Ala Gly Asp  Val Glu Glu
    2045                 2050                 2055

Asn Pro  Gly Pro Ser Glu Leu  Ile Lys Glu Asn Met  His Met Lys
    2060                 2065                 2070

Leu Tyr  Met Glu Gly Thr Val  Asp Asn His His Phe  Lys Cys Thr
    2075                 2080                 2085

Ser Glu  Gly Glu Gly Lys Pro  Tyr Glu Gly Thr Gln  Thr Met Arg
    2090                 2095                 2100

Ile Lys  Val Val Glu Gly Gly  Pro Leu Pro Phe Ala  Phe Asp Ile
    2105                 2110                 2115

Leu Ala  Thr Ser Phe Leu Tyr  Gly Ser Lys Thr Phe  Ile Asn His
    2120                 2125                 2130

Thr Gln  Gly Ile Pro Asp Phe  Phe Lys Gln Ser Phe  Pro Glu Gly
    2135                 2140                 2145

Phe Thr  Trp Glu Arg Val Thr  Thr Tyr Glu Asp Gly  Gly Val Leu
    2150                 2155                 2160

Thr Ala  Thr Gln Asp Thr Ser  Leu Gln Asp Gly Cys  Leu Ile Tyr
    2165                 2170                 2175

Asn Val  Lys Ile Arg Gly Val  Asn Phe Thr Ser Asn  Gly Pro Val
    2180                 2185                 2190

Met Gln  Lys Lys Thr Leu Gly  Trp Glu Ala Phe Thr  Glu Thr Leu
    2195                 2200                 2205

Tyr Pro  Ala Asp Gly Gly Leu  Glu Gly Arg Asn Asp  Met Ala Leu
    2210                 2215                 2220

Lys Leu  Val Gly Gly Ser His  Leu Ile Ala Asn Ile  Lys Thr Thr
    2225                 2230                 2235

Tyr Arg  Ser Lys Lys Pro Ala  Lys Asn Leu Lys Met  Pro Gly Val
    2240                 2245                 2250

Tyr Tyr  Val Asp Tyr Arg Leu  Glu Arg Ile Lys Glu  Ala Asn Asn
    2255                 2260                 2265

Glu Thr  Tyr Val Glu Gln His  Glu Val Ala Val Ala  Arg Tyr Cys
    2270                 2275                 2280

Asp Leu  Pro Ser Lys Leu Gly  His Lys Leu Asn
    2285                 2290
```

<210> SEQ ID NO 2
<211> LENGTH: 2296
<212> TYPE: PRT
<213> ORGANISM: Artificial sequence
<220> FEATURE:
<223> OTHER INFORMATION: Synthetic polypeptide

<400> SEQUENCE: 2

```
Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Gly Gly Ser Gly Gly Gly Ser Met Asp
65                  70                  75                  80

Lys Lys Tyr Ser Ile Gly Leu Ala Ile Gly Thr Asn Ser Val Gly Trp
                85                  90                  95
```

-continued

Ala Val Ile Thr Asp Glu Tyr Lys Val Pro Ser Lys Lys Phe Lys Val
100 105 110

Leu Gly Asn Thr Asp Arg His Ser Ile Lys Lys Asn Leu Ile Gly Ala
115 120 125

Leu Leu Phe Asp Ser Gly Glu Thr Ala Glu Ala Thr Arg Leu Lys Arg
130 135 140

Thr Ala Arg Arg Arg Tyr Thr Arg Arg Lys Asn Arg Ile Cys Tyr Leu
145 150 155 160

Gln Glu Ile Phe Ser Asn Glu Met Ala Lys Val Asp Asp Ser Phe Phe
165 170 175

His Arg Leu Glu Glu Ser Phe Leu Val Glu Glu Asp Lys Lys His Glu
180 185 190

Arg His Pro Ile Phe Gly Asn Ile Val Asp Glu Val Ala Tyr His Glu
195 200 205

Lys Tyr Pro Thr Ile Tyr His Leu Arg Lys Lys Leu Val Asp Ser Thr
210 215 220

Asp Lys Ala Asp Leu Arg Leu Ile Tyr Leu Ala Leu Ala His Met Ile
225 230 235 240

Lys Phe Arg Gly His Phe Leu Ile Glu Gly Asp Leu Asn Pro Asp Asn
245 250 255

Ser Asp Val Asp Lys Leu Phe Ile Gln Leu Val Gln Thr Tyr Asn Gln
260 265 270

Leu Phe Glu Glu Asn Pro Ile Asn Ala Ser Gly Val Asp Ala Lys Ala
275 280 285

Ile Leu Ser Ala Arg Leu Ser Lys Ser Arg Arg Leu Glu Asn Leu Ile
290 295 300

Ala Gln Leu Pro Gly Glu Lys Lys Asn Gly Leu Phe Gly Asn Leu Ile
305 310 315 320

Ala Leu Ser Leu Gly Leu Thr Pro Asn Phe Lys Ser Asn Phe Asp Leu
325 330 335

Ala Glu Asp Ala Lys Leu Gln Leu Ser Lys Asp Thr Tyr Asp Asp Asp
340 345 350

Leu Asp Asn Leu Leu Ala Gln Ile Gly Asp Gln Tyr Ala Asp Leu Phe
355 360 365

Leu Ala Ala Lys Asn Leu Ser Asp Ala Ile Leu Leu Ser Asp Ile Leu
370 375 380

Arg Val Asn Thr Glu Ile Thr Lys Ala Pro Leu Ser Ala Ser Met Ile
385 390 395 400

Lys Arg Tyr Asp Glu His His Gln Asp Leu Thr Leu Leu Lys Ala Leu
405 410 415

Val Arg Gln Gln Leu Pro Glu Lys Tyr Lys Glu Ile Phe Phe Asp Gln
420 425 430

Ser Lys Asn Gly Tyr Ala Gly Tyr Ile Asp Gly Gly Ala Ser Gln Glu
435 440 445

Glu Phe Tyr Lys Phe Ile Lys Pro Ile Leu Glu Lys Met Asp Gly Thr
450 455 460

Glu Glu Leu Leu Val Lys Leu Asn Arg Glu Asp Leu Leu Arg Lys Gln
465 470 475 480

Arg Thr Phe Asp Asn Gly Ser Ile Pro His Gln Ile His Leu Gly Glu
485 490 495

Leu His Ala Ile Leu Arg Arg Gln Glu Asp Phe Tyr Pro Phe Leu Lys
500 505 510

Asp Asn Arg Glu Lys Ile Glu Lys Ile Leu Thr Phe Arg Ile Pro Tyr

```
        515                 520                 525

Tyr Val Gly Pro Leu Ala Arg Gly Asn Ser Arg Phe Ala Trp Met Thr
    530                 535                 540

Arg Lys Ser Glu Glu Thr Ile Thr Pro Trp Asn Phe Glu Glu Val Val
545                 550                 555                 560

Asp Lys Gly Ala Ser Ala Gln Ser Phe Ile Glu Arg Met Thr Asn Phe
                565                 570                 575

Asp Lys Asn Leu Pro Asn Glu Lys Val Leu Pro Lys His Ser Leu Leu
            580                 585                 590

Tyr Glu Tyr Phe Thr Val Tyr Asn Glu Leu Thr Lys Val Lys Tyr Val
        595                 600                 605

Thr Glu Gly Met Arg Lys Pro Ala Phe Leu Ser Gly Glu Gln Lys Lys
    610                 615                 620

Ala Ile Val Asp Leu Leu Phe Lys Thr Asn Arg Lys Val Thr Val Lys
625                 630                 635                 640

Gln Leu Lys Glu Asp Tyr Phe Lys Lys Ile Glu Cys Phe Asp Ser Val
                645                 650                 655

Glu Ile Ser Gly Val Glu Asp Arg Phe Asn Ala Ser Leu Gly Thr Tyr
            660                 665                 670

His Asp Leu Leu Lys Ile Ile Lys Asp Lys Asp Phe Leu Asp Asn Glu
        675                 680                 685

Glu Asn Glu Asp Ile Leu Glu Asp Ile Val Leu Thr Leu Thr Leu Phe
    690                 695                 700

Glu Asp Arg Glu Met Ile Glu Glu Arg Leu Lys Thr Tyr Ala His Leu
705                 710                 715                 720

Phe Asp Asp Lys Val Met Lys Gln Leu Lys Arg Arg Arg Tyr Thr Gly
                725                 730                 735

Trp Gly Arg Leu Ser Arg Lys Leu Ile Asn Gly Ile Arg Asp Lys Gln
            740                 745                 750

Ser Gly Lys Thr Ile Leu Asp Phe Leu Lys Ser Asp Gly Phe Ala Asn
        755                 760                 765

Arg Asn Phe Met Gln Leu Ile His Asp Asp Ser Leu Thr Phe Lys Glu
    770                 775                 780

Asp Ile Gln Lys Ala Gln Val Ser Gly Gln Gly Asp Ser Leu His Glu
785                 790                 795                 800

His Ile Ala Asn Leu Ala Gly Ser Pro Ala Ile Lys Lys Gly Ile Leu
                805                 810                 815

Gln Thr Val Lys Val Val Asp Glu Leu Val Lys Val Met Gly Arg His
            820                 825                 830

Lys Pro Glu Asn Ile Val Ile Glu Met Ala Arg Glu Asn Gln Thr Thr
        835                 840                 845

Gln Lys Gly Gln Lys Asn Ser Arg Glu Arg Met Lys Arg Ile Glu Glu
    850                 855                 860

Gly Ile Lys Glu Leu Gly Ser Gln Ile Leu Lys Glu His Pro Val Glu
865                 870                 875                 880

Asn Thr Gln Leu Gln Asn Glu Lys Leu Tyr Leu Tyr Tyr Leu Gln Asn
                885                 890                 895

Gly Arg Asp Met Tyr Val Asp Gln Glu Leu Asp Ile Asn Arg Leu Ser
            900                 905                 910

Asp Tyr Asp Val Asp Ala Ile Val Pro Gln Ser Phe Leu Lys Asp Asp
        915                 920                 925

Ser Ile Asp Asn Lys Val Leu Thr Arg Ser Asp Lys Asn Arg Gly Lys
    930                 935                 940
```

```
Ser Asp Asn Val Pro Ser Glu Glu Val Val Lys Lys Met Lys Asn Tyr
945                 950                 955                 960

Trp Arg Gln Leu Leu Asn Ala Lys Leu Ile Thr Gln Arg Lys Phe Asp
                965                 970                 975

Asn Leu Thr Lys Ala Glu Arg Gly Gly Leu Ser Glu Leu Asp Lys Ala
            980                 985                 990

Gly Phe Ile Lys Arg Gln Leu Val  Glu Thr Arg Gln Ile  Thr Lys His
        995                 1000                 1005

Val Ala  Gln Ile Leu Asp Ser  Arg Met Asn Thr Lys  Tyr Asp Glu
    1010                 1015                 1020

Asn Asp  Lys Leu Ile Arg Glu  Val Lys Val Ile Thr  Leu Lys Ser
    1025                 1030                 1035

Lys Leu  Val Ser Asp Phe Arg  Lys Asp Phe Gln Phe  Tyr Lys Val
    1040                 1045                 1050

Arg Glu  Ile Asn Asn Tyr His  His Ala His Asp Ala  Tyr Leu Asn
    1055                 1060                 1065

Ala Val  Val Gly Thr Ala Leu  Ile Lys Lys Tyr Pro  Lys Leu Glu
    1070                 1075                 1080

Ser Glu  Phe Val Tyr Gly Asp  Tyr Lys Val Tyr Asp  Val Arg Lys
    1085                 1090                 1095

Met Ile  Ala Lys Ser Glu Gln  Glu Ile Gly Lys Ala  Thr Ala Lys
    1100                 1105                 1110

Tyr Phe  Phe Tyr Ser Asn Ile  Met Asn Phe Phe Lys  Thr Glu Ile
    1115                 1120                 1125

Thr Leu  Ala Asn Gly Glu Ile  Arg Lys Arg Pro Leu  Ile Glu Thr
    1130                 1135                 1140

Asn Gly  Glu Thr Gly Glu Ile  Val Trp Asp Lys Gly  Arg Asp Phe
    1145                 1150                 1155

Ala Thr  Val Arg Lys Val Leu  Ser Met Pro Gln Val  Asn Ile Val
    1160                 1165                 1170

Lys Lys  Thr Glu Val Gln Thr  Gly Gly Phe Ser Lys  Glu Ser Ile
    1175                 1180                 1185

Leu Pro  Lys Arg Asn Ser Asp  Lys Leu Ile Ala Arg  Lys Lys Asp
    1190                 1195                 1200

Trp Asp  Pro Lys Lys Tyr Gly  Gly Phe Asp Ser Pro  Thr Val Ala
    1205                 1210                 1215

Tyr Ser  Val Leu Val Val Ala  Lys Val Glu Lys Gly  Lys Ser Lys
    1220                 1225                 1230

Lys Leu  Lys Ser Val Lys Glu  Leu Leu Gly Ile Thr  Ile Met Glu
    1235                 1240                 1245

Arg Ser  Ser Phe Glu Lys Asn  Pro Ile Asp Phe Leu  Glu Ala Lys
    1250                 1255                 1260

Gly Tyr  Lys Glu Val Lys Lys  Asp Leu Ile Ile Lys  Leu Pro Lys
    1265                 1270                 1275

Tyr Ser  Leu Phe Glu Leu Glu  Asn Gly Arg Lys Arg  Met Leu Ala
    1280                 1285                 1290

Ser Ala  Gly Glu Leu Gln Lys  Gly Asn Glu Leu Ala  Leu Pro Ser
    1295                 1300                 1305

Lys Tyr  Val Asn Phe Leu Tyr  Leu Ala Ser His Tyr  Glu Lys Leu
    1310                 1315                 1320

Lys Gly  Ser Pro Glu Asp Asn  Glu Gln Lys Gln Leu  Phe Val Glu
    1325                 1330                 1335
```

```
Gln His Lys His Tyr Leu Asp Glu Ile Ile Glu Gln Ile Ser Glu
    1340                1345                1350

Phe Ser Lys Arg Val Ile Leu Ala Asp Ala Asn Leu Asp Lys Val
    1355                1360                1365

Leu Ser Ala Tyr Asn Lys His Arg Asp Lys Pro Ile Arg Glu Gln
    1370                1375                1380

Ala Glu Asn Ile Ile His Leu Phe Thr Leu Thr Asn Leu Gly Ala
    1385                1390                1395

Pro Ala Ala Phe Lys Tyr Phe Asp Thr Thr Ile Asp Arg Lys Arg
    1400                1405                1410

Tyr Thr Ser Thr Lys Glu Val Leu Asp Ala Thr Leu Ile His Gln
    1415                1420                1425

Ser Ile Thr Gly Leu Tyr Glu Thr Arg Ile Asp Leu Ser Gln Leu
    1430                1435                1440

Gly Gly Asp Ser Arg Ala Asp Tyr Pro Tyr Asp Val Pro Asp Tyr
    1445                1450                1455

Ala Ser Gly Ser Pro Lys Lys Lys Arg Lys Val Ser Pro Gly Ser
    1460                1465                1470

Gly Ser Glu Thr Pro Gly Thr Ser Glu Ser Ala Thr Pro Glu Ser
    1475                1480                1485

Asn His Asp Gln Glu Phe Asp Pro Pro Lys Val Tyr Pro Pro Val
    1490                1495                1500

Pro Ala Glu Lys Arg Lys Pro Ile Arg Val Leu Ser Leu Phe Asp
    1505                1510                1515

Gly Ile Ala Thr Gly Leu Leu Val Leu Lys Asp Leu Gly Ile Gln
    1520                1525                1530

Val Asp Arg Tyr Ile Ala Ser Glu Val Cys Glu Asp Ser Ile Thr
    1535                1540                1545

Val Gly Met Val Arg His Gln Gly Lys Ile Met Tyr Val Gly Asp
    1550                1555                1560

Val Arg Ser Val Thr Gln Lys His Ile Gln Glu Trp Gly Pro Phe
    1565                1570                1575

Asp Leu Val Ile Gly Gly Ser Pro Cys Asn Asp Leu Ser Ile Val
    1580                1585                1590

Asn Pro Ala Arg Lys Gly Leu Tyr Glu Gly Thr Gly Arg Leu Phe
    1595                1600                1605

Phe Glu Phe Tyr Arg Leu Leu His Asp Ala Arg Pro Lys Glu Gly
    1610                1615                1620

Asp Asp Arg Pro Phe Phe Trp Leu Phe Glu Asn Val Val Ala Met
    1625                1630                1635

Gly Val Ser Asp Lys Arg Asp Ile Ser Arg Phe Leu Glu Ser Asn
    1640                1645                1650

Pro Val Met Ile Asp Ala Lys Glu Val Ser Ala Ala His Arg Ala
    1655                1660                1665

Arg Tyr Phe Trp Gly Asn Leu Pro Gly Met Asn Arg Pro Leu Ala
    1670                1675                1680

Ser Thr Val Asn Asp Lys Leu Glu Leu Gln Glu Cys Leu Glu His
    1685                1690                1695

Gly Arg Ile Ala Lys Phe Ser Lys Val Arg Thr Ile Thr Thr Arg
    1700                1705                1710

Ser Asn Ser Ile Lys Gln Gly Lys Asp Gln His Phe Pro Val Phe
    1715                1720                1725

Met Asn Glu Lys Glu Asp Ile Leu Trp Cys Thr Glu Met Glu Arg
```

```
    1730                1735                1740

Val Phe  Gly Phe Pro Val His  Tyr Thr Asp Val Ser  Asn Met Ser
    1745                1750                1755

Arg Leu  Ala Arg Gln Arg Leu  Leu Gly Arg Ser Trp  Ser Val Pro
    1760                1765                1770

Val Ile  Arg His Leu Phe Ala  Pro Leu Lys Glu Tyr  Phe Ala Cys
    1775                1780                1785

Val Ser  Ser Gly Asn Ser Asn  Ala Asn Ser Arg Gly  Pro Ser Phe
    1790                1795                1800

Ser Ser  Gly Leu Val Pro Leu  Ser Leu Arg Gly Ser  His Met Gly
    1805                1810                1815

Pro Met  Glu Ile Tyr Lys Thr  Val Ser Ala Trp Lys  Arg Gln Pro
    1820                1825                1830

Val Arg  Val Leu Ser Leu Phe  Arg Asn Ile Asp Lys  Val Leu Lys
    1835                1840                1845

Ser Leu  Gly Phe Leu Glu Ser  Gly Ser Gly Ser Gly  Gly Gly Thr
    1850                1855                1860

Leu Lys  Tyr Val Glu Asp Val  Thr Asn Val Val Arg  Arg Asp Val
    1865                1870                1875

Glu Lys  Trp Gly Pro Phe Asp  Leu Val Tyr Gly Ser  Thr Gln Pro
    1880                1885                1890

Leu Gly  Ser Ser Cys Asp Arg  Cys Pro Gly Trp Tyr  Met Phe Gln
    1895                1900                1905

Phe His  Arg Ile Leu Gln Tyr  Ala Leu Pro Arg Gln  Glu Ser Gln
    1910                1915                1920

Arg Pro  Phe Phe Trp Ile Phe  Met Asp Asn Leu Leu  Leu Thr Glu
    1925                1930                1935

Asp Asp  Gln Glu Thr Thr Thr  Arg Phe Leu Gln Thr  Glu Ala Val
    1940                1945                1950

Thr Leu  Gln Asp Val Arg Gly  Arg Asp Tyr Gln Asn  Ala Met Arg
    1955                1960                1965

Val Trp  Ser Asn Ile Pro Gly  Leu Lys Ser Lys His  Ala Pro Leu
    1970                1975                1980

Thr Pro  Lys Glu Glu Glu Tyr  Leu Gln Ala Gln Val  Arg Ser Arg
    1985                1990                1995

Ser Lys  Leu Asp Ala Pro Lys  Val Asp Leu Leu Val  Lys Asn Cys
    2000                2005                2010

Leu Leu  Pro Leu Arg Glu Tyr  Phe Lys Tyr Phe Ser  Gln Asn Ser
    2015                2020                2025

Leu Pro  Leu Ser Arg Ala Asp  Pro Lys Lys Lys Arg  Lys Val Gly
    2030                2035                2040

Ser Gly  Ala Thr Asn Phe Ser  Leu Leu Lys Gln Ala  Gly Asp Val
    2045                2050                2055

Glu Glu  Asn Pro Gly Pro Ser  Glu Leu Ile Lys Glu  Asn Met His
    2060                2065                2070

Met Lys  Leu Tyr Met Glu Gly  Thr Val Asp Asn His  His Phe Lys
    2075                2080                2085

Cys Thr  Ser Glu Gly Glu Gly  Lys Pro Tyr Glu Gly  Thr Gln Thr
    2090                2095                2100

Met Arg  Ile Lys Val Val Glu  Gly Gly Pro Leu Pro  Phe Ala Phe
    2105                2110                2115

Asp Ile  Leu Ala Thr Ser Phe  Leu Tyr Gly Ser Lys  Thr Phe Ile
    2120                2125                2130
```

```
Asn His  Thr Gln Gly Ile Pro  Asp Phe Phe Lys Gln  Ser Phe Pro
    2135                 2140                 2145

Glu Gly  Phe Thr Trp Glu Arg  Val Thr Thr Tyr Glu  Asp Gly Gly
    2150                 2155                 2160

Val Leu  Thr Ala Thr Gln Asp  Thr Ser Leu Gln Asp  Gly Cys Leu
    2165                 2170                 2175

Ile Tyr  Asn Val Lys Ile Arg  Gly Val Asn Phe Thr  Ser Asn Gly
    2180                 2185                 2190

Pro Val  Met Gln Lys Lys Thr  Leu Gly Trp Glu Ala  Phe Thr Glu
    2195                 2200                 2205

Thr Leu  Tyr Pro Ala Asp Gly  Gly Leu Glu Gly Arg  Asn Asp Met
    2210                 2215                 2220

Ala Leu  Lys Leu Val Gly Gly  Ser His Leu Ile Ala  Asn Ile Lys
    2225                 2230                 2235

Thr Thr  Tyr Arg Ser Lys Lys  Pro Ala Lys Asn Leu  Lys Met Pro
    2240                 2245                 2250

Gly Val  Tyr Tyr Val Asp Tyr  Arg Leu Glu Arg Ile  Lys Glu Ala
    2255                 2260                 2265

Asn Asn  Glu Thr Tyr Val Glu  Gln His Glu Val Ala  Val Ala Arg
    2270                 2275                 2280

Tyr Cys  Asp Leu Pro Ser Lys  Leu Gly His Lys Leu  Asn
    2285                 2290                 2295


<210> SEQ ID NO 3
<211> LENGTH: 2316
<212> TYPE: PRT
<213> ORGANISM: Artificial sequence
<220> FEATURE:
<223> OTHER INFORMATION: Synthetic polypeptide

<400> SEQUENCE: 3

Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Gly Gly Ser Gly Gly Gly Ser Met Asp
65                  70                  75                  80

Lys Lys Tyr Ser Ile Gly Leu Ala Ile Gly Thr Asn Ser Val Gly Trp
                85                  90                  95

Ala Val Ile Thr Asp Glu Tyr Lys Val Pro Ser Lys Lys Phe Lys Val
            100                 105                 110

Leu Gly Asn Thr Asp Arg His Ser Ile Lys Lys Asn Leu Ile Gly Ala
        115                 120                 125

Leu Leu Phe Asp Ser Gly Glu Thr Ala Glu Ala Thr Arg Leu Lys Arg
    130                 135                 140

Thr Ala Arg Arg Arg Tyr Thr Arg Arg Lys Asn Arg Ile Cys Tyr Leu
145                 150                 155                 160

Gln Glu Ile Phe Ser Asn Glu Met Ala Lys Val Asp Asp Ser Phe Phe
                165                 170                 175

His Arg Leu Glu Glu Ser Phe Leu Val Glu Glu Asp Lys Lys His Glu
            180                 185                 190
```

```
Arg His Pro Ile Phe Gly Asn Ile Val Asp Glu Val Ala Tyr His Glu
        195                 200                 205

Lys Tyr Pro Thr Ile Tyr His Leu Arg Lys Lys Leu Val Asp Ser Thr
    210                 215                 220

Asp Lys Ala Asp Leu Arg Leu Ile Tyr Leu Ala Leu Ala His Met Ile
225                 230                 235                 240

Lys Phe Arg Gly His Phe Leu Ile Glu Gly Asp Leu Asn Pro Asp Asn
                245                 250                 255

Ser Asp Val Asp Lys Leu Phe Ile Gln Leu Val Gln Thr Tyr Asn Gln
            260                 265                 270

Leu Phe Glu Glu Asn Pro Ile Asn Ala Ser Gly Val Asp Ala Lys Ala
        275                 280                 285

Ile Leu Ser Ala Arg Leu Ser Lys Ser Arg Arg Leu Glu Asn Leu Ile
    290                 295                 300

Ala Gln Leu Pro Gly Glu Lys Lys Asn Gly Leu Phe Gly Asn Leu Ile
305                 310                 315                 320

Ala Leu Ser Leu Gly Leu Thr Pro Asn Phe Lys Ser Asn Phe Asp Leu
                325                 330                 335

Ala Glu Asp Ala Lys Leu Gln Leu Ser Lys Asp Thr Tyr Asp Asp Asp
            340                 345                 350

Leu Asp Asn Leu Leu Ala Gln Ile Gly Asp Gln Tyr Ala Asp Leu Phe
        355                 360                 365

Leu Ala Ala Lys Asn Leu Ser Asp Ala Ile Leu Leu Ser Asp Ile Leu
    370                 375                 380

Arg Val Asn Thr Glu Ile Thr Lys Ala Pro Leu Ser Ala Ser Met Ile
385                 390                 395                 400

Lys Arg Tyr Asp Glu His His Gln Asp Leu Thr Leu Leu Lys Ala Leu
                405                 410                 415

Val Arg Gln Gln Leu Pro Glu Lys Tyr Lys Glu Ile Phe Phe Asp Gln
            420                 425                 430

Ser Lys Asn Gly Tyr Ala Gly Tyr Ile Asp Gly Gly Ala Ser Gln Glu
        435                 440                 445

Glu Phe Tyr Lys Phe Ile Lys Pro Ile Leu Glu Lys Met Asp Gly Thr
    450                 455                 460

Glu Glu Leu Leu Val Lys Leu Asn Arg Glu Asp Leu Leu Arg Lys Gln
465                 470                 475                 480

Arg Thr Phe Asp Asn Gly Ser Ile Pro His Gln Ile His Leu Gly Glu
                485                 490                 495

Leu His Ala Ile Leu Arg Arg Gln Glu Asp Phe Tyr Pro Phe Leu Lys
            500                 505                 510

Asp Asn Arg Glu Lys Ile Glu Lys Ile Leu Thr Phe Arg Ile Pro Tyr
        515                 520                 525

Tyr Val Gly Pro Leu Ala Arg Gly Asn Ser Arg Phe Ala Trp Met Thr
    530                 535                 540

Arg Lys Ser Glu Glu Thr Ile Thr Pro Trp Asn Phe Glu Glu Val Val
545                 550                 555                 560

Asp Lys Gly Ala Ser Ala Gln Ser Phe Ile Glu Arg Met Thr Asn Phe
                565                 570                 575

Asp Lys Asn Leu Pro Asn Glu Lys Val Leu Pro Lys His Ser Leu Leu
            580                 585                 590

Tyr Glu Tyr Phe Thr Val Tyr Asn Glu Leu Thr Lys Val Lys Tyr Val
        595                 600                 605
```

```
Thr Glu Gly Met Arg Lys Pro Ala Phe Leu Ser Gly Glu Gln Lys Lys
    610                 615                 620

Ala Ile Val Asp Leu Leu Phe Lys Thr Asn Arg Lys Val Thr Val Lys
625                 630                 635                 640

Gln Leu Lys Glu Asp Tyr Phe Lys Lys Ile Glu Cys Phe Asp Ser Val
                645                 650                 655

Glu Ile Ser Gly Val Glu Asp Arg Phe Asn Ala Ser Leu Gly Thr Tyr
            660                 665                 670

His Asp Leu Leu Lys Ile Ile Lys Asp Lys Asp Phe Leu Asp Asn Glu
        675                 680                 685

Glu Asn Glu Asp Ile Leu Glu Asp Ile Val Leu Thr Leu Thr Leu Phe
    690                 695                 700

Glu Asp Arg Glu Met Ile Glu Glu Arg Leu Lys Thr Tyr Ala His Leu
705                 710                 715                 720

Phe Asp Asp Lys Val Met Lys Gln Leu Lys Arg Arg Arg Tyr Thr Gly
                725                 730                 735

Trp Gly Arg Leu Ser Arg Lys Leu Ile Asn Gly Ile Arg Asp Lys Gln
            740                 745                 750

Ser Gly Lys Thr Ile Leu Asp Phe Leu Lys Ser Asp Gly Phe Ala Asn
        755                 760                 765

Arg Asn Phe Met Gln Leu Ile His Asp Asp Ser Leu Thr Phe Lys Glu
    770                 775                 780

Asp Ile Gln Lys Ala Gln Val Ser Gly Gln Gly Asp Ser Leu His Glu
785                 790                 795                 800

His Ile Ala Asn Leu Ala Gly Ser Pro Ala Ile Lys Lys Gly Ile Leu
                805                 810                 815

Gln Thr Val Lys Val Val Asp Glu Leu Val Lys Val Met Gly Arg His
            820                 825                 830

Lys Pro Glu Asn Ile Val Ile Glu Met Ala Arg Glu Asn Gln Thr Thr
        835                 840                 845

Gln Lys Gly Gln Lys Asn Ser Arg Glu Arg Met Lys Arg Ile Glu Glu
    850                 855                 860

Gly Ile Lys Glu Leu Gly Ser Gln Ile Leu Lys Glu His Pro Val Glu
865                 870                 875                 880

Asn Thr Gln Leu Gln Asn Glu Lys Leu Tyr Leu Tyr Tyr Leu Gln Asn
                885                 890                 895

Gly Arg Asp Met Tyr Val Asp Gln Glu Leu Asp Ile Asn Arg Leu Ser
            900                 905                 910

Asp Tyr Asp Val Asp Ala Ile Val Pro Gln Ser Phe Leu Lys Asp Asp
        915                 920                 925

Ser Ile Asp Asn Lys Val Leu Thr Arg Ser Asp Lys Asn Arg Gly Lys
    930                 935                 940

Ser Asp Asn Val Pro Ser Glu Glu Val Val Lys Lys Met Lys Asn Tyr
945                 950                 955                 960

Trp Arg Gln Leu Leu Asn Ala Lys Leu Ile Thr Gln Arg Lys Phe Asp
                965                 970                 975

Asn Leu Thr Lys Ala Glu Arg Gly Gly Leu Ser Glu Leu Asp Lys Ala
            980                 985                 990

Gly Phe Ile Lys Arg Gln Leu Val  Glu Thr Arg Gln Ile  Thr Lys His
        995                 1000                1005

Val Ala  Gln Ile Leu Asp Ser  Arg Met Asn Thr Lys  Tyr Asp Glu
    1010                1015                1020

Asn Asp  Lys Leu Ile Arg Glu  Val Lys Val Ile Thr  Leu Lys Ser
```

```
    1025                1030                1035

Lys Leu  Val Ser Asp Phe Arg  Lys Asp Phe Gln Phe  Tyr Lys Val
    1040                1045                1050

Arg Glu  Ile Asn Asn Tyr His  His Ala His Asp Ala  Tyr Leu Asn
    1055                1060                1065

Ala Val  Val Gly Thr Ala Leu  Ile Lys Lys Tyr Pro  Lys Leu Glu
    1070                1075                1080

Ser Glu  Phe Val Tyr Gly Asp  Tyr Lys Val Tyr Asp  Val Arg Lys
    1085                1090                1095

Met Ile  Ala Lys Ser Glu Gln  Glu Ile Gly Lys Ala  Thr Ala Lys
    1100                1105                1110

Tyr Phe  Phe Tyr Ser Asn Ile  Met Asn Phe Phe Lys  Thr Glu Ile
    1115                1120                1125

Thr Leu  Ala Asn Gly Glu Ile  Arg Lys Arg Pro Leu  Ile Glu Thr
    1130                1135                1140

Asn Gly  Glu Thr Gly Glu Ile  Val Trp Asp Lys Gly  Arg Asp Phe
    1145                1150                1155

Ala Thr  Val Arg Lys Val Leu  Ser Met Pro Gln Val  Asn Ile Val
    1160                1165                1170

Lys Lys  Thr Glu Val Gln Thr  Gly Gly Phe Ser Lys  Glu Ser Ile
    1175                1180                1185

Leu Pro  Lys Arg Asn Ser Asp  Lys Leu Ile Ala Arg  Lys Lys Asp
    1190                1195                1200

Trp Asp  Pro Lys Lys Tyr Gly  Gly Phe Asp Ser Pro  Thr Val Ala
    1205                1210                1215

Tyr Ser  Val Leu Val Val Ala  Lys Val Glu Lys Gly  Lys Ser Lys
    1220                1225                1230

Lys Leu  Lys Ser Val Lys Glu  Leu Leu Gly Ile Thr  Ile Met Glu
    1235                1240                1245

Arg Ser  Ser Phe Glu Lys Asn  Pro Ile Asp Phe Leu  Glu Ala Lys
    1250                1255                1260

Gly Tyr  Lys Glu Val Lys Lys  Asp Leu Ile Ile Lys  Leu Pro Lys
    1265                1270                1275

Tyr Ser  Leu Phe Glu Leu Glu  Asn Gly Arg Lys Arg  Met Leu Ala
    1280                1285                1290

Ser Ala  Gly Glu Leu Gln Lys  Gly Asn Glu Leu Ala  Leu Pro Ser
    1295                1300                1305

Lys Tyr  Val Asn Phe Leu Tyr  Leu Ala Ser His Tyr  Glu Lys Leu
    1310                1315                1320

Lys Gly  Ser Pro Glu Asp Asn  Glu Gln Lys Gln Leu  Phe Val Glu
    1325                1330                1335

Gln His  Lys His Tyr Leu Asp  Glu Ile Ile Glu Gln  Ile Ser Glu
    1340                1345                1350

Phe Ser  Lys Arg Val Ile Leu  Ala Asp Ala Asn Leu  Asp Lys Val
    1355                1360                1365

Leu Ser  Ala Tyr Asn Lys His  Arg Asp Lys Pro Ile  Arg Glu Gln
    1370                1375                1380

Ala Glu  Asn Ile Ile His Leu  Phe Thr Leu Thr Asn  Leu Gly Ala
    1385                1390                1395

Pro Ala  Ala Phe Lys Tyr Phe  Asp Thr Thr Ile Asp  Arg Lys Arg
    1400                1405                1410

Tyr Thr  Ser Thr Lys Glu Val  Leu Asp Ala Thr Leu  Ile His Gln
    1415                1420                1425
```

```
Ser Ile  Thr Gly Leu Tyr Glu  Thr Arg Ile Asp Leu  Ser Gln Leu
    1430                 1435                 1440

Gly Gly  Asp Ser Arg Ala Asp  Tyr Pro Tyr Asp Val  Pro Asp Tyr
    1445                 1450                 1455

Ala Ser  Gly Ser Pro Lys Lys  Lys Arg Lys Val Glu  Ala Ser Gly
    1460                 1465                 1470

Ser Gly  Arg Ala Ser Pro Gly  Ile Pro Gly Ser Thr  Arg Asn His
    1475                 1480                 1485

Asp Gln  Glu Phe Asp Pro Pro  Lys Val Tyr Pro Pro  Val Pro Ala
    1490                 1495                 1500

Glu Lys  Arg Lys Pro Ile Arg  Val Leu Ser Leu Phe  Asp Gly Ile
    1505                 1510                 1515

Ala Thr  Gly Leu Leu Val Leu  Lys Asp Leu Gly Ile  Gln Val Asp
    1520                 1525                 1530

Arg Tyr  Ile Ala Ser Glu Val  Cys Glu Asp Ser Ile  Thr Val Gly
    1535                 1540                 1545

Met Val  Arg His Gln Gly Lys  Ile Met Tyr Val Gly  Asp Val Arg
    1550                 1555                 1560

Ser Val  Thr Gln Lys His Ile  Gln Glu Trp Gly Pro  Phe Asp Leu
    1565                 1570                 1575

Val Ile  Gly Gly Ser Pro Cys  Asn Asp Leu Ser Ile  Val Asn Pro
    1580                 1585                 1590

Ala Arg  Lys Gly Leu Tyr Glu  Gly Thr Gly Arg Leu  Phe Phe Glu
    1595                 1600                 1605

Phe Tyr  Arg Leu Leu His Asp  Ala Arg Pro Lys Glu  Gly Asp Asp
    1610                 1615                 1620

Arg Pro  Phe Phe Trp Leu Phe  Glu Asn Val Val Ala  Met Gly Val
    1625                 1630                 1635

Ser Asp  Lys Arg Asp Ile Ser  Arg Phe Leu Glu Ser  Asn Pro Val
    1640                 1645                 1650

Met Ile  Asp Ala Lys Glu Val  Ser Ala Ala His Arg  Ala Arg Tyr
    1655                 1660                 1665

Phe Trp  Gly Asn Leu Pro Gly  Met Asn Arg Pro Leu  Ala Ser Thr
    1670                 1675                 1680

Val Asn  Asp Lys Leu Glu Leu  Gln Glu Cys Leu Glu  His Gly Arg
    1685                 1690                 1695

Ile Ala  Lys Phe Ser Lys Val  Arg Thr Ile Thr Thr  Arg Ser Asn
    1700                 1705                 1710

Ser Ile  Lys Gln Gly Lys Asp  Gln His Phe Pro Val  Phe Met Asn
    1715                 1720                 1725

Glu Lys  Glu Asp Ile Leu Trp  Cys Thr Glu Met Glu  Arg Val Phe
    1730                 1735                 1740

Gly Phe  Pro Val His Tyr Thr  Asp Val Ser Asn Met  Ser Arg Leu
    1745                 1750                 1755

Ala Arg  Gln Arg Leu Leu Gly  Arg Ser Trp Ser Val  Pro Val Ile
    1760                 1765                 1770

Arg His  Leu Phe Ala Pro Leu  Lys Glu Tyr Phe Ala  Cys Val Ser
    1775                 1780                 1785

Ser Gly  Asn Ser Asn Ala Asn  Ser Arg Gly Pro Ser  Phe Ser Ser
    1790                 1795                 1800

Gly Leu  Val Pro Leu Ser Leu  Arg Gly Ser His Met  Gly Pro Met
    1805                 1810                 1815
```

```
Glu Ile  Tyr Lys Thr Val Ser  Ala Trp Lys Arg Gln  Pro Val Arg
    1820                 1825                 1830

Val Leu  Ser Leu Phe Arg Asn  Ile Asp Lys Val Leu  Lys Ser Leu
    1835                 1840                 1845

Gly Phe  Leu Glu Ser Gly Ser  Gly Ser Gly Gly Gly  Thr Leu Lys
    1850                 1855                 1860

Tyr Val  Glu Asp Val Thr Asn  Val Val Arg Arg Asp  Val Glu Lys
    1865                 1870                 1875

Trp Gly  Pro Phe Asp Leu Val  Tyr Gly Ser Thr Gln  Pro Leu Gly
    1880                 1885                 1890

Ser Ser  Cys Asp Arg Cys Pro  Gly Trp Tyr Met Phe  Gln Phe His
    1895                 1900                 1905

Arg Ile  Leu Gln Tyr Ala Leu  Pro Arg Gln Glu Ser  Gln Arg Pro
    1910                 1915                 1920

Phe Phe  Trp Ile Phe Met Asp  Asn Leu Leu Leu Thr  Glu Asp Asp
    1925                 1930                 1935

Gln Glu  Thr Thr Thr Arg Phe  Leu Gln Thr Glu Ala  Val Thr Leu
    1940                 1945                 1950

Gln Asp  Val Arg Gly Arg Asp  Tyr Gln Asn Ala Met  Arg Val Trp
    1955                 1960                 1965

Ser Asn  Ile Pro Gly Leu Lys  Ser Lys His Ala Pro  Leu Thr Pro
    1970                 1975                 1980

Lys Glu  Glu Glu Tyr Leu Gln  Ala Gln Val Arg Ser  Arg Ser Lys
    1985                 1990                 1995

Leu Asp  Ala Pro Lys Val Asp  Leu Leu Val Lys Asn  Cys Leu Leu
    2000                 2005                 2010

Pro Leu  Arg Glu Tyr Phe Lys  Tyr Phe Ser Gln Asn  Ser Leu Pro
    2015                 2020                 2025

Leu Ser  Arg Ala Asp Pro Lys  Lys Lys Arg Lys Val  Gly Ser Gly
    2030                 2035                 2040

Ala Thr  Asn Phe Ser Leu Leu  Lys Gln Ala Gly Asp  Val Glu Glu
    2045                 2050                 2055

Asn Pro  Gly Pro Gly Ser Gly  Ala Thr Asn Phe Ser  Leu Leu Lys
    2060                 2065                 2070

Gln Ala  Gly Asp Val Glu Glu  Asn Pro Gly Pro Ser  Glu Leu Ile
    2075                 2080                 2085

Lys Glu  Asn Met His Met Lys  Leu Tyr Met Glu Gly  Thr Val Asp
    2090                 2095                 2100

Asn His  His Phe Lys Cys Thr  Ser Glu Gly Glu Gly  Lys Pro Tyr
    2105                 2110                 2115

Glu Gly  Thr Gln Thr Met Arg  Ile Lys Val Val Glu  Gly Gly Pro
    2120                 2125                 2130

Leu Pro  Phe Ala Phe Asp Ile  Leu Ala Thr Ser Phe  Leu Tyr Gly
    2135                 2140                 2145

Ser Lys  Thr Phe Ile Asn His  Thr Gln Gly Ile Pro  Asp Phe Phe
    2150                 2155                 2160

Lys Gln  Ser Phe Pro Glu Gly  Phe Thr Trp Glu Arg  Val Thr Thr
    2165                 2170                 2175

Tyr Glu  Asp Gly Gly Val Leu  Thr Ala Thr Gln Asp  Thr Ser Leu
    2180                 2185                 2190

Gln Asp  Gly Cys Leu Ile Tyr  Asn Val Lys Ile Arg  Gly Val Asn
    2195                 2200                 2205

Phe Thr  Ser Asn Gly Pro Val  Met Gln Lys Lys Thr  Leu Gly Trp
```

```
    2210                2215                2220

Glu Ala  Phe Thr Glu Thr Leu  Tyr Pro Ala Asp Gly  Gly Leu Glu
    2225                2230                2235

Gly Arg  Asn Asp Met Ala Leu  Lys Leu Val Gly Gly  Ser His Leu
    2240                2245                2250

Ile Ala  Asn Ile Lys Thr Thr  Tyr Arg Ser Lys Lys  Pro Ala Lys
    2255                2260                2265

Asn Leu  Lys Met Pro Gly Val  Tyr Tyr Val Asp Tyr  Arg Leu Glu
    2270                2275                2280

Arg Ile  Lys Glu Ala Asn Asn  Glu Thr Tyr Val Glu  Gln His Glu
    2285                2290                2295

Val Ala  Val Ala Arg Tyr Cys  Asp Leu Pro Ser Lys  Leu Gly His
    2300                2305                2310

Lys Leu  Asn
    2315


<210> SEQ ID NO 4
<211> LENGTH: 2318
<212> TYPE: PRT
<213> ORGANISM: Artificial sequence
<220> FEATURE:
<223> OTHER INFORMATION: Synthetic polypeptide

<400> SEQUENCE: 4

Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Gly Gly Ser Gly Gly Gly Ser Met Asp
65                  70                  75                  80

Lys Lys Tyr Ser Ile Gly Leu Ala Ile Gly Thr Asn Ser Val Gly Trp
                85                  90                  95

Ala Val Ile Thr Asp Glu Tyr Lys Val Pro Ser Lys Lys Phe Lys Val
            100                 105                 110

Leu Gly Asn Thr Asp Arg His Ser Ile Lys Lys Asn Leu Ile Gly Ala
        115                 120                 125

Leu Leu Phe Asp Ser Gly Glu Thr Ala Glu Ala Thr Arg Leu Lys Arg
    130                 135                 140

Thr Ala Arg Arg Arg Tyr Thr Arg Arg Lys Asn Arg Ile Cys Tyr Leu
145                 150                 155                 160

Gln Glu Ile Phe Ser Asn Glu Met Ala Lys Val Asp Asp Ser Phe Phe
                165                 170                 175

His Arg Leu Glu Glu Ser Phe Leu Val Glu Glu Asp Lys Lys His Glu
            180                 185                 190

Arg His Pro Ile Phe Gly Asn Ile Val Asp Glu Val Ala Tyr His Glu
        195                 200                 205

Lys Tyr Pro Thr Ile Tyr His Leu Arg Lys Lys Leu Val Asp Ser Thr
    210                 215                 220

Asp Lys Ala Asp Leu Arg Leu Ile Tyr Leu Ala Leu Ala His Met Ile
225                 230                 235                 240

Lys Phe Arg Gly His Phe Leu Ile Glu Gly Asp Leu Asn Pro Asp Asn
```

```
                245                 250                 255

Ser Asp Val Asp Lys Leu Phe Ile Gln Leu Val Gln Thr Tyr Asn Gln
            260                 265                 270

Leu Phe Glu Glu Asn Pro Ile Asn Ala Ser Gly Val Asp Ala Lys Ala
        275                 280                 285

Ile Leu Ser Ala Arg Leu Ser Lys Ser Arg Arg Leu Glu Asn Leu Ile
    290                 295                 300

Ala Gln Leu Pro Gly Glu Lys Lys Asn Gly Leu Phe Gly Asn Leu Ile
305                 310                 315                 320

Ala Leu Ser Leu Gly Leu Thr Pro Asn Phe Lys Ser Asn Phe Asp Leu
                325                 330                 335

Ala Glu Asp Ala Lys Leu Gln Leu Ser Lys Asp Thr Tyr Asp Asp Asp
            340                 345                 350

Leu Asp Asn Leu Leu Ala Gln Ile Gly Asp Gln Tyr Ala Asp Leu Phe
        355                 360                 365

Leu Ala Ala Lys Asn Leu Ser Asp Ala Ile Leu Leu Ser Asp Ile Leu
    370                 375                 380

Arg Val Asn Thr Glu Ile Thr Lys Ala Pro Leu Ser Ala Ser Met Ile
385                 390                 395                 400

Lys Arg Tyr Asp Glu His His Gln Asp Leu Thr Leu Leu Lys Ala Leu
                405                 410                 415

Val Arg Gln Gln Leu Pro Glu Lys Tyr Lys Glu Ile Phe Phe Asp Gln
            420                 425                 430

Ser Lys Asn Gly Tyr Ala Gly Tyr Ile Asp Gly Gly Ala Ser Gln Glu
        435                 440                 445

Glu Phe Tyr Lys Phe Ile Lys Pro Ile Leu Glu Lys Met Asp Gly Thr
    450                 455                 460

Glu Glu Leu Leu Val Lys Leu Asn Arg Glu Asp Leu Leu Arg Lys Gln
465                 470                 475                 480

Arg Thr Phe Asp Asn Gly Ser Ile Pro His Gln Ile His Leu Gly Glu
                485                 490                 495

Leu His Ala Ile Leu Arg Arg Gln Glu Asp Phe Tyr Pro Phe Leu Lys
            500                 505                 510

Asp Asn Arg Glu Lys Ile Glu Lys Ile Leu Thr Phe Arg Ile Pro Tyr
        515                 520                 525

Tyr Val Gly Pro Leu Ala Arg Gly Asn Ser Arg Phe Ala Trp Met Thr
    530                 535                 540

Arg Lys Ser Glu Glu Thr Ile Thr Pro Trp Asn Phe Glu Glu Val Val
545                 550                 555                 560

Asp Lys Gly Ala Ser Ala Gln Ser Phe Ile Glu Arg Met Thr Asn Phe
                565                 570                 575

Asp Lys Asn Leu Pro Asn Glu Lys Val Leu Pro Lys His Ser Leu Leu
            580                 585                 590

Tyr Glu Tyr Phe Thr Val Tyr Asn Glu Leu Thr Lys Val Lys Tyr Val
        595                 600                 605

Thr Glu Gly Met Arg Lys Pro Ala Phe Leu Ser Gly Glu Gln Lys Lys
    610                 615                 620

Ala Ile Val Asp Leu Leu Phe Lys Thr Asn Arg Lys Val Thr Val Lys
625                 630                 635                 640

Gln Leu Lys Glu Asp Tyr Phe Lys Lys Ile Glu Cys Phe Asp Ser Val
                645                 650                 655

Glu Ile Ser Gly Val Glu Asp Arg Phe Asn Ala Ser Leu Gly Thr Tyr
            660                 665                 670
```

```
His Asp Leu Leu Lys Ile Ile Lys Asp Lys Asp Phe Leu Asp Asn Glu
        675                 680                 685

Glu Asn Glu Asp Ile Leu Glu Asp Ile Val Leu Thr Leu Thr Leu Phe
    690                 695                 700

Glu Asp Arg Glu Met Ile Glu Glu Arg Leu Lys Thr Tyr Ala His Leu
705                 710                 715                 720

Phe Asp Asp Lys Val Met Lys Gln Leu Lys Arg Arg Arg Tyr Thr Gly
                725                 730                 735

Trp Gly Arg Leu Ser Arg Lys Leu Ile Asn Gly Ile Arg Asp Lys Gln
            740                 745                 750

Ser Gly Lys Thr Ile Leu Asp Phe Leu Lys Ser Asp Gly Phe Ala Asn
        755                 760                 765

Arg Asn Phe Met Gln Leu Ile His Asp Asp Ser Leu Thr Phe Lys Glu
    770                 775                 780

Asp Ile Gln Lys Ala Gln Val Ser Gly Gln Gly Asp Ser Leu His Glu
785                 790                 795                 800

His Ile Ala Asn Leu Ala Gly Ser Pro Ala Ile Lys Lys Gly Ile Leu
                805                 810                 815

Gln Thr Val Lys Val Val Asp Glu Leu Val Lys Val Met Gly Arg His
            820                 825                 830

Lys Pro Glu Asn Ile Val Ile Glu Met Ala Arg Glu Asn Gln Thr Thr
        835                 840                 845

Gln Lys Gly Gln Lys Asn Ser Arg Glu Arg Met Lys Arg Ile Glu Glu
    850                 855                 860

Gly Ile Lys Glu Leu Gly Ser Gln Ile Leu Lys Glu His Pro Val Glu
865                 870                 875                 880

Asn Thr Gln Leu Gln Asn Glu Lys Leu Tyr Leu Tyr Tyr Leu Gln Asn
                885                 890                 895

Gly Arg Asp Met Tyr Val Asp Gln Glu Leu Asp Ile Asn Arg Leu Ser
            900                 905                 910

Asp Tyr Asp Val Asp Ala Ile Val Pro Gln Ser Phe Leu Lys Asp Asp
        915                 920                 925

Ser Ile Asp Asn Lys Val Leu Thr Arg Ser Asp Lys Asn Arg Gly Lys
    930                 935                 940

Ser Asp Asn Val Pro Ser Glu Glu Val Val Lys Lys Met Lys Asn Tyr
945                 950                 955                 960

Trp Arg Gln Leu Leu Asn Ala Lys Leu Ile Thr Gln Arg Lys Phe Asp
                965                 970                 975

Asn Leu Thr Lys Ala Glu Arg Gly Gly Leu Ser Glu Leu Asp Lys Ala
            980                 985                 990

Gly Phe Ile Lys Arg Gln Leu Val  Glu Thr Arg Gln Ile  Thr Lys His
        995                 1000                1005

Val Ala  Gln Ile Leu Asp Ser  Arg Met Asn Thr Lys  Tyr Asp Glu
    1010                1015                1020

Asn Asp  Lys Leu Ile Arg Glu  Val Lys Val Ile Thr  Leu Lys Ser
    1025                1030                1035

Lys Leu  Val Ser Asp Phe Arg  Lys Asp Phe Gln Phe  Tyr Lys Val
    1040                1045                1050

Arg Glu  Ile Asn Asn Tyr His  His Ala His Asp Ala  Tyr Leu Asn
    1055                1060                1065

Ala Val  Val Gly Thr Ala Leu  Ile Lys Lys Tyr Pro  Lys Leu Glu
    1070                1075                1080
```

```
Ser Glu  Phe Val Tyr Gly Asp  Tyr Lys Val Tyr Asp  Val Arg Lys
    1085                 1090                 1095

Met Ile  Ala Lys Ser Glu Gln  Glu Ile Gly Lys Ala  Thr Ala Lys
    1100                 1105                 1110

Tyr Phe  Phe Tyr Ser Asn Ile  Met Asn Phe Phe Lys  Thr Glu Ile
    1115                 1120                 1125

Thr Leu  Ala Asn Gly Glu Ile  Arg Lys Arg Pro Leu  Ile Glu Thr
    1130                 1135                 1140

Asn Gly  Glu Thr Gly Glu Ile  Val Trp Asp Lys Gly  Arg Asp Phe
    1145                 1150                 1155

Ala Thr  Val Arg Lys Val Leu  Ser Met Pro Gln Val  Asn Ile Val
    1160                 1165                 1170

Lys Lys  Thr Glu Val Gln Thr  Gly Gly Phe Ser Lys  Glu Ser Ile
    1175                 1180                 1185

Leu Pro  Lys Arg Asn Ser Asp  Lys Leu Ile Ala Arg  Lys Lys Asp
    1190                 1195                 1200

Trp Asp  Pro Lys Lys Tyr Gly  Gly Phe Asp Ser Pro  Thr Val Ala
    1205                 1210                 1215

Tyr Ser  Val Leu Val Val Ala  Lys Val Glu Lys Gly  Lys Ser Lys
    1220                 1225                 1230

Lys Leu  Lys Ser Val Lys Glu  Leu Leu Gly Ile Thr  Ile Met Glu
    1235                 1240                 1245

Arg Ser  Ser Phe Glu Lys Asn  Pro Ile Asp Phe Leu  Glu Ala Lys
    1250                 1255                 1260

Gly Tyr  Lys Glu Val Lys Lys  Asp Leu Ile Ile Lys  Leu Pro Lys
    1265                 1270                 1275

Tyr Ser  Leu Phe Glu Leu Glu  Asn Gly Arg Lys Arg  Met Leu Ala
    1280                 1285                 1290

Ser Ala  Gly Glu Leu Gln Lys  Gly Asn Glu Leu Ala  Leu Pro Ser
    1295                 1300                 1305

Lys Tyr  Val Asn Phe Leu Tyr  Leu Ala Ser His Tyr  Glu Lys Leu
    1310                 1315                 1320

Lys Gly  Ser Pro Glu Asp Asn  Glu Gln Lys Gln Leu  Phe Val Glu
    1325                 1330                 1335

Gln His  Lys His Tyr Leu Asp  Glu Ile Ile Glu Gln  Ile Ser Glu
    1340                 1345                 1350

Phe Ser  Lys Arg Val Ile Leu  Ala Asp Ala Asn Leu  Asp Lys Val
    1355                 1360                 1365

Leu Ser  Ala Tyr Asn Lys His  Arg Asp Lys Pro Ile  Arg Glu Gln
    1370                 1375                 1380

Ala Glu  Asn Ile Ile His Leu  Phe Thr Leu Thr Asn  Leu Gly Ala
    1385                 1390                 1395

Pro Ala  Ala Phe Lys Tyr Phe  Asp Thr Thr Ile Asp  Arg Lys Arg
    1400                 1405                 1410

Tyr Thr  Ser Thr Lys Glu Val  Leu Asp Ala Thr Leu  Ile His Gln
    1415                 1420                 1425

Ser Ile  Thr Gly Leu Tyr Glu  Thr Arg Ile Asp Leu  Ser Gln Leu
    1430                 1435                 1440

Gly Gly  Asp Ser Arg Ala Asp  Tyr Pro Tyr Asp Val  Pro Asp Tyr
    1445                 1450                 1455

Ala Ser  Gly Ser Pro Lys Lys  Lys Arg Lys Val Ser  Pro Gly Ser
    1460                 1465                 1470

Gly Ser  Glu Thr Pro Gly Thr  Ser Glu Ser Ala Thr  Pro Glu Ser
```

1475 1480 1485

Asn His Asp Gln Glu Phe Asp Pro Pro Lys Val Tyr Pro Pro Val
1490 1495 1500

Pro Ala Glu Lys Arg Lys Pro Ile Arg Val Leu Ser Leu Phe Asp
1505 1510 1515

Gly Ile Ala Thr Gly Leu Leu Val Leu Lys Asp Leu Gly Ile Gln
1520 1525 1530

Val Asp Arg Tyr Ile Ala Ser Glu Val Cys Glu Asp Ser Ile Thr
1535 1540 1545

Val Gly Met Val Arg His Gln Gly Lys Ile Met Tyr Val Gly Asp
1550 1555 1560

Val Arg Ser Val Thr Gln Lys His Ile Gln Glu Trp Gly Pro Phe
1565 1570 1575

Asp Leu Val Ile Gly Gly Ser Pro Cys Asn Asp Leu Ser Ile Val
1580 1585 1590

Asn Pro Ala Arg Lys Gly Leu Tyr Glu Gly Thr Gly Arg Leu Phe
1595 1600 1605

Phe Glu Phe Tyr Arg Leu Leu His Asp Ala Arg Pro Lys Glu Gly
1610 1615 1620

Asp Asp Arg Pro Phe Phe Trp Leu Phe Glu Asn Val Val Ala Met
1625 1630 1635

Gly Val Ser Asp Lys Arg Asp Ile Ser Arg Phe Leu Glu Ser Asn
1640 1645 1650

Pro Val Met Ile Asp Ala Lys Glu Val Ser Ala Ala His Arg Ala
1655 1660 1665

Arg Tyr Phe Trp Gly Asn Leu Pro Gly Met Asn Arg Pro Leu Ala
1670 1675 1680

Ser Thr Val Asn Asp Lys Leu Glu Leu Gln Glu Cys Leu Glu His
1685 1690 1695

Gly Arg Ile Ala Lys Phe Ser Lys Val Arg Thr Ile Thr Thr Arg
1700 1705 1710

Ser Asn Ser Ile Lys Gln Gly Lys Asp Gln His Phe Pro Val Phe
1715 1720 1725

Met Asn Glu Lys Glu Asp Ile Leu Trp Cys Thr Glu Met Glu Arg
1730 1735 1740

Val Phe Gly Phe Pro Val His Tyr Thr Asp Val Ser Asn Met Ser
1745 1750 1755

Arg Leu Ala Arg Gln Arg Leu Leu Gly Arg Ser Trp Ser Val Pro
1760 1765 1770

Val Ile Arg His Leu Phe Ala Pro Leu Lys Glu Tyr Phe Ala Cys
1775 1780 1785

Val Ser Ser Gly Asn Ser Asn Ala Asn Ser Arg Gly Pro Ser Phe
1790 1795 1800

Ser Ser Gly Leu Val Pro Leu Ser Leu Arg Gly Ser His Met Gly
1805 1810 1815

Pro Met Glu Ile Tyr Lys Thr Val Ser Ala Trp Lys Arg Gln Pro
1820 1825 1830

Val Arg Val Leu Ser Leu Phe Arg Asn Ile Asp Lys Val Leu Lys
1835 1840 1845

Ser Leu Gly Phe Leu Glu Ser Gly Ser Gly Ser Gly Gly Gly Thr
1850 1855 1860

Leu Lys Tyr Val Glu Asp Val Thr Asn Val Val Arg Arg Asp Val
1865 1870 1875

```
Glu Lys  Trp Gly Pro Phe Asp  Leu Val Tyr Gly Ser  Thr Gln Pro
    1880                 1885                 1890

Leu Gly  Ser Ser Cys Asp Arg  Cys Pro Gly Trp Tyr  Met Phe Gln
    1895                 1900                 1905

Phe His  Arg Ile Leu Gln Tyr  Ala Leu Pro Arg Gln  Glu Ser Gln
    1910                 1915                 1920

Arg Pro  Phe Phe Trp Ile Phe  Met Asp Asn Leu Leu  Leu Thr Glu
    1925                 1930                 1935

Asp Asp  Gln Glu Thr Thr Thr  Arg Phe Leu Gln Thr  Glu Ala Val
    1940                 1945                 1950

Thr Leu  Gln Asp Val Arg Gly  Arg Asp Tyr Gln Asn  Ala Met Arg
    1955                 1960                 1965

Val Trp  Ser Asn Ile Pro Gly  Leu Lys Ser Lys His  Ala Pro Leu
    1970                 1975                 1980

Thr Pro  Lys Glu Glu Glu Tyr  Leu Gln Ala Gln Val  Arg Ser Arg
    1985                 1990                 1995

Ser Lys  Leu Asp Ala Pro Lys  Val Asp Leu Leu Val  Lys Asn Cys
    2000                 2005                 2010

Leu Leu  Pro Leu Arg Glu Tyr  Phe Lys Tyr Phe Ser  Gln Asn Ser
    2015                 2020                 2025

Leu Pro  Leu Ser Arg Ala Asp  Pro Lys Lys Lys Arg  Lys Val Gly
    2030                 2035                 2040

Ser Gly  Ala Thr Asn Phe Ser  Leu Leu Lys Gln Ala  Gly Asp Val
    2045                 2050                 2055

Glu Glu  Asn Pro Gly Pro Gly  Ser Gly Ala Thr Asn  Phe Ser Leu
    2060                 2065                 2070

Leu Lys  Gln Ala Gly Asp Val  Glu Glu Asn Pro Gly  Pro Ser Glu
    2075                 2080                 2085

Leu Ile  Lys Glu Asn Met His  Met Lys Leu Tyr Met  Glu Gly Thr
    2090                 2095                 2100

Val Asp  Asn His His Phe Lys  Cys Thr Ser Glu Gly  Glu Gly Lys
    2105                 2110                 2115

Pro Tyr  Glu Gly Thr Gln Thr  Met Arg Ile Lys Val  Val Glu Gly
    2120                 2125                 2130

Gly Pro  Leu Pro Phe Ala Phe  Asp Ile Leu Ala Thr  Ser Phe Leu
    2135                 2140                 2145

Tyr Gly  Ser Lys Thr Phe Ile  Asn His Thr Gln Gly  Ile Pro Asp
    2150                 2155                 2160

Phe Phe  Lys Gln Ser Phe Pro  Glu Gly Phe Thr Trp  Glu Arg Val
    2165                 2170                 2175

Thr Thr  Tyr Glu Asp Gly Gly  Val Leu Thr Ala Thr  Gln Asp Thr
    2180                 2185                 2190

Ser Leu  Gln Asp Gly Cys Leu  Ile Tyr Asn Val Lys  Ile Arg Gly
    2195                 2200                 2205

Val Asn  Phe Thr Ser Asn Gly  Pro Val Met Gln Lys  Lys Thr Leu
    2210                 2215                 2220

Gly Trp  Glu Ala Phe Thr Glu  Thr Leu Tyr Pro Ala  Asp Gly Gly
    2225                 2230                 2235

Leu Glu  Gly Arg Asn Asp Met  Ala Leu Lys Leu Val  Gly Gly Ser
    2240                 2245                 2250

His Leu  Ile Ala Asn Ile Lys  Thr Thr Tyr Arg Ser  Lys Lys Pro
    2255                 2260                 2265
```

```
Ala Lys  Asn Leu Lys Met Pro  Gly Val Tyr Tyr Val  Asp Tyr Arg
    2270                2275                2280

Leu Glu  Arg Ile Lys Glu Ala  Asn Asn Glu Thr Tyr  Val Glu Gln
    2285                2290                2295

His Glu  Val Ala Val Ala Arg  Tyr Cys Asp Leu Pro  Ser Lys Leu
    2300                2305                2310

Gly His  Lys Leu Asn
    2315


<210> SEQ ID NO 5
<211> LENGTH: 2360
<212> TYPE: PRT
<213> ORGANISM: Artificial sequence
<220> FEATURE:
<223> OTHER INFORMATION: Synthetic polypeptide

<400> SEQUENCE: 5

Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Gly Gly Ser Gly Gly Gly Ser Met Asp
65                  70                  75                  80

Lys Lys Tyr Ser Ile Gly Leu Ala Ile Gly Thr Asn Ser Val Gly Trp
                85                  90                  95

Ala Val Ile Thr Asp Glu Tyr Lys Val Pro Ser Lys Lys Phe Lys Val
            100                 105                 110

Leu Gly Asn Thr Asp Arg His Ser Ile Lys Lys Asn Leu Ile Gly Ala
        115                 120                 125

Leu Leu Phe Asp Ser Gly Glu Thr Ala Glu Ala Thr Arg Leu Lys Arg
    130                 135                 140

Thr Ala Arg Arg Arg Tyr Thr Arg Arg Lys Asn Arg Ile Cys Tyr Leu
145                 150                 155                 160

Gln Glu Ile Phe Ser Asn Glu Met Ala Lys Val Asp Asp Ser Phe Phe
                165                 170                 175

His Arg Leu Glu Glu Ser Phe Leu Val Glu Glu Asp Lys Lys His Glu
            180                 185                 190

Arg His Pro Ile Phe Gly Asn Ile Val Asp Glu Val Ala Tyr His Glu
        195                 200                 205

Lys Tyr Pro Thr Ile Tyr His Leu Arg Lys Lys Leu Val Asp Ser Thr
    210                 215                 220

Asp Lys Ala Asp Leu Arg Leu Ile Tyr Leu Ala Leu Ala His Met Ile
225                 230                 235                 240

Lys Phe Arg Gly His Phe Leu Ile Glu Gly Asp Leu Asn Pro Asp Asn
                245                 250                 255

Ser Asp Val Asp Lys Leu Phe Ile Gln Leu Val Gln Thr Tyr Asn Gln
            260                 265                 270

Leu Phe Glu Glu Asn Pro Ile Asn Ala Ser Gly Val Asp Ala Lys Ala
        275                 280                 285

Ile Leu Ser Ala Arg Leu Ser Lys Ser Arg Arg Leu Glu Asn Leu Ile
    290                 295                 300
```

```
Ala Gln Leu Pro Gly Glu Lys Lys Asn Gly Leu Phe Gly Asn Leu Ile
305                 310                 315                 320

Ala Leu Ser Leu Gly Leu Thr Pro Asn Phe Lys Ser Asn Phe Asp Leu
                325                 330                 335

Ala Glu Asp Ala Lys Leu Gln Leu Ser Lys Asp Thr Tyr Asp Asp Asp
            340                 345                 350

Leu Asp Asn Leu Leu Ala Gln Ile Gly Asp Gln Tyr Ala Asp Leu Phe
        355                 360                 365

Leu Ala Ala Lys Asn Leu Ser Asp Ala Ile Leu Leu Ser Asp Ile Leu
    370                 375                 380

Arg Val Asn Thr Glu Ile Thr Lys Ala Pro Leu Ser Ala Ser Met Ile
385                 390                 395                 400

Lys Arg Tyr Asp Glu His His Gln Asp Leu Thr Leu Leu Lys Ala Leu
                405                 410                 415

Val Arg Gln Gln Leu Pro Glu Lys Tyr Lys Glu Ile Phe Phe Asp Gln
            420                 425                 430

Ser Lys Asn Gly Tyr Ala Gly Tyr Ile Asp Gly Gly Ala Ser Gln Glu
        435                 440                 445

Glu Phe Tyr Lys Phe Ile Lys Pro Ile Leu Glu Lys Met Asp Gly Thr
    450                 455                 460

Glu Glu Leu Leu Val Lys Leu Asn Arg Glu Asp Leu Leu Arg Lys Gln
465                 470                 475                 480

Arg Thr Phe Asp Asn Gly Ser Ile Pro His Gln Ile His Leu Gly Glu
                485                 490                 495

Leu His Ala Ile Leu Arg Arg Gln Glu Asp Phe Tyr Pro Phe Leu Lys
            500                 505                 510

Asp Asn Arg Glu Lys Ile Glu Lys Ile Leu Thr Phe Arg Ile Pro Tyr
        515                 520                 525

Tyr Val Gly Pro Leu Ala Arg Gly Asn Ser Arg Phe Ala Trp Met Thr
    530                 535                 540

Arg Lys Ser Glu Glu Thr Ile Thr Pro Trp Asn Phe Glu Glu Val Val
545                 550                 555                 560

Asp Lys Gly Ala Ser Ala Gln Ser Phe Ile Glu Arg Met Thr Asn Phe
                565                 570                 575

Asp Lys Asn Leu Pro Asn Glu Lys Val Leu Pro Lys His Ser Leu Leu
            580                 585                 590

Tyr Glu Tyr Phe Thr Val Tyr Asn Glu Leu Thr Lys Val Lys Tyr Val
        595                 600                 605

Thr Glu Gly Met Arg Lys Pro Ala Phe Leu Ser Gly Glu Gln Lys Lys
    610                 615                 620

Ala Ile Val Asp Leu Leu Phe Lys Thr Asn Arg Lys Val Thr Val Lys
625                 630                 635                 640

Gln Leu Lys Glu Asp Tyr Phe Lys Lys Ile Glu Cys Phe Asp Ser Val
                645                 650                 655

Glu Ile Ser Gly Val Glu Asp Arg Phe Asn Ala Ser Leu Gly Thr Tyr
            660                 665                 670

His Asp Leu Leu Lys Ile Ile Lys Asp Lys Asp Phe Leu Asp Asn Glu
        675                 680                 685

Glu Asn Glu Asp Ile Leu Glu Asp Ile Val Leu Thr Leu Thr Leu Phe
    690                 695                 700

Glu Asp Arg Glu Met Ile Glu Glu Arg Leu Lys Thr Tyr Ala His Leu
705                 710                 715                 720

Phe Asp Asp Lys Val Met Lys Gln Leu Lys Arg Arg Arg Tyr Thr Gly
```

-continued

```
                725                 730                 735

Trp Gly Arg Leu Ser Arg Lys Leu Ile Asn Gly Ile Arg Asp Lys Gln
            740                 745                 750

Ser Gly Lys Thr Ile Leu Asp Phe Leu Lys Ser Asp Gly Phe Ala Asn
        755                 760                 765

Arg Asn Phe Met Gln Leu Ile His Asp Asp Ser Leu Thr Phe Lys Glu
    770                 775                 780

Asp Ile Gln Lys Ala Gln Val Ser Gly Gln Gly Asp Ser Leu His Glu
785                 790                 795                 800

His Ile Ala Asn Leu Ala Gly Ser Pro Ala Ile Lys Lys Gly Ile Leu
                805                 810                 815

Gln Thr Val Lys Val Val Asp Glu Leu Val Lys Val Met Gly Arg His
            820                 825                 830

Lys Pro Glu Asn Ile Val Ile Glu Met Ala Arg Glu Asn Gln Thr Thr
        835                 840                 845

Gln Lys Gly Gln Lys Asn Ser Arg Glu Arg Met Lys Arg Ile Glu Glu
    850                 855                 860

Gly Ile Lys Glu Leu Gly Ser Gln Ile Leu Lys Glu His Pro Val Glu
865                 870                 875                 880

Asn Thr Gln Leu Gln Asn Glu Lys Leu Tyr Leu Tyr Tyr Leu Gln Asn
                885                 890                 895

Gly Arg Asp Met Tyr Val Asp Gln Glu Leu Asp Ile Asn Arg Leu Ser
            900                 905                 910

Asp Tyr Asp Val Asp Ala Ile Val Pro Gln Ser Phe Leu Lys Asp Asp
        915                 920                 925

Ser Ile Asp Asn Lys Val Leu Thr Arg Ser Asp Lys Asn Arg Gly Lys
    930                 935                 940

Ser Asp Asn Val Pro Ser Glu Glu Val Val Lys Lys Met Lys Asn Tyr
945                 950                 955                 960

Trp Arg Gln Leu Leu Asn Ala Lys Leu Ile Thr Gln Arg Lys Phe Asp
                965                 970                 975

Asn Leu Thr Lys Ala Glu Arg Gly Gly Leu Ser Glu Leu Asp Lys Ala
            980                 985                 990

Gly Phe Ile Lys Arg Gln Leu Val  Glu Thr Arg Gln Ile  Thr Lys His
        995                 1000                1005

Val Ala  Gln Ile Leu Asp Ser  Arg Met Asn Thr Lys  Tyr Asp Glu
    1010                1015                1020

Asn Asp  Lys Leu Ile Arg Glu  Val Lys Val Ile Thr  Leu Lys Ser
    1025                1030                1035

Lys Leu  Val Ser Asp Phe Arg  Lys Asp Phe Gln Phe  Tyr Lys Val
    1040                1045                1050

Arg Glu  Ile Asn Asn Tyr His  His Ala His Asp Ala  Tyr Leu Asn
    1055                1060                1065

Ala Val  Val Gly Thr Ala Leu  Ile Lys Lys Tyr Pro  Lys Leu Glu
    1070                1075                1080

Ser Glu  Phe Val Tyr Gly Asp  Tyr Lys Val Tyr Asp  Val Arg Lys
    1085                1090                1095

Met Ile  Ala Lys Ser Glu Gln  Glu Ile Gly Lys Ala  Thr Ala Lys
    1100                1105                1110

Tyr Phe  Phe Tyr Ser Asn Ile  Met Asn Phe Phe Lys  Thr Glu Ile
    1115                1120                1125

Thr Leu  Ala Asn Gly Glu Ile  Arg Lys Arg Pro Leu  Ile Glu Thr
    1130                1135                1140
```

-continued

```
Asn Gly  Glu Thr Gly Glu Ile  Val Trp Asp Lys Gly  Arg Asp Phe
    1145                 1150                 1155

Ala Thr  Val Arg Lys Val Leu  Ser Met Pro Gln Val  Asn Ile Val
    1160                 1165                 1170

Lys Lys  Thr Glu Val Gln Thr  Gly Gly Phe Ser Lys  Glu Ser Ile
    1175                 1180                 1185

Leu Pro  Lys Arg Asn Ser Asp  Lys Leu Ile Ala Arg  Lys Lys Asp
    1190                 1195                 1200

Trp Asp  Pro Lys Lys Tyr Gly  Gly Phe Asp Ser Pro  Thr Val Ala
    1205                 1210                 1215

Tyr Ser  Val Leu Val Val Ala  Lys Val Glu Lys Gly  Lys Ser Lys
    1220                 1225                 1230

Lys Leu  Lys Ser Val Lys Glu  Leu Leu Gly Ile Thr  Ile Met Glu
    1235                 1240                 1245

Arg Ser  Ser Phe Glu Lys Asn  Pro Ile Asp Phe Leu  Glu Ala Lys
    1250                 1255                 1260

Gly Tyr  Lys Glu Val Lys Lys  Asp Leu Ile Ile Lys  Leu Pro Lys
    1265                 1270                 1275

Tyr Ser  Leu Phe Glu Leu Glu  Asn Gly Arg Lys Arg  Met Leu Ala
    1280                 1285                 1290

Ser Ala  Gly Glu Leu Gln Lys  Gly Asn Glu Leu Ala  Leu Pro Ser
    1295                 1300                 1305

Lys Tyr  Val Asn Phe Leu Tyr  Leu Ala Ser His Tyr  Glu Lys Leu
    1310                 1315                 1320

Lys Gly  Ser Pro Glu Asp Asn  Glu Gln Lys Gln Leu  Phe Val Glu
    1325                 1330                 1335

Gln His  Lys His Tyr Leu Asp  Glu Ile Ile Glu Gln  Ile Ser Glu
    1340                 1345                 1350

Phe Ser  Lys Arg Val Ile Leu  Ala Asp Ala Asn Leu  Asp Lys Val
    1355                 1360                 1365

Leu Ser  Ala Tyr Asn Lys His  Arg Asp Lys Pro Ile  Arg Glu Gln
    1370                 1375                 1380

Ala Glu  Asn Ile Ile His Leu  Phe Thr Leu Thr Asn  Leu Gly Ala
    1385                 1390                 1395

Pro Ala  Ala Phe Lys Tyr Phe  Asp Thr Thr Ile Asp  Arg Lys Arg
    1400                 1405                 1410

Tyr Thr  Ser Thr Lys Glu Val  Leu Asp Ala Thr Leu  Ile His Gln
    1415                 1420                 1425

Ser Ile  Thr Gly Leu Tyr Glu  Thr Arg Ile Asp Leu  Ser Gln Leu
    1430                 1435                 1440

Gly Gly  Asp Ser Arg Ala Asp  Tyr Pro Tyr Asp Val  Pro Asp Tyr
    1445                 1450                 1455

Ala Ser  Gly Ser Pro Lys Lys  Lys Arg Lys Val Ser  Pro Gly Gly
    1460                 1465                 1470

Gly Pro  Ser Ser Gly Ala Pro  Pro Pro Ser Gly Gly  Ser Pro Ala
    1475                 1480                 1485

Gly Ser  Pro Thr Ser Thr Glu  Glu Gly Thr Ser Glu  Ser Ala Thr
    1490                 1495                 1500

Pro Glu  Ser Gly Pro Gly Thr  Ser Thr Glu Pro Ser  Glu Gly Ser
    1505                 1510                 1515

Ala Pro  Gly Ser Pro Ala Gly  Ser Pro Thr Ser Thr  Glu Glu Gly
    1520                 1525                 1530
```

```
Thr Ser  Thr Glu Pro Ser Glu  Gly Ser Ala Pro Gly  Thr Ser Thr
    1535                 1540                 1545

Glu Pro  Ser Glu Asn His Asp  Gln Glu Phe Asp Pro  Pro Lys Val
    1550                 1555                 1560

Tyr Pro  Pro Val Pro Ala Glu  Lys Arg Lys Pro Ile  Arg Val Leu
    1565                 1570                 1575

Ser Leu  Phe Asp Gly Ile Ala  Thr Gly Leu Leu Val  Leu Lys Asp
    1580                 1585                 1590

Leu Gly  Ile Gln Val Asp Arg  Tyr Ile Ala Ser Glu  Val Cys Glu
    1595                 1600                 1605

Asp Ser  Ile Thr Val Gly Met  Val Arg His Gln Gly  Lys Ile Met
    1610                 1615                 1620

Tyr Val  Gly Asp Val Arg Ser  Val Thr Gln Lys His  Ile Gln Glu
    1625                 1630                 1635

Trp Gly  Pro Phe Asp Leu Val  Ile Gly Gly Ser Pro  Cys Asn Asp
    1640                 1645                 1650

Leu Ser  Ile Val Asn Pro Ala  Arg Lys Gly Leu Tyr  Glu Gly Thr
    1655                 1660                 1665

Gly Arg  Leu Phe Phe Glu Phe  Tyr Arg Leu Leu His  Asp Ala Arg
    1670                 1675                 1680

Pro Lys  Glu Gly Asp Asp Arg  Pro Phe Phe Trp Leu  Phe Glu Asn
    1685                 1690                 1695

Val Val  Ala Met Gly Val Ser  Asp Lys Arg Asp Ile  Ser Arg Phe
    1700                 1705                 1710

Leu Glu  Ser Asn Pro Val Met  Ile Asp Ala Lys Glu  Val Ser Ala
    1715                 1720                 1725

Ala His  Arg Ala Arg Tyr Phe  Trp Gly Asn Leu Pro  Gly Met Asn
    1730                 1735                 1740

Arg Pro  Leu Ala Ser Thr Val  Asn Asp Lys Leu Glu  Leu Gln Glu
    1745                 1750                 1755

Cys Leu  Glu His Gly Arg Ile  Ala Lys Phe Ser Lys  Val Arg Thr
    1760                 1765                 1770

Ile Thr  Thr Arg Ser Asn Ser  Ile Lys Gln Gly Lys  Asp Gln His
    1775                 1780                 1785

Phe Pro  Val Phe Met Asn Glu  Lys Glu Asp Ile Leu  Trp Cys Thr
    1790                 1795                 1800

Glu Met  Glu Arg Val Phe Gly  Phe Pro Val His Tyr  Thr Asp Val
    1805                 1810                 1815

Ser Asn  Met Ser Arg Leu Ala  Arg Gln Arg Leu Leu  Gly Arg Ser
    1820                 1825                 1830

Trp Ser  Val Pro Val Ile Arg  His Leu Phe Ala Pro  Leu Lys Glu
    1835                 1840                 1845

Tyr Phe  Ala Cys Val Ser Ser  Gly Asn Ser Asn Ala  Asn Ser Arg
    1850                 1855                 1860

Gly Pro  Ser Phe Ser Ser Gly  Leu Val Pro Leu Ser  Leu Arg Gly
    1865                 1870                 1875

Ser His  Met Gly Pro Met Glu  Ile Tyr Lys Thr Val  Ser Ala Trp
    1880                 1885                 1890

Lys Arg  Gln Pro Val Arg Val  Leu Ser Leu Phe Arg  Asn Ile Asp
    1895                 1900                 1905

Lys Val  Leu Lys Ser Leu Gly  Phe Leu Glu Ser Gly  Ser Gly Ser
    1910                 1915                 1920

Gly Gly  Gly Thr Leu Lys Tyr  Val Glu Asp Val Thr  Asn Val Val
```

```
    1925                1930                1935

Arg Arg  Asp Val Glu Lys Trp  Gly Pro Phe Asp Leu  Val Tyr Gly
    1940                1945                1950

Ser Thr  Gln Pro Leu Gly Ser  Ser Cys Asp Arg Cys  Pro Gly Trp
    1955                1960                1965

Tyr Met  Phe Gln Phe His Arg  Ile Leu Gln Tyr Ala  Leu Pro Arg
    1970                1975                1980

Gln Glu  Ser Gln Arg Pro Phe  Phe Trp Ile Phe Met  Asp Asn Leu
    1985                1990                1995

Leu Leu  Thr Glu Asp Asp Gln  Glu Thr Thr Thr Arg  Phe Leu Gln
    2000                2005                2010

Thr Glu  Ala Val Thr Leu Gln  Asp Val Arg Gly Arg  Asp Tyr Gln
    2015                2020                2025

Asn Ala  Met Arg Val Trp Ser  Asn Ile Pro Gly Leu  Lys Ser Lys
    2030                2035                2040

His Ala  Pro Leu Thr Pro Lys  Glu Glu Glu Tyr Leu  Gln Ala Gln
    2045                2050                2055

Val Arg  Ser Arg Ser Lys Leu  Asp Ala Pro Lys Val  Asp Leu Leu
    2060                2065                2070

Val Lys  Asn Cys Leu Leu Pro  Leu Arg Glu Tyr Phe  Lys Tyr Phe
    2075                2080                2085

Ser Gln  Asn Ser Leu Pro Leu  Ser Arg Ala Asp Pro  Lys Lys Lys
    2090                2095                2100

Arg Lys  Val Gly Ser Gly Ala  Thr Asn Phe Ser Leu  Leu Lys Gln
    2105                2110                2115

Ala Gly  Asp Val Glu Glu Asn  Pro Gly Pro Ser Glu  Leu Ile Lys
    2120                2125                2130

Glu Asn  Met His Met Lys Leu  Tyr Met Glu Gly Thr  Val Asp Asn
    2135                2140                2145

His His  Phe Lys Cys Thr Ser  Glu Gly Glu Gly Lys  Pro Tyr Glu
    2150                2155                2160

Gly Thr  Gln Thr Met Arg Ile  Lys Val Val Glu Gly  Gly Pro Leu
    2165                2170                2175

Pro Phe  Ala Phe Asp Ile Leu  Ala Thr Ser Phe Leu  Tyr Gly Ser
    2180                2185                2190

Lys Thr  Phe Ile Asn His Thr  Gln Gly Ile Pro Asp  Phe Phe Lys
    2195                2200                2205

Gln Ser  Phe Pro Glu Gly Phe  Thr Trp Glu Arg Val  Thr Thr Tyr
    2210                2215                2220

Glu Asp  Gly Gly Val Leu Thr  Ala Thr Gln Asp Thr  Ser Leu Gln
    2225                2230                2235

Asp Gly  Cys Leu Ile Tyr Asn  Val Lys Ile Arg Gly  Val Asn Phe
    2240                2245                2250

Thr Ser  Asn Gly Pro Val Met  Gln Lys Lys Thr Leu  Gly Trp Glu
    2255                2260                2265

Ala Phe  Thr Glu Thr Leu Tyr  Pro Ala Asp Gly Gly  Leu Glu Gly
    2270                2275                2280

Arg Asn  Asp Met Ala Leu Lys  Leu Val Gly Gly Ser  His Leu Ile
    2285                2290                2295

Ala Asn  Ile Lys Thr Thr Tyr  Arg Ser Lys Lys Pro  Ala Lys Asn
    2300                2305                2310

Leu Lys  Met Pro Gly Val Tyr  Tyr Val Asp Tyr Arg  Leu Glu Arg
    2315                2320                2325
```

Ile Lys Glu Ala Asn Asn Glu Thr Tyr Val Glu Gln His Glu Val
2330 2335 2340

Ala Val Ala Arg Tyr Cys Asp Leu Pro Ser Lys Leu Gly His Lys
2345 2350 2355

Leu Asn
2360

<210> SEQ ID NO 6
<211> LENGTH: 2382
<212> TYPE: PRT
<213> ORGANISM: Artificial sequence
<220> FEATURE:
<223> OTHER INFORMATION: Synthetic polypeptide

<400> SEQUENCE: 6

Asp Ala Lys Ser Leu Thr Ala Trp Ser Arg Thr Leu Val Thr Phe Lys
1 5 10 15

Asp Val Phe Val Asp Phe Thr Arg Glu Glu Trp Lys Leu Leu Asp Thr
20 25 30

Ala Gln Gln Ile Val Tyr Arg Asn Val Met Leu Glu Asn Tyr Lys Asn
35 40 45

Leu Val Ser Leu Gly Tyr Gln Leu Thr Lys Pro Asp Val Ile Leu Arg
50 55 60

Leu Glu Lys Gly Glu Glu Pro Gly Gly Ser Gly Gly Gly Ser Met Asp
65 70 75 80

Lys Lys Tyr Ser Ile Gly Leu Ala Ile Gly Thr Asn Ser Val Gly Trp
85 90 95

Ala Val Ile Thr Asp Glu Tyr Lys Val Pro Ser Lys Lys Phe Lys Val
100 105 110

Leu Gly Asn Thr Asp Arg His Ser Ile Lys Lys Asn Leu Ile Gly Ala
115 120 125

Leu Leu Phe Asp Ser Gly Glu Thr Ala Glu Ala Thr Arg Leu Lys Arg
130 135 140

Thr Ala Arg Arg Arg Tyr Thr Arg Arg Lys Asn Arg Ile Cys Tyr Leu
145 150 155 160

Gln Glu Ile Phe Ser Asn Glu Met Ala Lys Val Asp Asp Ser Phe Phe
165 170 175

His Arg Leu Glu Glu Ser Phe Leu Val Glu Glu Asp Lys Lys His Glu
180 185 190

Arg His Pro Ile Phe Gly Asn Ile Val Asp Glu Val Ala Tyr His Glu
195 200 205

Lys Tyr Pro Thr Ile Tyr His Leu Arg Lys Lys Leu Val Asp Ser Thr
210 215 220

Asp Lys Ala Asp Leu Arg Leu Ile Tyr Leu Ala Leu Ala His Met Ile
225 230 235 240

Lys Phe Arg Gly His Phe Leu Ile Glu Gly Asp Leu Asn Pro Asp Asn
245 250 255

Ser Asp Val Asp Lys Leu Phe Ile Gln Leu Val Gln Thr Tyr Asn Gln
260 265 270

Leu Phe Glu Glu Asn Pro Ile Asn Ala Ser Gly Val Asp Ala Lys Ala
275 280 285

Ile Leu Ser Ala Arg Leu Ser Lys Ser Arg Arg Leu Glu Asn Leu Ile
290 295 300

Ala Gln Leu Pro Gly Glu Lys Lys Asn Gly Leu Phe Gly Asn Leu Ile
305 310 315 320

```
Ala Leu Ser Leu Gly Leu Thr Pro Asn Phe Lys Ser Asn Phe Asp Leu
                325                 330                 335

Ala Glu Asp Ala Lys Leu Gln Leu Ser Lys Asp Thr Tyr Asp Asp Asp
            340                 345                 350

Leu Asp Asn Leu Leu Ala Gln Ile Gly Asp Gln Tyr Ala Asp Leu Phe
        355                 360                 365

Leu Ala Ala Lys Asn Leu Ser Asp Ala Ile Leu Leu Ser Asp Ile Leu
    370                 375                 380

Arg Val Asn Thr Glu Ile Thr Lys Ala Pro Leu Ser Ala Ser Met Ile
385                 390                 395                 400

Lys Arg Tyr Asp Glu His His Gln Asp Leu Thr Leu Leu Lys Ala Leu
                405                 410                 415

Val Arg Gln Gln Leu Pro Glu Lys Tyr Lys Glu Ile Phe Phe Asp Gln
            420                 425                 430

Ser Lys Asn Gly Tyr Ala Gly Tyr Ile Asp Gly Gly Ala Ser Gln Glu
        435                 440                 445

Glu Phe Tyr Lys Phe Ile Lys Pro Ile Leu Glu Lys Met Asp Gly Thr
    450                 455                 460

Glu Glu Leu Leu Val Lys Leu Asn Arg Glu Asp Leu Leu Arg Lys Gln
465                 470                 475                 480

Arg Thr Phe Asp Asn Gly Ser Ile Pro His Gln Ile His Leu Gly Glu
                485                 490                 495

Leu His Ala Ile Leu Arg Arg Gln Glu Asp Phe Tyr Pro Phe Leu Lys
            500                 505                 510

Asp Asn Arg Glu Lys Ile Glu Lys Ile Leu Thr Phe Arg Ile Pro Tyr
        515                 520                 525

Tyr Val Gly Pro Leu Ala Arg Gly Asn Ser Arg Phe Ala Trp Met Thr
    530                 535                 540

Arg Lys Ser Glu Glu Thr Ile Thr Pro Trp Asn Phe Glu Glu Val Val
545                 550                 555                 560

Asp Lys Gly Ala Ser Ala Gln Ser Phe Ile Glu Arg Met Thr Asn Phe
                565                 570                 575

Asp Lys Asn Leu Pro Asn Glu Lys Val Leu Pro Lys His Ser Leu Leu
            580                 585                 590

Tyr Glu Tyr Phe Thr Val Tyr Asn Glu Leu Thr Lys Val Lys Tyr Val
        595                 600                 605

Thr Glu Gly Met Arg Lys Pro Ala Phe Leu Ser Gly Glu Gln Lys Lys
    610                 615                 620

Ala Ile Val Asp Leu Leu Phe Lys Thr Asn Arg Lys Val Thr Val Lys
625                 630                 635                 640

Gln Leu Lys Glu Asp Tyr Phe Lys Lys Ile Glu Cys Phe Asp Ser Val
                645                 650                 655

Glu Ile Ser Gly Val Glu Asp Arg Phe Asn Ala Ser Leu Gly Thr Tyr
            660                 665                 670

His Asp Leu Leu Lys Ile Ile Lys Asp Lys Asp Phe Leu Asp Asn Glu
        675                 680                 685

Glu Asn Glu Asp Ile Leu Glu Asp Ile Val Leu Thr Leu Thr Leu Phe
    690                 695                 700

Glu Asp Arg Glu Met Ile Glu Glu Arg Leu Lys Thr Tyr Ala His Leu
705                 710                 715                 720

Phe Asp Asp Lys Val Met Lys Gln Leu Lys Arg Arg Arg Tyr Thr Gly
                725                 730                 735
```

```
Trp Gly Arg Leu Ser Arg Lys Leu Ile Asn Gly Ile Arg Asp Lys Gln
            740                 745                 750

Ser Gly Lys Thr Ile Leu Asp Phe Leu Lys Ser Asp Gly Phe Ala Asn
        755                 760                 765

Arg Asn Phe Met Gln Leu Ile His Asp Asp Ser Leu Thr Phe Lys Glu
    770                 775                 780

Asp Ile Gln Lys Ala Gln Val Ser Gly Gln Gly Asp Ser Leu His Glu
785                 790                 795                 800

His Ile Ala Asn Leu Ala Gly Ser Pro Ala Ile Lys Lys Gly Ile Leu
                805                 810                 815

Gln Thr Val Lys Val Val Asp Glu Leu Val Lys Val Met Gly Arg His
            820                 825                 830

Lys Pro Glu Asn Ile Val Ile Glu Met Ala Arg Glu Asn Gln Thr Thr
        835                 840                 845

Gln Lys Gly Gln Lys Asn Ser Arg Glu Arg Met Lys Arg Ile Glu Glu
    850                 855                 860

Gly Ile Lys Glu Leu Gly Ser Gln Ile Leu Lys Glu His Pro Val Glu
865                 870                 875                 880

Asn Thr Gln Leu Gln Asn Glu Lys Leu Tyr Leu Tyr Tyr Leu Gln Asn
                885                 890                 895

Gly Arg Asp Met Tyr Val Asp Gln Glu Leu Asp Ile Asn Arg Leu Ser
            900                 905                 910

Asp Tyr Asp Val Asp Ala Ile Val Pro Gln Ser Phe Leu Lys Asp Asp
        915                 920                 925

Ser Ile Asp Asn Lys Val Leu Thr Arg Ser Asp Lys Asn Arg Gly Lys
    930                 935                 940

Ser Asp Asn Val Pro Ser Glu Glu Val Val Lys Lys Met Lys Asn Tyr
945                 950                 955                 960

Trp Arg Gln Leu Leu Asn Ala Lys Leu Ile Thr Gln Arg Lys Phe Asp
                965                 970                 975

Asn Leu Thr Lys Ala Glu Arg Gly Gly Leu Ser Glu Leu Asp Lys Ala
            980                 985                 990

Gly Phe Ile Lys Arg Gln Leu Val  Glu Thr Arg Gln Ile  Thr Lys His
        995                 1000                1005

Val Ala  Gln Ile Leu Asp Ser  Arg Met Asn Thr Lys  Tyr Asp Glu
    1010                1015                1020

Asn Asp  Lys Leu Ile Arg Glu  Val Lys Val Ile Thr  Leu Lys Ser
    1025                1030                1035

Lys Leu  Val Ser Asp Phe Arg  Lys Asp Phe Gln Phe  Tyr Lys Val
    1040                1045                1050

Arg Glu  Ile Asn Asn Tyr His  His Ala His Asp Ala  Tyr Leu Asn
    1055                1060                1065

Ala Val  Val Gly Thr Ala Leu  Ile Lys Lys Tyr Pro  Lys Leu Glu
    1070                1075                1080

Ser Glu  Phe Val Tyr Gly Asp  Tyr Lys Val Tyr Asp  Val Arg Lys
    1085                1090                1095

Met Ile  Ala Lys Ser Glu Gln  Glu Ile Gly Lys Ala  Thr Ala Lys
    1100                1105                1110

Tyr Phe  Phe Tyr Ser Asn Ile  Met Asn Phe Phe Lys  Thr Glu Ile
    1115                1120                1125

Thr Leu  Ala Asn Gly Glu Ile  Arg Lys Arg Pro Leu  Ile Glu Thr
    1130                1135                1140

Asn Gly  Glu Thr Gly Glu Ile  Val Trp Asp Lys Gly  Arg Asp Phe
```

```
    1145                1150                1155

Ala Thr  Val Arg Lys Val Leu  Ser Met Pro Gln Val  Asn Ile Val
    1160                1165                1170

Lys Lys  Thr Glu Val Gln Thr  Gly Gly Phe Ser Lys  Glu Ser Ile
    1175                1180                1185

Leu Pro  Lys Arg Asn Ser Asp  Lys Leu Ile Ala Arg  Lys Lys Asp
    1190                1195                1200

Trp Asp  Pro Lys Lys Tyr Gly  Gly Phe Asp Ser Pro  Thr Val Ala
    1205                1210                1215

Tyr Ser  Val Leu Val Val Ala  Lys Val Glu Lys Gly  Lys Ser Lys
    1220                1225                1230

Lys Leu  Lys Ser Val Lys Glu  Leu Leu Gly Ile Thr  Ile Met Glu
    1235                1240                1245

Arg Ser  Ser Phe Glu Lys Asn  Pro Ile Asp Phe Leu  Glu Ala Lys
    1250                1255                1260

Gly Tyr  Lys Glu Val Lys Lys  Asp Leu Ile Ile Lys  Leu Pro Lys
    1265                1270                1275

Tyr Ser  Leu Phe Glu Leu Glu  Asn Gly Arg Lys Arg  Met Leu Ala
    1280                1285                1290

Ser Ala  Gly Glu Leu Gln Lys  Gly Asn Glu Leu Ala  Leu Pro Ser
    1295                1300                1305

Lys Tyr  Val Asn Phe Leu Tyr  Leu Ala Ser His Tyr  Glu Lys Leu
    1310                1315                1320

Lys Gly  Ser Pro Glu Asp Asn  Glu Gln Lys Gln Leu  Phe Val Glu
    1325                1330                1335

Gln His  Lys His Tyr Leu Asp  Glu Ile Ile Glu Gln  Ile Ser Glu
    1340                1345                1350

Phe Ser  Lys Arg Val Ile Leu  Ala Asp Ala Asn Leu  Asp Lys Val
    1355                1360                1365

Leu Ser  Ala Tyr Asn Lys His  Arg Asp Lys Pro Ile  Arg Glu Gln
    1370                1375                1380

Ala Glu  Asn Ile Ile His Leu  Phe Thr Leu Thr Asn  Leu Gly Ala
    1385                1390                1395

Pro Ala  Ala Phe Lys Tyr Phe  Asp Thr Thr Ile Asp  Arg Lys Arg
    1400                1405                1410

Tyr Thr  Ser Thr Lys Glu Val  Leu Asp Ala Thr Leu  Ile His Gln
    1415                1420                1425

Ser Ile  Thr Gly Leu Tyr Glu  Thr Arg Ile Asp Leu  Ser Gln Leu
    1430                1435                1440

Gly Gly  Asp Ser Arg Ala Asp  Tyr Pro Tyr Asp Val  Pro Asp Tyr
    1445                1450                1455

Ala Ser  Gly Ser Pro Lys Lys  Lys Arg Lys Val Ser  Pro Gly Gly
    1460                1465                1470

Gly Pro  Ser Ser Gly Ala Pro  Pro Pro Ser Gly Gly  Ser Pro Ala
    1475                1480                1485

Gly Ser  Pro Thr Ser Thr Glu  Glu Gly Thr Ser Glu  Ser Ala Thr
    1490                1495                1500

Pro Glu  Ser Gly Pro Gly Thr  Ser Thr Glu Pro Ser  Glu Gly Ser
    1505                1510                1515

Ala Pro  Gly Ser Pro Ala Gly  Ser Pro Thr Ser Thr  Glu Glu Gly
    1520                1525                1530

Thr Ser  Thr Glu Pro Ser Glu  Gly Ser Ala Pro Gly  Thr Ser Thr
    1535                1540                1545
```

```
Glu Pro  Ser Glu Asn His Asp  Gln Glu Phe Asp Pro  Pro Lys Val
    1550                 1555                 1560

Tyr Pro  Pro Val Pro Ala Glu  Lys Arg Lys Pro Ile  Arg Val Leu
    1565                 1570                 1575

Ser Leu  Phe Asp Gly Ile Ala  Thr Gly Leu Leu Val  Leu Lys Asp
    1580                 1585                 1590

Leu Gly  Ile Gln Val Asp Arg  Tyr Ile Ala Ser Glu  Val Cys Glu
    1595                 1600                 1605

Asp Ser  Ile Thr Val Gly Met  Val Arg His Gln Gly  Lys Ile Met
    1610                 1615                 1620

Tyr Val  Gly Asp Val Arg Ser  Val Thr Gln Lys His  Ile Gln Glu
    1625                 1630                 1635

Trp Gly  Pro Phe Asp Leu Val  Ile Gly Gly Ser Pro  Cys Asn Asp
    1640                 1645                 1650

Leu Ser  Ile Val Asn Pro Ala  Arg Lys Gly Leu Tyr  Glu Gly Thr
    1655                 1660                 1665

Gly Arg  Leu Phe Phe Glu Phe  Tyr Arg Leu Leu His  Asp Ala Arg
    1670                 1675                 1680

Pro Lys  Glu Gly Asp Asp Arg  Pro Phe Phe Trp Leu  Phe Glu Asn
    1685                 1690                 1695

Val Val  Ala Met Gly Val Ser  Asp Lys Arg Asp Ile  Ser Arg Phe
    1700                 1705                 1710

Leu Glu  Ser Asn Pro Val Met  Ile Asp Ala Lys Glu  Val Ser Ala
    1715                 1720                 1725

Ala His  Arg Ala Arg Tyr Phe  Trp Gly Asn Leu Pro  Gly Met Asn
    1730                 1735                 1740

Arg Pro  Leu Ala Ser Thr Val  Asn Asp Lys Leu Glu  Leu Gln Glu
    1745                 1750                 1755

Cys Leu  Glu His Gly Arg Ile  Ala Lys Phe Ser Lys  Val Arg Thr
    1760                 1765                 1770

Ile Thr  Thr Arg Ser Asn Ser  Ile Lys Gln Gly Lys  Asp Gln His
    1775                 1780                 1785

Phe Pro  Val Phe Met Asn Glu  Lys Glu Asp Ile Leu  Trp Cys Thr
    1790                 1795                 1800

Glu Met  Glu Arg Val Phe Gly  Phe Pro Val His Tyr  Thr Asp Val
    1805                 1810                 1815

Ser Asn  Met Ser Arg Leu Ala  Arg Gln Arg Leu Leu  Gly Arg Ser
    1820                 1825                 1830

Trp Ser  Val Pro Val Ile Arg  His Leu Phe Ala Pro  Leu Lys Glu
    1835                 1840                 1845

Tyr Phe  Ala Cys Val Ser Ser  Gly Asn Ser Asn Ala  Asn Ser Arg
    1850                 1855                 1860

Gly Pro  Ser Phe Ser Ser Gly  Leu Val Pro Leu Ser  Leu Arg Gly
    1865                 1870                 1875

Ser His  Met Gly Pro Met Glu  Ile Tyr Lys Thr Val  Ser Ala Trp
    1880                 1885                 1890

Lys Arg  Gln Pro Val Arg Val  Leu Ser Leu Phe Arg  Asn Ile Asp
    1895                 1900                 1905

Lys Val  Leu Lys Ser Leu Gly  Phe Leu Glu Ser Gly  Ser Gly Ser
    1910                 1915                 1920

Gly Gly  Gly Thr Leu Lys Tyr  Val Glu Asp Val Thr  Asn Val Val
    1925                 1930                 1935
```

```
Arg Arg  Asp Val Glu Lys Trp  Gly Pro Phe Asp Leu  Val Tyr Gly
    1940                 1945                 1950

Ser Thr  Gln Pro Leu Gly Ser  Ser Cys Asp Arg Cys  Pro Gly Trp
    1955                 1960                 1965

Tyr Met  Phe Gln Phe His Arg  Ile Leu Gln Tyr Ala  Leu Pro Arg
    1970                 1975                 1980

Gln Glu  Ser Gln Arg Pro Phe  Phe Trp Ile Phe Met  Asp Asn Leu
    1985                 1990                 1995

Leu Leu  Thr Glu Asp Asp Gln  Glu Thr Thr Thr Arg  Phe Leu Gln
    2000                 2005                 2010

Thr Glu  Ala Val Thr Leu Gln  Asp Val Arg Gly Arg  Asp Tyr Gln
    2015                 2020                 2025

Asn Ala  Met Arg Val Trp Ser  Asn Ile Pro Gly Leu  Lys Ser Lys
    2030                 2035                 2040

His Ala  Pro Leu Thr Pro Lys  Glu Glu Glu Tyr Leu  Gln Ala Gln
    2045                 2050                 2055

Val Arg  Ser Arg Ser Lys Leu  Asp Ala Pro Lys Val  Asp Leu Leu
    2060                 2065                 2070

Val Lys  Asn Cys Leu Leu Pro  Leu Arg Glu Tyr Phe  Lys Tyr Phe
    2075                 2080                 2085

Ser Gln  Asn Ser Leu Pro Leu  Ser Arg Ala Asp Pro  Lys Lys Lys
    2090                 2095                 2100

Arg Lys  Val Gly Ser Gly Ala  Thr Asn Phe Ser Leu  Leu Lys Gln
    2105                 2110                 2115

Ala Gly  Asp Val Glu Glu Asn  Pro Gly Pro Gly Ser  Gly Ala Thr
    2120                 2125                 2130

Asn Phe  Ser Leu Leu Lys Gln  Ala Gly Asp Val Glu  Glu Asn Pro
    2135                 2140                 2145

Gly Pro  Ser Glu Leu Ile Lys  Glu Asn Met His Met  Lys Leu Tyr
    2150                 2155                 2160

Met Glu  Gly Thr Val Asp Asn  His His Phe Lys Cys  Thr Ser Glu
    2165                 2170                 2175

Gly Glu  Gly Lys Pro Tyr Glu  Gly Thr Gln Thr Met  Arg Ile Lys
    2180                 2185                 2190

Val Val  Glu Gly Gly Pro Leu  Pro Phe Ala Phe Asp  Ile Leu Ala
    2195                 2200                 2205

Thr Ser  Phe Leu Tyr Gly Ser  Lys Thr Phe Ile Asn  His Thr Gln
    2210                 2215                 2220

Gly Ile  Pro Asp Phe Phe Lys  Gln Ser Phe Pro Glu  Gly Phe Thr
    2225                 2230                 2235

Trp Glu  Arg Val Thr Thr Tyr  Glu Asp Gly Gly Val  Leu Thr Ala
    2240                 2245                 2250

Thr Gln  Asp Thr Ser Leu Gln  Asp Gly Cys Leu Ile  Tyr Asn Val
    2255                 2260                 2265

Lys Ile  Arg Gly Val Asn Phe  Thr Ser Asn Gly Pro  Val Met Gln
    2270                 2275                 2280

Lys Lys  Thr Leu Gly Trp Glu  Ala Phe Thr Glu Thr  Leu Tyr Pro
    2285                 2290                 2295

Ala Asp  Gly Gly Leu Glu Gly  Arg Asn Asp Met Ala  Leu Lys Leu
    2300                 2305                 2310

Val Gly  Gly Ser His Leu Ile  Ala Asn Ile Lys Thr  Thr Tyr Arg
    2315                 2320                 2325

Ser Lys  Lys Pro Ala Lys Asn  Leu Lys Met Pro Gly  Val Tyr Tyr
```

```
    2330                2335                2340

Val Asp  Tyr Arg Leu Glu Arg  Ile Lys Glu Ala Asn  Asn Glu Thr
    2345                2350                2355

Tyr Val  Glu Gln His Glu Val  Ala Val Ala Arg Tyr  Cys Asp Leu
    2360                2365                2370

Pro Ser  Lys Leu Gly His Lys  Leu Asn
    2375                2380


<210> SEQ ID NO 7
<211> LENGTH: 2303
<212> TYPE: PRT
<213> ORGANISM: Artificial sequence
<220> FEATURE:
<223> OTHER INFORMATION: Synthetic polypeptide

<400> SEQUENCE: 7

Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Ser Gly Ser Glu Thr Pro Gly Thr Ser
65                  70                  75                  80

Glu Ser Ala Thr Pro Glu Ser Met Asp Lys Lys Tyr Ser Ile Gly Leu
                85                  90                  95

Ala Ile Gly Thr Asn Ser Val Gly Trp Ala Val Ile Thr Asp Glu Tyr
            100                 105                 110

Lys Val Pro Ser Lys Lys Phe Lys Val Leu Gly Asn Thr Asp Arg His
        115                 120                 125

Ser Ile Lys Lys Asn Leu Ile Gly Ala Leu Leu Phe Asp Ser Gly Glu
    130                 135                 140

Thr Ala Glu Ala Thr Arg Leu Lys Arg Thr Ala Arg Arg Arg Tyr Thr
145                 150                 155                 160

Arg Arg Lys Asn Arg Ile Cys Tyr Leu Gln Glu Ile Phe Ser Asn Glu
                165                 170                 175

Met Ala Lys Val Asp Asp Ser Phe Phe His Arg Leu Glu Glu Ser Phe
            180                 185                 190

Leu Val Glu Glu Asp Lys Lys His Glu Arg His Pro Ile Phe Gly Asn
        195                 200                 205

Ile Val Asp Glu Val Ala Tyr His Glu Lys Tyr Pro Thr Ile Tyr His
    210                 215                 220

Leu Arg Lys Lys Leu Val Asp Ser Thr Asp Lys Ala Asp Leu Arg Leu
225                 230                 235                 240

Ile Tyr Leu Ala Leu Ala His Met Ile Lys Phe Arg Gly His Phe Leu
                245                 250                 255

Ile Glu Gly Asp Leu Asn Pro Asp Asn Ser Asp Val Asp Lys Leu Phe
            260                 265                 270

Ile Gln Leu Val Gln Thr Tyr Asn Gln Leu Phe Glu Glu Asn Pro Ile
        275                 280                 285

Asn Ala Ser Gly Val Asp Ala Lys Ala Ile Leu Ser Ala Arg Leu Ser
    290                 295                 300

Lys Ser Arg Arg Leu Glu Asn Leu Ile Ala Gln Leu Pro Gly Glu Lys
```

305 310 315 320

Lys Asn Gly Leu Phe Gly Asn Leu Ile Ala Leu Ser Leu Gly Leu Thr
325 330 335

Pro Asn Phe Lys Ser Asn Phe Asp Leu Ala Glu Asp Ala Lys Leu Gln
340 345 350

Leu Ser Lys Asp Thr Tyr Asp Asp Asp Leu Asp Asn Leu Leu Ala Gln
355 360 365

Ile Gly Asp Gln Tyr Ala Asp Leu Phe Leu Ala Ala Lys Asn Leu Ser
370 375 380

Asp Ala Ile Leu Leu Ser Asp Ile Leu Arg Val Asn Thr Glu Ile Thr
385 390 395 400

Lys Ala Pro Leu Ser Ala Ser Met Ile Lys Arg Tyr Asp Glu His His
405 410 415

Gln Asp Leu Thr Leu Leu Lys Ala Leu Val Arg Gln Gln Leu Pro Glu
420 425 430

Lys Tyr Lys Glu Ile Phe Phe Asp Gln Ser Lys Asn Gly Tyr Ala Gly
435 440 445

Tyr Ile Asp Gly Gly Ala Ser Gln Glu Glu Phe Tyr Lys Phe Ile Lys
450 455 460

Pro Ile Leu Glu Lys Met Asp Gly Thr Glu Glu Leu Leu Val Lys Leu
465 470 475 480

Asn Arg Glu Asp Leu Leu Arg Lys Gln Arg Thr Phe Asp Asn Gly Ser
485 490 495

Ile Pro His Gln Ile His Leu Gly Glu Leu His Ala Ile Leu Arg Arg
500 505 510

Gln Glu Asp Phe Tyr Pro Phe Leu Lys Asp Asn Arg Glu Lys Ile Glu
515 520 525

Lys Ile Leu Thr Phe Arg Ile Pro Tyr Tyr Val Gly Pro Leu Ala Arg
530 535 540

Gly Asn Ser Arg Phe Ala Trp Met Thr Arg Lys Ser Glu Glu Thr Ile
545 550 555 560

Thr Pro Trp Asn Phe Glu Glu Val Val Asp Lys Gly Ala Ser Ala Gln
565 570 575

Ser Phe Ile Glu Arg Met Thr Asn Phe Asp Lys Asn Leu Pro Asn Glu
580 585 590

Lys Val Leu Pro Lys His Ser Leu Leu Tyr Glu Tyr Phe Thr Val Tyr
595 600 605

Asn Glu Leu Thr Lys Val Lys Tyr Val Thr Glu Gly Met Arg Lys Pro
610 615 620

Ala Phe Leu Ser Gly Glu Gln Lys Lys Ala Ile Val Asp Leu Leu Phe
625 630 635 640

Lys Thr Asn Arg Lys Val Thr Val Lys Gln Leu Lys Glu Asp Tyr Phe
645 650 655

Lys Lys Ile Glu Cys Phe Asp Ser Val Glu Ile Ser Gly Val Glu Asp
660 665 670

Arg Phe Asn Ala Ser Leu Gly Thr Tyr His Asp Leu Leu Lys Ile Ile
675 680 685

Lys Asp Lys Asp Phe Leu Asp Asn Glu Glu Asn Glu Asp Ile Leu Glu
690 695 700

Asp Ile Val Leu Thr Leu Thr Leu Phe Glu Asp Arg Glu Met Ile Glu
705 710 715 720

Glu Arg Leu Lys Thr Tyr Ala His Leu Phe Asp Asp Lys Val Met Lys
725 730 735

```
Gln Leu Lys Arg Arg Arg Tyr Thr Gly Trp Gly Arg Leu Ser Arg Lys
            740                 745                 750

Leu Ile Asn Gly Ile Arg Asp Lys Gln Ser Gly Lys Thr Ile Leu Asp
        755                 760                 765

Phe Leu Lys Ser Asp Gly Phe Ala Asn Arg Asn Phe Met Gln Leu Ile
    770                 775                 780

His Asp Asp Ser Leu Thr Phe Lys Glu Asp Ile Gln Lys Ala Gln Val
785                 790                 795                 800

Ser Gly Gln Gly Asp Ser Leu His Glu His Ile Ala Asn Leu Ala Gly
                805                 810                 815

Ser Pro Ala Ile Lys Lys Gly Ile Leu Gln Thr Val Lys Val Val Asp
            820                 825                 830

Glu Leu Val Lys Val Met Gly Arg His Lys Pro Glu Asn Ile Val Ile
        835                 840                 845

Glu Met Ala Arg Glu Asn Gln Thr Thr Gln Lys Gly Gln Lys Asn Ser
    850                 855                 860

Arg Glu Arg Met Lys Arg Ile Glu Glu Gly Ile Lys Glu Leu Gly Ser
865                 870                 875                 880

Gln Ile Leu Lys Glu His Pro Val Glu Asn Thr Gln Leu Gln Asn Glu
                885                 890                 895

Lys Leu Tyr Leu Tyr Tyr Leu Gln Asn Gly Arg Asp Met Tyr Val Asp
            900                 905                 910

Gln Glu Leu Asp Ile Asn Arg Leu Ser Asp Tyr Asp Val Asp Ala Ile
        915                 920                 925

Val Pro Gln Ser Phe Leu Lys Asp Asp Ser Ile Asp Asn Lys Val Leu
    930                 935                 940

Thr Arg Ser Asp Lys Asn Arg Gly Lys Ser Asp Asn Val Pro Ser Glu
945                 950                 955                 960

Glu Val Val Lys Lys Met Lys Asn Tyr Trp Arg Gln Leu Leu Asn Ala
                965                 970                 975

Lys Leu Ile Thr Gln Arg Lys Phe Asp Asn Leu Thr Lys Ala Glu Arg
            980                 985                 990

Gly Gly Leu Ser Glu Leu Asp Lys  Ala Gly Phe Ile Lys  Arg Gln Leu
        995                 1000                1005

Val Glu  Thr Arg Gln Ile Thr  Lys His Val Ala Gln  Ile Leu Asp
    1010                1015                1020

Ser Arg  Met Asn Thr Lys Tyr  Asp Glu Asn Asp Lys  Leu Ile Arg
    1025                1030                1035

Glu Val  Lys Val Ile Thr Leu  Lys Ser Lys Leu Val  Ser Asp Phe
    1040                1045                1050

Arg Lys  Asp Phe Gln Phe Tyr  Lys Val Arg Glu Ile  Asn Asn Tyr
    1055                1060                1065

His His  Ala His Asp Ala Tyr  Leu Asn Ala Val Val  Gly Thr Ala
    1070                1075                1080

Leu Ile  Lys Lys Tyr Pro Lys  Leu Glu Ser Glu Phe  Val Tyr Gly
    1085                1090                1095

Asp Tyr  Lys Val Tyr Asp Val  Arg Lys Met Ile Ala  Lys Ser Glu
    1100                1105                1110

Gln Glu  Ile Gly Lys Ala Thr  Ala Lys Tyr Phe Phe  Tyr Ser Asn
    1115                1120                1125

Ile Met  Asn Phe Phe Lys Thr  Glu Ile Thr Leu Ala  Asn Gly Glu
    1130                1135                1140
```

```
Ile Arg  Lys Arg Pro Leu Ile  Glu Thr Asn Gly Glu  Thr Gly Glu
    1145                 1150                 1155

Ile Val  Trp Asp Lys Gly Arg  Asp Phe Ala Thr Val  Arg Lys Val
    1160                 1165                 1170

Leu Ser  Met Pro Gln Val Asn  Ile Val Lys Lys Thr  Glu Val Gln
    1175                 1180                 1185

Thr Gly  Gly Phe Ser Lys Glu  Ser Ile Leu Pro Lys  Arg Asn Ser
    1190                 1195                 1200

Asp Lys  Leu Ile Ala Arg Lys  Lys Asp Trp Asp Pro  Lys Lys Tyr
    1205                 1210                 1215

Gly Gly  Phe Asp Ser Pro Thr  Val Ala Tyr Ser Val  Leu Val Val
    1220                 1225                 1230

Ala Lys  Val Glu Lys Gly Lys  Ser Lys Lys Leu Lys  Ser Val Lys
    1235                 1240                 1245

Glu Leu  Leu Gly Ile Thr Ile  Met Glu Arg Ser Ser  Phe Glu Lys
    1250                 1255                 1260

Asn Pro  Ile Asp Phe Leu Glu  Ala Lys Gly Tyr Lys  Glu Val Lys
    1265                 1270                 1275

Lys Asp  Leu Ile Ile Lys Leu  Pro Lys Tyr Ser Leu  Phe Glu Leu
    1280                 1285                 1290

Glu Asn  Gly Arg Lys Arg Met  Leu Ala Ser Ala Gly  Glu Leu Gln
    1295                 1300                 1305

Lys Gly  Asn Glu Leu Ala Leu  Pro Ser Lys Tyr Val  Asn Phe Leu
    1310                 1315                 1320

Tyr Leu  Ala Ser His Tyr Glu  Lys Leu Lys Gly Ser  Pro Glu Asp
    1325                 1330                 1335

Asn Glu  Gln Lys Gln Leu Phe  Val Glu Gln His Lys  His Tyr Leu
    1340                 1345                 1350

Asp Glu  Ile Ile Glu Gln Ile  Ser Glu Phe Ser Lys  Arg Val Ile
    1355                 1360                 1365

Leu Ala  Asp Ala Asn Leu Asp  Lys Val Leu Ser Ala  Tyr Asn Lys
    1370                 1375                 1380

His Arg  Asp Lys Pro Ile Arg  Glu Gln Ala Glu Asn  Ile Ile His
    1385                 1390                 1395

Leu Phe  Thr Leu Thr Asn Leu  Gly Ala Pro Ala Ala  Phe Lys Tyr
    1400                 1405                 1410

Phe Asp  Thr Thr Ile Asp Arg  Lys Arg Tyr Thr Ser  Thr Lys Glu
    1415                 1420                 1425

Val Leu  Asp Ala Thr Leu Ile  His Gln Ser Ile Thr  Gly Leu Tyr
    1430                 1435                 1440

Glu Thr  Arg Ile Asp Leu Ser  Gln Leu Gly Gly Asp  Ser Arg Ala
    1445                 1450                 1455

Asp Tyr  Pro Tyr Asp Val Pro  Asp Tyr Ala Ser Gly  Ser Pro Lys
    1460                 1465                 1470

Lys Lys  Arg Lys Val Glu Ala  Ser Gly Ser Gly Arg  Ala Ser Pro
    1475                 1480                 1485

Gly Ile  Pro Gly Ser Thr Arg  Asn His Asp Gln Glu  Phe Asp Pro
    1490                 1495                 1500

Pro Lys  Val Tyr Pro Pro Val  Pro Ala Glu Lys Arg  Lys Pro Ile
    1505                 1510                 1515

Arg Val  Leu Ser Leu Phe Asp  Gly Ile Ala Thr Gly  Leu Leu Val
    1520                 1525                 1530

Leu Lys  Asp Leu Gly Ile Gln  Val Asp Arg Tyr Ile  Ala Ser Glu
```

```
    1535                1540                1545

Val Cys  Glu Asp Ser Ile Thr  Val Gly Met Val Arg  His Gln Gly
    1550                1555                1560

Lys Ile  Met Tyr Val Gly Asp  Val Arg Ser Val Thr  Gln Lys His
    1565                1570                1575

Ile Gln  Glu Trp Gly Pro Phe  Asp Leu Val Ile Gly  Gly Ser Pro
    1580                1585                1590

Cys Asn  Asp Leu Ser Ile Val  Asn Pro Ala Arg Lys  Gly Leu Tyr
    1595                1600                1605

Glu Gly  Thr Gly Arg Leu Phe  Phe Glu Phe Tyr Arg  Leu Leu His
    1610                1615                1620

Asp Ala  Arg Pro Lys Glu Gly  Asp Asp Arg Pro Phe  Phe Trp Leu
    1625                1630                1635

Phe Glu  Asn Val Val Ala Met  Gly Val Ser Asp Lys  Arg Asp Ile
    1640                1645                1650

Ser Arg  Phe Leu Glu Ser Asn  Pro Val Met Ile Asp  Ala Lys Glu
    1655                1660                1665

Val Ser  Ala Ala His Arg Ala  Arg Tyr Phe Trp Gly  Asn Leu Pro
    1670                1675                1680

Gly Met  Asn Arg Pro Leu Ala  Ser Thr Val Asn Asp  Lys Leu Glu
    1685                1690                1695

Leu Gln  Glu Cys Leu Glu His  Gly Arg Ile Ala Lys  Phe Ser Lys
    1700                1705                1710

Val Arg  Thr Ile Thr Thr Arg  Ser Asn Ser Ile Lys  Gln Gly Lys
    1715                1720                1725

Asp Gln  His Phe Pro Val Phe  Met Asn Glu Lys Glu  Asp Ile Leu
    1730                1735                1740

Trp Cys  Thr Glu Met Glu Arg  Val Phe Gly Phe Pro  Val His Tyr
    1745                1750                1755

Thr Asp  Val Ser Asn Met Ser  Arg Leu Ala Arg Gln  Arg Leu Leu
    1760                1765                1770

Gly Arg  Ser Trp Ser Val Pro  Val Ile Arg His Leu  Phe Ala Pro
    1775                1780                1785

Leu Lys  Glu Tyr Phe Ala Cys  Val Ser Ser Gly Asn  Ser Asn Ala
    1790                1795                1800

Asn Ser  Arg Gly Pro Ser Phe  Ser Ser Gly Leu Val  Pro Leu Ser
    1805                1810                1815

Leu Arg  Gly Ser His Met Gly  Pro Met Glu Ile Tyr  Lys Thr Val
    1820                1825                1830

Ser Ala  Trp Lys Arg Gln Pro  Val Arg Val Leu Ser  Leu Phe Arg
    1835                1840                1845

Asn Ile  Asp Lys Val Leu Lys  Ser Leu Gly Phe Leu  Glu Ser Gly
    1850                1855                1860

Ser Gly  Ser Gly Gly Gly Thr  Leu Lys Tyr Val Glu  Asp Val Thr
    1865                1870                1875

Asn Val  Val Arg Arg Asp Val  Glu Lys Trp Gly Pro  Phe Asp Leu
    1880                1885                1890

Val Tyr  Gly Ser Thr Gln Pro  Leu Gly Ser Ser Cys  Asp Arg Cys
    1895                1900                1905

Pro Gly  Trp Tyr Met Phe Gln  Phe His Arg Ile Leu  Gln Tyr Ala
    1910                1915                1920

Leu Pro  Arg Gln Glu Ser Gln  Arg Pro Phe Phe Trp  Ile Phe Met
    1925                1930                1935
```

Asp Asn Leu Leu Leu Thr Glu Asp Asp Gln Glu Thr Thr Thr Arg
1940 1945 1950

Phe Leu Gln Thr Glu Ala Val Thr Leu Gln Asp Val Arg Gly Arg
1955 1960 1965

Asp Tyr Gln Asn Ala Met Arg Val Trp Ser Asn Ile Pro Gly Leu
1970 1975 1980

Lys Ser Lys His Ala Pro Leu Thr Pro Lys Glu Glu Glu Tyr Leu
1985 1990 1995

Gln Ala Gln Val Arg Ser Arg Ser Lys Leu Asp Ala Pro Lys Val
2000 2005 2010

Asp Leu Leu Val Lys Asn Cys Leu Leu Pro Leu Arg Glu Tyr Phe
2015 2020 2025

Lys Tyr Phe Ser Gln Asn Ser Leu Pro Leu Ser Arg Ala Asp Pro
2030 2035 2040

Lys Lys Lys Arg Lys Val Gly Ser Gly Ala Thr Asn Phe Ser Leu
2045 2050 2055

Leu Lys Gln Ala Gly Asp Val Glu Glu Asn Pro Gly Pro Ser Glu
2060 2065 2070

Leu Ile Lys Glu Asn Met His Met Lys Leu Tyr Met Glu Gly Thr
2075 2080 2085

Val Asp Asn His His Phe Lys Cys Thr Ser Glu Gly Glu Gly Lys
2090 2095 2100

Pro Tyr Glu Gly Thr Gln Thr Met Arg Ile Lys Val Val Glu Gly
2105 2110 2115

Gly Pro Leu Pro Phe Ala Phe Asp Ile Leu Ala Thr Ser Phe Leu
2120 2125 2130

Tyr Gly Ser Lys Thr Phe Ile Asn His Thr Gln Gly Ile Pro Asp
2135 2140 2145

Phe Phe Lys Gln Ser Phe Pro Glu Gly Phe Thr Trp Glu Arg Val
2150 2155 2160

Thr Thr Tyr Glu Asp Gly Gly Val Leu Thr Ala Thr Gln Asp Thr
2165 2170 2175

Ser Leu Gln Asp Gly Cys Leu Ile Tyr Asn Val Lys Ile Arg Gly
2180 2185 2190

Val Asn Phe Thr Ser Asn Gly Pro Val Met Gln Lys Lys Thr Leu
2195 2200 2205

Gly Trp Glu Ala Phe Thr Glu Thr Leu Tyr Pro Ala Asp Gly Gly
2210 2215 2220

Leu Glu Gly Arg Asn Asp Met Ala Leu Lys Leu Val Gly Gly Ser
2225 2230 2235

His Leu Ile Ala Asn Ile Lys Thr Thr Tyr Arg Ser Lys Lys Pro
2240 2245 2250

Ala Lys Asn Leu Lys Met Pro Gly Val Tyr Tyr Val Asp Tyr Arg
2255 2260 2265

Leu Glu Arg Ile Lys Glu Ala Asn Asn Glu Thr Tyr Val Glu Gln
2270 2275 2280

His Glu Val Ala Val Ala Arg Tyr Cys Asp Leu Pro Ser Lys Leu
2285 2290 2295

Gly His Lys Leu Asn
2300

<210> SEQ ID NO 8
<211> LENGTH: 2325

<212> TYPE: PRT
<213> ORGANISM: Artificial sequence
<220> FEATURE:
<223> OTHER INFORMATION: Synthetic polypeptide

<400> SEQUENCE: 8

```
Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Ser Gly Ser Glu Thr Pro Gly Thr Ser
65                  70                  75                  80

Glu Ser Ala Thr Pro Glu Ser Met Asp Lys Lys Tyr Ser Ile Gly Leu
                85                  90                  95

Ala Ile Gly Thr Asn Ser Val Gly Trp Ala Val Ile Thr Asp Glu Tyr
            100                 105                 110

Lys Val Pro Ser Lys Lys Phe Lys Val Leu Gly Asn Thr Asp Arg His
        115                 120                 125

Ser Ile Lys Lys Asn Leu Ile Gly Ala Leu Leu Phe Asp Ser Gly Glu
    130                 135                 140

Thr Ala Glu Ala Thr Arg Leu Lys Arg Thr Ala Arg Arg Arg Tyr Thr
145                 150                 155                 160

Arg Arg Lys Asn Arg Ile Cys Tyr Leu Gln Glu Ile Phe Ser Asn Glu
                165                 170                 175

Met Ala Lys Val Asp Asp Ser Phe Phe His Arg Leu Glu Glu Ser Phe
            180                 185                 190

Leu Val Glu Glu Asp Lys Lys His Glu Arg His Pro Ile Phe Gly Asn
        195                 200                 205

Ile Val Asp Glu Val Ala Tyr His Glu Lys Tyr Pro Thr Ile Tyr His
    210                 215                 220

Leu Arg Lys Lys Leu Val Asp Ser Thr Asp Lys Ala Asp Leu Arg Leu
225                 230                 235                 240

Ile Tyr Leu Ala Leu Ala His Met Ile Lys Phe Arg Gly His Phe Leu
                245                 250                 255

Ile Glu Gly Asp Leu Asn Pro Asp Asn Ser Asp Val Asp Lys Leu Phe
            260                 265                 270

Ile Gln Leu Val Gln Thr Tyr Asn Gln Leu Phe Glu Glu Asn Pro Ile
        275                 280                 285

Asn Ala Ser Gly Val Asp Ala Lys Ala Ile Leu Ser Ala Arg Leu Ser
    290                 295                 300

Lys Ser Arg Arg Leu Glu Asn Leu Ile Ala Gln Leu Pro Gly Glu Lys
305                 310                 315                 320

Lys Asn Gly Leu Phe Gly Asn Leu Ile Ala Leu Ser Leu Gly Leu Thr
                325                 330                 335

Pro Asn Phe Lys Ser Asn Phe Asp Leu Ala Glu Asp Ala Lys Leu Gln
            340                 345                 350

Leu Ser Lys Asp Thr Tyr Asp Asp Asp Leu Asp Asn Leu Leu Ala Gln
        355                 360                 365

Ile Gly Asp Gln Tyr Ala Asp Leu Phe Leu Ala Ala Lys Asn Leu Ser
    370                 375                 380
```

```
Asp Ala Ile Leu Leu Ser Asp Ile Leu Arg Val Asn Thr Glu Ile Thr
385                 390                 395                 400

Lys Ala Pro Leu Ser Ala Ser Met Ile Lys Arg Tyr Asp Glu His His
                405                 410                 415

Gln Asp Leu Thr Leu Leu Lys Ala Leu Val Arg Gln Gln Leu Pro Glu
            420                 425                 430

Lys Tyr Lys Glu Ile Phe Phe Asp Gln Ser Lys Asn Gly Tyr Ala Gly
        435                 440                 445

Tyr Ile Asp Gly Gly Ala Ser Gln Glu Glu Phe Tyr Lys Phe Ile Lys
    450                 455                 460

Pro Ile Leu Glu Lys Met Asp Gly Thr Glu Glu Leu Leu Val Lys Leu
465                 470                 475                 480

Asn Arg Glu Asp Leu Leu Arg Lys Gln Arg Thr Phe Asp Asn Gly Ser
                485                 490                 495

Ile Pro His Gln Ile His Leu Gly Glu Leu His Ala Ile Leu Arg Arg
            500                 505                 510

Gln Glu Asp Phe Tyr Pro Phe Leu Lys Asp Asn Arg Glu Lys Ile Glu
        515                 520                 525

Lys Ile Leu Thr Phe Arg Ile Pro Tyr Tyr Val Gly Pro Leu Ala Arg
    530                 535                 540

Gly Asn Ser Arg Phe Ala Trp Met Thr Arg Lys Ser Glu Glu Thr Ile
545                 550                 555                 560

Thr Pro Trp Asn Phe Glu Glu Val Val Asp Lys Gly Ala Ser Ala Gln
                565                 570                 575

Ser Phe Ile Glu Arg Met Thr Asn Phe Asp Lys Asn Leu Pro Asn Glu
            580                 585                 590

Lys Val Leu Pro Lys His Ser Leu Leu Tyr Glu Tyr Phe Thr Val Tyr
        595                 600                 605

Asn Glu Leu Thr Lys Val Lys Tyr Val Thr Glu Gly Met Arg Lys Pro
    610                 615                 620

Ala Phe Leu Ser Gly Glu Gln Lys Lys Ala Ile Val Asp Leu Leu Phe
625                 630                 635                 640

Lys Thr Asn Arg Lys Val Thr Val Lys Gln Leu Lys Glu Asp Tyr Phe
                645                 650                 655

Lys Lys Ile Glu Cys Phe Asp Ser Val Glu Ile Ser Gly Val Glu Asp
            660                 665                 670

Arg Phe Asn Ala Ser Leu Gly Thr Tyr His Asp Leu Leu Lys Ile Ile
        675                 680                 685

Lys Asp Lys Asp Phe Leu Asp Asn Glu Glu Asn Glu Asp Ile Leu Glu
    690                 695                 700

Asp Ile Val Leu Thr Leu Thr Leu Phe Glu Asp Arg Glu Met Ile Glu
705                 710                 715                 720

Glu Arg Leu Lys Thr Tyr Ala His Leu Phe Asp Asp Lys Val Met Lys
                725                 730                 735

Gln Leu Lys Arg Arg Arg Tyr Thr Gly Trp Gly Arg Leu Ser Arg Lys
            740                 745                 750

Leu Ile Asn Gly Ile Arg Asp Lys Gln Ser Gly Lys Thr Ile Leu Asp
        755                 760                 765

Phe Leu Lys Ser Asp Gly Phe Ala Asn Arg Asn Phe Met Gln Leu Ile
    770                 775                 780

His Asp Asp Ser Leu Thr Phe Lys Glu Asp Ile Gln Lys Ala Gln Val
785                 790                 795                 800

Ser Gly Gln Gly Asp Ser Leu His Glu His Ile Ala Asn Leu Ala Gly
```

```
                805                 810                 815

Ser Pro Ala Ile Lys Lys Gly Ile Leu Gln Thr Val Lys Val Val Asp
            820                 825                 830

Glu Leu Val Lys Val Met Gly Arg His Lys Pro Glu Asn Ile Val Ile
        835                 840                 845

Glu Met Ala Arg Glu Asn Gln Thr Thr Gln Lys Gly Gln Lys Asn Ser
    850                 855                 860

Arg Glu Arg Met Lys Arg Ile Glu Glu Gly Ile Lys Glu Leu Gly Ser
865                 870                 875                 880

Gln Ile Leu Lys Glu His Pro Val Glu Asn Thr Gln Leu Gln Asn Glu
                885                 890                 895

Lys Leu Tyr Leu Tyr Tyr Leu Gln Asn Gly Arg Asp Met Tyr Val Asp
            900                 905                 910

Gln Glu Leu Asp Ile Asn Arg Leu Ser Asp Tyr Asp Val Asp Ala Ile
        915                 920                 925

Val Pro Gln Ser Phe Leu Lys Asp Asp Ser Ile Asp Asn Lys Val Leu
    930                 935                 940

Thr Arg Ser Asp Lys Asn Arg Gly Lys Ser Asp Asn Val Pro Ser Glu
945                 950                 955                 960

Glu Val Val Lys Lys Met Lys Asn Tyr Trp Arg Gln Leu Leu Asn Ala
                965                 970                 975

Lys Leu Ile Thr Gln Arg Lys Phe Asp Asn Leu Thr Lys Ala Glu Arg
            980                 985                 990

Gly Gly Leu Ser Glu Leu Asp Lys  Ala Gly Phe Ile Lys  Arg Gln Leu
        995                 1000                1005

Val Glu  Thr Arg Gln Ile Thr  Lys His Val Ala Gln  Ile Leu Asp
    1010                1015                1020

Ser Arg  Met Asn Thr Lys Tyr  Asp Glu Asn Asp Lys  Leu Ile Arg
    1025                1030                1035

Glu Val  Lys Val Ile Thr Leu  Lys Ser Lys Leu Val  Ser Asp Phe
    1040                1045                1050

Arg Lys  Asp Phe Gln Phe Tyr  Lys Val Arg Glu Ile  Asn Asn Tyr
    1055                1060                1065

His His  Ala His Asp Ala Tyr  Leu Asn Ala Val Val  Gly Thr Ala
    1070                1075                1080

Leu Ile  Lys Lys Tyr Pro Lys  Leu Glu Ser Glu Phe  Val Tyr Gly
    1085                1090                1095

Asp Tyr  Lys Val Tyr Asp Val  Arg Lys Met Ile Ala  Lys Ser Glu
    1100                1105                1110

Gln Glu  Ile Gly Lys Ala Thr  Ala Lys Tyr Phe Phe  Tyr Ser Asn
    1115                1120                1125

Ile Met  Asn Phe Phe Lys Thr  Glu Ile Thr Leu Ala  Asn Gly Glu
    1130                1135                1140

Ile Arg  Lys Arg Pro Leu Ile  Glu Thr Asn Gly Glu  Thr Gly Glu
    1145                1150                1155

Ile Val  Trp Asp Lys Gly Arg  Asp Phe Ala Thr Val  Arg Lys Val
    1160                1165                1170

Leu Ser  Met Pro Gln Val Asn  Ile Val Lys Lys Thr  Glu Val Gln
    1175                1180                1185

Thr Gly  Gly Phe Ser Lys Glu  Ser Ile Leu Pro Lys  Arg Asn Ser
    1190                1195                1200

Asp Lys  Leu Ile Ala Arg Lys  Lys Asp Trp Asp Pro  Lys Lys Tyr
    1205                1210                1215
```

```
Gly Gly Phe Asp Ser Pro Thr Val Ala Tyr Ser Val Leu Val Val
    1220                1225                1230

Ala Lys Val Glu Lys Gly Lys Ser Lys Lys Leu Lys Ser Val Lys
    1235                1240                1245

Glu Leu Leu Gly Ile Thr Ile Met Glu Arg Ser Ser Phe Glu Lys
    1250                1255                1260

Asn Pro Ile Asp Phe Leu Glu Ala Lys Gly Tyr Lys Glu Val Lys
    1265                1270                1275

Lys Asp Leu Ile Ile Lys Leu Pro Lys Tyr Ser Leu Phe Glu Leu
    1280                1285                1290

Glu Asn Gly Arg Lys Arg Met Leu Ala Ser Ala Gly Glu Leu Gln
    1295                1300                1305

Lys Gly Asn Glu Leu Ala Leu Pro Ser Lys Tyr Val Asn Phe Leu
    1310                1315                1320

Tyr Leu Ala Ser His Tyr Glu Lys Leu Lys Gly Ser Pro Glu Asp
    1325                1330                1335

Asn Glu Gln Lys Gln Leu Phe Val Glu Gln His Lys His Tyr Leu
    1340                1345                1350

Asp Glu Ile Ile Glu Gln Ile Ser Glu Phe Ser Lys Arg Val Ile
    1355                1360                1365

Leu Ala Asp Ala Asn Leu Asp Lys Val Leu Ser Ala Tyr Asn Lys
    1370                1375                1380

His Arg Asp Lys Pro Ile Arg Glu Gln Ala Glu Asn Ile Ile His
    1385                1390                1395

Leu Phe Thr Leu Thr Asn Leu Gly Ala Pro Ala Ala Phe Lys Tyr
    1400                1405                1410

Phe Asp Thr Thr Ile Asp Arg Lys Arg Tyr Thr Ser Thr Lys Glu
    1415                1420                1425

Val Leu Asp Ala Thr Leu Ile His Gln Ser Ile Thr Gly Leu Tyr
    1430                1435                1440

Glu Thr Arg Ile Asp Leu Ser Gln Leu Gly Gly Asp Ser Arg Ala
    1445                1450                1455

Asp Tyr Pro Tyr Asp Val Pro Asp Tyr Ala Ser Gly Ser Pro Lys
    1460                1465                1470

Lys Lys Arg Lys Val Glu Ala Ser Gly Ser Gly Arg Ala Ser Pro
    1475                1480                1485

Gly Ile Pro Gly Ser Thr Arg Asn His Asp Gln Glu Phe Asp Pro
    1490                1495                1500

Pro Lys Val Tyr Pro Pro Val Pro Ala Glu Lys Arg Lys Pro Ile
    1505                1510                1515

Arg Val Leu Ser Leu Phe Asp Gly Ile Ala Thr Gly Leu Leu Val
    1520                1525                1530

Leu Lys Asp Leu Gly Ile Gln Val Asp Arg Tyr Ile Ala Ser Glu
    1535                1540                1545

Val Cys Glu Asp Ser Ile Thr Val Gly Met Val Arg His Gln Gly
    1550                1555                1560

Lys Ile Met Tyr Val Gly Asp Val Arg Ser Val Thr Gln Lys His
    1565                1570                1575

Ile Gln Glu Trp Gly Pro Phe Asp Leu Val Ile Gly Gly Ser Pro
    1580                1585                1590

Cys Asn Asp Leu Ser Ile Val Asn Pro Ala Arg Lys Gly Leu Tyr
    1595                1600                1605
```

```
Glu Gly  Thr Gly Arg Leu Phe  Phe Glu Phe Tyr Arg  Leu Leu His
    1610                 1615                 1620

Asp Ala  Arg Pro Lys Glu Gly  Asp Asp Arg Pro Phe  Phe Trp Leu
    1625                 1630                 1635

Phe Glu  Asn Val Val Ala Met  Gly Val Ser Asp Lys  Arg Asp Ile
    1640                 1645                 1650

Ser Arg  Phe Leu Glu Ser Asn  Pro Val Met Ile Asp  Ala Lys Glu
    1655                 1660                 1665

Val Ser  Ala Ala His Arg Ala  Arg Tyr Phe Trp Gly  Asn Leu Pro
    1670                 1675                 1680

Gly Met  Asn Arg Pro Leu Ala  Ser Thr Val Asn Asp  Lys Leu Glu
    1685                 1690                 1695

Leu Gln  Glu Cys Leu Glu His  Gly Arg Ile Ala Lys  Phe Ser Lys
    1700                 1705                 1710

Val Arg  Thr Ile Thr Thr Arg  Ser Asn Ser Ile Lys  Gln Gly Lys
    1715                 1720                 1725

Asp Gln  His Phe Pro Val Phe  Met Asn Glu Lys Glu  Asp Ile Leu
    1730                 1735                 1740

Trp Cys  Thr Glu Met Glu Arg  Val Phe Gly Phe Pro  Val His Tyr
    1745                 1750                 1755

Thr Asp  Val Ser Asn Met Ser  Arg Leu Ala Arg Gln  Arg Leu Leu
    1760                 1765                 1770

Gly Arg  Ser Trp Ser Val Pro  Val Ile Arg His Leu  Phe Ala Pro
    1775                 1780                 1785

Leu Lys  Glu Tyr Phe Ala Cys  Val Ser Ser Gly Asn  Ser Asn Ala
    1790                 1795                 1800

Asn Ser  Arg Gly Pro Ser Phe  Ser Ser Gly Leu Val  Pro Leu Ser
    1805                 1810                 1815

Leu Arg  Gly Ser His Met Gly  Pro Met Glu Ile Tyr  Lys Thr Val
    1820                 1825                 1830

Ser Ala  Trp Lys Arg Gln Pro  Val Arg Val Leu Ser  Leu Phe Arg
    1835                 1840                 1845

Asn Ile  Asp Lys Val Leu Lys  Ser Leu Gly Phe Leu  Glu Ser Gly
    1850                 1855                 1860

Ser Gly  Ser Gly Gly Gly Thr  Leu Lys Tyr Val Glu  Asp Val Thr
    1865                 1870                 1875

Asn Val  Val Arg Arg Asp Val  Glu Lys Trp Gly Pro  Phe Asp Leu
    1880                 1885                 1890

Val Tyr  Gly Ser Thr Gln Pro  Leu Gly Ser Ser Cys  Asp Arg Cys
    1895                 1900                 1905

Pro Gly  Trp Tyr Met Phe Gln  Phe His Arg Ile Leu  Gln Tyr Ala
    1910                 1915                 1920

Leu Pro  Arg Gln Glu Ser Gln  Arg Pro Phe Phe Trp  Ile Phe Met
    1925                 1930                 1935

Asp Asn  Leu Leu Leu Thr Glu  Asp Asp Gln Glu Thr  Thr Thr Arg
    1940                 1945                 1950

Phe Leu  Gln Thr Glu Ala Val  Thr Leu Gln Asp Val  Arg Gly Arg
    1955                 1960                 1965

Asp Tyr  Gln Asn Ala Met Arg  Val Trp Ser Asn Ile  Pro Gly Leu
    1970                 1975                 1980

Lys Ser  Lys His Ala Pro Leu  Thr Pro Lys Glu Glu  Glu Tyr Leu
    1985                 1990                 1995

Gln Ala  Gln Val Arg Ser Arg  Ser Lys Leu Asp Ala  Pro Lys Val
```

```
    2000                2005                2010

Asp Leu  Leu Val Lys Asn Cys  Leu Leu Pro Leu Arg  Glu Tyr Phe
    2015                2020                2025

Lys Tyr  Phe Ser Gln Asn Ser  Leu Pro Leu Ser Arg  Ala Asp Pro
    2030                2035                2040

Lys Lys  Lys Arg Lys Val Gly  Ser Gly Ala Thr Asn  Phe Ser Leu
    2045                2050                2055

Leu Lys  Gln Ala Gly Asp Val  Glu Glu Asn Pro Gly  Pro Gly Ser
    2060                2065                2070

Gly Ala  Thr Asn Phe Ser Leu  Leu Lys Gln Ala Gly  Asp Val Glu
    2075                2080                2085

Glu Asn  Pro Gly Pro Ser Glu  Leu Ile Lys Glu Asn  Met His Met
    2090                2095                2100

Lys Leu  Tyr Met Glu Gly Thr  Val Asp Asn His His  Phe Lys Cys
    2105                2110                2115

Thr Ser  Glu Gly Glu Gly Lys  Pro Tyr Glu Gly Thr  Gln Thr Met
    2120                2125                2130

Arg Ile  Lys Val Val Glu Gly  Gly Pro Leu Pro Phe  Ala Phe Asp
    2135                2140                2145

Ile Leu  Ala Thr Ser Phe Leu  Tyr Gly Ser Lys Thr  Phe Ile Asn
    2150                2155                2160

His Thr  Gln Gly Ile Pro Asp  Phe Phe Lys Gln Ser  Phe Pro Glu
    2165                2170                2175

Gly Phe  Thr Trp Glu Arg Val  Thr Thr Tyr Glu Asp  Gly Gly Val
    2180                2185                2190

Leu Thr  Ala Thr Gln Asp Thr  Ser Leu Gln Asp Gly  Cys Leu Ile
    2195                2200                2205

Tyr Asn  Val Lys Ile Arg Gly  Val Asn Phe Thr Ser  Asn Gly Pro
    2210                2215                2220

Val Met  Gln Lys Lys Thr Leu  Gly Trp Glu Ala Phe  Thr Glu Thr
    2225                2230                2235

Leu Tyr  Pro Ala Asp Gly Gly  Leu Glu Gly Arg Asn  Asp Met Ala
    2240                2245                2250

Leu Lys  Leu Val Gly Gly Ser  His Leu Ile Ala Asn  Ile Lys Thr
    2255                2260                2265

Thr Tyr  Arg Ser Lys Lys Pro  Ala Lys Asn Leu Lys  Met Pro Gly
    2270                2275                2280

Val Tyr  Tyr Val Asp Tyr Arg  Leu Glu Arg Ile Lys  Glu Ala Asn
    2285                2290                2295

Asn Glu  Thr Tyr Val Glu Gln  His Glu Val Ala Val  Ala Arg Tyr
    2300                2305                2310

Cys Asp  Leu Pro Ser Lys Leu  Gly His Lys Leu Asn
    2315                2320                2325
```

<210> SEQ ID NO 9
<211> LENGTH: 2367
<212> TYPE: PRT
<213> ORGANISM: Artificial sequence
<220> FEATURE:
<223> OTHER INFORMATION: Synthetic polypeptide

<400> SEQUENCE: 9

```
Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
```

```
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Gly Gly Pro Ser Ser Gly Ala Pro Pro
65                  70                  75                  80

Pro Ser Gly Gly Ser Pro Ala Gly Ser Pro Thr Ser Thr Glu Glu Gly
                85                  90                  95

Thr Ser Glu Ser Ala Thr Pro Glu Ser Gly Pro Gly Thr Ser Thr Glu
            100                 105                 110

Pro Ser Glu Gly Ser Ala Pro Gly Ser Pro Ala Gly Ser Pro Thr Ser
        115                 120                 125

Thr Glu Glu Gly Thr Ser Thr Glu Pro Ser Glu Gly Ser Ala Pro Gly
    130                 135                 140

Thr Ser Thr Glu Pro Ser Glu Met Asp Lys Lys Tyr Ser Ile Gly Leu
145                 150                 155                 160

Ala Ile Gly Thr Asn Ser Val Gly Trp Ala Val Ile Thr Asp Glu Tyr
                165                 170                 175

Lys Val Pro Ser Lys Lys Phe Lys Val Leu Gly Asn Thr Asp Arg His
            180                 185                 190

Ser Ile Lys Lys Asn Leu Ile Gly Ala Leu Leu Phe Asp Ser Gly Glu
        195                 200                 205

Thr Ala Glu Ala Thr Arg Leu Lys Arg Thr Ala Arg Arg Arg Tyr Thr
    210                 215                 220

Arg Arg Lys Asn Arg Ile Cys Tyr Leu Gln Glu Ile Phe Ser Asn Glu
225                 230                 235                 240

Met Ala Lys Val Asp Asp Ser Phe Phe His Arg Leu Glu Glu Ser Phe
                245                 250                 255

Leu Val Glu Glu Asp Lys Lys His Glu Arg His Pro Ile Phe Gly Asn
            260                 265                 270

Ile Val Asp Glu Val Ala Tyr His Glu Lys Tyr Pro Thr Ile Tyr His
        275                 280                 285

Leu Arg Lys Lys Leu Val Asp Ser Thr Asp Lys Ala Asp Leu Arg Leu
    290                 295                 300

Ile Tyr Leu Ala Leu Ala His Met Ile Lys Phe Arg Gly His Phe Leu
305                 310                 315                 320

Ile Glu Gly Asp Leu Asn Pro Asp Asn Ser Asp Val Asp Lys Leu Phe
                325                 330                 335

Ile Gln Leu Val Gln Thr Tyr Asn Gln Leu Phe Glu Glu Asn Pro Ile
            340                 345                 350

Asn Ala Ser Gly Val Asp Ala Lys Ala Ile Leu Ser Ala Arg Leu Ser
        355                 360                 365

Lys Ser Arg Arg Leu Glu Asn Leu Ile Ala Gln Leu Pro Gly Glu Lys
    370                 375                 380

Lys Asn Gly Leu Phe Gly Asn Leu Ile Ala Leu Ser Leu Gly Leu Thr
385                 390                 395                 400

Pro Asn Phe Lys Ser Asn Phe Asp Leu Ala Glu Asp Ala Lys Leu Gln
                405                 410                 415

Leu Ser Lys Asp Thr Tyr Asp Asp Asp Leu Asp Asn Leu Leu Ala Gln
            420                 425                 430

Ile Gly Asp Gln Tyr Ala Asp Leu Phe Leu Ala Ala Lys Asn Leu Ser
        435                 440                 445
```

Asp Ala Ile Leu Leu Ser Asp Ile Leu Arg Val Asn Thr Glu Ile Thr
    450                 455                 460

Lys Ala Pro Leu Ser Ala Ser Met Ile Lys Arg Tyr Asp Glu His His
465                 470                 475                 480

Gln Asp Leu Thr Leu Leu Lys Ala Leu Val Arg Gln Gln Leu Pro Glu
                485                 490                 495

Lys Tyr Lys Glu Ile Phe Phe Asp Gln Ser Lys Asn Gly Tyr Ala Gly
            500                 505                 510

Tyr Ile Asp Gly Gly Ala Ser Gln Glu Glu Phe Tyr Lys Phe Ile Lys
        515                 520                 525

Pro Ile Leu Glu Lys Met Asp Gly Thr Glu Glu Leu Leu Val Lys Leu
    530                 535                 540

Asn Arg Glu Asp Leu Leu Arg Lys Gln Arg Thr Phe Asp Asn Gly Ser
545                 550                 555                 560

Ile Pro His Gln Ile His Leu Gly Glu Leu His Ala Ile Leu Arg Arg
                565                 570                 575

Gln Glu Asp Phe Tyr Pro Phe Leu Lys Asp Asn Arg Glu Lys Ile Glu
            580                 585                 590

Lys Ile Leu Thr Phe Arg Ile Pro Tyr Tyr Val Gly Pro Leu Ala Arg
        595                 600                 605

Gly Asn Ser Arg Phe Ala Trp Met Thr Arg Lys Ser Glu Glu Thr Ile
    610                 615                 620

Thr Pro Trp Asn Phe Glu Glu Val Val Asp Lys Gly Ala Ser Ala Gln
625                 630                 635                 640

Ser Phe Ile Glu Arg Met Thr Asn Phe Asp Lys Asn Leu Pro Asn Glu
                645                 650                 655

Lys Val Leu Pro Lys His Ser Leu Leu Tyr Glu Tyr Phe Thr Val Tyr
            660                 665                 670

Asn Glu Leu Thr Lys Val Lys Tyr Val Thr Glu Gly Met Arg Lys Pro
        675                 680                 685

Ala Phe Leu Ser Gly Glu Gln Lys Lys Ala Ile Val Asp Leu Leu Phe
    690                 695                 700

Lys Thr Asn Arg Lys Val Thr Val Lys Gln Leu Lys Glu Asp Tyr Phe
705                 710                 715                 720

Lys Lys Ile Glu Cys Phe Asp Ser Val Glu Ile Ser Gly Val Glu Asp
                725                 730                 735

Arg Phe Asn Ala Ser Leu Gly Thr Tyr His Asp Leu Leu Lys Ile Ile
            740                 745                 750

Lys Asp Lys Asp Phe Leu Asp Asn Glu Glu Asn Glu Asp Ile Leu Glu
        755                 760                 765

Asp Ile Val Leu Thr Leu Thr Leu Phe Glu Asp Arg Glu Met Ile Glu
    770                 775                 780

Glu Arg Leu Lys Thr Tyr Ala His Leu Phe Asp Asp Lys Val Met Lys
785                 790                 795                 800

Gln Leu Lys Arg Arg Arg Tyr Thr Gly Trp Gly Arg Leu Ser Arg Lys
                805                 810                 815

Leu Ile Asn Gly Ile Arg Asp Lys Gln Ser Gly Lys Thr Ile Leu Asp
            820                 825                 830

Phe Leu Lys Ser Asp Gly Phe Ala Asn Arg Asn Phe Met Gln Leu Ile
        835                 840                 845

His Asp Asp Ser Leu Thr Phe Lys Glu Asp Ile Gln Lys Ala Gln Val
    850                 855                 860

```
Ser Gly Gln Gly Asp Ser Leu His Glu His Ile Ala Asn Leu Ala Gly
865                 870                 875                 880

Ser Pro Ala Ile Lys Lys Gly Ile Leu Gln Thr Val Lys Val Val Asp
                885                 890                 895

Glu Leu Val Lys Val Met Gly Arg His Lys Pro Glu Asn Ile Val Ile
            900                 905                 910

Glu Met Ala Arg Glu Asn Gln Thr Thr Gln Lys Gly Gln Lys Asn Ser
        915                 920                 925

Arg Glu Arg Met Lys Arg Ile Glu Glu Gly Ile Lys Glu Leu Gly Ser
    930                 935                 940

Gln Ile Leu Lys Glu His Pro Val Glu Asn Thr Gln Leu Gln Asn Glu
945                 950                 955                 960

Lys Leu Tyr Leu Tyr Tyr Leu Gln Asn Gly Arg Asp Met Tyr Val Asp
                965                 970                 975

Gln Glu Leu Asp Ile Asn Arg Leu Ser Asp Tyr Asp Val Asp Ala Ile
            980                 985                 990

Val Pro Gln Ser Phe Leu Lys Asp  Asp Ser Ile Asp Asn  Lys Val Leu
        995                 1000                1005

Thr Arg  Ser Asp Lys Asn Arg  Gly Lys Ser Asp Asn  Val Pro Ser
    1010                1015                1020

Glu Glu  Val Val Lys Lys Met  Lys Asn Tyr Trp Arg  Gln Leu Leu
    1025                1030                1035

Asn Ala  Lys Leu Ile Thr Gln  Arg Lys Phe Asp Asn  Leu Thr Lys
    1040                1045                1050

Ala Glu  Arg Gly Gly Leu Ser  Glu Leu Asp Lys Ala  Gly Phe Ile
    1055                1060                1065

Lys Arg  Gln Leu Val Glu Thr  Arg Gln Ile Thr Lys  His Val Ala
    1070                1075                1080

Gln Ile  Leu Asp Ser Arg Met  Asn Thr Lys Tyr Asp  Glu Asn Asp
    1085                1090                1095

Lys Leu  Ile Arg Glu Val Lys  Val Ile Thr Leu Lys  Ser Lys Leu
    1100                1105                1110

Val Ser  Asp Phe Arg Lys Asp  Phe Gln Phe Tyr Lys  Val Arg Glu
    1115                1120                1125

Ile Asn  Asn Tyr His His Ala  His Asp Ala Tyr Leu  Asn Ala Val
    1130                1135                1140

Val Gly  Thr Ala Leu Ile Lys  Lys Tyr Pro Lys Leu  Glu Ser Glu
    1145                1150                1155

Phe Val  Tyr Gly Asp Tyr Lys  Val Tyr Asp Val Arg  Lys Met Ile
    1160                1165                1170

Ala Lys  Ser Glu Gln Glu Ile  Gly Lys Ala Thr Ala  Lys Tyr Phe
    1175                1180                1185

Phe Tyr  Ser Asn Ile Met Asn  Phe Phe Lys Thr Glu  Ile Thr Leu
    1190                1195                1200

Ala Asn  Gly Glu Ile Arg Lys  Arg Pro Leu Ile Glu  Thr Asn Gly
    1205                1210                1215

Glu Thr  Gly Glu Ile Val Trp  Asp Lys Gly Arg Asp  Phe Ala Thr
    1220                1225                1230

Val Arg  Lys Val Leu Ser Met  Pro Gln Val Asn Ile  Val Lys Lys
    1235                1240                1245

Thr Glu  Val Gln Thr Gly Gly  Phe Ser Lys Glu Ser  Ile Leu Pro
    1250                1255                1260

Lys Arg  Asn Ser Asp Lys Leu  Ile Ala Arg Lys Lys  Asp Trp Asp
```

```
    1265                1270                1275

Pro Lys  Lys Tyr Gly Gly Phe  Asp Ser Pro Thr Val  Ala Tyr Ser
    1280                1285                1290

Val Leu  Val Val Ala Lys Val  Glu Lys Gly Lys Ser  Lys Lys Leu
    1295                1300                1305

Lys Ser  Val Lys Glu Leu Leu  Gly Ile Thr Ile Met  Glu Arg Ser
    1310                1315                1320

Ser Phe  Glu Lys Asn Pro Ile  Asp Phe Leu Glu Ala  Lys Gly Tyr
    1325                1330                1335

Lys Glu  Val Lys Lys Asp Leu  Ile Ile Lys Leu Pro  Lys Tyr Ser
    1340                1345                1350

Leu Phe  Glu Leu Glu Asn Gly  Arg Lys Arg Met Leu  Ala Ser Ala
    1355                1360                1365

Gly Glu  Leu Gln Lys Gly Asn  Glu Leu Ala Leu Pro  Ser Lys Tyr
    1370                1375                1380

Val Asn  Phe Leu Tyr Leu Ala  Ser His Tyr Glu Lys  Leu Lys Gly
    1385                1390                1395

Ser Pro  Glu Asp Asn Glu Gln  Lys Gln Leu Phe Val  Glu Gln His
    1400                1405                1410

Lys His  Tyr Leu Asp Glu Ile  Ile Glu Gln Ile Ser  Glu Phe Ser
    1415                1420                1425

Lys Arg  Val Ile Leu Ala Asp  Ala Asn Leu Asp Lys  Val Leu Ser
    1430                1435                1440

Ala Tyr  Asn Lys His Arg Asp  Lys Pro Ile Arg Glu  Gln Ala Glu
    1445                1450                1455

Asn Ile  Ile His Leu Phe Thr  Leu Thr Asn Leu Gly  Ala Pro Ala
    1460                1465                1470

Ala Phe  Lys Tyr Phe Asp Thr  Thr Ile Asp Arg Lys  Arg Tyr Thr
    1475                1480                1485

Ser Thr  Lys Glu Val Leu Asp  Ala Thr Leu Ile His  Gln Ser Ile
    1490                1495                1500

Thr Gly  Leu Tyr Glu Thr Arg  Ile Asp Leu Ser Gln  Leu Gly Gly
    1505                1510                1515

Asp Ser  Arg Ala Asp Tyr Pro  Tyr Asp Val Pro Asp  Tyr Ala Ser
    1520                1525                1530

Gly Ser  Pro Lys Lys Lys Arg  Lys Val Glu Ala Ser  Gly Ser Gly
    1535                1540                1545

Arg Ala  Ser Pro Gly Ile Pro  Gly Ser Thr Arg Asn  His Asp Gln
    1550                1555                1560

Glu Phe  Asp Pro Pro Lys Val  Tyr Pro Pro Val Pro  Ala Glu Lys
    1565                1570                1575

Arg Lys  Pro Ile Arg Val Leu  Ser Leu Phe Asp Gly  Ile Ala Thr
    1580                1585                1590

Gly Leu  Leu Val Leu Lys Asp  Leu Gly Ile Gln Val  Asp Arg Tyr
    1595                1600                1605

Ile Ala  Ser Glu Val Cys Glu  Asp Ser Ile Thr Val  Gly Met Val
    1610                1615                1620

Arg His  Gln Gly Lys Ile Met  Tyr Val Gly Asp Val  Arg Ser Val
    1625                1630                1635

Thr Gln  Lys His Ile Gln Glu  Trp Gly Pro Phe Asp  Leu Val Ile
    1640                1645                1650

Gly Gly  Ser Pro Cys Asn Asp  Leu Ser Ile Val Asn  Pro Ala Arg
    1655                1660                1665
```

```
Lys Gly Leu Tyr Glu Gly Thr Gly Arg Leu Phe Phe Glu Phe Tyr
    1670                1675                1680

Arg Leu Leu His Asp Ala Arg Pro Lys Glu Gly Asp Asp Arg Pro
    1685                1690                1695

Phe Phe Trp Leu Phe Glu Asn Val Val Ala Met Gly Val Ser Asp
    1700                1705                1710

Lys Arg Asp Ile Ser Arg Phe Leu Glu Ser Asn Pro Val Met Ile
    1715                1720                1725

Asp Ala Lys Glu Val Ser Ala Ala His Arg Ala Arg Tyr Phe Trp
    1730                1735                1740

Gly Asn Leu Pro Gly Met Asn Arg Pro Leu Ala Ser Thr Val Asn
    1745                1750                1755

Asp Lys Leu Glu Leu Gln Glu Cys Leu Glu His Gly Arg Ile Ala
    1760                1765                1770

Lys Phe Ser Lys Val Arg Thr Ile Thr Thr Arg Ser Asn Ser Ile
    1775                1780                1785

Lys Gln Gly Lys Asp Gln His Phe Pro Val Phe Met Asn Glu Lys
    1790                1795                1800

Glu Asp Ile Leu Trp Cys Thr Glu Met Glu Arg Val Phe Gly Phe
    1805                1810                1815

Pro Val His Tyr Thr Asp Val Ser Asn Met Ser Arg Leu Ala Arg
    1820                1825                1830

Gln Arg Leu Leu Gly Arg Ser Trp Ser Val Pro Val Ile Arg His
    1835                1840                1845

Leu Phe Ala Pro Leu Lys Glu Tyr Phe Ala Cys Val Ser Ser Gly
    1850                1855                1860

Asn Ser Asn Ala Asn Ser Arg Gly Pro Ser Phe Ser Ser Gly Leu
    1865                1870                1875

Val Pro Leu Ser Leu Arg Gly Ser His Met Gly Pro Met Glu Ile
    1880                1885                1890

Tyr Lys Thr Val Ser Ala Trp Lys Arg Gln Pro Val Arg Val Leu
    1895                1900                1905

Ser Leu Phe Arg Asn Ile Asp Lys Val Leu Lys Ser Leu Gly Phe
    1910                1915                1920

Leu Glu Ser Gly Ser Gly Ser Gly Gly Gly Thr Leu Lys Tyr Val
    1925                1930                1935

Glu Asp Val Thr Asn Val Val Arg Arg Asp Val Glu Lys Trp Gly
    1940                1945                1950

Pro Phe Asp Leu Val Tyr Gly Ser Thr Gln Pro Leu Gly Ser Ser
    1955                1960                1965

Cys Asp Arg Cys Pro Gly Trp Tyr Met Phe Gln Phe His Arg Ile
    1970                1975                1980

Leu Gln Tyr Ala Leu Pro Arg Gln Glu Ser Gln Arg Pro Phe Phe
    1985                1990                1995

Trp Ile Phe Met Asp Asn Leu Leu Leu Thr Glu Asp Asp Gln Glu
    2000                2005                2010

Thr Thr Thr Arg Phe Leu Gln Thr Glu Ala Val Thr Leu Gln Asp
    2015                2020                2025

Val Arg Gly Arg Asp Tyr Gln Asn Ala Met Arg Val Trp Ser Asn
    2030                2035                2040

Ile Pro Gly Leu Lys Ser Lys His Ala Pro Leu Thr Pro Lys Glu
    2045                2050                2055
```

```
Glu Glu  Tyr Leu Gln Ala Gln  Val Arg Ser Arg Ser  Lys Leu Asp
    2060                 2065                 2070

Ala Pro  Lys Val Asp Leu Leu  Val Lys Asn Cys Leu  Leu Pro Leu
    2075                 2080                 2085

Arg Glu  Tyr Phe Lys Tyr Phe  Ser Gln Asn Ser Leu  Pro Leu Ser
    2090                 2095                 2100

Arg Ala  Asp Pro Lys Lys Lys  Arg Lys Val Gly Ser  Gly Ala Thr
    2105                 2110                 2115

Asn Phe  Ser Leu Leu Lys Gln  Ala Gly Asp Val Glu  Glu Asn Pro
    2120                 2125                 2130

Gly Pro  Ser Glu Leu Ile Lys  Glu Asn Met His Met  Lys Leu Tyr
    2135                 2140                 2145

Met Glu  Gly Thr Val Asp Asn  His His Phe Lys Cys  Thr Ser Glu
    2150                 2155                 2160

Gly Glu  Gly Lys Pro Tyr Glu  Gly Thr Gln Thr Met  Arg Ile Lys
    2165                 2170                 2175

Val Val  Glu Gly Gly Pro Leu  Pro Phe Ala Phe Asp  Ile Leu Ala
    2180                 2185                 2190

Thr Ser  Phe Leu Tyr Gly Ser  Lys Thr Phe Ile Asn  His Thr Gln
    2195                 2200                 2205

Gly Ile  Pro Asp Phe Phe Lys  Gln Ser Phe Pro Glu  Gly Phe Thr
    2210                 2215                 2220

Trp Glu  Arg Val Thr Thr Tyr  Glu Asp Gly Gly Val  Leu Thr Ala
    2225                 2230                 2235

Thr Gln  Asp Thr Ser Leu Gln  Asp Gly Cys Leu Ile  Tyr Asn Val
    2240                 2245                 2250

Lys Ile  Arg Gly Val Asn Phe  Thr Ser Asn Gly Pro  Val Met Gln
    2255                 2260                 2265

Lys Lys  Thr Leu Gly Trp Glu  Ala Phe Thr Glu Thr  Leu Tyr Pro
    2270                 2275                 2280

Ala Asp  Gly Gly Leu Glu Gly  Arg Asn Asp Met Ala  Leu Lys Leu
    2285                 2290                 2295

Val Gly  Gly Ser His Leu Ile  Ala Asn Ile Lys Thr  Thr Tyr Arg
    2300                 2305                 2310

Ser Lys  Lys Pro Ala Lys Asn  Leu Lys Met Pro Gly  Val Tyr Tyr
    2315                 2320                 2325

Val Asp  Tyr Arg Leu Glu Arg  Ile Lys Glu Ala Asn  Asn Glu Thr
    2330                 2335                 2340

Tyr Val  Glu Gln His Glu Val  Ala Val Ala Arg Tyr  Cys Asp Leu
    2345                 2350                 2355

Pro Ser  Lys Leu Gly His Lys  Leu Asn
    2360                 2365
```

<210> SEQ ID NO 10
<211> LENGTH: 2389
<212> TYPE: PRT
<213> ORGANISM: Artificial sequence
<220> FEATURE:
<223> OTHER INFORMATION: Synthetic polypeptide

<400> SEQUENCE: 10

```
Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
            20                  25                  30
```

```
Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Gly Gly Pro Ser Ser Gly Ala Pro Pro
65                  70                  75                  80

Pro Ser Gly Gly Ser Pro Ala Gly Ser Pro Thr Ser Thr Glu Glu Gly
                85                  90                  95

Thr Ser Glu Ser Ala Thr Pro Glu Ser Gly Pro Gly Thr Ser Thr Glu
            100                 105                 110

Pro Ser Glu Gly Ser Ala Pro Gly Ser Pro Ala Gly Ser Pro Thr Ser
        115                 120                 125

Thr Glu Glu Gly Thr Ser Thr Glu Pro Ser Glu Gly Ser Ala Pro Gly
    130                 135                 140

Thr Ser Thr Glu Pro Ser Glu Met Asp Lys Lys Tyr Ser Ile Gly Leu
145                 150                 155                 160

Ala Ile Gly Thr Asn Ser Val Gly Trp Ala Val Ile Thr Asp Glu Tyr
                165                 170                 175

Lys Val Pro Ser Lys Lys Phe Lys Val Leu Gly Asn Thr Asp Arg His
            180                 185                 190

Ser Ile Lys Lys Asn Leu Ile Gly Ala Leu Leu Phe Asp Ser Gly Glu
        195                 200                 205

Thr Ala Glu Ala Thr Arg Leu Lys Arg Thr Ala Arg Arg Arg Tyr Thr
    210                 215                 220

Arg Arg Lys Asn Arg Ile Cys Tyr Leu Gln Glu Ile Phe Ser Asn Glu
225                 230                 235                 240

Met Ala Lys Val Asp Asp Ser Phe Phe His Arg Leu Glu Glu Ser Phe
                245                 250                 255

Leu Val Glu Glu Asp Lys Lys His Glu Arg His Pro Ile Phe Gly Asn
            260                 265                 270

Ile Val Asp Glu Val Ala Tyr His Glu Lys Tyr Pro Thr Ile Tyr His
        275                 280                 285

Leu Arg Lys Lys Leu Val Asp Ser Thr Asp Lys Ala Asp Leu Arg Leu
    290                 295                 300

Ile Tyr Leu Ala Leu Ala His Met Ile Lys Phe Arg Gly His Phe Leu
305                 310                 315                 320

Ile Glu Gly Asp Leu Asn Pro Asp Asn Ser Asp Val Asp Lys Leu Phe
                325                 330                 335

Ile Gln Leu Val Gln Thr Tyr Asn Gln Leu Phe Glu Glu Asn Pro Ile
            340                 345                 350

Asn Ala Ser Gly Val Asp Ala Lys Ala Ile Leu Ser Ala Arg Leu Ser
        355                 360                 365

Lys Ser Arg Arg Leu Glu Asn Leu Ile Ala Gln Leu Pro Gly Glu Lys
    370                 375                 380

Lys Asn Gly Leu Phe Gly Asn Leu Ile Ala Leu Ser Leu Gly Leu Thr
385                 390                 395                 400

Pro Asn Phe Lys Ser Asn Phe Asp Leu Ala Glu Asp Ala Lys Leu Gln
                405                 410                 415

Leu Ser Lys Asp Thr Tyr Asp Asp Asp Leu Asp Asn Leu Leu Ala Gln
            420                 425                 430

Ile Gly Asp Gln Tyr Ala Asp Leu Phe Leu Ala Ala Lys Asn Leu Ser
        435                 440                 445

Asp Ala Ile Leu Leu Ser Asp Ile Leu Arg Val Asn Thr Glu Ile Thr
```

```
    450                 455                 460

Lys Ala Pro Leu Ser Ala Ser Met Ile Lys Arg Tyr Asp Glu His His
465                 470                 475                 480

Gln Asp Leu Thr Leu Leu Lys Ala Leu Val Arg Gln Gln Leu Pro Glu
                485                 490                 495

Lys Tyr Lys Glu Ile Phe Phe Asp Gln Ser Lys Asn Gly Tyr Ala Gly
            500                 505                 510

Tyr Ile Asp Gly Gly Ala Ser Gln Glu Glu Phe Tyr Lys Phe Ile Lys
        515                 520                 525

Pro Ile Leu Glu Lys Met Asp Gly Thr Glu Glu Leu Leu Val Lys Leu
    530                 535                 540

Asn Arg Glu Asp Leu Leu Arg Lys Gln Arg Thr Phe Asp Asn Gly Ser
545                 550                 555                 560

Ile Pro His Gln Ile His Leu Gly Glu Leu His Ala Ile Leu Arg Arg
                565                 570                 575

Gln Glu Asp Phe Tyr Pro Phe Leu Lys Asp Asn Arg Glu Lys Ile Glu
            580                 585                 590

Lys Ile Leu Thr Phe Arg Ile Pro Tyr Tyr Val Gly Pro Leu Ala Arg
        595                 600                 605

Gly Asn Ser Arg Phe Ala Trp Met Thr Arg Lys Ser Glu Glu Thr Ile
    610                 615                 620

Thr Pro Trp Asn Phe Glu Glu Val Val Asp Lys Gly Ala Ser Ala Gln
625                 630                 635                 640

Ser Phe Ile Glu Arg Met Thr Asn Phe Asp Lys Asn Leu Pro Asn Glu
                645                 650                 655

Lys Val Leu Pro Lys His Ser Leu Leu Tyr Glu Tyr Phe Thr Val Tyr
            660                 665                 670

Asn Glu Leu Thr Lys Val Lys Tyr Val Thr Glu Gly Met Arg Lys Pro
        675                 680                 685

Ala Phe Leu Ser Gly Glu Gln Lys Lys Ala Ile Val Asp Leu Leu Phe
    690                 695                 700

Lys Thr Asn Arg Lys Val Thr Val Lys Gln Leu Lys Glu Asp Tyr Phe
705                 710                 715                 720

Lys Lys Ile Glu Cys Phe Asp Ser Val Glu Ile Ser Gly Val Glu Asp
                725                 730                 735

Arg Phe Asn Ala Ser Leu Gly Thr Tyr His Asp Leu Leu Lys Ile Ile
            740                 745                 750

Lys Asp Lys Asp Phe Leu Asp Asn Glu Glu Asn Glu Asp Ile Leu Glu
        755                 760                 765

Asp Ile Val Leu Thr Leu Thr Leu Phe Glu Asp Arg Glu Met Ile Glu
    770                 775                 780

Glu Arg Leu Lys Thr Tyr Ala His Leu Phe Asp Asp Lys Val Met Lys
785                 790                 795                 800

Gln Leu Lys Arg Arg Arg Tyr Thr Gly Trp Gly Arg Leu Ser Arg Lys
                805                 810                 815

Leu Ile Asn Gly Ile Arg Asp Lys Gln Ser Gly Lys Thr Ile Leu Asp
            820                 825                 830

Phe Leu Lys Ser Asp Gly Phe Ala Asn Arg Asn Phe Met Gln Leu Ile
        835                 840                 845

His Asp Asp Ser Leu Thr Phe Lys Glu Asp Ile Gln Lys Ala Gln Val
    850                 855                 860

Ser Gly Gln Gly Asp Ser Leu His Glu His Ile Ala Asn Leu Ala Gly
865                 870                 875                 880
```

```
Ser Pro Ala Ile Lys Lys Gly Ile Leu Gln Thr Val Lys Val Val Asp
                885                 890                 895

Glu Leu Val Lys Val Met Gly Arg His Lys Pro Glu Asn Ile Val Ile
            900                 905                 910

Glu Met Ala Arg Glu Asn Gln Thr Thr Gln Lys Gly Gln Lys Asn Ser
        915                 920                 925

Arg Glu Arg Met Lys Arg Ile Glu Glu Gly Ile Lys Glu Leu Gly Ser
    930                 935                 940

Gln Ile Leu Lys Glu His Pro Val Glu Asn Thr Gln Leu Gln Asn Glu
945                 950                 955                 960

Lys Leu Tyr Leu Tyr Tyr Leu Gln Asn Gly Arg Asp Met Tyr Val Asp
                965                 970                 975

Gln Glu Leu Asp Ile Asn Arg Leu Ser Asp Tyr Asp Val Asp Ala Ile
            980                 985                 990

Val Pro Gln Ser Phe Leu Lys Asp  Asp Ser Ile Asp Asn  Lys Val Leu
        995                 1000                1005

Thr Arg  Ser Asp Lys Asn Arg  Gly Lys Ser Asp Asn  Val Pro Ser
    1010                1015                1020

Glu Glu  Val Val Lys Lys Met  Lys Asn Tyr Trp Arg  Gln Leu Leu
    1025                1030                1035

Asn Ala  Lys Leu Ile Thr Gln  Arg Lys Phe Asp Asn  Leu Thr Lys
    1040                1045                1050

Ala Glu  Arg Gly Gly Leu Ser  Glu Leu Asp Lys Ala  Gly Phe Ile
    1055                1060                1065

Lys Arg  Gln Leu Val Glu Thr  Arg Gln Ile Thr Lys  His Val Ala
    1070                1075                1080

Gln Ile  Leu Asp Ser Arg Met  Asn Thr Lys Tyr Asp  Glu Asn Asp
    1085                1090                1095

Lys Leu  Ile Arg Glu Val Lys  Val Ile Thr Leu Lys  Ser Lys Leu
    1100                1105                1110

Val Ser  Asp Phe Arg Lys Asp  Phe Gln Phe Tyr Lys  Val Arg Glu
    1115                1120                1125

Ile Asn  Asn Tyr His His Ala  His Asp Ala Tyr Leu  Asn Ala Val
    1130                1135                1140

Val Gly  Thr Ala Leu Ile Lys  Lys Tyr Pro Lys Leu  Glu Ser Glu
    1145                1150                1155

Phe Val  Tyr Gly Asp Tyr Lys  Val Tyr Asp Val Arg  Lys Met Ile
    1160                1165                1170

Ala Lys  Ser Glu Gln Glu Ile  Gly Lys Ala Thr Ala  Lys Tyr Phe
    1175                1180                1185

Phe Tyr  Ser Asn Ile Met Asn  Phe Phe Lys Thr Glu  Ile Thr Leu
    1190                1195                1200

Ala Asn  Gly Glu Ile Arg Lys  Arg Pro Leu Ile Glu  Thr Asn Gly
    1205                1210                1215

Glu Thr  Gly Glu Ile Val Trp  Asp Lys Gly Arg Asp  Phe Ala Thr
    1220                1225                1230

Val Arg  Lys Val Leu Ser Met  Pro Gln Val Asn Ile  Val Lys Lys
    1235                1240                1245

Thr Glu  Val Gln Thr Gly Gly  Phe Ser Lys Glu Ser  Ile Leu Pro
    1250                1255                1260

Lys Arg  Asn Ser Asp Lys Leu  Ile Ala Arg Lys Lys  Asp Trp Asp
    1265                1270                1275
```

```
Pro Lys Lys Tyr Gly Gly Phe Asp Ser Pro Thr Val Ala Tyr Ser
    1280                1285                1290

Val Leu Val Val Ala Lys Val Glu Lys Gly Lys Ser Lys Lys Leu
    1295                1300                1305

Lys Ser Val Lys Glu Leu Leu Gly Ile Thr Ile Met Glu Arg Ser
    1310                1315                1320

Ser Phe Glu Lys Asn Pro Ile Asp Phe Leu Glu Ala Lys Gly Tyr
    1325                1330                1335

Lys Glu Val Lys Lys Asp Leu Ile Ile Lys Leu Pro Lys Tyr Ser
    1340                1345                1350

Leu Phe Glu Leu Glu Asn Gly Arg Lys Arg Met Leu Ala Ser Ala
    1355                1360                1365

Gly Glu Leu Gln Lys Gly Asn Glu Leu Ala Leu Pro Ser Lys Tyr
    1370                1375                1380

Val Asn Phe Leu Tyr Leu Ala Ser His Tyr Glu Lys Leu Lys Gly
    1385                1390                1395

Ser Pro Glu Asp Asn Glu Gln Lys Gln Leu Phe Val Glu Gln His
    1400                1405                1410

Lys His Tyr Leu Asp Glu Ile Ile Glu Gln Ile Ser Glu Phe Ser
    1415                1420                1425

Lys Arg Val Ile Leu Ala Asp Ala Asn Leu Asp Lys Val Leu Ser
    1430                1435                1440

Ala Tyr Asn Lys His Arg Asp Lys Pro Ile Arg Glu Gln Ala Glu
    1445                1450                1455

Asn Ile Ile His Leu Phe Thr Leu Thr Asn Leu Gly Ala Pro Ala
    1460                1465                1470

Ala Phe Lys Tyr Phe Asp Thr Thr Ile Asp Arg Lys Arg Tyr Thr
    1475                1480                1485

Ser Thr Lys Glu Val Leu Asp Ala Thr Leu Ile His Gln Ser Ile
    1490                1495                1500

Thr Gly Leu Tyr Glu Thr Arg Ile Asp Leu Ser Gln Leu Gly Gly
    1505                1510                1515

Asp Ser Arg Ala Asp Tyr Pro Tyr Asp Val Pro Asp Tyr Ala Ser
    1520                1525                1530

Gly Ser Pro Lys Lys Lys Arg Lys Val Glu Ala Ser Gly Ser Gly
    1535                1540                1545

Arg Ala Ser Pro Gly Ile Pro Gly Ser Thr Arg Asn His Asp Gln
    1550                1555                1560

Glu Phe Asp Pro Pro Lys Val Tyr Pro Pro Val Pro Ala Glu Lys
    1565                1570                1575

Arg Lys Pro Ile Arg Val Leu Ser Leu Phe Asp Gly Ile Ala Thr
    1580                1585                1590

Gly Leu Leu Val Leu Lys Asp Leu Gly Ile Gln Val Asp Arg Tyr
    1595                1600                1605

Ile Ala Ser Glu Val Cys Glu Asp Ser Ile Thr Val Gly Met Val
    1610                1615                1620

Arg His Gln Gly Lys Ile Met Tyr Val Gly Asp Val Arg Ser Val
    1625                1630                1635

Thr Gln Lys His Ile Gln Glu Trp Gly Pro Phe Asp Leu Val Ile
    1640                1645                1650

Gly Gly Ser Pro Cys Asn Asp Leu Ser Ile Val Asn Pro Ala Arg
    1655                1660                1665

Lys Gly Leu Tyr Glu Gly Thr Gly Arg Leu Phe Phe Glu Phe Tyr
```

```
    1670                1675                1680

Arg Leu  Leu His Asp Ala Arg  Pro Lys Glu Gly Asp  Asp Arg Pro
    1685                1690                1695

Phe Phe  Trp Leu Phe Glu Asn  Val Val Ala Met Gly  Val Ser Asp
    1700                1705                1710

Lys Arg  Asp Ile Ser Arg Phe  Leu Glu Ser Asn Pro  Val Met Ile
    1715                1720                1725

Asp Ala  Lys Glu Val Ser Ala  Ala His Arg Ala Arg  Tyr Phe Trp
    1730                1735                1740

Gly Asn  Leu Pro Gly Met Asn  Arg Pro Leu Ala Ser  Thr Val Asn
    1745                1750                1755

Asp Lys  Leu Glu Leu Gln Glu  Cys Leu Glu His Gly  Arg Ile Ala
    1760                1765                1770

Lys Phe  Ser Lys Val Arg Thr  Ile Thr Thr Arg Ser  Asn Ser Ile
    1775                1780                1785

Lys Gln  Gly Lys Asp Gln His  Phe Pro Val Phe Met  Asn Glu Lys
    1790                1795                1800

Glu Asp  Ile Leu Trp Cys Thr  Glu Met Glu Arg Val  Phe Gly Phe
    1805                1810                1815

Pro Val  His Tyr Thr Asp Val  Ser Asn Met Ser Arg  Leu Ala Arg
    1820                1825                1830

Gln Arg  Leu Leu Gly Arg Ser  Trp Ser Val Pro Val  Ile Arg His
    1835                1840                1845

Leu Phe  Ala Pro Leu Lys Glu  Tyr Phe Ala Cys Val  Ser Ser Gly
    1850                1855                1860

Asn Ser  Asn Ala Asn Ser Arg  Gly Pro Ser Phe Ser  Ser Gly Leu
    1865                1870                1875

Val Pro  Leu Ser Leu Arg Gly  Ser His Met Gly Pro  Met Glu Ile
    1880                1885                1890

Tyr Lys  Thr Val Ser Ala Trp  Lys Arg Gln Pro Val  Arg Val Leu
    1895                1900                1905

Ser Leu  Phe Arg Asn Ile Asp  Lys Val Leu Lys Ser  Leu Gly Phe
    1910                1915                1920

Leu Glu  Ser Gly Ser Gly Ser  Gly Gly Gly Thr Leu  Lys Tyr Val
    1925                1930                1935

Glu Asp  Val Thr Asn Val Val  Arg Arg Asp Val Glu  Lys Trp Gly
    1940                1945                1950

Pro Phe  Asp Leu Val Tyr Gly  Ser Thr Gln Pro Leu  Gly Ser Ser
    1955                1960                1965

Cys Asp  Arg Cys Pro Gly Trp  Tyr Met Phe Gln Phe  His Arg Ile
    1970                1975                1980

Leu Gln  Tyr Ala Leu Pro Arg  Gln Glu Ser Gln Arg  Pro Phe Phe
    1985                1990                1995

Trp Ile  Phe Met Asp Asn Leu  Leu Leu Thr Glu Asp  Asp Gln Glu
    2000                2005                2010

Thr Thr  Thr Arg Phe Leu Gln  Thr Glu Ala Val Thr  Leu Gln Asp
    2015                2020                2025

Val Arg  Gly Arg Asp Tyr Gln  Asn Ala Met Arg Val  Trp Ser Asn
    2030                2035                2040

Ile Pro  Gly Leu Lys Ser Lys  His Ala Pro Leu Thr  Pro Lys Glu
    2045                2050                2055

Glu Glu  Tyr Leu Gln Ala Gln  Val Arg Ser Arg Ser  Lys Leu Asp
    2060                2065                2070
```

```
Ala Pro  Lys Val Asp Leu Leu  Val Lys Asn Cys Leu  Leu Pro Leu
    2075                 2080                 2085

Arg Glu  Tyr Phe Lys Tyr Phe  Ser Gln Asn Ser Leu  Pro Leu Ser
    2090                 2095                 2100

Arg Ala  Asp Pro Lys Lys Lys  Arg Lys Val Gly Ser  Gly Ala Thr
    2105                 2110                 2115

Asn Phe  Ser Leu Leu Lys Gln  Ala Gly Asp Val Glu  Glu Asn Pro
    2120                 2125                 2130

Gly Pro  Gly Ser Gly Ala Thr  Asn Phe Ser Leu Leu  Lys Gln Ala
    2135                 2140                 2145

Gly Asp  Val Glu Glu Asn Pro  Gly Pro Ser Glu Leu  Ile Lys Glu
    2150                 2155                 2160

Asn Met  His Met Lys Leu Tyr  Met Glu Gly Thr Val  Asp Asn His
    2165                 2170                 2175

His Phe  Lys Cys Thr Ser Glu  Gly Glu Gly Lys Pro  Tyr Glu Gly
    2180                 2185                 2190

Thr Gln  Thr Met Arg Ile Lys  Val Val Glu Gly Gly  Pro Leu Pro
    2195                 2200                 2205

Phe Ala  Phe Asp Ile Leu Ala  Thr Ser Phe Leu Tyr  Gly Ser Lys
    2210                 2215                 2220

Thr Phe  Ile Asn His Thr Gln  Gly Ile Pro Asp Phe  Phe Lys Gln
    2225                 2230                 2235

Ser Phe  Pro Glu Gly Phe Thr  Trp Glu Arg Val Thr  Thr Tyr Glu
    2240                 2245                 2250

Asp Gly  Gly Val Leu Thr Ala  Thr Gln Asp Thr Ser  Leu Gln Asp
    2255                 2260                 2265

Gly Cys  Leu Ile Tyr Asn Val  Lys Ile Arg Gly Val  Asn Phe Thr
    2270                 2275                 2280

Ser Asn  Gly Pro Val Met Gln  Lys Lys Thr Leu Gly  Trp Glu Ala
    2285                 2290                 2295

Phe Thr  Glu Thr Leu Tyr Pro  Ala Asp Gly Gly Leu  Glu Gly Arg
    2300                 2305                 2310

Asn Asp  Met Ala Leu Lys Leu  Val Gly Gly Ser His  Leu Ile Ala
    2315                 2320                 2325

Asn Ile  Lys Thr Thr Tyr Arg  Ser Lys Lys Pro Ala  Lys Asn Leu
    2330                 2335                 2340

Lys Met  Pro Gly Val Tyr Tyr  Val Asp Tyr Arg Leu  Glu Arg Ile
    2345                 2350                 2355

Lys Glu  Ala Asn Asn Glu Thr  Tyr Val Glu Gln His  Glu Val Ala
    2360                 2365                 2370

Val Ala  Arg Tyr Cys Asp Leu  Pro Ser Lys Leu Gly  His Lys Leu
    2375                 2380                 2385

Asn
```

<210> SEQ ID NO 11
<211> LENGTH: 2369
<212> TYPE: PRT
<213> ORGANISM: Artificial sequence
<220> FEATURE:
<223> OTHER INFORMATION: Synthetic polypeptide

<400> SEQUENCE: 11

```
Asp Ala Lys Ser Leu Thr Ala Trp Ser Arg Thr Leu Val Thr Phe Lys
1               5                   10                  15
```

-continued

```
Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Ser Gly Ser Glu Thr Pro Gly Thr Ser
65                  70                  75                  80

Glu Ser Ala Thr Pro Glu Ser Met Asp Lys Lys Tyr Ser Ile Gly Leu
                85                  90                  95

Ala Ile Gly Thr Asn Ser Val Gly Trp Ala Val Ile Thr Asp Glu Tyr
            100                 105                 110

Lys Val Pro Ser Lys Lys Phe Lys Val Leu Gly Asn Thr Asp Arg His
        115                 120                 125

Ser Ile Lys Lys Asn Leu Ile Gly Ala Leu Leu Phe Asp Ser Gly Glu
    130                 135                 140

Thr Ala Glu Ala Thr Arg Leu Lys Arg Thr Ala Arg Arg Arg Tyr Thr
145                 150                 155                 160

Arg Arg Lys Asn Arg Ile Cys Tyr Leu Gln Glu Ile Phe Ser Asn Glu
                165                 170                 175

Met Ala Lys Val Asp Asp Ser Phe Phe His Arg Leu Glu Glu Ser Phe
            180                 185                 190

Leu Val Glu Glu Asp Lys Lys His Glu Arg His Pro Ile Phe Gly Asn
        195                 200                 205

Ile Val Asp Glu Val Ala Tyr His Glu Lys Tyr Pro Thr Ile Tyr His
    210                 215                 220

Leu Arg Lys Lys Leu Val Asp Ser Thr Asp Lys Ala Asp Leu Arg Leu
225                 230                 235                 240

Ile Tyr Leu Ala Leu Ala His Met Ile Lys Phe Arg Gly His Phe Leu
                245                 250                 255

Ile Glu Gly Asp Leu Asn Pro Asp Asn Ser Asp Val Asp Lys Leu Phe
            260                 265                 270

Ile Gln Leu Val Gln Thr Tyr Asn Gln Leu Phe Glu Glu Asn Pro Ile
        275                 280                 285

Asn Ala Ser Gly Val Asp Ala Lys Ala Ile Leu Ser Ala Arg Leu Ser
    290                 295                 300

Lys Ser Arg Arg Leu Glu Asn Leu Ile Ala Gln Leu Pro Gly Glu Lys
305                 310                 315                 320

Lys Asn Gly Leu Phe Gly Asn Leu Ile Ala Leu Ser Leu Gly Leu Thr
                325                 330                 335

Pro Asn Phe Lys Ser Asn Phe Asp Leu Ala Glu Asp Ala Lys Leu Gln
            340                 345                 350

Leu Ser Lys Asp Thr Tyr Asp Asp Asp Leu Asp Asn Leu Leu Ala Gln
        355                 360                 365

Ile Gly Asp Gln Tyr Ala Asp Leu Phe Leu Ala Ala Lys Asn Leu Ser
    370                 375                 380

Asp Ala Ile Leu Leu Ser Asp Ile Leu Arg Val Asn Thr Glu Ile Thr
385                 390                 395                 400

Lys Ala Pro Leu Ser Ala Ser Met Ile Lys Arg Tyr Asp Glu His His
                405                 410                 415

Gln Asp Leu Thr Leu Leu Lys Ala Leu Val Arg Gln Gln Leu Pro Glu
            420                 425                 430

Lys Tyr Lys Glu Ile Phe Phe Asp Gln Ser Lys Asn Gly Tyr Ala Gly
```

```
        435                 440                 445

Tyr Ile Asp Gly Gly Ala Ser Gln Glu Glu Phe Tyr Lys Phe Ile Lys
    450                 455                 460

Pro Ile Leu Glu Lys Met Asp Gly Thr Glu Glu Leu Leu Val Lys Leu
465                 470                 475                 480

Asn Arg Glu Asp Leu Leu Arg Lys Gln Arg Thr Phe Asp Asn Gly Ser
                485                 490                 495

Ile Pro His Gln Ile His Leu Gly Glu Leu His Ala Ile Leu Arg Arg
            500                 505                 510

Gln Glu Asp Phe Tyr Pro Phe Leu Lys Asp Asn Arg Glu Lys Ile Glu
        515                 520                 525

Lys Ile Leu Thr Phe Arg Ile Pro Tyr Tyr Val Gly Pro Leu Ala Arg
    530                 535                 540

Gly Asn Ser Arg Phe Ala Trp Met Thr Arg Lys Ser Glu Glu Thr Ile
545                 550                 555                 560

Thr Pro Trp Asn Phe Glu Glu Val Val Asp Lys Gly Ala Ser Ala Gln
                565                 570                 575

Ser Phe Ile Glu Arg Met Thr Asn Phe Asp Lys Asn Leu Pro Asn Glu
            580                 585                 590

Lys Val Leu Pro Lys His Ser Leu Leu Tyr Glu Tyr Phe Thr Val Tyr
        595                 600                 605

Asn Glu Leu Thr Lys Val Lys Tyr Val Thr Glu Gly Met Arg Lys Pro
    610                 615                 620

Ala Phe Leu Ser Gly Glu Gln Lys Lys Ala Ile Val Asp Leu Leu Phe
625                 630                 635                 640

Lys Thr Asn Arg Lys Val Thr Val Lys Gln Leu Lys Glu Asp Tyr Phe
                645                 650                 655

Lys Lys Ile Glu Cys Phe Asp Ser Val Glu Ile Ser Gly Val Glu Asp
            660                 665                 670

Arg Phe Asn Ala Ser Leu Gly Thr Tyr His Asp Leu Leu Lys Ile Ile
        675                 680                 685

Lys Asp Lys Asp Phe Leu Asp Asn Glu Glu Asn Glu Asp Ile Leu Glu
    690                 695                 700

Asp Ile Val Leu Thr Leu Thr Leu Phe Glu Asp Arg Glu Met Ile Glu
705                 710                 715                 720

Glu Arg Leu Lys Thr Tyr Ala His Leu Phe Asp Asp Lys Val Met Lys
                725                 730                 735

Gln Leu Lys Arg Arg Arg Tyr Thr Gly Trp Gly Arg Leu Ser Arg Lys
            740                 745                 750

Leu Ile Asn Gly Ile Arg Asp Lys Gln Ser Gly Lys Thr Ile Leu Asp
        755                 760                 765

Phe Leu Lys Ser Asp Gly Phe Ala Asn Arg Asn Phe Met Gln Leu Ile
    770                 775                 780

His Asp Asp Ser Leu Thr Phe Lys Glu Asp Ile Gln Lys Ala Gln Val
785                 790                 795                 800

Ser Gly Gln Gly Asp Ser Leu His Glu His Ile Ala Asn Leu Ala Gly
                805                 810                 815

Ser Pro Ala Ile Lys Lys Gly Ile Leu Gln Thr Val Lys Val Val Asp
            820                 825                 830

Glu Leu Val Lys Val Met Gly Arg His Lys Pro Glu Asn Ile Val Ile
        835                 840                 845

Glu Met Ala Arg Glu Asn Gln Thr Thr Gln Lys Gly Gln Lys Asn Ser
    850                 855                 860
```

```
Arg Glu Arg Met Lys Arg Ile Glu Glu Gly Ile Lys Glu Leu Gly Ser
865                 870                 875                 880

Gln Ile Leu Lys Glu His Pro Val Glu Asn Thr Gln Leu Gln Asn Glu
                885                 890                 895

Lys Leu Tyr Leu Tyr Tyr Leu Gln Asn Gly Arg Asp Met Tyr Val Asp
            900                 905                 910

Gln Glu Leu Asp Ile Asn Arg Leu Ser Asp Tyr Asp Val Asp Ala Ile
        915                 920                 925

Val Pro Gln Ser Phe Leu Lys Asp Asp Ser Ile Asp Asn Lys Val Leu
    930                 935                 940

Thr Arg Ser Asp Lys Asn Arg Gly Lys Ser Asp Asn Val Pro Ser Glu
945                 950                 955                 960

Glu Val Val Lys Lys Met Lys Asn Tyr Trp Arg Gln Leu Leu Asn Ala
                965                 970                 975

Lys Leu Ile Thr Gln Arg Lys Phe Asp Asn Leu Thr Lys Ala Glu Arg
            980                 985                 990

Gly Gly Leu Ser Glu Leu Asp Lys  Ala Gly Phe Ile Lys  Arg Gln Leu
        995                 1000                 1005

Val Glu  Thr Arg Gln Ile Thr  Lys His Val Ala Gln  Ile Leu Asp
    1010                 1015                 1020

Ser Arg  Met Asn Thr Lys Tyr  Asp Glu Asn Asp Lys  Leu Ile Arg
    1025                 1030                 1035

Glu Val  Lys Val Ile Thr Leu  Lys Ser Lys Leu Val  Ser Asp Phe
    1040                 1045                 1050

Arg Lys  Asp Phe Gln Phe Tyr  Lys Val Arg Glu Ile  Asn Asn Tyr
    1055                 1060                 1065

His His  Ala His Asp Ala Tyr  Leu Asn Ala Val Val  Gly Thr Ala
    1070                 1075                 1080

Leu Ile  Lys Lys Tyr Pro Lys  Leu Glu Ser Glu Phe  Val Tyr Gly
    1085                 1090                 1095

Asp Tyr  Lys Val Tyr Asp Val  Arg Lys Met Ile Ala  Lys Ser Glu
    1100                 1105                 1110

Gln Glu  Ile Gly Lys Ala Thr  Ala Lys Tyr Phe Phe  Tyr Ser Asn
    1115                 1120                 1125

Ile Met  Asn Phe Phe Lys Thr  Glu Ile Thr Leu Ala  Asn Gly Glu
    1130                 1135                 1140

Ile Arg  Lys Arg Pro Leu Ile  Glu Thr Asn Gly Glu  Thr Gly Glu
    1145                 1150                 1155

Ile Val  Trp Asp Lys Gly Arg  Asp Phe Ala Thr Val  Arg Lys Val
    1160                 1165                 1170

Leu Ser  Met Pro Gln Val Asn  Ile Val Lys Lys Thr  Glu Val Gln
    1175                 1180                 1185

Thr Gly  Gly Phe Ser Lys Glu  Ser Ile Leu Pro Lys  Arg Asn Ser
    1190                 1195                 1200

Asp Lys  Leu Ile Ala Arg Lys  Lys Asp Trp Asp Pro  Lys Lys Tyr
    1205                 1210                 1215

Gly Gly  Phe Asp Ser Pro Thr  Val Ala Tyr Ser Val  Leu Val Val
    1220                 1225                 1230

Ala Lys  Val Glu Lys Gly Lys  Ser Lys Lys Leu Lys  Ser Val Lys
    1235                 1240                 1245

Glu Leu  Leu Gly Ile Thr Ile  Met Glu Arg Ser Ser  Phe Glu Lys
    1250                 1255                 1260
```

-continued

```
Asn Pro  Ile Asp Phe Leu Glu  Ala Lys Gly Tyr Lys  Glu Val Lys
    1265                 1270                 1275

Lys Asp  Leu Ile Ile Lys Leu  Pro Lys Tyr Ser Leu  Phe Glu Leu
    1280                 1285                 1290

Glu Asn  Gly Arg Lys Arg Met  Leu Ala Ser Ala Gly  Glu Leu Gln
    1295                 1300                 1305

Lys Gly  Asn Glu Leu Ala Leu  Pro Ser Lys Tyr Val  Asn Phe Leu
    1310                 1315                 1320

Tyr Leu  Ala Ser His Tyr Glu  Lys Leu Lys Gly Ser  Pro Glu Asp
    1325                 1330                 1335

Asn Glu  Gln Lys Gln Leu Phe  Val Glu Gln His Lys  His Tyr Leu
    1340                 1345                 1350

Asp Glu  Ile Ile Glu Gln Ile  Ser Glu Phe Ser Lys  Arg Val Ile
    1355                 1360                 1365

Leu Ala  Asp Ala Asn Leu Asp  Lys Val Leu Ser Ala  Tyr Asn Lys
    1370                 1375                 1380

His Arg  Asp Lys Pro Ile Arg  Glu Gln Ala Glu Asn  Ile Ile His
    1385                 1390                 1395

Leu Phe  Thr Leu Thr Asn Leu  Gly Ala Pro Ala Ala  Phe Lys Tyr
    1400                 1405                 1410

Phe Asp  Thr Thr Ile Asp Arg  Lys Arg Tyr Thr Ser  Thr Lys Glu
    1415                 1420                 1425

Val Leu  Asp Ala Thr Leu Ile  His Gln Ser Ile Thr  Gly Leu Tyr
    1430                 1435                 1440

Glu Thr  Arg Ile Asp Leu Ser  Gln Leu Gly Gly Asp  Ser Arg Ala
    1445                 1450                 1455

Asp Tyr  Pro Tyr Asp Val Pro  Asp Tyr Ala Ser Gly  Ser Pro Lys
    1460                 1465                 1470

Lys Lys  Arg Lys Val Ser Pro  Gly Gly Gly Pro Ser  Ser Gly Ala
    1475                 1480                 1485

Pro Pro  Pro Ser Gly Gly Ser  Pro Ala Gly Ser Pro  Thr Ser Thr
    1490                 1495                 1500

Glu Glu  Gly Thr Ser Glu Ser  Ala Thr Pro Glu Ser  Gly Pro Gly
    1505                 1510                 1515

Thr Ser  Thr Glu Pro Ser Glu  Gly Ser Ala Pro Gly  Ser Pro Ala
    1520                 1525                 1530

Gly Ser  Pro Thr Ser Thr Glu  Glu Gly Thr Ser Thr  Glu Pro Ser
    1535                 1540                 1545

Glu Gly  Ser Ala Pro Gly Thr  Ser Thr Glu Pro Ser  Glu Asn His
    1550                 1555                 1560

Asp Gln  Glu Phe Asp Pro Pro  Lys Val Tyr Pro Pro  Val Pro Ala
    1565                 1570                 1575

Glu Lys  Arg Lys Pro Ile Arg  Val Leu Ser Leu Phe  Asp Gly Ile
    1580                 1585                 1590

Ala Thr  Gly Leu Leu Val Leu  Lys Asp Leu Gly Ile  Gln Val Asp
    1595                 1600                 1605

Arg Tyr  Ile Ala Ser Glu Val  Cys Glu Asp Ser Ile  Thr Val Gly
    1610                 1615                 1620

Met Val  Arg His Gln Gly Lys  Ile Met Tyr Val Gly  Asp Val Arg
    1625                 1630                 1635

Ser Val  Thr Gln Lys His Ile  Gln Glu Trp Gly Pro  Phe Asp Leu
    1640                 1645                 1650

Val Ile  Gly Gly Ser Pro Cys  Asn Asp Leu Ser Ile  Val Asn Pro
```

```
    1655                1660                1665

Ala Arg  Lys Gly Leu Tyr Glu  Gly Thr Gly Arg Leu  Phe Phe Glu
    1670                1675                1680

Phe Tyr  Arg Leu Leu His Asp  Ala Arg Pro Lys Glu  Gly Asp Asp
    1685                1690                1695

Arg Pro  Phe Phe Trp Leu Phe  Glu Asn Val Val Ala  Met Gly Val
    1700                1705                1710

Ser Asp  Lys Arg Asp Ile Ser  Arg Phe Leu Glu Ser  Asn Pro Val
    1715                1720                1725

Met Ile  Asp Ala Lys Glu Val  Ser Ala Ala His Arg  Ala Arg Tyr
    1730                1735                1740

Phe Trp  Gly Asn Leu Pro Gly  Met Asn Arg Pro Leu  Ala Ser Thr
    1745                1750                1755

Val Asn  Asp Lys Leu Glu Leu  Gln Glu Cys Leu Glu  His Gly Arg
    1760                1765                1770

Ile Ala  Lys Phe Ser Lys Val  Arg Thr Ile Thr Thr  Arg Ser Asn
    1775                1780                1785

Ser Ile  Lys Gln Gly Lys Asp  Gln His Phe Pro Val  Phe Met Asn
    1790                1795                1800

Glu Lys  Glu Asp Ile Leu Trp  Cys Thr Glu Met Glu  Arg Val Phe
    1805                1810                1815

Gly Phe  Pro Val His Tyr Thr  Asp Val Ser Asn Met  Ser Arg Leu
    1820                1825                1830

Ala Arg  Gln Arg Leu Leu Gly  Arg Ser Trp Ser Val  Pro Val Ile
    1835                1840                1845

Arg His  Leu Phe Ala Pro Leu  Lys Glu Tyr Phe Ala  Cys Val Ser
    1850                1855                1860

Ser Gly  Asn Ser Asn Ala Asn  Ser Arg Gly Pro Ser  Phe Ser Ser
    1865                1870                1875

Gly Leu  Val Pro Leu Ser Leu  Arg Gly Ser His Met  Gly Pro Met
    1880                1885                1890

Glu Ile  Tyr Lys Thr Val Ser  Ala Trp Lys Arg Gln  Pro Val Arg
    1895                1900                1905

Val Leu  Ser Leu Phe Arg Asn  Ile Asp Lys Val Leu  Lys Ser Leu
    1910                1915                1920

Gly Phe  Leu Glu Ser Gly Ser  Gly Ser Gly Gly Gly  Thr Leu Lys
    1925                1930                1935

Tyr Val  Glu Asp Val Thr Asn  Val Val Arg Arg Asp  Val Glu Lys
    1940                1945                1950

Trp Gly  Pro Phe Asp Leu Val  Tyr Gly Ser Thr Gln  Pro Leu Gly
    1955                1960                1965

Ser Ser  Cys Asp Arg Cys Pro  Gly Trp Tyr Met Phe  Gln Phe His
    1970                1975                1980

Arg Ile  Leu Gln Tyr Ala Leu  Pro Arg Gln Glu Ser  Gln Arg Pro
    1985                1990                1995

Phe Phe  Trp Ile Phe Met Asp  Asn Leu Leu Leu Thr  Glu Asp Asp
    2000                2005                2010

Gln Glu  Thr Thr Thr Arg Phe  Leu Gln Thr Glu Ala  Val Thr Leu
    2015                2020                2025

Gln Asp  Val Arg Gly Arg Asp  Tyr Gln Asn Ala Met  Arg Val Trp
    2030                2035                2040

Ser Asn  Ile Pro Gly Leu Lys  Ser Lys His Ala Pro  Leu Thr Pro
    2045                2050                2055
```

Lys Glu Glu Glu Tyr Leu Gln Ala Gln Val Arg Ser Arg Ser Lys
2060 2065 2070

Leu Asp Ala Pro Lys Val Asp Leu Leu Val Lys Asn Cys Leu Leu
2075 2080 2085

Pro Leu Arg Glu Tyr Phe Lys Tyr Phe Ser Gln Asn Ser Leu Pro
2090 2095 2100

Leu Ser Arg Ala Asp Pro Lys Lys Lys Arg Lys Val Gly Ser Gly
2105 2110 2115

Ala Thr Asn Phe Ser Leu Leu Lys Gln Ala Gly Asp Val Glu Glu
2120 2125 2130

Asn Pro Gly Pro Ser Glu Leu Ile Lys Glu Asn Met His Met Lys
2135 2140 2145

Leu Tyr Met Glu Gly Thr Val Asp Asn His His Phe Lys Cys Thr
2150 2155 2160

Ser Glu Gly Glu Gly Lys Pro Tyr Glu Gly Thr Gln Thr Met Arg
2165 2170 2175

Ile Lys Val Val Glu Gly Gly Pro Leu Pro Phe Ala Phe Asp Ile
2180 2185 2190

Leu Ala Thr Ser Phe Leu Tyr Gly Ser Lys Thr Phe Ile Asn His
2195 2200 2205

Thr Gln Gly Ile Pro Asp Phe Phe Lys Gln Ser Phe Pro Glu Gly
2210 2215 2220

Phe Thr Trp Glu Arg Val Thr Thr Tyr Glu Asp Gly Gly Val Leu
2225 2230 2235

Thr Ala Thr Gln Asp Thr Ser Leu Gln Asp Gly Cys Leu Ile Tyr
2240 2245 2250

Asn Val Lys Ile Arg Gly Val Asn Phe Thr Ser Asn Gly Pro Val
2255 2260 2265

Met Gln Lys Lys Thr Leu Gly Trp Glu Ala Phe Thr Glu Thr Leu
2270 2275 2280

Tyr Pro Ala Asp Gly Gly Leu Glu Gly Arg Asn Asp Met Ala Leu
2285 2290 2295

Lys Leu Val Gly Gly Ser His Leu Ile Ala Asn Ile Lys Thr Thr
2300 2305 2310

Tyr Arg Ser Lys Lys Pro Ala Lys Asn Leu Lys Met Pro Gly Val
2315 2320 2325

Tyr Tyr Val Asp Tyr Arg Leu Glu Arg Ile Lys Glu Ala Asn Asn
2330 2335 2340

Glu Thr Tyr Val Glu Gln His Glu Val Ala Val Ala Arg Tyr Cys
2345 2350 2355

Asp Leu Pro Ser Lys Leu Gly His Lys Leu Asn
2360 2365

<210> SEQ ID NO 12
<211> LENGTH: 2391
<212> TYPE: PRT
<213> ORGANISM: Artificial sequence
<220> FEATURE:
<223> OTHER INFORMATION: Synthetic polypeptide

<400> SEQUENCE: 12

Asp Ala Lys Ser Leu Thr Ala Trp Ser Arg Thr Leu Val Thr Phe Lys
1 5 10 15

Asp Val Phe Val Asp Phe Thr Arg Glu Glu Trp Lys Leu Leu Asp Thr
20 25 30

```
Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Ser Gly Ser Glu Thr Pro Gly Thr Ser
65                  70                  75                  80

Glu Ser Ala Thr Pro Glu Ser Met Asp Lys Lys Tyr Ser Ile Gly Leu
                85                  90                  95

Ala Ile Gly Thr Asn Ser Val Gly Trp Ala Val Ile Thr Asp Glu Tyr
            100                 105                 110

Lys Val Pro Ser Lys Lys Phe Lys Val Leu Gly Asn Thr Asp Arg His
        115                 120                 125

Ser Ile Lys Lys Asn Leu Ile Gly Ala Leu Leu Phe Asp Ser Gly Glu
    130                 135                 140

Thr Ala Glu Ala Thr Arg Leu Lys Arg Thr Ala Arg Arg Arg Tyr Thr
145                 150                 155                 160

Arg Arg Lys Asn Arg Ile Cys Tyr Leu Gln Glu Ile Phe Ser Asn Glu
                165                 170                 175

Met Ala Lys Val Asp Asp Ser Phe Phe His Arg Leu Glu Glu Ser Phe
            180                 185                 190

Leu Val Glu Glu Asp Lys Lys His Glu Arg His Pro Ile Phe Gly Asn
        195                 200                 205

Ile Val Asp Glu Val Ala Tyr His Glu Lys Tyr Pro Thr Ile Tyr His
    210                 215                 220

Leu Arg Lys Lys Leu Val Asp Ser Thr Asp Lys Ala Asp Leu Arg Leu
225                 230                 235                 240

Ile Tyr Leu Ala Leu Ala His Met Ile Lys Phe Arg Gly His Phe Leu
                245                 250                 255

Ile Glu Gly Asp Leu Asn Pro Asp Asn Ser Asp Val Asp Lys Leu Phe
            260                 265                 270

Ile Gln Leu Val Gln Thr Tyr Asn Gln Leu Phe Glu Glu Asn Pro Ile
        275                 280                 285

Asn Ala Ser Gly Val Asp Ala Lys Ala Ile Leu Ser Ala Arg Leu Ser
    290                 295                 300

Lys Ser Arg Arg Leu Glu Asn Leu Ile Ala Gln Leu Pro Gly Glu Lys
305                 310                 315                 320

Lys Asn Gly Leu Phe Gly Asn Leu Ile Ala Leu Ser Leu Gly Leu Thr
                325                 330                 335

Pro Asn Phe Lys Ser Asn Phe Asp Leu Ala Glu Asp Ala Lys Leu Gln
            340                 345                 350

Leu Ser Lys Asp Thr Tyr Asp Asp Asp Leu Asp Asn Leu Leu Ala Gln
        355                 360                 365

Ile Gly Asp Gln Tyr Ala Asp Leu Phe Leu Ala Ala Lys Asn Leu Ser
    370                 375                 380

Asp Ala Ile Leu Leu Ser Asp Ile Leu Arg Val Asn Thr Glu Ile Thr
385                 390                 395                 400

Lys Ala Pro Leu Ser Ala Ser Met Ile Lys Arg Tyr Asp Glu His His
                405                 410                 415

Gln Asp Leu Thr Leu Leu Lys Ala Leu Val Arg Gln Gln Leu Pro Glu
            420                 425                 430

Lys Tyr Lys Glu Ile Phe Phe Asp Gln Ser Lys Asn Gly Tyr Ala Gly
        435                 440                 445
```

```
Tyr Ile Asp Gly Gly Ala Ser Gln Glu Glu Phe Tyr Lys Phe Ile Lys
    450                 455                 460

Pro Ile Leu Glu Lys Met Asp Gly Thr Glu Glu Leu Leu Val Lys Leu
465                 470                 475                 480

Asn Arg Glu Asp Leu Leu Arg Lys Gln Arg Thr Phe Asp Asn Gly Ser
                485                 490                 495

Ile Pro His Gln Ile His Leu Gly Glu Leu His Ala Ile Leu Arg Arg
            500                 505                 510

Gln Glu Asp Phe Tyr Pro Phe Leu Lys Asp Asn Arg Glu Lys Ile Glu
        515                 520                 525

Lys Ile Leu Thr Phe Arg Ile Pro Tyr Tyr Val Gly Pro Leu Ala Arg
    530                 535                 540

Gly Asn Ser Arg Phe Ala Trp Met Thr Arg Lys Ser Glu Glu Thr Ile
545                 550                 555                 560

Thr Pro Trp Asn Phe Glu Glu Val Val Asp Lys Gly Ala Ser Ala Gln
                565                 570                 575

Ser Phe Ile Glu Arg Met Thr Asn Phe Asp Lys Asn Leu Pro Asn Glu
            580                 585                 590

Lys Val Leu Pro Lys His Ser Leu Leu Tyr Glu Tyr Phe Thr Val Tyr
        595                 600                 605

Asn Glu Leu Thr Lys Val Lys Tyr Val Thr Glu Gly Met Arg Lys Pro
    610                 615                 620

Ala Phe Leu Ser Gly Glu Gln Lys Lys Ala Ile Val Asp Leu Leu Phe
625                 630                 635                 640

Lys Thr Asn Arg Lys Val Thr Val Lys Gln Leu Lys Glu Asp Tyr Phe
                645                 650                 655

Lys Lys Ile Glu Cys Phe Asp Ser Val Glu Ile Ser Gly Val Glu Asp
            660                 665                 670

Arg Phe Asn Ala Ser Leu Gly Thr Tyr His Asp Leu Leu Lys Ile Ile
        675                 680                 685

Lys Asp Lys Asp Phe Leu Asp Asn Glu Glu Asn Glu Asp Ile Leu Glu
    690                 695                 700

Asp Ile Val Leu Thr Leu Thr Leu Phe Glu Asp Arg Glu Met Ile Glu
705                 710                 715                 720

Glu Arg Leu Lys Thr Tyr Ala His Leu Phe Asp Asp Lys Val Met Lys
                725                 730                 735

Gln Leu Lys Arg Arg Arg Tyr Thr Gly Trp Gly Arg Leu Ser Arg Lys
            740                 745                 750

Leu Ile Asn Gly Ile Arg Asp Lys Gln Ser Gly Lys Thr Ile Leu Asp
        755                 760                 765

Phe Leu Lys Ser Asp Gly Phe Ala Asn Arg Asn Phe Met Gln Leu Ile
    770                 775                 780

His Asp Asp Ser Leu Thr Phe Lys Glu Asp Ile Gln Lys Ala Gln Val
785                 790                 795                 800

Ser Gly Gln Gly Asp Ser Leu His Glu His Ile Ala Asn Leu Ala Gly
                805                 810                 815

Ser Pro Ala Ile Lys Lys Gly Ile Leu Gln Thr Val Lys Val Val Asp
            820                 825                 830

Glu Leu Val Lys Val Met Gly Arg His Lys Pro Glu Asn Ile Val Ile
        835                 840                 845

Glu Met Ala Arg Glu Asn Gln Thr Thr Gln Lys Gly Gln Lys Asn Ser
    850                 855                 860

Arg Glu Arg Met Lys Arg Ile Glu Glu Gly Ile Lys Glu Leu Gly Ser
```

```
865                 870                 875                 880

Gln Ile Leu Lys Glu His Pro Val Glu Asn Thr Gln Leu Gln Asn Glu
                885                 890                 895

Lys Leu Tyr Leu Tyr Tyr Leu Gln Asn Gly Arg Asp Met Tyr Val Asp
            900                 905                 910

Gln Glu Leu Asp Ile Asn Arg Leu Ser Asp Tyr Asp Val Asp Ala Ile
        915                 920                 925

Val Pro Gln Ser Phe Leu Lys Asp Asp Ser Ile Asp Asn Lys Val Leu
    930                 935                 940

Thr Arg Ser Asp Lys Asn Arg Gly Lys Ser Asp Asn Val Pro Ser Glu
945                 950                 955                 960

Glu Val Val Lys Lys Met Lys Asn Tyr Trp Arg Gln Leu Leu Asn Ala
                965                 970                 975

Lys Leu Ile Thr Gln Arg Lys Phe Asp Asn Leu Thr Lys Ala Glu Arg
            980                 985                 990

Gly Gly Leu Ser Glu Leu Asp Lys  Ala Gly Phe Ile Lys  Arg Gln Leu
        995                 1000                1005

Val Glu  Thr Arg Gln Ile Thr  Lys His Val Ala Gln  Ile Leu Asp
    1010                1015                1020

Ser Arg  Met Asn Thr Lys Tyr  Asp Glu Asn Asp Lys  Leu Ile Arg
    1025                1030                1035

Glu Val  Lys Val Ile Thr Leu  Lys Ser Lys Leu Val  Ser Asp Phe
    1040                1045                1050

Arg Lys  Asp Phe Gln Phe Tyr  Lys Val Arg Glu Ile  Asn Asn Tyr
    1055                1060                1065

His His  Ala His Asp Ala Tyr  Leu Asn Ala Val Val  Gly Thr Ala
    1070                1075                1080

Leu Ile  Lys Lys Tyr Pro Lys  Leu Glu Ser Glu Phe  Val Tyr Gly
    1085                1090                1095

Asp Tyr  Lys Val Tyr Asp Val  Arg Lys Met Ile Ala  Lys Ser Glu
    1100                1105                1110

Gln Glu  Ile Gly Lys Ala Thr  Ala Lys Tyr Phe Phe  Tyr Ser Asn
    1115                1120                1125

Ile Met  Asn Phe Phe Lys Thr  Glu Ile Thr Leu Ala  Asn Gly Glu
    1130                1135                1140

Ile Arg  Lys Arg Pro Leu Ile  Glu Thr Asn Gly Glu  Thr Gly Glu
    1145                1150                1155

Ile Val  Trp Asp Lys Gly Arg  Asp Phe Ala Thr Val  Arg Lys Val
    1160                1165                1170

Leu Ser  Met Pro Gln Val Asn  Ile Val Lys Lys Thr  Glu Val Gln
    1175                1180                1185

Thr Gly  Gly Phe Ser Lys Glu  Ser Ile Leu Pro Lys  Arg Asn Ser
    1190                1195                1200

Asp Lys  Leu Ile Ala Arg Lys  Lys Asp Trp Asp Pro  Lys Lys Tyr
    1205                1210                1215

Gly Gly  Phe Asp Ser Pro Thr  Val Ala Tyr Ser Val  Leu Val Val
    1220                1225                1230

Ala Lys  Val Glu Lys Gly Lys  Ser Lys Lys Leu Lys  Ser Val Lys
    1235                1240                1245

Glu Leu  Leu Gly Ile Thr Ile  Met Glu Arg Ser Ser  Phe Glu Lys
    1250                1255                1260

Asn Pro  Ile Asp Phe Leu Glu  Ala Lys Gly Tyr Lys  Glu Val Lys
    1265                1270                1275
```

Lys Asp Leu Ile Ile Lys Leu Pro Lys Tyr Ser Leu Phe Glu Leu
1280 1285 1290

Glu Asn Gly Arg Lys Arg Met Leu Ala Ser Ala Gly Glu Leu Gln
1295 1300 1305

Lys Gly Asn Glu Leu Ala Leu Pro Ser Lys Tyr Val Asn Phe Leu
1310 1315 1320

Tyr Leu Ala Ser His Tyr Glu Lys Leu Lys Gly Ser Pro Glu Asp
1325 1330 1335

Asn Glu Gln Lys Gln Leu Phe Val Glu Gln His Lys His Tyr Leu
1340 1345 1350

Asp Glu Ile Ile Glu Gln Ile Ser Glu Phe Ser Lys Arg Val Ile
1355 1360 1365

Leu Ala Asp Ala Asn Leu Asp Lys Val Leu Ser Ala Tyr Asn Lys
1370 1375 1380

His Arg Asp Lys Pro Ile Arg Glu Gln Ala Glu Asn Ile Ile His
1385 1390 1395

Leu Phe Thr Leu Thr Asn Leu Gly Ala Pro Ala Ala Phe Lys Tyr
1400 1405 1410

Phe Asp Thr Thr Ile Asp Arg Lys Arg Tyr Thr Ser Thr Lys Glu
1415 1420 1425

Val Leu Asp Ala Thr Leu Ile His Gln Ser Ile Thr Gly Leu Tyr
1430 1435 1440

Glu Thr Arg Ile Asp Leu Ser Gln Leu Gly Gly Asp Ser Arg Ala
1445 1450 1455

Asp Tyr Pro Tyr Asp Val Pro Asp Tyr Ala Ser Gly Ser Pro Lys
1460 1465 1470

Lys Lys Arg Lys Val Ser Pro Gly Gly Gly Pro Ser Ser Gly Ala
1475 1480 1485

Pro Pro Pro Ser Gly Gly Ser Pro Ala Gly Ser Pro Thr Ser Thr
1490 1495 1500

Glu Glu Gly Thr Ser Glu Ser Ala Thr Pro Glu Ser Gly Pro Gly
1505 1510 1515

Thr Ser Thr Glu Pro Ser Glu Gly Ser Ala Pro Gly Ser Pro Ala
1520 1525 1530

Gly Ser Pro Thr Ser Thr Glu Glu Gly Thr Ser Thr Glu Pro Ser
1535 1540 1545

Glu Gly Ser Ala Pro Gly Thr Ser Thr Glu Pro Ser Glu Asn His
1550 1555 1560

Asp Gln Glu Phe Asp Pro Pro Lys Val Tyr Pro Pro Val Pro Ala
1565 1570 1575

Glu Lys Arg Lys Pro Ile Arg Val Leu Ser Leu Phe Asp Gly Ile
1580 1585 1590

Ala Thr Gly Leu Leu Val Leu Lys Asp Leu Gly Ile Gln Val Asp
1595 1600 1605

Arg Tyr Ile Ala Ser Glu Val Cys Glu Asp Ser Ile Thr Val Gly
1610 1615 1620

Met Val Arg His Gln Gly Lys Ile Met Tyr Val Gly Asp Val Arg
1625 1630 1635

Ser Val Thr Gln Lys His Ile Gln Glu Trp Gly Pro Phe Asp Leu
1640 1645 1650

Val Ile Gly Gly Ser Pro Cys Asn Asp Leu Ser Ile Val Asn Pro
1655 1660 1665

```
Ala Arg Lys Gly Leu Tyr Glu Gly Thr Gly Arg Leu Phe Phe Glu
    1670                1675                1680

Phe Tyr Arg Leu Leu His Asp Ala Arg Pro Lys Glu Gly Asp Asp
    1685                1690                1695

Arg Pro Phe Phe Trp Leu Phe Glu Asn Val Val Ala Met Gly Val
    1700                1705                1710

Ser Asp Lys Arg Asp Ile Ser Arg Phe Leu Glu Ser Asn Pro Val
    1715                1720                1725

Met Ile Asp Ala Lys Glu Val Ser Ala Ala His Arg Ala Arg Tyr
    1730                1735                1740

Phe Trp Gly Asn Leu Pro Gly Met Asn Arg Pro Leu Ala Ser Thr
    1745                1750                1755

Val Asn Asp Lys Leu Glu Leu Gln Glu Cys Leu Glu His Gly Arg
    1760                1765                1770

Ile Ala Lys Phe Ser Lys Val Arg Thr Ile Thr Thr Arg Ser Asn
    1775                1780                1785

Ser Ile Lys Gln Gly Lys Asp Gln His Phe Pro Val Phe Met Asn
    1790                1795                1800

Glu Lys Glu Asp Ile Leu Trp Cys Thr Glu Met Glu Arg Val Phe
    1805                1810                1815

Gly Phe Pro Val His Tyr Thr Asp Val Ser Asn Met Ser Arg Leu
    1820                1825                1830

Ala Arg Gln Arg Leu Leu Gly Arg Ser Trp Ser Val Pro Val Ile
    1835                1840                1845

Arg His Leu Phe Ala Pro Leu Lys Glu Tyr Phe Ala Cys Val Ser
    1850                1855                1860

Ser Gly Asn Ser Asn Ala Asn Ser Arg Gly Pro Ser Phe Ser Ser
    1865                1870                1875

Gly Leu Val Pro Leu Ser Leu Arg Gly Ser His Met Gly Pro Met
    1880                1885                1890

Glu Ile Tyr Lys Thr Val Ser Ala Trp Lys Arg Gln Pro Val Arg
    1895                1900                1905

Val Leu Ser Leu Phe Arg Asn Ile Asp Lys Val Leu Lys Ser Leu
    1910                1915                1920

Gly Phe Leu Glu Ser Gly Ser Gly Ser Gly Gly Gly Thr Leu Lys
    1925                1930                1935

Tyr Val Glu Asp Val Thr Asn Val Val Arg Arg Asp Val Glu Lys
    1940                1945                1950

Trp Gly Pro Phe Asp Leu Val Tyr Gly Ser Thr Gln Pro Leu Gly
    1955                1960                1965

Ser Ser Cys Asp Arg Cys Pro Gly Trp Tyr Met Phe Gln Phe His
    1970                1975                1980

Arg Ile Leu Gln Tyr Ala Leu Pro Arg Gln Glu Ser Gln Arg Pro
    1985                1990                1995

Phe Phe Trp Ile Phe Met Asp Asn Leu Leu Leu Thr Glu Asp Asp
    2000                2005                2010

Gln Glu Thr Thr Thr Arg Phe Leu Gln Thr Glu Ala Val Thr Leu
    2015                2020                2025

Gln Asp Val Arg Gly Arg Asp Tyr Gln Asn Ala Met Arg Val Trp
    2030                2035                2040

Ser Asn Ile Pro Gly Leu Lys Ser Lys His Ala Pro Leu Thr Pro
    2045                2050                2055

Lys Glu Glu Glu Tyr Leu Gln Ala Gln Val Arg Ser Arg Ser Lys
```

2060 2065 2070

Leu Asp Ala Pro Lys Val Asp Leu Leu Val Lys Asn Cys Leu Leu
2075 2080 2085

Pro Leu Arg Glu Tyr Phe Lys Tyr Phe Ser Gln Asn Ser Leu Pro
2090 2095 2100

Leu Ser Arg Ala Asp Pro Lys Lys Lys Arg Lys Val Gly Ser Gly
2105 2110 2115

Ala Thr Asn Phe Ser Leu Leu Lys Gln Ala Gly Asp Val Glu Glu
2120 2125 2130

Asn Pro Gly Pro Gly Ser Gly Ala Thr Asn Phe Ser Leu Leu Lys
2135 2140 2145

Gln Ala Gly Asp Val Glu Glu Asn Pro Gly Pro Ser Glu Leu Ile
2150 2155 2160

Lys Glu Asn Met His Met Lys Leu Tyr Met Glu Gly Thr Val Asp
2165 2170 2175

Asn His His Phe Lys Cys Thr Ser Glu Gly Glu Gly Lys Pro Tyr
2180 2185 2190

Glu Gly Thr Gln Thr Met Arg Ile Lys Val Val Glu Gly Gly Pro
2195 2200 2205

Leu Pro Phe Ala Phe Asp Ile Leu Ala Thr Ser Phe Leu Tyr Gly
2210 2215 2220

Ser Lys Thr Phe Ile Asn His Thr Gln Gly Ile Pro Asp Phe Phe
2225 2230 2235

Lys Gln Ser Phe Pro Glu Gly Phe Thr Trp Glu Arg Val Thr Thr
2240 2245 2250

Tyr Glu Asp Gly Gly Val Leu Thr Ala Thr Gln Asp Thr Ser Leu
2255 2260 2265

Gln Asp Gly Cys Leu Ile Tyr Asn Val Lys Ile Arg Gly Val Asn
2270 2275 2280

Phe Thr Ser Asn Gly Pro Val Met Gln Lys Lys Thr Leu Gly Trp
2285 2290 2295

Glu Ala Phe Thr Glu Thr Leu Tyr Pro Ala Asp Gly Gly Leu Glu
2300 2305 2310

Gly Arg Asn Asp Met Ala Leu Lys Leu Val Gly Gly Ser His Leu
2315 2320 2325

Ile Ala Asn Ile Lys Thr Thr Tyr Arg Ser Lys Lys Pro Ala Lys
2330 2335 2340

Asn Leu Lys Met Pro Gly Val Tyr Tyr Val Asp Tyr Arg Leu Glu
2345 2350 2355

Arg Ile Lys Glu Ala Asn Asn Glu Thr Tyr Val Glu Gln His Glu
2360 2365 2370

Val Ala Val Ala Arg Tyr Cys Asp Leu Pro Ser Lys Leu Gly His
2375 2380 2385

Lys Leu Asn
2390

<210> SEQ ID NO 13
<211> LENGTH: 2369
<212> TYPE: PRT
<213> ORGANISM: Artificial sequence
<220> FEATURE:
<223> OTHER INFORMATION: Synthetic polypeptide

<400> SEQUENCE: 13

Asp Ala Lys Ser Leu Thr Ala Trp Ser Arg Thr Leu Val Thr Phe Lys

-continued

```
1               5                   10                  15

Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Gly Gly Pro Ser Ser Gly Ala Pro Pro
65                  70                  75                  80

Pro Ser Gly Gly Ser Pro Ala Gly Ser Pro Thr Ser Thr Glu Glu Gly
                85                  90                  95

Thr Ser Glu Ser Ala Thr Pro Glu Ser Gly Pro Gly Thr Ser Thr Glu
            100                 105                 110

Pro Ser Glu Gly Ser Ala Pro Gly Ser Pro Ala Gly Ser Pro Thr Ser
        115                 120                 125

Thr Glu Glu Gly Thr Ser Thr Glu Pro Ser Glu Gly Ser Ala Pro Gly
    130                 135                 140

Thr Ser Thr Glu Pro Ser Glu Met Asp Lys Lys Tyr Ser Ile Gly Leu
145                 150                 155                 160

Ala Ile Gly Thr Asn Ser Val Gly Trp Ala Val Ile Thr Asp Glu Tyr
                165                 170                 175

Lys Val Pro Ser Lys Lys Phe Lys Val Leu Gly Asn Thr Asp Arg His
            180                 185                 190

Ser Ile Lys Lys Asn Leu Ile Gly Ala Leu Leu Phe Asp Ser Gly Glu
        195                 200                 205

Thr Ala Glu Ala Thr Arg Leu Lys Arg Thr Ala Arg Arg Arg Tyr Thr
    210                 215                 220

Arg Arg Lys Asn Arg Ile Cys Tyr Leu Gln Glu Ile Phe Ser Asn Glu
225                 230                 235                 240

Met Ala Lys Val Asp Asp Ser Phe Phe His Arg Leu Glu Glu Ser Phe
                245                 250                 255

Leu Val Glu Glu Asp Lys Lys His Glu Arg His Pro Ile Phe Gly Asn
            260                 265                 270

Ile Val Asp Glu Val Ala Tyr His Glu Lys Tyr Pro Thr Ile Tyr His
        275                 280                 285

Leu Arg Lys Lys Leu Val Asp Ser Thr Asp Lys Ala Asp Leu Arg Leu
    290                 295                 300

Ile Tyr Leu Ala Leu Ala His Met Ile Lys Phe Arg Gly His Phe Leu
305                 310                 315                 320

Ile Glu Gly Asp Leu Asn Pro Asp Asn Ser Asp Val Asp Lys Leu Phe
                325                 330                 335

Ile Gln Leu Val Gln Thr Tyr Asn Gln Leu Phe Glu Glu Asn Pro Ile
            340                 345                 350

Asn Ala Ser Gly Val Asp Ala Lys Ala Ile Leu Ser Ala Arg Leu Ser
        355                 360                 365

Lys Ser Arg Arg Leu Glu Asn Leu Ile Ala Gln Leu Pro Gly Glu Lys
    370                 375                 380

Lys Asn Gly Leu Phe Gly Asn Leu Ile Ala Leu Ser Leu Gly Leu Thr
385                 390                 395                 400

Pro Asn Phe Lys Ser Asn Phe Asp Leu Ala Glu Asp Ala Lys Leu Gln
                405                 410                 415

Leu Ser Lys Asp Thr Tyr Asp Asp Asp Leu Asp Asn Leu Leu Ala Gln
            420                 425                 430
```

```
Ile Gly Asp Gln Tyr Ala Asp Leu Phe Leu Ala Ala Lys Asn Leu Ser
        435                 440                 445

Asp Ala Ile Leu Leu Ser Asp Ile Leu Arg Val Asn Thr Glu Ile Thr
    450                 455                 460

Lys Ala Pro Leu Ser Ala Ser Met Ile Lys Arg Tyr Asp Glu His His
465                 470                 475                 480

Gln Asp Leu Thr Leu Leu Lys Ala Leu Val Arg Gln Gln Leu Pro Glu
                485                 490                 495

Lys Tyr Lys Glu Ile Phe Phe Asp Gln Ser Lys Asn Gly Tyr Ala Gly
            500                 505                 510

Tyr Ile Asp Gly Gly Ala Ser Gln Glu Glu Phe Tyr Lys Phe Ile Lys
        515                 520                 525

Pro Ile Leu Glu Lys Met Asp Gly Thr Glu Glu Leu Leu Val Lys Leu
    530                 535                 540

Asn Arg Glu Asp Leu Leu Arg Lys Gln Arg Thr Phe Asp Asn Gly Ser
545                 550                 555                 560

Ile Pro His Gln Ile His Leu Gly Glu Leu His Ala Ile Leu Arg Arg
                565                 570                 575

Gln Glu Asp Phe Tyr Pro Phe Leu Lys Asp Asn Arg Glu Lys Ile Glu
            580                 585                 590

Lys Ile Leu Thr Phe Arg Ile Pro Tyr Tyr Val Gly Pro Leu Ala Arg
        595                 600                 605

Gly Asn Ser Arg Phe Ala Trp Met Thr Arg Lys Ser Glu Glu Thr Ile
    610                 615                 620

Thr Pro Trp Asn Phe Glu Glu Val Val Asp Lys Gly Ala Ser Ala Gln
625                 630                 635                 640

Ser Phe Ile Glu Arg Met Thr Asn Phe Asp Lys Asn Leu Pro Asn Glu
                645                 650                 655

Lys Val Leu Pro Lys His Ser Leu Leu Tyr Glu Tyr Phe Thr Val Tyr
            660                 665                 670

Asn Glu Leu Thr Lys Val Lys Tyr Val Thr Glu Gly Met Arg Lys Pro
        675                 680                 685

Ala Phe Leu Ser Gly Glu Gln Lys Lys Ala Ile Val Asp Leu Leu Phe
    690                 695                 700

Lys Thr Asn Arg Lys Val Thr Val Lys Gln Leu Lys Glu Asp Tyr Phe
705                 710                 715                 720

Lys Lys Ile Glu Cys Phe Asp Ser Val Glu Ile Ser Gly Val Glu Asp
                725                 730                 735

Arg Phe Asn Ala Ser Leu Gly Thr Tyr His Asp Leu Leu Lys Ile Ile
            740                 745                 750

Lys Asp Lys Asp Phe Leu Asp Asn Glu Glu Asn Glu Asp Ile Leu Glu
        755                 760                 765

Asp Ile Val Leu Thr Leu Thr Leu Phe Glu Asp Arg Glu Met Ile Glu
    770                 775                 780

Glu Arg Leu Lys Thr Tyr Ala His Leu Phe Asp Asp Lys Val Met Lys
785                 790                 795                 800

Gln Leu Lys Arg Arg Arg Tyr Thr Gly Trp Gly Arg Leu Ser Arg Lys
                805                 810                 815

Leu Ile Asn Gly Ile Arg Asp Lys Gln Ser Gly Lys Thr Ile Leu Asp
            820                 825                 830

Phe Leu Lys Ser Asp Gly Phe Ala Asn Arg Asn Phe Met Gln Leu Ile
        835                 840                 845
```

```
His Asp Asp Ser Leu Thr Phe Lys Glu Asp Ile Gln Lys Ala Gln Val
    850                 855                 860

Ser Gly Gln Gly Asp Ser Leu His Glu His Ile Ala Asn Leu Ala Gly
865                 870                 875                 880

Ser Pro Ala Ile Lys Lys Gly Ile Leu Gln Thr Val Lys Val Val Asp
                885                 890                 895

Glu Leu Val Lys Val Met Gly Arg His Lys Pro Glu Asn Ile Val Ile
            900                 905                 910

Glu Met Ala Arg Glu Asn Gln Thr Thr Gln Lys Gly Gln Lys Asn Ser
        915                 920                 925

Arg Glu Arg Met Lys Arg Ile Glu Glu Gly Ile Lys Glu Leu Gly Ser
    930                 935                 940

Gln Ile Leu Lys Glu His Pro Val Glu Asn Thr Gln Leu Gln Asn Glu
945                 950                 955                 960

Lys Leu Tyr Leu Tyr Tyr Leu Gln Asn Gly Arg Asp Met Tyr Val Asp
                965                 970                 975

Gln Glu Leu Asp Ile Asn Arg Leu Ser Asp Tyr Asp Val Asp Ala Ile
            980                 985                 990

Val Pro Gln Ser Phe Leu Lys Asp  Asp Ser Ile Asp Asn  Lys Val Leu
        995                 1000                1005

Thr Arg  Ser Asp Lys Asn Arg  Gly Lys Ser Asp Asn  Val Pro Ser
    1010                1015                1020

Glu Glu  Val Val Lys Lys Met  Lys Asn Tyr Trp Arg  Gln Leu Leu
    1025                1030                1035

Asn Ala  Lys Leu Ile Thr Gln  Arg Lys Phe Asp Asn  Leu Thr Lys
    1040                1045                1050

Ala Glu  Arg Gly Gly Leu Ser  Glu Leu Asp Lys Ala  Gly Phe Ile
    1055                1060                1065

Lys Arg  Gln Leu Val Glu Thr  Arg Gln Ile Thr Lys  His Val Ala
    1070                1075                1080

Gln Ile  Leu Asp Ser Arg Met  Asn Thr Lys Tyr Asp  Glu Asn Asp
    1085                1090                1095

Lys Leu  Ile Arg Glu Val Lys  Val Ile Thr Leu Lys  Ser Lys Leu
    1100                1105                1110

Val Ser  Asp Phe Arg Lys Asp  Phe Gln Phe Tyr Lys  Val Arg Glu
    1115                1120                1125

Ile Asn  Asn Tyr His His Ala  His Asp Ala Tyr Leu  Asn Ala Val
    1130                1135                1140

Val Gly  Thr Ala Leu Ile Lys  Lys Tyr Pro Lys Leu  Glu Ser Glu
    1145                1150                1155

Phe Val  Tyr Gly Asp Tyr Lys  Val Tyr Asp Val Arg  Lys Met Ile
    1160                1165                1170

Ala Lys  Ser Glu Gln Glu Ile  Gly Lys Ala Thr Ala  Lys Tyr Phe
    1175                1180                1185

Phe Tyr  Ser Asn Ile Met Asn  Phe Phe Lys Thr Glu  Ile Thr Leu
    1190                1195                1200

Ala Asn  Gly Glu Ile Arg Lys  Arg Pro Leu Ile Glu  Thr Asn Gly
    1205                1210                1215

Glu Thr  Gly Glu Ile Val Trp  Asp Lys Gly Arg Asp  Phe Ala Thr
    1220                1225                1230

Val Arg  Lys Val Leu Ser Met  Pro Gln Val Asn Ile  Val Lys Lys
    1235                1240                1245

Thr Glu  Val Gln Thr Gly Gly  Phe Ser Lys Glu Ser  Ile Leu Pro
```

```
    1250                1255                1260

Lys Arg  Asn Ser Asp Lys Leu  Ile Ala Arg Lys Lys  Asp Trp Asp
    1265                1270                1275

Pro Lys  Lys Tyr Gly Gly Phe  Asp Ser Pro Thr Val  Ala Tyr Ser
    1280                1285                1290

Val Leu  Val Val Ala Lys Val  Glu Lys Gly Lys Ser  Lys Lys Leu
    1295                1300                1305

Lys Ser  Val Lys Glu Leu Leu  Gly Ile Thr Ile Met  Glu Arg Ser
    1310                1315                1320

Ser Phe  Glu Lys Asn Pro Ile  Asp Phe Leu Glu Ala  Lys Gly Tyr
    1325                1330                1335

Lys Glu  Val Lys Lys Asp Leu  Ile Ile Lys Leu Pro  Lys Tyr Ser
    1340                1345                1350

Leu Phe  Glu Leu Glu Asn Gly  Arg Lys Arg Met Leu  Ala Ser Ala
    1355                1360                1365

Gly Glu  Leu Gln Lys Gly Asn  Glu Leu Ala Leu Pro  Ser Lys Tyr
    1370                1375                1380

Val Asn  Phe Leu Tyr Leu Ala  Ser His Tyr Glu Lys  Leu Lys Gly
    1385                1390                1395

Ser Pro  Glu Asp Asn Glu Gln  Lys Gln Leu Phe Val  Glu Gln His
    1400                1405                1410

Lys His  Tyr Leu Asp Glu Ile  Ile Glu Gln Ile Ser  Glu Phe Ser
    1415                1420                1425

Lys Arg  Val Ile Leu Ala Asp  Ala Asn Leu Asp Lys  Val Leu Ser
    1430                1435                1440

Ala Tyr  Asn Lys His Arg Asp  Lys Pro Ile Arg Glu  Gln Ala Glu
    1445                1450                1455

Asn Ile  Ile His Leu Phe Thr  Leu Thr Asn Leu Gly  Ala Pro Ala
    1460                1465                1470

Ala Phe  Lys Tyr Phe Asp Thr  Thr Ile Asp Arg Lys  Arg Tyr Thr
    1475                1480                1485

Ser Thr  Lys Glu Val Leu Asp  Ala Thr Leu Ile His  Gln Ser Ile
    1490                1495                1500

Thr Gly  Leu Tyr Glu Thr Arg  Ile Asp Leu Ser Gln  Leu Gly Gly
    1505                1510                1515

Asp Ser  Arg Ala Asp Tyr Pro  Tyr Asp Val Pro Asp  Tyr Ala Ser
    1520                1525                1530

Gly Ser  Pro Lys Lys Lys Arg  Lys Val Ser Pro Gly  Ser Gly Ser
    1535                1540                1545

Glu Thr  Pro Gly Thr Ser Glu  Ser Ala Thr Pro Glu  Ser Asn His
    1550                1555                1560

Asp Gln  Glu Phe Asp Pro Pro  Lys Val Tyr Pro Pro  Val Pro Ala
    1565                1570                1575

Glu Lys  Arg Lys Pro Ile Arg  Val Leu Ser Leu Phe  Asp Gly Ile
    1580                1585                1590

Ala Thr  Gly Leu Leu Val Leu  Lys Asp Leu Gly Ile  Gln Val Asp
    1595                1600                1605

Arg Tyr  Ile Ala Ser Glu Val  Cys Glu Asp Ser Ile  Thr Val Gly
    1610                1615                1620

Met Val  Arg His Gln Gly Lys  Ile Met Tyr Val Gly  Asp Val Arg
    1625                1630                1635

Ser Val  Thr Gln Lys His Ile  Gln Glu Trp Gly Pro  Phe Asp Leu
    1640                1645                1650
```

```
Val Ile  Gly Gly Ser Pro Cys  Asn Asp Leu Ser Ile  Val Asn Pro
    1655                 1660                 1665

Ala Arg  Lys Gly Leu Tyr Glu  Gly Thr Gly Arg Leu  Phe Phe Glu
    1670                 1675                 1680

Phe Tyr  Arg Leu Leu His Asp  Ala Arg Pro Lys Glu  Gly Asp Asp
    1685                 1690                 1695

Arg Pro  Phe Phe Trp Leu Phe  Glu Asn Val Val Ala  Met Gly Val
    1700                 1705                 1710

Ser Asp  Lys Arg Asp Ile Ser  Arg Phe Leu Glu Ser  Asn Pro Val
    1715                 1720                 1725

Met Ile  Asp Ala Lys Glu Val  Ser Ala Ala His Arg  Ala Arg Tyr
    1730                 1735                 1740

Phe Trp  Gly Asn Leu Pro Gly  Met Asn Arg Pro Leu  Ala Ser Thr
    1745                 1750                 1755

Val Asn  Asp Lys Leu Glu Leu  Gln Glu Cys Leu Glu  His Gly Arg
    1760                 1765                 1770

Ile Ala  Lys Phe Ser Lys Val  Arg Thr Ile Thr Thr  Arg Ser Asn
    1775                 1780                 1785

Ser Ile  Lys Gln Gly Lys Asp  Gln His Phe Pro Val  Phe Met Asn
    1790                 1795                 1800

Glu Lys  Glu Asp Ile Leu Trp  Cys Thr Glu Met Glu  Arg Val Phe
    1805                 1810                 1815

Gly Phe  Pro Val His Tyr Thr  Asp Val Ser Asn Met  Ser Arg Leu
    1820                 1825                 1830

Ala Arg  Gln Arg Leu Leu Gly  Arg Ser Trp Ser Val  Pro Val Ile
    1835                 1840                 1845

Arg His  Leu Phe Ala Pro Leu  Lys Glu Tyr Phe Ala  Cys Val Ser
    1850                 1855                 1860

Ser Gly  Asn Ser Asn Ala Asn  Ser Arg Gly Pro Ser  Phe Ser Ser
    1865                 1870                 1875

Gly Leu  Val Pro Leu Ser Leu  Arg Gly Ser His Met  Gly Pro Met
    1880                 1885                 1890

Glu Ile  Tyr Lys Thr Val Ser  Ala Trp Lys Arg Gln  Pro Val Arg
    1895                 1900                 1905

Val Leu  Ser Leu Phe Arg Asn  Ile Asp Lys Val Leu  Lys Ser Leu
    1910                 1915                 1920

Gly Phe  Leu Glu Ser Gly Ser  Gly Ser Gly Gly Gly  Thr Leu Lys
    1925                 1930                 1935

Tyr Val  Glu Asp Val Thr Asn  Val Val Arg Arg Asp  Val Glu Lys
    1940                 1945                 1950

Trp Gly  Pro Phe Asp Leu Val  Tyr Gly Ser Thr Gln  Pro Leu Gly
    1955                 1960                 1965

Ser Ser  Cys Asp Arg Cys Pro  Gly Trp Tyr Met Phe  Gln Phe His
    1970                 1975                 1980

Arg Ile  Leu Gln Tyr Ala Leu  Pro Arg Gln Glu Ser  Gln Arg Pro
    1985                 1990                 1995

Phe Phe  Trp Ile Phe Met Asp  Asn Leu Leu Leu Thr  Glu Asp Asp
    2000                 2005                 2010

Gln Glu  Thr Thr Thr Arg Phe  Leu Gln Thr Glu Ala  Val Thr Leu
    2015                 2020                 2025

Gln Asp  Val Arg Gly Arg Asp  Tyr Gln Asn Ala Met  Arg Val Trp
    2030                 2035                 2040
```

```
Ser Asn  Ile Pro Gly Leu Lys  Ser Lys His Ala Pro  Leu Thr Pro
    2045                 2050                 2055

Lys Glu  Glu Glu Tyr Leu Gln  Ala Gln Val Arg Ser  Arg Ser Lys
    2060                 2065                 2070

Leu Asp  Ala Pro Lys Val Asp  Leu Leu Val Lys Asn  Cys Leu Leu
    2075                 2080                 2085

Pro Leu  Arg Glu Tyr Phe Lys  Tyr Phe Ser Gln Asn  Ser Leu Pro
    2090                 2095                 2100

Leu Ser  Arg Ala Asp Pro Lys  Lys Lys Arg Lys Val  Gly Ser Gly
    2105                 2110                 2115

Ala Thr  Asn Phe Ser Leu Leu  Lys Gln Ala Gly Asp  Val Glu Glu
    2120                 2125                 2130

Asn Pro  Gly Pro Ser Glu Leu  Ile Lys Glu Asn Met  His Met Lys
    2135                 2140                 2145

Leu Tyr  Met Glu Gly Thr Val  Asp Asn His His Phe  Lys Cys Thr
    2150                 2155                 2160

Ser Glu  Gly Glu Gly Lys Pro  Tyr Glu Gly Thr Gln  Thr Met Arg
    2165                 2170                 2175

Ile Lys  Val Val Glu Gly Gly  Pro Leu Pro Phe Ala  Phe Asp Ile
    2180                 2185                 2190

Leu Ala  Thr Ser Phe Leu Tyr  Gly Ser Lys Thr Phe  Ile Asn His
    2195                 2200                 2205

Thr Gln  Gly Ile Pro Asp Phe  Phe Lys Gln Ser Phe  Pro Glu Gly
    2210                 2215                 2220

Phe Thr  Trp Glu Arg Val Thr  Thr Tyr Glu Asp Gly  Gly Val Leu
    2225                 2230                 2235

Thr Ala  Thr Gln Asp Thr Ser  Leu Gln Asp Gly Cys  Leu Ile Tyr
    2240                 2245                 2250

Asn Val  Lys Ile Arg Gly Val  Asn Phe Thr Ser Asn  Gly Pro Val
    2255                 2260                 2265

Met Gln  Lys Lys Thr Leu Gly  Trp Glu Ala Phe Thr  Glu Thr Leu
    2270                 2275                 2280

Tyr Pro  Ala Asp Gly Gly Leu  Glu Gly Arg Asn Asp  Met Ala Leu
    2285                 2290                 2295

Lys Leu  Val Gly Gly Ser His  Leu Ile Ala Asn Ile  Lys Thr Thr
    2300                 2305                 2310

Tyr Arg  Ser Lys Lys Pro Ala  Lys Asn Leu Lys Met  Pro Gly Val
    2315                 2320                 2325

Tyr Tyr  Val Asp Tyr Arg Leu  Glu Arg Ile Lys Glu  Ala Asn Asn
    2330                 2335                 2340

Glu Thr  Tyr Val Glu Gln His  Glu Val Ala Val Ala  Arg Tyr Cys
    2345                 2350                 2355

Asp Leu  Pro Ser Lys Leu Gly  His Lys Leu Asn
    2360                 2365
```

<210> SEQ ID NO 14
<211> LENGTH: 2391
<212> TYPE: PRT
<213> ORGANISM: Artificial sequence
<220> FEATURE:
<223> OTHER INFORMATION: Synthetic polypeptide

<400> SEQUENCE: 14

```
Asp Ala Lys Ser Leu Thr Ala Trp Ser Arg Thr Leu Val Thr Phe Lys
1               5                   10                  15
```

```
Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Gly Gly Pro Ser Ser Gly Ala Pro Pro
65                  70                  75                  80

Pro Ser Gly Gly Ser Pro Ala Gly Ser Pro Thr Ser Thr Glu Glu Gly
                85                  90                  95

Thr Ser Glu Ser Ala Thr Pro Glu Ser Gly Pro Gly Thr Ser Thr Glu
            100                 105                 110

Pro Ser Glu Gly Ser Ala Pro Gly Ser Pro Ala Gly Ser Pro Thr Ser
        115                 120                 125

Thr Glu Glu Gly Thr Ser Thr Glu Pro Ser Glu Gly Ser Ala Pro Gly
    130                 135                 140

Thr Ser Thr Glu Pro Ser Glu Met Asp Lys Lys Tyr Ser Ile Gly Leu
145                 150                 155                 160

Ala Ile Gly Thr Asn Ser Val Gly Trp Ala Val Ile Thr Asp Glu Tyr
                165                 170                 175

Lys Val Pro Ser Lys Lys Phe Lys Val Leu Gly Asn Thr Asp Arg His
            180                 185                 190

Ser Ile Lys Lys Asn Leu Ile Gly Ala Leu Leu Phe Asp Ser Gly Glu
        195                 200                 205

Thr Ala Glu Ala Thr Arg Leu Lys Arg Thr Ala Arg Arg Arg Tyr Thr
    210                 215                 220

Arg Arg Lys Asn Arg Ile Cys Tyr Leu Gln Glu Ile Phe Ser Asn Glu
225                 230                 235                 240

Met Ala Lys Val Asp Asp Ser Phe Phe His Arg Leu Glu Glu Ser Phe
                245                 250                 255

Leu Val Glu Glu Asp Lys Lys His Glu Arg His Pro Ile Phe Gly Asn
            260                 265                 270

Ile Val Asp Glu Val Ala Tyr His Glu Lys Tyr Pro Thr Ile Tyr His
        275                 280                 285

Leu Arg Lys Lys Leu Val Asp Ser Thr Asp Lys Ala Asp Leu Arg Leu
    290                 295                 300

Ile Tyr Leu Ala Leu Ala His Met Ile Lys Phe Arg Gly His Phe Leu
305                 310                 315                 320

Ile Glu Gly Asp Leu Asn Pro Asp Asn Ser Asp Val Asp Lys Leu Phe
                325                 330                 335

Ile Gln Leu Val Gln Thr Tyr Asn Gln Leu Phe Glu Glu Asn Pro Ile
            340                 345                 350

Asn Ala Ser Gly Val Asp Ala Lys Ala Ile Leu Ser Ala Arg Leu Ser
        355                 360                 365

Lys Ser Arg Arg Leu Glu Asn Leu Ile Ala Gln Leu Pro Gly Glu Lys
    370                 375                 380

Lys Asn Gly Leu Phe Gly Asn Leu Ile Ala Leu Ser Leu Gly Leu Thr
385                 390                 395                 400

Pro Asn Phe Lys Ser Asn Phe Asp Leu Ala Glu Asp Ala Lys Leu Gln
                405                 410                 415

Leu Ser Lys Asp Thr Tyr Asp Asp Asp Leu Asp Asn Leu Leu Ala Gln
            420                 425                 430

Ile Gly Asp Gln Tyr Ala Asp Leu Phe Leu Ala Ala Lys Asn Leu Ser
```

```
        435                 440                 445

Asp Ala Ile Leu Leu Ser Asp Ile Leu Arg Val Asn Thr Glu Ile Thr
    450                 455                 460

Lys Ala Pro Leu Ser Ala Ser Met Ile Lys Arg Tyr Asp Glu His His
465                 470                 475                 480

Gln Asp Leu Thr Leu Leu Lys Ala Leu Val Arg Gln Gln Leu Pro Glu
                485                 490                 495

Lys Tyr Lys Glu Ile Phe Phe Asp Gln Ser Lys Asn Gly Tyr Ala Gly
            500                 505                 510

Tyr Ile Asp Gly Gly Ala Ser Gln Glu Glu Phe Tyr Lys Phe Ile Lys
        515                 520                 525

Pro Ile Leu Glu Lys Met Asp Gly Thr Glu Glu Leu Leu Val Lys Leu
    530                 535                 540

Asn Arg Glu Asp Leu Leu Arg Lys Gln Arg Thr Phe Asp Asn Gly Ser
545                 550                 555                 560

Ile Pro His Gln Ile His Leu Gly Glu Leu His Ala Ile Leu Arg Arg
                565                 570                 575

Gln Glu Asp Phe Tyr Pro Phe Leu Lys Asp Asn Arg Glu Lys Ile Glu
            580                 585                 590

Lys Ile Leu Thr Phe Arg Ile Pro Tyr Tyr Val Gly Pro Leu Ala Arg
        595                 600                 605

Gly Asn Ser Arg Phe Ala Trp Met Thr Arg Lys Ser Glu Glu Thr Ile
    610                 615                 620

Thr Pro Trp Asn Phe Glu Glu Val Val Asp Lys Gly Ala Ser Ala Gln
625                 630                 635                 640

Ser Phe Ile Glu Arg Met Thr Asn Phe Asp Lys Asn Leu Pro Asn Glu
                645                 650                 655

Lys Val Leu Pro Lys His Ser Leu Leu Tyr Glu Tyr Phe Thr Val Tyr
            660                 665                 670

Asn Glu Leu Thr Lys Val Lys Tyr Val Thr Glu Gly Met Arg Lys Pro
        675                 680                 685

Ala Phe Leu Ser Gly Glu Gln Lys Lys Ala Ile Val Asp Leu Leu Phe
    690                 695                 700

Lys Thr Asn Arg Lys Val Thr Val Lys Gln Leu Lys Glu Asp Tyr Phe
705                 710                 715                 720

Lys Lys Ile Glu Cys Phe Asp Ser Val Glu Ile Ser Gly Val Glu Asp
                725                 730                 735

Arg Phe Asn Ala Ser Leu Gly Thr Tyr His Asp Leu Leu Lys Ile Ile
            740                 745                 750

Lys Asp Lys Asp Phe Leu Asp Asn Glu Glu Asn Glu Asp Ile Leu Glu
        755                 760                 765

Asp Ile Val Leu Thr Leu Thr Leu Phe Glu Asp Arg Glu Met Ile Glu
    770                 775                 780

Glu Arg Leu Lys Thr Tyr Ala His Leu Phe Asp Asp Lys Val Met Lys
785                 790                 795                 800

Gln Leu Lys Arg Arg Arg Tyr Thr Gly Trp Gly Arg Leu Ser Arg Lys
                805                 810                 815

Leu Ile Asn Gly Ile Arg Asp Lys Gln Ser Gly Lys Thr Ile Leu Asp
            820                 825                 830

Phe Leu Lys Ser Asp Gly Phe Ala Asn Arg Asn Phe Met Gln Leu Ile
        835                 840                 845

His Asp Asp Ser Leu Thr Phe Lys Glu Asp Ile Gln Lys Ala Gln Val
    850                 855                 860
```

```
Ser Gly Gln Gly Asp Ser Leu His Glu His Ile Ala Asn Leu Ala Gly
865                 870                 875                 880

Ser Pro Ala Ile Lys Lys Gly Ile Leu Gln Thr Val Lys Val Val Asp
                885                 890                 895

Glu Leu Val Lys Val Met Gly Arg His Lys Pro Glu Asn Ile Val Ile
            900                 905                 910

Glu Met Ala Arg Glu Asn Gln Thr Thr Gln Lys Gly Gln Lys Asn Ser
        915                 920                 925

Arg Glu Arg Met Lys Arg Ile Glu Glu Gly Ile Lys Glu Leu Gly Ser
    930                 935                 940

Gln Ile Leu Lys Glu His Pro Val Glu Asn Thr Gln Leu Gln Asn Glu
945                 950                 955                 960

Lys Leu Tyr Leu Tyr Tyr Leu Gln Asn Gly Arg Asp Met Tyr Val Asp
                965                 970                 975

Gln Glu Leu Asp Ile Asn Arg Leu Ser Asp Tyr Asp Val Asp Ala Ile
            980                 985                 990

Val Pro Gln Ser Phe Leu Lys Asp  Asp Ser Ile Asp Asn  Lys Val Leu
        995                 1000                1005

Thr Arg  Ser Asp Lys Asn Arg  Gly Lys Ser Asp Asn  Val Pro Ser
    1010                 1015                1020

Glu Glu  Val Val Lys Lys Met  Lys Asn Tyr Trp Arg  Gln Leu Leu
    1025                 1030                1035

Asn Ala  Lys Leu Ile Thr Gln  Arg Lys Phe Asp Asn  Leu Thr Lys
    1040                 1045                1050

Ala Glu  Arg Gly Gly Leu Ser  Glu Leu Asp Lys Ala  Gly Phe Ile
    1055                 1060                1065

Lys Arg  Gln Leu Val Glu Thr  Arg Gln Ile Thr Lys  His Val Ala
    1070                 1075                1080

Gln Ile  Leu Asp Ser Arg Met  Asn Thr Lys Tyr Asp  Glu Asn Asp
    1085                 1090                1095

Lys Leu  Ile Arg Glu Val Lys  Val Ile Thr Leu Lys  Ser Lys Leu
    1100                 1105                1110

Val Ser  Asp Phe Arg Lys Asp  Phe Gln Phe Tyr Lys  Val Arg Glu
    1115                 1120                1125

Ile Asn  Asn Tyr His His Ala  His Asp Ala Tyr Leu  Asn Ala Val
    1130                 1135                1140

Val Gly  Thr Ala Leu Ile Lys  Lys Tyr Pro Lys Leu  Glu Ser Glu
    1145                 1150                1155

Phe Val  Tyr Gly Asp Tyr Lys  Val Tyr Asp Val Arg  Lys Met Ile
    1160                 1165                1170

Ala Lys  Ser Glu Gln Glu Ile  Gly Lys Ala Thr Ala  Lys Tyr Phe
    1175                 1180                1185

Phe Tyr  Ser Asn Ile Met Asn  Phe Phe Lys Thr Glu  Ile Thr Leu
    1190                 1195                1200

Ala Asn  Gly Glu Ile Arg Lys  Arg Pro Leu Ile Glu  Thr Asn Gly
    1205                 1210                1215

Glu Thr  Gly Glu Ile Val Trp  Asp Lys Gly Arg Asp  Phe Ala Thr
    1220                 1225                1230

Val Arg  Lys Val Leu Ser Met  Pro Gln Val Asn Ile  Val Lys Lys
    1235                 1240                1245

Thr Glu  Val Gln Thr Gly Gly  Phe Ser Lys Glu Ser  Ile Leu Pro
    1250                 1255                1260
```

```
Lys Arg  Asn Ser Asp Lys Leu  Ile Ala Arg Lys Lys  Asp Trp Asp
    1265                 1270                 1275

Pro Lys  Lys Tyr Gly Gly Phe  Asp Ser Pro Thr Val  Ala Tyr Ser
    1280                 1285                 1290

Val Leu  Val Val Ala Lys Val  Glu Lys Gly Lys Ser  Lys Lys Leu
    1295                 1300                 1305

Lys Ser  Val Lys Glu Leu Leu  Gly Ile Thr Ile Met  Glu Arg Ser
    1310                 1315                 1320

Ser Phe  Glu Lys Asn Pro Ile  Asp Phe Leu Glu Ala  Lys Gly Tyr
    1325                 1330                 1335

Lys Glu  Val Lys Lys Asp Leu  Ile Ile Lys Leu Pro  Lys Tyr Ser
    1340                 1345                 1350

Leu Phe  Glu Leu Glu Asn Gly  Arg Lys Arg Met Leu  Ala Ser Ala
    1355                 1360                 1365

Gly Glu  Leu Gln Lys Gly Asn  Glu Leu Ala Leu Pro  Ser Lys Tyr
    1370                 1375                 1380

Val Asn  Phe Leu Tyr Leu Ala  Ser His Tyr Glu Lys  Leu Lys Gly
    1385                 1390                 1395

Ser Pro  Glu Asp Asn Glu Gln  Lys Gln Leu Phe Val  Glu Gln His
    1400                 1405                 1410

Lys His  Tyr Leu Asp Glu Ile  Ile Glu Gln Ile Ser  Glu Phe Ser
    1415                 1420                 1425

Lys Arg  Val Ile Leu Ala Asp  Ala Asn Leu Asp Lys  Val Leu Ser
    1430                 1435                 1440

Ala Tyr  Asn Lys His Arg Asp  Lys Pro Ile Arg Glu  Gln Ala Glu
    1445                 1450                 1455

Asn Ile  Ile His Leu Phe Thr  Leu Thr Asn Leu Gly  Ala Pro Ala
    1460                 1465                 1470

Ala Phe  Lys Tyr Phe Asp Thr  Thr Ile Asp Arg Lys  Arg Tyr Thr
    1475                 1480                 1485

Ser Thr  Lys Glu Val Leu Asp  Ala Thr Leu Ile His  Gln Ser Ile
    1490                 1495                 1500

Thr Gly  Leu Tyr Glu Thr Arg  Ile Asp Leu Ser Gln  Leu Gly Gly
    1505                 1510                 1515

Asp Ser  Arg Ala Asp Tyr Pro  Tyr Asp Val Pro Asp  Tyr Ala Ser
    1520                 1525                 1530

Gly Ser  Pro Lys Lys Lys Arg  Lys Val Ser Pro Gly  Ser Gly Ser
    1535                 1540                 1545

Glu Thr  Pro Gly Thr Ser Glu  Ser Ala Thr Pro Glu  Ser Asn His
    1550                 1555                 1560

Asp Gln  Glu Phe Asp Pro Pro  Lys Val Tyr Pro Pro  Val Pro Ala
    1565                 1570                 1575

Glu Lys  Arg Lys Pro Ile Arg  Val Leu Ser Leu Phe  Asp Gly Ile
    1580                 1585                 1590

Ala Thr  Gly Leu Leu Val Leu  Lys Asp Leu Gly Ile  Gln Val Asp
    1595                 1600                 1605

Arg Tyr  Ile Ala Ser Glu Val  Cys Glu Asp Ser Ile  Thr Val Gly
    1610                 1615                 1620

Met Val  Arg His Gln Gly Lys  Ile Met Tyr Val Gly  Asp Val Arg
    1625                 1630                 1635

Ser Val  Thr Gln Lys His Ile  Gln Glu Trp Gly Pro  Phe Asp Leu
    1640                 1645                 1650

Val Ile  Gly Gly Ser Pro Cys  Asn Asp Leu Ser Ile  Val Asn Pro
```

```
    1655                1660                1665

Ala Arg Lys Gly Leu Tyr Glu Gly Thr Gly Arg Leu Phe Phe Glu
    1670                1675                1680

Phe Tyr Arg Leu Leu His Asp Ala Arg Pro Lys Glu Gly Asp Asp
    1685                1690                1695

Arg Pro Phe Phe Trp Leu Phe Glu Asn Val Val Ala Met Gly Val
    1700                1705                1710

Ser Asp Lys Arg Asp Ile Ser Arg Phe Leu Glu Ser Asn Pro Val
    1715                1720                1725

Met Ile Asp Ala Lys Glu Val Ser Ala Ala His Arg Ala Arg Tyr
    1730                1735                1740

Phe Trp Gly Asn Leu Pro Gly Met Asn Arg Pro Leu Ala Ser Thr
    1745                1750                1755

Val Asn Asp Lys Leu Glu Leu Gln Glu Cys Leu Glu His Gly Arg
    1760                1765                1770

Ile Ala Lys Phe Ser Lys Val Arg Thr Ile Thr Thr Arg Ser Asn
    1775                1780                1785

Ser Ile Lys Gln Gly Lys Asp Gln His Phe Pro Val Phe Met Asn
    1790                1795                1800

Glu Lys Glu Asp Ile Leu Trp Cys Thr Glu Met Glu Arg Val Phe
    1805                1810                1815

Gly Phe Pro Val His Tyr Thr Asp Val Ser Asn Met Ser Arg Leu
    1820                1825                1830

Ala Arg Gln Arg Leu Leu Gly Arg Ser Trp Ser Val Pro Val Ile
    1835                1840                1845

Arg His Leu Phe Ala Pro Leu Lys Glu Tyr Phe Ala Cys Val Ser
    1850                1855                1860

Ser Gly Asn Ser Asn Ala Asn Ser Arg Gly Pro Ser Phe Ser Ser
    1865                1870                1875

Gly Leu Val Pro Leu Ser Leu Arg Gly Ser His Met Gly Pro Met
    1880                1885                1890

Glu Ile Tyr Lys Thr Val Ser Ala Trp Lys Arg Gln Pro Val Arg
    1895                1900                1905

Val Leu Ser Leu Phe Arg Asn Ile Asp Lys Val Leu Lys Ser Leu
    1910                1915                1920

Gly Phe Leu Glu Ser Gly Ser Gly Ser Gly Gly Gly Thr Leu Lys
    1925                1930                1935

Tyr Val Glu Asp Val Thr Asn Val Val Arg Arg Asp Val Glu Lys
    1940                1945                1950

Trp Gly Pro Phe Asp Leu Val Tyr Gly Ser Thr Gln Pro Leu Gly
    1955                1960                1965

Ser Ser Cys Asp Arg Cys Pro Gly Trp Tyr Met Phe Gln Phe His
    1970                1975                1980

Arg Ile Leu Gln Tyr Ala Leu Pro Arg Gln Glu Ser Gln Arg Pro
    1985                1990                1995

Phe Phe Trp Ile Phe Met Asp Asn Leu Leu Leu Thr Glu Asp Asp
    2000                2005                2010

Gln Glu Thr Thr Thr Arg Phe Leu Gln Thr Glu Ala Val Thr Leu
    2015                2020                2025

Gln Asp Val Arg Gly Arg Asp Tyr Gln Asn Ala Met Arg Val Trp
    2030                2035                2040

Ser Asn Ile Pro Gly Leu Lys Ser Lys His Ala Pro Leu Thr Pro
    2045                2050                2055
```

Lys Glu Glu Glu Tyr Leu Gln Ala Gln Val Arg Ser Arg Ser Lys
    2060                2065                2070

Leu Asp Ala Pro Lys Val Asp Leu Leu Val Lys Asn Cys Leu Leu
    2075                2080                2085

Pro Leu Arg Glu Tyr Phe Lys Tyr Phe Ser Gln Asn Ser Leu Pro
    2090                2095                2100

Leu Ser Arg Ala Asp Pro Lys Lys Lys Arg Lys Val Gly Ser Gly
    2105                2110                2115

Ala Thr Asn Phe Ser Leu Leu Lys Gln Ala Gly Asp Val Glu Glu
    2120                2125                2130

Asn Pro Gly Pro Gly Ser Gly Ala Thr Asn Phe Ser Leu Leu Lys
    2135                2140                2145

Gln Ala Gly Asp Val Glu Glu Asn Pro Gly Pro Ser Glu Leu Ile
    2150                2155                2160

Lys Glu Asn Met His Met Lys Leu Tyr Met Glu Gly Thr Val Asp
    2165                2170                2175

Asn His His Phe Lys Cys Thr Ser Glu Gly Glu Gly Lys Pro Tyr
    2180                2185                2190

Glu Gly Thr Gln Thr Met Arg Ile Lys Val Val Glu Gly Gly Pro
    2195                2200                2205

Leu Pro Phe Ala Phe Asp Ile Leu Ala Thr Ser Phe Leu Tyr Gly
    2210                2215                2220

Ser Lys Thr Phe Ile Asn His Thr Gln Gly Ile Pro Asp Phe Phe
    2225                2230                2235

Lys Gln Ser Phe Pro Glu Gly Phe Thr Trp Glu Arg Val Thr Thr
    2240                2245                2250

Tyr Glu Asp Gly Gly Val Leu Thr Ala Thr Gln Asp Thr Ser Leu
    2255                2260                2265

Gln Asp Gly Cys Leu Ile Tyr Asn Val Lys Ile Arg Gly Val Asn
    2270                2275                2280

Phe Thr Ser Asn Gly Pro Val Met Gln Lys Lys Thr Leu Gly Trp
    2285                2290                2295

Glu Ala Phe Thr Glu Thr Leu Tyr Pro Ala Asp Gly Gly Leu Glu
    2300                2305                2310

Gly Arg Asn Asp Met Ala Leu Lys Leu Val Gly Gly Ser His Leu
    2315                2320                2325

Ile Ala Asn Ile Lys Thr Thr Tyr Arg Ser Lys Lys Pro Ala Lys
    2330                2335                2340

Asn Leu Lys Met Pro Gly Val Tyr Tyr Val Asp Tyr Arg Leu Glu
    2345                2350                2355

Arg Ile Lys Glu Ala Asn Asn Glu Thr Tyr Val Glu Gln His Glu
    2360                2365                2370

Val Ala Val Ala Arg Tyr Cys Asp Leu Pro Ser Lys Leu Gly His
    2375                2380                2385

Lys Leu Asn
    2390

<210> SEQ ID NO 15
<211> LENGTH: 2345
<212> TYPE: PRT
<213> ORGANISM: Artificial sequence
<220> FEATURE:
<223> OTHER INFORMATION: Synthetic polypeptide

<400> SEQUENCE: 15

```
Asn His Asp Gln Glu Phe Asp Pro Pro Lys Val Tyr Pro Pro Val Pro
1               5                   10                  15

Ala Glu Lys Arg Lys Pro Ile Arg Val Leu Ser Leu Phe Asp Gly Ile
            20                  25                  30

Ala Thr Gly Leu Leu Val Leu Lys Asp Leu Gly Ile Gln Val Asp Arg
        35                  40                  45

Tyr Ile Ala Ser Glu Val Cys Glu Asp Ser Ile Thr Val Gly Met Val
    50                  55                  60

Arg His Gln Gly Lys Ile Met Tyr Val Gly Asp Val Arg Ser Val Thr
65                  70                  75                  80

Gln Lys His Ile Gln Glu Trp Gly Pro Phe Asp Leu Val Ile Gly Gly
                85                  90                  95

Ser Pro Cys Asn Asp Leu Ser Ile Val Asn Pro Ala Arg Lys Gly Leu
            100                 105                 110

Tyr Glu Gly Thr Gly Arg Leu Phe Phe Glu Phe Tyr Arg Leu Leu His
        115                 120                 125

Asp Ala Arg Pro Lys Glu Gly Asp Asp Arg Pro Phe Phe Trp Leu Phe
    130                 135                 140

Glu Asn Val Val Ala Met Gly Val Ser Asp Lys Arg Asp Ile Ser Arg
145                 150                 155                 160

Phe Leu Glu Ser Asn Pro Val Met Ile Asp Ala Lys Glu Val Ser Ala
                165                 170                 175

Ala His Arg Ala Arg Tyr Phe Trp Gly Asn Leu Pro Gly Met Asn Arg
            180                 185                 190

Pro Leu Ala Ser Thr Val Asn Asp Lys Leu Glu Leu Gln Glu Cys Leu
        195                 200                 205

Glu His Gly Arg Ile Ala Lys Phe Ser Lys Val Arg Thr Ile Thr Thr
    210                 215                 220

Arg Ser Asn Ser Ile Lys Gln Gly Lys Asp Gln His Phe Pro Val Phe
225                 230                 235                 240

Met Asn Glu Lys Glu Asp Ile Leu Trp Cys Thr Glu Met Glu Arg Val
                245                 250                 255

Phe Gly Phe Pro Val His Tyr Thr Asp Val Ser Asn Met Ser Arg Leu
            260                 265                 270

Ala Arg Gln Arg Leu Leu Gly Arg Ser Trp Ser Val Pro Val Ile Arg
        275                 280                 285

His Leu Phe Ala Pro Leu Lys Glu Tyr Phe Ala Cys Val Ser Ser Gly
    290                 295                 300

Asn Ser Asn Ala Asn Ser Arg Gly Pro Ser Phe Ser Ser Gly Leu Val
305                 310                 315                 320

Pro Leu Ser Leu Arg Gly Ser His Met Gly Pro Met Glu Ile Tyr Lys
                325                 330                 335

Thr Val Ser Ala Trp Lys Arg Gln Pro Val Arg Val Leu Ser Leu Phe
            340                 345                 350

Arg Asn Ile Asp Lys Val Leu Lys Ser Leu Gly Phe Leu Glu Ser Gly
        355                 360                 365

Ser Gly Ser Gly Gly Gly Thr Leu Lys Tyr Val Glu Asp Val Thr Asn
    370                 375                 380

Val Val Arg Arg Asp Val Glu Lys Trp Gly Pro Phe Asp Leu Val Tyr
385                 390                 395                 400

Gly Ser Thr Gln Pro Leu Gly Ser Ser Cys Asp Arg Cys Pro Gly Trp
                405                 410                 415
```

```
Tyr Met Phe Gln Phe His Arg Ile Leu Gln Tyr Ala Leu Pro Arg Gln
            420                 425                 430

Glu Ser Gln Arg Pro Phe Phe Trp Ile Phe Met Asp Asn Leu Leu Leu
        435                 440                 445

Thr Glu Asp Asp Gln Glu Thr Thr Thr Arg Phe Leu Gln Thr Glu Ala
    450                 455                 460

Val Thr Leu Gln Asp Val Arg Gly Arg Asp Tyr Gln Asn Ala Met Arg
465                 470                 475                 480

Val Trp Ser Asn Ile Pro Gly Leu Lys Ser Lys His Ala Pro Leu Thr
                485                 490                 495

Pro Lys Glu Glu Glu Tyr Leu Gln Ala Gln Val Arg Ser Arg Ser Lys
            500                 505                 510

Leu Asp Ala Pro Lys Val Asp Leu Leu Val Lys Asn Cys Leu Leu Pro
        515                 520                 525

Leu Arg Glu Tyr Phe Lys Tyr Phe Ser Gln Asn Ser Leu Pro Leu Gly
    530                 535                 540

Gly Pro Ser Ser Gly Ala Pro Pro Pro Ser Gly Gly Ser Pro Ala Gly
545                 550                 555                 560

Ser Pro Thr Ser Thr Glu Glu Gly Thr Ser Glu Ser Ala Thr Pro Glu
                565                 570                 575

Ser Gly Pro Gly Thr Ser Thr Glu Pro Ser Glu Gly Ser Ala Pro Gly
            580                 585                 590

Ser Pro Ala Gly Ser Pro Thr Ser Thr Glu Glu Gly Thr Ser Thr Glu
        595                 600                 605

Pro Ser Glu Gly Ser Ala Pro Gly Thr Ser Thr Glu Pro Ser Glu Met
    610                 615                 620

Asp Lys Lys Tyr Ser Ile Gly Leu Ala Ile Gly Thr Asn Ser Val Gly
625                 630                 635                 640

Trp Ala Val Ile Thr Asp Glu Tyr Lys Val Pro Ser Lys Lys Phe Lys
                645                 650                 655

Val Leu Gly Asn Thr Asp Arg His Ser Ile Lys Lys Asn Leu Ile Gly
            660                 665                 670

Ala Leu Leu Phe Asp Ser Gly Glu Thr Ala Glu Ala Thr Arg Leu Lys
        675                 680                 685

Arg Thr Ala Arg Arg Arg Tyr Thr Arg Arg Lys Asn Arg Ile Cys Tyr
    690                 695                 700

Leu Gln Glu Ile Phe Ser Asn Glu Met Ala Lys Val Asp Asp Ser Phe
705                 710                 715                 720

Phe His Arg Leu Glu Glu Ser Phe Leu Val Glu Glu Asp Lys Lys His
                725                 730                 735

Glu Arg His Pro Ile Phe Gly Asn Ile Val Asp Glu Val Ala Tyr His
            740                 745                 750

Glu Lys Tyr Pro Thr Ile Tyr His Leu Arg Lys Lys Leu Val Asp Ser
        755                 760                 765

Thr Asp Lys Ala Asp Leu Arg Leu Ile Tyr Leu Ala Leu Ala His Met
    770                 775                 780

Ile Lys Phe Arg Gly His Phe Leu Ile Glu Gly Asp Leu Asn Pro Asp
785                 790                 795                 800

Asn Ser Asp Val Asp Lys Leu Phe Ile Gln Leu Val Gln Thr Tyr Asn
                805                 810                 815

Gln Leu Phe Glu Glu Asn Pro Ile Asn Ala Ser Gly Val Asp Ala Lys
            820                 825                 830

Ala Ile Leu Ser Ala Arg Leu Ser Lys Ser Arg Arg Leu Glu Asn Leu
```

```
        835                 840                 845

Ile Ala Gln Leu Pro Gly Glu Lys Lys Asn Gly Leu Phe Gly Asn Leu
    850                 855                 860

Ile Ala Leu Ser Leu Gly Leu Thr Pro Asn Phe Lys Ser Asn Phe Asp
865                 870                 875                 880

Leu Ala Glu Asp Ala Lys Leu Gln Leu Ser Lys Asp Thr Tyr Asp Asp
                885                 890                 895

Asp Leu Asp Asn Leu Leu Ala Gln Ile Gly Asp Gln Tyr Ala Asp Leu
            900                 905                 910

Phe Leu Ala Ala Lys Asn Leu Ser Asp Ala Ile Leu Leu Ser Asp Ile
        915                 920                 925

Leu Arg Val Asn Thr Glu Ile Thr Lys Ala Pro Leu Ser Ala Ser Met
    930                 935                 940

Ile Lys Arg Tyr Asp Glu His His Gln Asp Leu Thr Leu Leu Lys Ala
945                 950                 955                 960

Leu Val Arg Gln Gln Leu Pro Glu Lys Tyr Lys Glu Ile Phe Phe Asp
                965                 970                 975

Gln Ser Lys Asn Gly Tyr Ala Gly Tyr Ile Asp Gly Gly Ala Ser Gln
            980                 985                 990

Glu Glu Phe Tyr Lys Phe Ile Lys  Pro Ile Leu Glu Lys  Met Asp Gly
        995                 1000                1005

Thr Glu  Glu Leu Leu Val Lys  Leu Asn Arg Glu Asp  Leu Leu Arg
    1010                1015                1020

Lys Gln  Arg Thr Phe Asp Asn  Gly Ser Ile Pro His  Gln Ile His
    1025                1030                1035

Leu Gly  Glu Leu His Ala Ile  Leu Arg Arg Gln Glu  Asp Phe Tyr
    1040                1045                1050

Pro Phe  Leu Lys Asp Asn Arg  Glu Lys Ile Glu Lys  Ile Leu Thr
    1055                1060                1065

Phe Arg  Ile Pro Tyr Tyr Val  Gly Pro Leu Ala Arg  Gly Asn Ser
    1070                1075                1080

Arg Phe  Ala Trp Met Thr Arg  Lys Ser Glu Glu Thr  Ile Thr Pro
    1085                1090                1095

Trp Asn  Phe Glu Glu Val Val  Asp Lys Gly Ala Ser  Ala Gln Ser
    1100                1105                1110

Phe Ile  Glu Arg Met Thr Asn  Phe Asp Lys Asn Leu  Pro Asn Glu
    1115                1120                1125

Lys Val  Leu Pro Lys His Ser  Leu Leu Tyr Glu Tyr  Phe Thr Val
    1130                1135                1140

Tyr Asn  Glu Leu Thr Lys Val  Lys Tyr Val Thr Glu  Gly Met Arg
    1145                1150                1155

Lys Pro  Ala Phe Leu Ser Gly  Glu Gln Lys Lys Ala  Ile Val Asp
    1160                1165                1170

Leu Leu  Phe Lys Thr Asn Arg  Lys Val Thr Val Lys  Gln Leu Lys
    1175                1180                1185

Glu Asp  Tyr Phe Lys Lys Ile  Glu Cys Phe Asp Ser  Val Glu Ile
    1190                1195                1200

Ser Gly  Val Glu Asp Arg Phe  Asn Ala Ser Leu Gly  Thr Tyr His
    1205                1210                1215

Asp Leu  Leu Lys Ile Ile Lys  Asp Lys Asp Phe Leu  Asp Asn Glu
    1220                1225                1230

Glu Asn  Glu Asp Ile Leu Glu  Asp Ile Val Leu Thr  Leu Thr Leu
    1235                1240                1245
```

```
Phe Glu  Asp Arg Glu Met Ile  Glu Glu Arg Leu Lys  Thr Tyr Ala
    1250                 1255                 1260

His Leu  Phe Asp Asp Lys Val  Met Lys Gln Leu Lys  Arg Arg Arg
    1265                 1270                 1275

Tyr Thr  Gly Trp Gly Arg Leu  Ser Arg Lys Leu Ile  Asn Gly Ile
    1280                 1285                 1290

Arg Asp  Lys Gln Ser Gly Lys  Thr Ile Leu Asp Phe  Leu Lys Ser
    1295                 1300                 1305

Asp Gly  Phe Ala Asn Arg Asn  Phe Met Gln Leu Ile  His Asp Asp
    1310                 1315                 1320

Ser Leu  Thr Phe Lys Glu Asp  Ile Gln Lys Ala Gln  Val Ser Gly
    1325                 1330                 1335

Gln Gly  Asp Ser Leu His Glu  His Ile Ala Asn Leu  Ala Gly Ser
    1340                 1345                 1350

Pro Ala  Ile Lys Lys Gly Ile  Leu Gln Thr Val Lys  Val Val Asp
    1355                 1360                 1365

Glu Leu  Val Lys Val Met Gly  Arg His Lys Pro Glu  Asn Ile Val
    1370                 1375                 1380

Ile Glu  Met Ala Arg Glu Asn  Gln Thr Thr Gln Lys  Gly Gln Lys
    1385                 1390                 1395

Asn Ser  Arg Glu Arg Met Lys  Arg Ile Glu Glu Gly  Ile Lys Glu
    1400                 1405                 1410

Leu Gly  Ser Gln Ile Leu Lys  Glu His Pro Val Glu  Asn Thr Gln
    1415                 1420                 1425

Leu Gln  Asn Glu Lys Leu Tyr  Leu Tyr Tyr Leu Gln  Asn Gly Arg
    1430                 1435                 1440

Asp Met  Tyr Val Asp Gln Glu  Leu Asp Ile Asn Arg  Leu Ser Asp
    1445                 1450                 1455

Tyr Asp  Val Asp Ala Ile Val  Pro Gln Ser Phe Leu  Lys Asp Asp
    1460                 1465                 1470

Ser Ile  Asp Asn Lys Val Leu  Thr Arg Ser Asp Lys  Asn Arg Gly
    1475                 1480                 1485

Lys Ser  Asp Asn Val Pro Ser  Glu Glu Val Val Lys  Lys Met Lys
    1490                 1495                 1500

Asn Tyr  Trp Arg Gln Leu Leu  Asn Ala Lys Leu Ile  Thr Gln Arg
    1505                 1510                 1515

Lys Phe  Asp Asn Leu Thr Lys  Ala Glu Arg Gly Gly  Leu Ser Glu
    1520                 1525                 1530

Leu Asp  Lys Ala Gly Phe Ile  Lys Arg Gln Leu Val  Glu Thr Arg
    1535                 1540                 1545

Gln Ile  Thr Lys His Val Ala  Gln Ile Leu Asp Ser  Arg Met Asn
    1550                 1555                 1560

Thr Lys  Tyr Asp Glu Asn Asp  Lys Leu Ile Arg Glu  Val Lys Val
    1565                 1570                 1575

Ile Thr  Leu Lys Ser Lys Leu  Val Ser Asp Phe Arg  Lys Asp Phe
    1580                 1585                 1590

Gln Phe  Tyr Lys Val Arg Glu  Ile Asn Asn Tyr His  His Ala His
    1595                 1600                 1605

Asp Ala  Tyr Leu Asn Ala Val  Val Gly Thr Ala Leu  Ile Lys Lys
    1610                 1615                 1620

Tyr Pro  Lys Leu Glu Ser Glu  Phe Val Tyr Gly Asp  Tyr Lys Val
    1625                 1630                 1635
```

Tyr Asp Val Arg Lys Met Ile Ala Lys Ser Glu Gln Glu Ile Gly
1640 1645 1650

Lys Ala Thr Ala Lys Tyr Phe Phe Tyr Ser Asn Ile Met Asn Phe
1655 1660 1665

Phe Lys Thr Glu Ile Thr Leu Ala Asn Gly Glu Ile Arg Lys Arg
1670 1675 1680

Pro Leu Ile Glu Thr Asn Gly Glu Thr Gly Glu Ile Val Trp Asp
1685 1690 1695

Lys Gly Arg Asp Phe Ala Thr Val Arg Lys Val Leu Ser Met Pro
1700 1705 1710

Gln Val Asn Ile Val Lys Lys Thr Glu Val Gln Thr Gly Gly Phe
1715 1720 1725

Ser Lys Glu Ser Ile Leu Pro Lys Arg Asn Ser Asp Lys Leu Ile
1730 1735 1740

Ala Arg Lys Lys Asp Trp Asp Pro Lys Lys Tyr Gly Gly Phe Asp
1745 1750 1755

Ser Pro Thr Val Ala Tyr Ser Val Leu Val Val Ala Lys Val Glu
1760 1765 1770

Lys Gly Lys Ser Lys Lys Leu Lys Ser Val Lys Glu Leu Leu Gly
1775 1780 1785

Ile Thr Ile Met Glu Arg Ser Ser Phe Glu Lys Asn Pro Ile Asp
1790 1795 1800

Phe Leu Glu Ala Lys Gly Tyr Lys Glu Val Lys Lys Asp Leu Ile
1805 1810 1815

Ile Lys Leu Pro Lys Tyr Ser Leu Phe Glu Leu Glu Asn Gly Arg
1820 1825 1830

Lys Arg Met Leu Ala Ser Ala Gly Glu Leu Gln Lys Gly Asn Glu
1835 1840 1845

Leu Ala Leu Pro Ser Lys Tyr Val Asn Phe Leu Tyr Leu Ala Ser
1850 1855 1860

His Tyr Glu Lys Leu Lys Gly Ser Pro Glu Asp Asn Glu Gln Lys
1865 1870 1875

Gln Leu Phe Val Glu Gln His Lys His Tyr Leu Asp Glu Ile Ile
1880 1885 1890

Glu Gln Ile Ser Glu Phe Ser Lys Arg Val Ile Leu Ala Asp Ala
1895 1900 1905

Asn Leu Asp Lys Val Leu Ser Ala Tyr Asn Lys His Arg Asp Lys
1910 1915 1920

Pro Ile Arg Glu Gln Ala Glu Asn Ile Ile His Leu Phe Thr Leu
1925 1930 1935

Thr Asn Leu Gly Ala Pro Ala Ala Phe Lys Tyr Phe Asp Thr Thr
1940 1945 1950

Ile Asp Arg Lys Arg Tyr Thr Ser Thr Lys Glu Val Leu Asp Ala
1955 1960 1965

Thr Leu Ile His Gln Ser Ile Thr Gly Leu Tyr Glu Thr Arg Ile
1970 1975 1980

Asp Leu Ser Gln Leu Gly Gly Asp Ala Tyr Pro Tyr Asp Val Pro
1985 1990 1995

Asp Tyr Ala Ser Leu Gly Ser Gly Ser Pro Lys Lys Lys Arg Lys
2000 2005 2010

Val Glu Asp Pro Lys Lys Lys Arg Lys Val Asp Gly Ile Gly Ser
2015 2020 2025

Gly Ser Asn Gly Ser Ser Gly Ser Ser Glu Leu Ile Lys Glu Asn 2030 2035 2040

Met His Met Lys Leu Tyr Met Glu Gly Thr Val Asp Asn His His
2045 2050 2055

Phe Lys Cys Thr Ser Glu Gly Glu Gly Lys Pro Tyr Glu Gly Thr
2060 2065 2070

Gln Thr Met Arg Ile Lys Val Val Glu Gly Gly Pro Leu Pro Phe
2075 2080 2085

Ala Phe Asp Ile Leu Ala Thr Ser Phe Leu Tyr Gly Ser Lys Thr
2090 2095 2100

Phe Ile Asn His Thr Gln Gly Ile Pro Asp Phe Phe Lys Gln Ser
2105 2110 2115

Phe Pro Glu Gly Phe Thr Trp Glu Arg Val Thr Thr Tyr Glu Asp
2120 2125 2130

Gly Gly Val Leu Thr Ala Thr Gln Asp Thr Ser Leu Gln Asp Gly
2135 2140 2145

Cys Leu Ile Tyr Asn Val Lys Ile Arg Gly Val Asn Phe Thr Ser
2150 2155 2160

Asn Gly Pro Val Met Gln Lys Lys Thr Leu Gly Trp Glu Ala Phe
2165 2170 2175

Thr Glu Thr Leu Tyr Pro Ala Asp Gly Gly Leu Glu Gly Arg Asn
2180 2185 2190

Asp Met Ala Leu Lys Leu Val Gly Gly Ser His Leu Ile Ala Asn
2195 2200 2205

Ile Lys Thr Thr Tyr Arg Ser Lys Lys Pro Ala Lys Asn Leu Lys
2210 2215 2220

Met Pro Gly Val Tyr Tyr Val Asp Tyr Arg Leu Glu Arg Ile Lys
2225 2230 2235

Glu Ala Asn Asn Glu Thr Tyr Val Glu Gln His Glu Val Ala Val
2240 2245 2250

Ala Arg Tyr Cys Asp Leu Pro Ser Lys Leu Gly His Lys Leu Asn
2255 2260 2265

Gly Gly Gly Gly Gly Met Asp Ala Lys Ser Leu Thr Ala Trp Ser
2270 2275 2280

Arg Thr Leu Val Thr Phe Lys Asp Val Phe Val Asp Phe Thr Arg
2285 2290 2295

Glu Glu Trp Lys Leu Leu Asp Thr Ala Gln Gln Ile Val Tyr Arg
2300 2305 2310

Asn Val Met Leu Glu Asn Tyr Lys Asn Leu Val Ser Leu Gly Tyr
2315 2320 2325

Gln Leu Thr Lys Pro Asp Val Ile Leu Arg Leu Glu Lys Gly Glu
2330 2335 2340

Glu Pro
2345

<210> SEQ ID NO 16
<211> LENGTH: 71
<212> TYPE: PRT
<213> ORGANISM: Artificial sequence
<220> FEATURE:
<223> OTHER INFORMATION: Synthetic polypeptide

<400> SEQUENCE: 16

Asp Ala Lys Ser Leu Thr Ala Trp Ser Arg Thr Leu Val Thr Phe Lys
1 5 10 15

Asp Val Phe Val Asp Phe Thr Arg Glu Glu Trp Lys Leu Leu Asp Thr

```
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro
65                  70


<210> SEQ ID NO 17
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 17

Gly Gly Ser Gly Gly Gly Ser
1               5


<210> SEQ ID NO 18
<211> LENGTH: 3
<212> TYPE: PRT
<213> ORGANISM: Artificial sequence
<220> FEATURE:
<223> OTHER INFORMATION: Synthetic polypeptide

<400> SEQUENCE: 18

Ser Gly Ser
1


<210> SEQ ID NO 19
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 19

Glu Ala Ser Gly Ser Gly Arg Ala Ser Pro Gly Ile Pro Gly Ser Thr
1               5                   10                  15

Arg


<210> SEQ ID NO 20
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 20

Ser Arg Ala Asp
1


<210> SEQ ID NO 21
<211> LENGTH: 3
<212> TYPE: PRT
<213> ORGANISM: Artificial sequence
<220> FEATURE:
<223> OTHER INFORMATION: Synthetic polypeptide

<400> SEQUENCE: 21

Gly Ser Gly
1
```

<210> SEQ ID NO 22
<211> LENGTH: 3
<212> TYPE: PRT
<213> ORGANISM: Artificial sequence
<220> FEATURE:
<223> OTHER INFORMATION: Synthetic polypeptide

<400> SEQUENCE: 22

Ser Pro Gly
1

<210> SEQ ID NO 23
<211> LENGTH: 1368
<212> TYPE: PRT
<213> ORGANISM: Artificial sequence
<220> FEATURE:
<223> OTHER INFORMATION: Synthetic polypeptide

<400> SEQUENCE: 23

Met Asp Lys Lys Tyr Ser Ile Gly Leu Ala Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala
195 200 205

Lys Ala Ile Leu Ser Ala Arg Leu Ser Lys Ser Arg Arg Leu Glu Asn
210 215 220

Leu Ile Ala Gln Leu Pro Gly Glu Lys Lys Asn Gly Leu Phe Gly Asn
225 230 235 240

Leu Ile Ala Leu Ser Leu Gly Leu Thr Pro Asn Phe Lys Ser Asn Phe
245 250 255

Asp Leu Ala Glu Asp Ala Lys Leu Gln Leu Ser Lys Asp Thr Tyr Asp
260 265 270

Asp Asp Leu Asp Asn Leu Leu Ala Gln Ile Gly Asp Gln Tyr Ala Asp
275 280 285

Leu Phe Leu Ala Ala Lys Asn Leu Ser Asp Ala Ile Leu Leu Ser Asp
290 295 300

```
Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
```

```
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140
```

Leu Val Val Ala Lys Val Glu Lys Gly Lys Ser Lys Lys Leu Lys
1145 1150 1155

Ser Val Lys Glu Leu Leu Gly Ile Thr Ile Met Glu Arg Ser Ser
1160 1165 1170

Phe Glu Lys Asn Pro Ile Asp Phe Leu Glu Ala Lys Gly Tyr Lys
1175 1180 1185

Glu Val Lys Lys Asp Leu Ile Ile Lys Leu Pro Lys Tyr Ser Leu
1190 1195 1200

Phe Glu Leu Glu Asn Gly Arg Lys Arg Met Leu Ala Ser Ala Gly
1205 1210 1215

Glu Leu Gln Lys Gly Asn Glu Leu Ala Leu Pro Ser Lys Tyr Val
1220 1225 1230

Asn Phe Leu Tyr Leu Ala Ser His Tyr Glu Lys Leu Lys Gly Ser
1235 1240 1245

Pro Glu Asp Asn Glu Gln Lys Gln Leu Phe Val Glu Gln His Lys
1250 1255 1260

His Tyr Leu Asp Glu Ile Ile Glu Gln Ile Ser Glu Phe Ser Lys
1265 1270 1275

Arg Val Ile Leu Ala Asp Ala Asn Leu Asp Lys Val Leu Ser Ala
1280 1285 1290

Tyr Asn Lys His Arg Asp Lys Pro Ile Arg Glu Gln Ala Glu Asn
1295 1300 1305

Ile Ile His Leu Phe Thr Leu Thr Asn Leu Gly Ala Pro Ala Ala
1310 1315 1320

Phe Lys Tyr Phe Asp Thr Thr Ile Asp Arg Lys Arg Tyr Thr Ser
1325 1330 1335

Thr Lys Glu Val Leu Asp Ala Thr Leu Ile His Gln Ser Ile Thr
1340 1345 1350

Gly Leu Tyr Glu Thr Arg Ile Asp Leu Ser Gln Leu Gly Gly Asp
1355 1360 1365

<210> SEQ ID NO 24
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 24

Tyr Pro Tyr Asp Val Pro Asp Tyr Ala
1 5

<210> SEQ ID NO 25
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 25

Pro Lys Lys Lys Arg Lys Val
1 5

<210> SEQ ID NO 26
<211> LENGTH: 301
<212> TYPE: PRT
<213> ORGANISM: Artificial sequence
<220> FEATURE:
<223> OTHER INFORMATION: Synthetic polypeptide

<400> SEQUENCE: 26

```
Asn His Asp Gln Glu Phe Asp Pro Pro Lys Val Tyr Pro Pro Val Pro
1               5                   10                  15

Ala Glu Lys Arg Lys Pro Ile Arg Val Leu Ser Leu Phe Asp Gly Ile
            20                  25                  30

Ala Thr Gly Leu Leu Val Leu Lys Asp Leu Gly Ile Gln Val Asp Arg
        35                  40                  45

Tyr Ile Ala Ser Glu Val Cys Glu Asp Ser Ile Thr Val Gly Met Val
    50                  55                  60

Arg His Gln Gly Lys Ile Met Tyr Val Gly Asp Val Arg Ser Val Thr
65                  70                  75                  80

Gln Lys His Ile Gln Glu Trp Gly Pro Phe Asp Leu Val Ile Gly Gly
                85                  90                  95

Ser Pro Cys Asn Asp Leu Ser Ile Val Asn Pro Ala Arg Lys Gly Leu
            100                 105                 110

Tyr Glu Gly Thr Gly Arg Leu Phe Phe Glu Phe Tyr Arg Leu Leu His
        115                 120                 125

Asp Ala Arg Pro Lys Glu Gly Asp Asp Arg Pro Phe Phe Trp Leu Phe
    130                 135                 140

Glu Asn Val Val Ala Met Gly Val Ser Asp Lys Arg Asp Ile Ser Arg
145                 150                 155                 160

Phe Leu Glu Ser Asn Pro Val Met Ile Asp Ala Lys Glu Val Ser Ala
                165                 170                 175

Ala His Arg Ala Arg Tyr Phe Trp Gly Asn Leu Pro Gly Met Asn Arg
            180                 185                 190

Pro Leu Ala Ser Thr Val Asn Asp Lys Leu Glu Leu Gln Glu Cys Leu
        195                 200                 205

Glu His Gly Arg Ile Ala Lys Phe Ser Lys Val Arg Thr Ile Thr Thr
    210                 215                 220

Arg Ser Asn Ser Ile Lys Gln Gly Lys Asp Gln His Phe Pro Val Phe
225                 230                 235                 240

Met Asn Glu Lys Glu Asp Ile Leu Trp Cys Thr Glu Met Glu Arg Val
                245                 250                 255

Phe Gly Phe Pro Val His Tyr Thr Asp Val Ser Asn Met Ser Arg Leu
            260                 265                 270

Ala Arg Gln Arg Leu Leu Gly Arg Ser Trp Ser Val Pro Val Ile Arg
        275                 280                 285

His Leu Phe Ala Pro Leu Lys Glu Tyr Phe Ala Cys Val
    290                 295                 300
```

<210> SEQ ID NO 27
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 27

```
Ser Ser Gly Asn Ser Asn Ala Asn Ser Arg Gly Pro Ser Phe Ser Ser
1               5                   10                  15

Gly Leu Val Pro Leu Ser Leu Arg Gly Ser His
            20                  25
```

<210> SEQ ID NO 28
<211> LENGTH: 215

<212> TYPE: PRT
<213> ORGANISM: Artificial sequence
<220> FEATURE:
<223> OTHER INFORMATION: Synthetic polypeptide

<400> SEQUENCE: 28

Met Gly Pro Met Glu Ile Tyr Lys Thr Val Ser Ala Trp Lys Arg Gln
1 5 10 15

Pro Val Arg Val Leu Ser Leu Phe Arg Asn Ile Asp Lys Val Leu Lys
20 25 30

Ser Leu Gly Phe Leu Glu Ser Gly Ser Gly Ser Gly Gly Gly Thr Leu
35 40 45

Lys Tyr Val Glu Asp Val Thr Asn Val Val Arg Arg Asp Val Glu Lys
50 55 60

Trp Gly Pro Phe Asp Leu Val Tyr Gly Ser Thr Gln Pro Leu Gly Ser
65 70 75 80

Ser Cys Asp Arg Cys Pro Gly Trp Tyr Met Phe Gln Phe His Arg Ile
85 90 95

Leu Gln Tyr Ala Leu Pro Arg Gln Glu Ser Gln Arg Pro Phe Phe Trp
100 105 110

Ile Phe Met Asp Asn Leu Leu Leu Thr Glu Asp Asp Gln Glu Thr Thr
115 120 125

Thr Arg Phe Leu Gln Thr Glu Ala Val Thr Leu Gln Asp Val Arg Gly
130 135 140

Arg Asp Tyr Gln Asn Ala Met Arg Val Trp Ser Asn Ile Pro Gly Leu
145 150 155 160

Lys Ser Lys His Ala Pro Leu Thr Pro Lys Glu Glu Glu Tyr Leu Gln
165 170 175

Ala Gln Val Arg Ser Arg Ser Lys Leu Asp Ala Pro Lys Val Asp Leu
180 185 190

Leu Val Lys Asn Cys Leu Leu Pro Leu Arg Glu Tyr Phe Lys Tyr Phe
195 200 205

Ser Gln Asn Ser Leu Pro Leu
210 215

<210> SEQ ID NO 29
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 29

Ala Thr Asn Phe Ser Leu Leu Lys Gln Ala Gly Asp Val Glu Glu Asn
1 5 10 15

Pro Gly Pro

<210> SEQ ID NO 30
<211> LENGTH: 232
<212> TYPE: PRT
<213> ORGANISM: Artificial sequence
<220> FEATURE:
<223> OTHER INFORMATION: Synthetic polypeptide

<400> SEQUENCE: 30

Ser Glu Leu Ile Lys Glu Asn Met His Met Lys Leu Tyr Met Glu Gly
1 5 10 15

Thr Val Asp Asn His His Phe Lys Cys Thr Ser Glu Gly Glu Gly Lys
20 25 30

Pro Tyr Glu Gly Thr Gln Thr Met Arg Ile Lys Val Val Glu Gly Gly
35 40 45

Pro Leu Pro Phe Ala Phe Asp Ile Leu Ala Thr Ser Phe Leu Tyr Gly
50 55 60

Ser Lys Thr Phe Ile Asn His Thr Gln Gly Ile Pro Asp Phe Phe Lys
65 70 75 80

Gln Ser Phe Pro Glu Gly Phe Thr Trp Glu Arg Val Thr Thr Tyr Glu
85 90 95

Asp Gly Gly Val Leu Thr Ala Thr Gln Asp Thr Ser Leu Gln Asp Gly
100 105 110

Cys Leu Ile Tyr Asn Val Lys Ile Arg Gly Val Asn Phe Thr Ser Asn
115 120 125

Gly Pro Val Met Gln Lys Lys Thr Leu Gly Trp Glu Ala Phe Thr Glu
130 135 140

Thr Leu Tyr Pro Ala Asp Gly Gly Leu Glu Gly Arg Asn Asp Met Ala
145 150 155 160

Leu Lys Leu Val Gly Gly Ser His Leu Ile Ala Asn Ile Lys Thr Thr
165 170 175

Tyr Arg Ser Lys Lys Pro Ala Lys Asn Leu Lys Met Pro Gly Val Tyr
180 185 190

Tyr Val Asp Tyr Arg Leu Glu Arg Ile Lys Glu Ala Asn Asn Glu Thr
195 200 205

Tyr Val Glu Gln His Glu Val Ala Val Ala Arg Tyr Cys Asp Leu Pro
210 215 220

Ser Lys Leu Gly His Lys Leu Asn
225 230

<210> SEQ ID NO 31
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 31

Ser Gly Ser Glu Thr Pro Gly Thr Ser Glu Ser Ala Thr Pro Glu Ser
1 5 10 15

<210> SEQ ID NO 32
<211> LENGTH: 80
<212> TYPE: PRT
<213> ORGANISM: Artificial sequence
<220> FEATURE:
<223> OTHER INFORMATION: Synthetic polypeptide

<400> SEQUENCE: 32

Gly Gly Pro Ser Ser Gly Ala Pro Pro Pro Ser Gly Gly Ser Pro Ala
1 5 10 15

Gly Ser Pro Thr Ser Thr Glu Glu Gly Thr Ser Glu Ser Ala Thr Pro
20 25 30

Glu Ser Gly Pro Gly Thr Ser Thr Glu Pro Ser Glu Gly Ser Ala Pro
35 40 45

Gly Ser Pro Ala Gly Ser Pro Thr Ser Thr Glu Glu Gly Thr Ser Thr
50 55 60

Glu Pro Ser Glu Gly Ser Ala Pro Gly Thr Ser Thr Glu Pro Ser Glu
65 70 75 80

<210> SEQ ID NO 33
<211> LENGTH: 543
<212> TYPE: PRT
<213> ORGANISM: Artificial sequence
<220> FEATURE:
<223> OTHER INFORMATION: Synthetic polypeptide

<400> SEQUENCE: 33

```
Asn His Asp Gln Glu Phe Asp Pro Pro Lys Val Tyr Pro Pro Val Pro
1               5                   10                  15

Ala Glu Lys Arg Lys Pro Ile Arg Val Leu Ser Leu Phe Asp Gly Ile
            20                  25                  30

Ala Thr Gly Leu Leu Val Leu Lys Asp Leu Gly Ile Gln Val Asp Arg
        35                  40                  45

Tyr Ile Ala Ser Glu Val Cys Glu Asp Ser Ile Thr Val Gly Met Val
    50                  55                  60

Arg His Gln Gly Lys Ile Met Tyr Val Gly Asp Val Arg Ser Val Thr
65                  70                  75                  80

Gln Lys His Ile Gln Glu Trp Gly Pro Phe Asp Leu Val Ile Gly Gly
                85                  90                  95

Ser Pro Cys Asn Asp Leu Ser Ile Val Asn Pro Ala Arg Lys Gly Leu
            100                 105                 110

Tyr Glu Gly Thr Gly Arg Leu Phe Phe Glu Phe Tyr Arg Leu Leu His
        115                 120                 125

Asp Ala Arg Pro Lys Glu Gly Asp Asp Arg Pro Phe Phe Trp Leu Phe
    130                 135                 140

Glu Asn Val Val Ala Met Gly Val Ser Asp Lys Arg Asp Ile Ser Arg
145                 150                 155                 160

Phe Leu Glu Ser Asn Pro Val Met Ile Asp Ala Lys Glu Val Ser Ala
                165                 170                 175

Ala His Arg Ala Arg Tyr Phe Trp Gly Asn Leu Pro Gly Met Asn Arg
            180                 185                 190

Pro Leu Ala Ser Thr Val Asn Asp Lys Leu Glu Leu Gln Glu Cys Leu
        195                 200                 205

Glu His Gly Arg Ile Ala Lys Phe Ser Lys Val Arg Thr Ile Thr Thr
    210                 215                 220

Arg Ser Asn Ser Ile Lys Gln Gly Lys Asp Gln His Phe Pro Val Phe
225                 230                 235                 240

Met Asn Glu Lys Glu Asp Ile Leu Trp Cys Thr Glu Met Glu Arg Val
                245                 250                 255

Phe Gly Phe Pro Val His Tyr Thr Asp Val Ser Asn Met Ser Arg Leu
            260                 265                 270

Ala Arg Gln Arg Leu Leu Gly Arg Ser Trp Ser Val Pro Val Ile Arg
        275                 280                 285

His Leu Phe Ala Pro Leu Lys Glu Tyr Phe Ala Cys Val Ser Ser Gly
    290                 295                 300

Asn Ser Asn Ala Asn Ser Arg Gly Pro Ser Phe Ser Ser Gly Leu Val
305                 310                 315                 320

Pro Leu Ser Leu Arg Gly Ser His Met Gly Pro Met Glu Ile Tyr Lys
                325                 330                 335

Thr Val Ser Ala Trp Lys Arg Gln Pro Val Arg Val Leu Ser Leu Phe
            340                 345                 350

Arg Asn Ile Asp Lys Val Leu Lys Ser Leu Gly Phe Leu Glu Ser Gly
        355                 360                 365

Ser Gly Ser Gly Gly Gly Thr Leu Lys Tyr Val Glu Asp Val Thr Asn
```

```
    370                 375                 380

Val Val Arg Arg Asp Val Glu Lys Trp Gly Pro Phe Asp Leu Val Tyr
385                 390                 395                 400

Gly Ser Thr Gln Pro Leu Gly Ser Ser Cys Asp Arg Cys Pro Gly Trp
                405                 410                 415

Tyr Met Phe Gln Phe His Arg Ile Leu Gln Tyr Ala Leu Pro Arg Gln
            420                 425                 430

Glu Ser Gln Arg Pro Phe Phe Trp Ile Phe Met Asp Asn Leu Leu Leu
        435                 440                 445

Thr Glu Asp Asp Gln Glu Thr Thr Thr Arg Phe Leu Gln Thr Glu Ala
    450                 455                 460

Val Thr Leu Gln Asp Val Arg Gly Arg Asp Tyr Gln Asn Ala Met Arg
465                 470                 475                 480

Val Trp Ser Asn Ile Pro Gly Leu Lys Ser Lys His Ala Pro Leu Thr
                485                 490                 495

Pro Lys Glu Glu Glu Tyr Leu Gln Ala Gln Val Arg Ser Arg Ser Lys
            500                 505                 510

Leu Asp Ala Pro Lys Val Asp Leu Leu Val Lys Asn Cys Leu Leu Pro
        515                 520                 525

Leu Arg Glu Tyr Phe Lys Tyr Phe Ser Gln Asn Ser Leu Pro Leu
    530                 535                 540
```

<210> SEQ ID NO 34
<211> LENGTH: 1307
<212> TYPE: PRT
<213> ORGANISM: Artificial sequence
<220> FEATURE:
<223> OTHER INFORMATION: Synthetic polypeptide

<400> SEQUENCE: 34

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
```

```
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620
```

```
Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Ala Asn Leu Asn Phe Gly Phe Lys  Ser Lys Arg Thr Gly  Ile Ala Glu
        995                 1000                1005

Lys Ala  Val Tyr Gln Gln Phe  Glu Lys Met Leu Ile  Asp Lys Leu
    1010                1015                1020

Asn Cys  Leu Val Leu Lys Asp  Tyr Pro Ala Glu Lys  Val Gly Gly
    1025                1030                1035
```

Val Leu Asn Pro Tyr Gln Leu Thr Asp Gln Phe Thr Ser Phe Ala
1040 1045 1050

Lys Met Gly Thr Gln Ser Gly Phe Leu Phe Tyr Val Pro Ala Pro
1055 1060 1065

Tyr Thr Ser Lys Ile Asp Pro Leu Thr Gly Phe Val Asp Pro Phe
1070 1075 1080

Val Trp Lys Thr Ile Lys Asn His Glu Ser Arg Lys His Phe Leu
1085 1090 1095

Glu Gly Phe Asp Phe Leu His Tyr Asp Val Lys Thr Gly Asp Phe
1100 1105 1110

Ile Leu His Phe Lys Met Asn Arg Asn Leu Ser Phe Gln Arg Gly
1115 1120 1125

Leu Pro Gly Phe Met Pro Ala Trp Asp Ile Val Phe Glu Lys Asn
1130 1135 1140

Glu Thr Gln Phe Asp Ala Lys Gly Thr Pro Phe Ile Ala Gly Lys
1145 1150 1155

Arg Ile Val Pro Val Ile Glu Asn His Arg Phe Thr Gly Arg Tyr
1160 1165 1170

Arg Asp Leu Tyr Pro Ala Asn Glu Leu Ile Ala Leu Leu Glu Glu
1175 1180 1185

Lys Gly Ile Val Phe Arg Asp Gly Ser Asn Ile Leu Pro Lys Leu
1190 1195 1200

Leu Glu Asn Asp Asp Ser His Ala Ile Asp Thr Met Val Ala Leu
1205 1210 1215

Ile Arg Ser Val Leu Gln Met Arg Asn Ser Asn Ala Ala Thr Gly
1220 1225 1230

Glu Asp Tyr Ile Asn Ser Pro Val Arg Asp Leu Asn Gly Val Cys
1235 1240 1245

Phe Asp Ser Arg Phe Gln Asn Pro Glu Trp Pro Met Asp Ala Asp
1250 1255 1260

Ala Asn Gly Ala Tyr His Ile Ala Leu Lys Gly Gln Leu Leu Leu
1265 1270 1275

Asn His Leu Lys Glu Ser Lys Asp Leu Lys Leu Gln Asn Gly Ile
1280 1285 1290

Ser Asn Gln Asp Trp Leu Ala Tyr Ile Gln Glu Leu Arg Asn
1295 1300 1305

<210> SEQ ID NO 35
<211> LENGTH: 1228
<212> TYPE: PRT
<213> ORGANISM: Artificial sequence
<220> FEATURE:
<223> OTHER INFORMATION: Synthetic polypeptide

<400> SEQUENCE: 35

Met Ser Lys Leu Glu Lys Phe Thr Asn Cys Tyr Ser Leu Ser Lys Thr
1 5 10 15

Leu Arg Phe Lys Ala Ile Pro Val Gly Lys Thr Gln Glu Asn Ile Asp
20 25 30

Asn Lys Arg Leu Leu Val Glu Asp Glu Lys Arg Ala Glu Asp Tyr Lys
35 40 45

Gly Val Lys Lys Leu Leu Asp Arg Tyr Tyr Leu Ser Phe Ile Asn Asp
50 55 60

Val Leu His Ser Ile Lys Leu Lys Asn Leu Asn Asn Tyr Ile Ser Leu
65 70 75 80

-continued

```
Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
```

```
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Ala
            820                 825                 830

Arg Gly Glu Arg Asn Leu Leu Tyr Ile Val Val Val Asp Gly Lys Gly
        835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Ala Asp Leu Asn
        915                 920                 925
```

```
Ser Gly Phe Lys Asn Ser Arg Val Lys Val Glu Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu  Thr Ser Lys Ile Asp  Pro Ser Thr
        995                 1000                1005

Gly Phe  Val Asn Leu Leu Lys  Thr Lys Tyr Thr Ser  Ile Ala Asp
    1010                1015                1020

Ser Lys  Lys Phe Ile Ser Ser  Phe Asp Arg Ile Met  Tyr Val Pro
    1025                1030                1035

Glu Glu  Asp Leu Phe Glu Phe  Ala Leu Asp Tyr Lys  Asn Phe Ser
    1040                1045                1050

Arg Thr  Asp Ala Asp Tyr Ile  Lys Lys Trp Lys Leu  Tyr Ser Tyr
    1055                1060                1065

Gly Asn  Arg Ile Arg Ile Phe  Arg Asn Pro Lys Lys  Asn Asn Val
    1070                1075                1080

Phe Asp  Trp Glu Glu Val Cys  Leu Thr Ser Ala Tyr  Lys Glu Leu
    1085                1090                1095

Phe Asn  Lys Tyr Gly Ile Asn  Tyr Gln Gln Gly Asp  Ile Arg Ala
    1100                1105                1110

Leu Leu  Cys Glu Gln Ser Asp  Lys Ala Phe Tyr Ser  Ser Phe Met
    1115                1120                1125

Ala Leu  Met Ser Leu Met Leu  Gln Met Arg Asn Ser  Ile Thr Gly
    1130                1135                1140

Arg Thr  Asp Val Asp Phe Leu  Ile Ser Pro Val Lys  Asn Ser Asp
    1145                1150                1155

Gly Ile  Phe Tyr Asp Ser Arg  Asn Tyr Glu Ala Gln  Glu Asn Ala
    1160                1165                1170

Ile Leu  Pro Lys Asn Ala Asp  Ala Asn Gly Ala Tyr  Asn Ile Ala
    1175                1180                1185

Arg Lys  Val Leu Trp Ala Ile  Gly Gln Phe Lys Lys  Ala Glu Asp
    1190                1195                1200

Glu Lys  Leu Asp Lys Val Lys  Ile Ala Ile Ser Asn  Lys Glu Trp
    1205                1210                1215

Leu Glu  Tyr Ala Gln Thr Ser  Val Lys His
    1220                1225


<210> SEQ ID NO 36
<211> LENGTH: 1314
<212> TYPE: PRT
<213> ORGANISM: Artificial sequence
<220> FEATURE:
<223> OTHER INFORMATION: Synthetic polypeptide

<400> SEQUENCE: 36

Met Tyr Pro Tyr Asp Val Pro Asp Tyr Ala Ser Gly Ser Gly Met Ser
1               5                   10                  15

Ile Tyr Gln Glu Phe Val Asn Lys Tyr Ser Leu Ser Lys Thr Leu Arg
            20                  25                  30

Phe Glu Leu Ile Pro Gln Gly Lys Thr Leu Glu Asn Ile Lys Ala Arg
        35                  40                  45
```

```
Gly Leu Ile Leu Asp Asp Glu Lys Arg Ala Lys Asp Tyr Lys Lys Ala
    50                  55                  60

Lys Gln Ile Ile Asp Lys Tyr His Gln Phe Phe Ile Glu Glu Ile Leu
65                  70                  75                  80

Ser Ser Val Cys Ile Ser Glu Asp Leu Leu Gln Asn Tyr Ser Asp Val
                85                  90                  95

Tyr Phe Lys Leu Lys Lys Ser Asp Asp Asp Asn Leu Gln Lys Asp Phe
            100                 105                 110

Lys Ser Ala Lys Asp Thr Ile Lys Lys Gln Ile Ser Glu Tyr Ile Lys
        115                 120                 125

Asp Ser Glu Lys Phe Lys Asn Leu Phe Asn Gln Asn Leu Ile Asp Ala
    130                 135                 140

Lys Lys Gly Gln Glu Ser Asp Leu Ile Leu Trp Leu Lys Gln Ser Lys
145                 150                 155                 160

Asp Asn Gly Ile Glu Leu Phe Lys Ala Asn Ser Asp Ile Thr Asp Ile
                165                 170                 175

Asp Glu Ala Leu Glu Ile Ile Lys Ser Phe Lys Gly Trp Thr Thr Tyr
            180                 185                 190

Phe Lys Gly Phe His Glu Asn Arg Lys Asn Val Tyr Ser Ser Asn Asp
        195                 200                 205

Ile Pro Thr Ser Ile Ile Tyr Arg Ile Val Asp Asp Asn Leu Pro Lys
    210                 215                 220

Phe Leu Glu Asn Lys Ala Lys Tyr Glu Ser Leu Lys Asp Lys Ala Pro
225                 230                 235                 240

Glu Ala Ile Asn Tyr Glu Gln Ile Lys Lys Asp Leu Ala Glu Glu Leu
                245                 250                 255

Thr Phe Asp Ile Asp Tyr Lys Thr Ser Glu Val Asn Gln Arg Val Phe
            260                 265                 270

Ser Leu Asp Glu Val Phe Glu Ile Ala Asn Phe Asn Asn Tyr Leu Asn
        275                 280                 285

Gln Ser Gly Ile Thr Lys Phe Asn Thr Ile Ile Gly Gly Lys Phe Val
    290                 295                 300

Asn Gly Glu Asn Thr Lys Arg Lys Gly Ile Asn Glu Tyr Ile Asn Leu
305                 310                 315                 320

Tyr Ser Gln Gln Ile Asn Asp Lys Thr Leu Lys Lys Tyr Lys Met Ser
                325                 330                 335

Val Leu Phe Lys Gln Ile Leu Ser Asp Thr Glu Ser Lys Ser Phe Val
            340                 345                 350

Ile Asp Lys Leu Glu Asp Asp Ser Asp Val Val Thr Thr Met Gln Ser
        355                 360                 365

Phe Tyr Glu Gln Ile Ala Ala Phe Lys Thr Val Glu Glu Lys Ser Ile
    370                 375                 380

Lys Glu Thr Leu Ser Leu Leu Phe Asp Asp Leu Lys Ala Gln Lys Leu
385                 390                 395                 400

Asp Leu Ser Lys Ile Tyr Phe Lys Asn Asp Lys Ser Leu Thr Asp Leu
                405                 410                 415

Ser Gln Gln Val Phe Asp Asp Tyr Ser Val Ile Gly Thr Ala Val Leu
            420                 425                 430

Glu Tyr Ile Thr Gln Gln Ile Ala Pro Lys Asn Leu Asp Asn Pro Ser
        435                 440                 445

Lys Lys Glu Gln Glu Leu Ile Ala Lys Lys Thr Glu Lys Ala Lys Tyr
    450                 455                 460
```

```
Leu Ser Leu Glu Thr Ile Lys Leu Ala Leu Glu Glu Phe Asn Lys His
465                 470                 475                 480

Arg Asp Ile Asp Lys Gln Cys Arg Phe Glu Glu Ile Leu Ala Asn Phe
                485                 490                 495

Ala Ala Ile Pro Met Ile Phe Asp Glu Ile Ala Gln Asn Lys Asp Asn
            500                 505                 510

Leu Ala Gln Ile Ser Ile Lys Tyr Gln Asn Gln Gly Lys Lys Asp Leu
        515                 520                 525

Leu Gln Ala Ser Ala Glu Asp Asp Val Lys Ala Ile Lys Asp Leu Leu
    530                 535                 540

Asp Gln Thr Asn Asn Leu Leu His Lys Leu Lys Ile Phe His Ile Ser
545                 550                 555                 560

Gln Ser Glu Asp Lys Ala Asn Ile Leu Asp Lys Asp Glu His Phe Tyr
                565                 570                 575

Leu Val Phe Glu Glu Cys Tyr Phe Glu Leu Ala Asn Ile Val Pro Leu
            580                 585                 590

Tyr Asn Lys Ile Arg Asn Tyr Ile Thr Gln Lys Pro Tyr Ser Asp Glu
        595                 600                 605

Lys Phe Lys Leu Asn Phe Glu Asn Ser Thr Leu Ala Asn Gly Trp Asp
    610                 615                 620

Lys Asn Lys Glu Pro Asp Asn Thr Ala Ile Leu Phe Ile Lys Asp Asp
625                 630                 635                 640

Lys Tyr Tyr Leu Gly Val Met Asn Lys Lys Asn Asn Lys Ile Phe Asp
                645                 650                 655

Asp Lys Ala Ile Lys Glu Asn Lys Gly Glu Gly Tyr Lys Lys Ile Val
            660                 665                 670

Tyr Lys Leu Leu Pro Gly Ala Asn Lys Met Leu Pro Lys Val Phe Phe
        675                 680                 685

Ser Ala Lys Ser Ile Lys Phe Tyr Asn Pro Ser Glu Asp Ile Leu Arg
    690                 695                 700

Ile Arg Asn His Ser Thr His Thr Lys Asn Gly Ser Pro Gln Lys Gly
705                 710                 715                 720

Tyr Glu Lys Phe Glu Phe Asn Ile Glu Asp Cys Arg Lys Phe Ile Asp
                725                 730                 735

Phe Tyr Lys Gln Ser Ile Ser Lys His Pro Glu Trp Lys Asp Phe Gly
            740                 745                 750

Phe Arg Phe Ser Asp Thr Gln Arg Tyr Asn Ser Ile Asp Glu Phe Tyr
        755                 760                 765

Arg Glu Val Glu Asn Gln Gly Tyr Lys Leu Thr Phe Glu Asn Ile Ser
    770                 775                 780

Glu Ser Tyr Ile Asp Ser Val Val Asn Gln Gly Lys Leu Tyr Leu Phe
785                 790                 795                 800

Gln Ile Tyr Asn Lys Asp Phe Ser Ala Tyr Ser Lys Gly Arg Pro Asn
                805                 810                 815

Leu His Thr Leu Tyr Trp Lys Ala Leu Phe Asp Glu Arg Asn Leu Gln
            820                 825                 830

Asp Val Val Tyr Lys Leu Asn Gly Glu Ala Glu Leu Phe Tyr Arg Lys
        835                 840                 845

Gln Ser Ile Pro Lys Lys Ile Thr His Pro Ala Lys Glu Ala Ile Ala
    850                 855                 860

Asn Lys Asn Lys Asp Asn Pro Lys Lys Glu Ser Val Phe Glu Tyr Asp
865                 870                 875                 880

Leu Ile Lys Asp Lys Arg Phe Thr Glu Asp Lys Phe Phe Phe His Cys
```

```
                885                 890                 895

Pro Ile Thr Ile Asn Phe Lys Ser Ser Gly Ala Asn Lys Phe Asn Asp
            900                 905                 910

Glu Ile Asn Leu Leu Leu Lys Glu Lys Ala Asn Asp Val His Ile Leu
        915                 920                 925

Ser Ile Ala Arg Gly Glu Arg His Leu Ala Tyr Tyr Thr Leu Val Asp
    930                 935                 940

Gly Lys Gly Asn Ile Ile Lys Gln Asp Thr Phe Asn Ile Ile Gly Asn
945                 950                 955                 960

Asp Arg Met Lys Thr Asn Tyr His Asp Lys Leu Ala Ala Ile Glu Lys
                965                 970                 975

Asp Arg Asp Ser Ala Arg Lys Asp Trp Lys Lys Ile Asn Asn Ile Lys
            980                 985                 990

Glu Met Lys Glu Gly Tyr Leu Ser  Gln Val Val His Glu  Ile Ala Lys
        995                 1000                1005

Leu Val  Ile Glu Tyr Asn Ala  Ile Val Val Phe Glu  Asp Leu Asn
    1010                1015                1020

Phe Gly  Phe Lys Arg Gly Arg  Phe Lys Val Glu Lys  Gln Val Tyr
    1025                1030                1035

Gln Lys  Leu Glu Lys Met Leu  Ile Glu Lys Leu Asn  Tyr Leu Val
    1040                1045                1050

Phe Lys  Asp Asn Glu Phe Asp  Lys Thr Gly Gly Val  Leu Arg Ala
    1055                1060                1065

Tyr Gln  Leu Thr Ala Pro Phe  Glu Thr Phe Lys Lys  Met Gly Lys
    1070                1075                1080

Gln Thr  Gly Ile Ile Tyr Tyr  Val Pro Ala Gly Phe  Thr Ser Lys
    1085                1090                1095

Ile Cys  Pro Val Thr Gly Phe  Val Asn Gln Leu Tyr  Pro Lys Tyr
    1100                1105                1110

Glu Ser  Val Ser Lys Ser Gln  Glu Phe Phe Ser Lys  Phe Asp Lys
    1115                1120                1125

Ile Cys  Tyr Asn Leu Asp Lys  Gly Tyr Phe Glu Phe  Ser Phe Asp
    1130                1135                1140

Tyr Lys  Asn Phe Gly Asp Lys  Ala Ala Lys Gly Lys  Trp Thr Ile
    1145                1150                1155

Ala Ser  Phe Gly Ser Arg Leu  Ile Asn Phe Arg Asn  Ser Asp Lys
    1160                1165                1170

Asn His  Asn Trp Asp Thr Arg  Glu Val Tyr Pro Thr  Lys Glu Leu
    1175                1180                1185

Glu Lys  Leu Leu Lys Asp Tyr  Ser Ile Glu Tyr Gly  His Gly Glu
    1190                1195                1200

Cys Ile  Lys Ala Ala Ile Cys  Gly Glu Ser Asp Lys  Lys Phe Phe
    1205                1210                1215

Ala Lys  Leu Thr Ser Val Leu  Asn Thr Ile Leu Gln  Met Arg Asn
    1220                1225                1230

Ser Lys  Thr Gly Thr Glu Leu  Asp Tyr Leu Ile Ser  Pro Val Ala
    1235                1240                1245

Asp Val  Asn Gly Asn Phe Phe  Asp Ser Arg Gln Ala  Pro Lys Asn
    1250                1255                1260

Met Pro  Gln Asp Ala Asp Ala  Asn Gly Ala Tyr His  Ile Gly Leu
    1265                1270                1275

Lys Gly  Leu Met Leu Leu Gly  Arg Ile Lys Asn Asn  Gln Glu Gly
    1280                1285                1290
```

```
Lys Lys  Leu Asn Leu Val Ile  Lys Asn Glu Glu Tyr  Phe Glu Phe
    1295                1300                1305

Val Gln  Asn Arg Asn Asn
    1310


<210> SEQ ID NO 37
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 37

actgcggaaa tttgagcgt                                                19


<210> SEQ ID NO 38
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 38

acgctcaaat ttccgcagt                                                19


<210> SEQ ID NO 39
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 39

aggcaatggc tgcacatgc                                                19


<210> SEQ ID NO 40
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 40

gcatgtgcag ccattgcct                                                19


<210> SEQ ID NO 41
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 41

gacgcttggt tctgaggag                                                19


<210> SEQ ID NO 42
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 42

ctcctcagaa ccaagcgtc                                                19
```

<210> SEQ ID NO 43
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 43
tccggaaacg cattcctct 19

<210> SEQ ID NO 44
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 44
agaggaatgc gtttccgga 19

<210> SEQ ID NO 45
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 45
ccgcgtcagc ccggcccgg 19

<210> SEQ ID NO 46
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 46
ccgggccggg ctgacgcgg 19

<210> SEQ ID NO 47
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 47
cgactcccgc tgggcctct 19

<210> SEQ ID NO 48
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 48
agaggcccag cgggagtcg 19

<210> SEQ ID NO 49
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 49
ccgttgcgcg ctcgctctc 19

<210> SEQ ID NO 50
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 50
gagagcgagc gcgcaacgg 19

<210> SEQ ID NO 51
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 51
ccgcgcatcc tgccaggcc 19

<210> SEQ ID NO 52
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 52
ggcctggcag gatgcgcgg 19

<210> SEQ ID NO 53
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 53
ccaacttggc gcgtttcgg 19

<210> SEQ ID NO 54
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 54
ccgaaacgcg ccaagttgg 19

<210> SEQ ID NO 55
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 55
accacgcgtc cgagtccgg 19

<210> SEQ ID NO 56

<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 56
ccggactcgg acgcgtggt 19

<210> SEQ ID NO 57
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 57
tgctcattgt ccctggaca 19

<210> SEQ ID NO 58
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 58
tgtccaggga caatgagca 19

<210> SEQ ID NO 59
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 59
ggacaccctg ctcattgtc 19

<210> SEQ ID NO 60
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 60
gacaatgagc agggtgtcc 19

<210> SEQ ID NO 61
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 61
accggcagcc tgcgcgtcc 19

<210> SEQ ID NO 62
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 62
ggacgcgcag gctgccggt 19

<210> SEQ ID NO 63
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 63
cgatgggcac ccactgctc 19

<210> SEQ ID NO 64
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 64
gagcagtggg tgcccatcg 19

<210> SEQ ID NO 65
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 65
ccttcacgtg gacgcgcag 19

<210> SEQ ID NO 66
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 66
ctgcgcgtcc acgtgaagg 19

<210> SEQ ID NO 67
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 67
cgtgaaggtg gaagccttc 19

<210> SEQ ID NO 68
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 68
gaaggcttcc accttcacg 19

<210> SEQ ID NO 69
<211> LENGTH: 19
<212> TYPE: DNA

<213> ORGANISM: Artificial sequence
<220> FEATURE:
<223> OTHER INFORMATION: Synthetic polynucleotide

<400> SEQUENCE: 69
ctccttggtc aggcgccgg 19

<210> SEQ ID NO 70
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 70
ccggcgcctg accaaggag 19

<210> SEQ ID NO 71
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 71
tggtcaggcg ccggttccg 19

<210> SEQ ID NO 72
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 72
cggaaccggc gcctgacca 19

<210> SEQ ID NO 73
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 73
tagaggtcgc cttctcctc 19

<210> SEQ ID NO 74
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 74
gaggagaagg cgacctcta 19

<210> SEQ ID NO 75
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 75
cgacgctcgg gtcgcggtg 19

<210> SEQ ID NO 76
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 76
caccgcgacc cgagcgtcg 19

<210> SEQ ID NO 77
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 77
atgctgtcgc cgcgcgggg 19

<210> SEQ ID NO 78
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 78
ccccgcgcgg cgacagcat 19

<210> SEQ ID NO 79
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 79
ctcaccctca ccggagcca 19

<210> SEQ ID NO 80
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 80
tggctccggt gagggtgag 19

<210> SEQ ID NO 81
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 81
ccgcaaactt tactcctta 19

<210> SEQ ID NO 82
<211> LENGTH: 19
<212> TYPE: DNA
<213> ORGANISM: Artificial sequence
<220> FEATURE:

<223> OTHER INFORMATION: Synthetic polynucleotide

<400> SEQUENCE: 82
taaggagtaa agtttgcgg 19

<210> SEQ ID NO 83
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 83
ctcctaagat tggcttcac 19

<210> SEQ ID NO 84
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 84
gtgaagccaa tcttaggag 19

<210> SEQ ID NO 85
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 85
ccggagccac tcctaagat 19

<210> SEQ ID NO 86
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 86
atcttaggag tggctccgg 19

<210> SEQ ID NO 87
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 87
ttctctaccc tacgtctca 19

<210> SEQ ID NO 88
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 88
tgagacgtag ggtagagaa 19

<210> SEQ ID NO 89
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 89
tacgtctcat tctccgcaa 19

<210> SEQ ID NO 90
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 90
ttgcggagaa tgagacgta 19

<210> SEQ ID NO 91
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 91
gctaggcctc cagcccttc 19

<210> SEQ ID NO 92
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 92
gaagggctgg aggcctagc 19

<210> SEQ ID NO 93
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 93
acaggtggcg ccgcaactt 19

<210> SEQ ID NO 94
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 94
aagttgcggc gccacctgt 19

<210> SEQ ID NO 95
<211> LENGTH: 19
<212> TYPE: DNA
<213> ORGANISM: Artificial sequence
<220> FEATURE:
<223> OTHER INFORMATION: Synthetic polynucleotide -continued

```
<400> SEQUENCE: 95

agccggaggc gcgagagtc                                                    19


<210> SEQ ID NO 96
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 96

gactctcgcg cctccggct                                                    19
```